(12) United States Patent
Niu et al.

(10) Patent No.: US 9,676,785 B2
(45) Date of Patent: Jun. 13, 2017

(54) HCV PROTEASE INHIBITORS AND USES THEREOF

(71) Applicant: Celgene CAR LLC, Pembroke (BM)

(72) Inventors: Deqiang Niu, Lexington, MA (US);
Russell C. Petter, Stow, MA (US);
Juswinder Singh, Ashland, MA (US);
Arthur F. Kluge, Lincoln, MA (US);
Lixin Qiao, Tewksbury, MA (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 14/331,161

(22) Filed: Jul. 14, 2014

(65) Prior Publication Data
US 2014/0323465 A1 Oct. 30, 2014

Related U.S. Application Data

(62) Division of application No. 12/339,770, filed on Dec. 19, 2008, now Pat. No. 8,778,877.

(60) Provisional application No. 61/016,110, filed on Dec. 21, 2007, provisional application No. 61/016,473, filed on Dec. 23, 2007, provisional application No. 61/075,001, filed on Jun. 23, 2008, provisional application No. 61/098,675, filed on Sep. 19, 2008.

(51) Int. Cl.
| | | |
|---|---|---|
| *C07D 403/14* | (2006.01) | |
| *C07D 487/16* | (2006.01) | |
| *C07K 5/078* | (2006.01) | |
| *C07K 5/083* | (2006.01) | |
| *C07K 5/087* | (2006.01) | |
| *C07K 5/08* | (2006.01) | |
| *A61K 31/4035* | (2006.01) | |
| *A61K 31/407* | (2006.01) | |
| *A61K 31/506* | (2006.01) | |
| *A61K 45/06* | (2006.01) | |
| *C07D 403/12* | (2006.01) | |
| *C07D 487/04* | (2006.01) | |
| *A61K 38/00* | (2006.01) | |

(52) U.S. Cl.
CPC .......... *C07D 487/16* (2013.01); *A61K 31/407* (2013.01); *A61K 31/4035* (2013.01); *A61K 31/506* (2013.01); *A61K 45/06* (2013.01); *C07D 403/12* (2013.01); *C07D 403/14* (2013.01); *C07D 487/04* (2013.01); *C07K 5/06165* (2013.01); *C07K 5/0806* (2013.01); *C07K 5/0812* (2013.01); *C07K 5/0827* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,018,020 A | 1/2000 | Attwood et al. | |
| 6,211,338 B1 | 4/2001 | Malcolm et al. | |
| 6,642,204 B2 | 11/2003 | Llinas-Brunet et al. | |
| 6,727,267 B2 | 4/2004 | Jaen et al. | |
| 6,800,434 B2 | 10/2004 | Saksena et al. | |
| 6,825,347 B2 | 11/2004 | Carpino et al. | |
| 6,867,185 B2 | 3/2005 | Campbell et al. | |
| 6,869,964 B2 | 3/2005 | Campbell et al. | |
| 6,872,805 B2 | 3/2005 | Campbell et al. | |
| 6,878,722 B2 | 4/2005 | Campbell et al. | |
| 6,894,072 B2 | 5/2005 | Arasappan et al. | |
| 6,908,901 B2 | 6/2005 | Bailey et al. | |
| 6,914,122 B2 | 7/2005 | Venkatraman et al. | |
| 6,919,423 B2 | 7/2005 | Llinas-Brunet | |
| 6,995,174 B2 | 2/2006 | Wang et al. | |
| 7,041,698 B2 | 5/2006 | Ripka et al. | |
| 7,091,184 B2 | 8/2006 | Llinas-Brunet et al. | |
| 7,122,627 B2 | 10/2006 | Priestley et al. | |
| 7,132,504 B2 | 11/2006 | Scola et al. | |
| 7,135,462 B2 | 11/2006 | Scola et al. | |
| 7,148,347 B2 | 12/2006 | Brandenburg et al. | |
| 7,189,844 B2 | 3/2007 | Gallou et al. | |
| 7,208,600 B2 | 4/2007 | Cottrell et al. | |
| 7,253,160 B2 | 8/2007 | Njoroge et al. | |
| 7,273,851 B2 | 9/2007 | Miao et al. | |
| 7,273,885 B2 | 9/2007 | Pitlik et al. | |
| 7,309,708 B2 | 12/2007 | Tu et al. | |
| 7,323,447 B2 | 1/2008 | Sin et al. | |
| 7,402,568 B2 | 7/2008 | Or et al. | |
| 7,449,479 B2 | 11/2008 | Wang et al. | |
| 7,470,664 B2 | 12/2008 | Holloway et al. | |
| 7,491,794 B2 | 2/2009 | Blatt et al. | |
| 7,582,605 B2 | 9/2009 | Moore et al. | |
| 7,605,126 B2 | 10/2009 | Niu et al. | |
| 7,635,683 B2 | 12/2009 | Gai et al. | |
| 7,662,779 B2 | 2/2010 | Sun et al. | |
| 7,687,459 B2 | 3/2010 | Niu et al. | |
| 8,188,137 B2 | 5/2012 | Niu et al. | |
| 8,293,705 B2 | 10/2012 | Niu et al. | |

(Continued)

FOREIGN PATENT DOCUMENTS

| | | | |
|---|---|---|---|
| CN | 1668297 A | 9/2005 | |
| CN | 1902216 A | 1/2007 | |

(Continued)

OTHER PUBLICATIONS

Alberti, A. et al., J. Hepatology 31., (Suppl. 1): 17-24, 1999.
Blight, K.J. et al., Antiviral Ther. 3, Suppl. 3: 71-81, 1998.
De Francesco, R. et al., Advances in the development of new therapeutic agents targeting the NS3-4A serine protease or the NS5B RNA-dependent RNA polymerase of the hepatitis C virus, Advanced Drug Delivery Reviews, 59(12):1242-1262 (2007).
Hepatitis C Support Project, "HCV: Genotype & Quasispecies", Version 2.0, pp. 1-3, Feb. 2006.

(Continued)

*Primary Examiner* — Thomas S Heard
(74) *Attorney, Agent, or Firm* — Choate, Hall & Stewart LLP; John P. Rearick; Nicholas J. Pace

(57) ABSTRACT

The present invention provides compounds, pharmaceutically acceptable compositions thereof, and methods of using the same.

32 Claims, 11 Drawing Sheets

(56) References Cited

U.S. PATENT DOCUMENTS

| | | |
|---|---|---|
| 8,309,685 B2 | 11/2012 | Petter et al. |
| 8,524,760 B2 | 9/2013 | Niu et al. |
| 8,603,737 B2 | 12/2013 | Hagel et al. |
| 8,741,837 B2 | 6/2014 | Niu et al. |
| 8,778,877 B2 | 7/2014 | Niu et al. |
| 8,980,935 B2 | 3/2015 | Niu et al. |
| 9,163,061 B2 | 10/2015 | Petter et al. |
| 2003/0064499 A1 | 4/2003 | Houghton et al. |
| 2004/0072761 A1 | 4/2004 | Campbell et al. |
| 2004/0162318 A1 | 8/2004 | Saha et al. |
| 2004/0180815 A1 | 9/2004 | Nakajima et al. |
| 2004/0265917 A1 | 12/2004 | Benjamin et al. |
| 2005/0014136 A1 | 1/2005 | Depla et al. |
| 2005/0020503 A1 | 1/2005 | Llinas-Brunet et al. |
| 2005/0053617 A1 | 3/2005 | Depla et al. |
| 2005/0143316 A1 | 6/2005 | Tu et al. |
| 2005/0267018 A1 | 12/2005 | Blatt et al. |
| 2005/0267151 A1 | 12/2005 | Busacca et al. |
| 2006/0019905 A1 | 1/2006 | Bailey et al. |
| 2006/0046956 A1 | 3/2006 | Sannigrahi et al. |
| 2006/0121563 A1 | 6/2006 | Prassler et al. |
| 2006/0122123 A1 | 6/2006 | Chaudhary et al. |
| 2006/0142204 A1 | 6/2006 | Halfon et al. |
| 2006/0183694 A1 | 8/2006 | Sin et al. |
| 2006/0199773 A1 | 9/2006 | Sausker et al. |
| 2006/0205638 A1 | 9/2006 | Busacca et al. |
| 2006/0258868 A1 | 11/2006 | Bailey et al. |
| 2006/0276405 A1 | 12/2006 | Albrecht |
| 2006/0276406 A1 | 12/2006 | Gupta et al. |
| 2006/0276407 A1 | 12/2006 | Albrecht et al. |
| 2006/0281688 A1 | 12/2006 | Zhang et al. |
| 2006/0281689 A1 | 12/2006 | Malcolm |
| 2006/0287248 A1 | 12/2006 | Malcolm |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0021351 A1 | 1/2007 | White et al. |
| 2007/0027071 A1 | 2/2007 | Holloway et al. |
| 2007/0054842 A1 | 3/2007 | Blatt et al. |
| 2007/0054864 A1 | 3/2007 | Graupe et al. |
| 2007/0072809 A1 | 3/2007 | Cho et al. |
| 2007/0099825 A1 | 5/2007 | D'Andrea et al. |
| 2007/0224167 A1 | 9/2007 | Emini et al. |
| 2007/0237818 A1 | 10/2007 | Malcolm et al. |
| 2007/0243166 A1 | 10/2007 | Llinas-Brunet et al. |
| 2008/0032936 A1 | 2/2008 | Gai et al. |
| 2008/0119461 A1 | 5/2008 | Sin et al. |
| 2008/0152619 A1 | 6/2008 | Sin et al. |
| 2009/0081636 A1 | 3/2009 | Huang |
| 2009/0176858 A1 | 7/2009 | Niu et al. |
| 2009/0180981 A1 | 7/2009 | Niu et al. |
| 2009/0274656 A1 | 11/2009 | Wang et al. |
| 2009/0306085 A1 | 12/2009 | Petter et al. |
| 2010/0041591 A1 | 2/2010 | Niu et al. |
| 2010/0041674 A1 | 2/2010 | Niu et al. |
| 2010/0069294 A1 | 3/2010 | Petter et al. |
| 2010/0074890 A1 | 3/2010 | Hagel et al. |
| 2012/0190614 A1 | 7/2012 | Niu et al. |
| 2013/0017991 A1 | 1/2013 | Niu et al. |
| 2013/0131105 A1 | 5/2013 | Petter et al. |
| 2013/0338062 A1 | 12/2013 | Niu et al. |
| 2015/0031106 A1 | 1/2015 | Niu et al. |
| 2015/0175657 A1 | 6/2015 | Niu et al. |
| 2016/0235805 A1 | 8/2016 | Petter et al. |
| 2016/0243249 A1 | 8/2016 | Petter et al. |
| 2016/0326216 A1 | 11/2016 | Niu et al. |

FOREIGN PATENT DOCUMENTS

| | | |
|---|---|---|
| JP | 2006-507264 A | 3/2006 |
| JP | 2006-511193 A | 4/2006 |
| JP | 2006-523714 A | 10/2006 |
| JP | 2006-528937 A | 12/2006 |
| JP | 2011-509243 A | 3/2011 |
| WO | WO-03/091411 A2 | 11/2003 |
| WO | WO-03099274 A1 | 12/2003 |
| WO | WO-2004/032827 A2 | 4/2004 |
| WO | WO-2004/033425 A1 | 4/2004 |
| WO | WO-2004/094452 A2 | 11/2004 |
| WO | WO-2004/103996 A1 | 12/2004 |
| WO | WO-2005037214 A2 | 4/2005 |
| WO | WO-2005/051980 A1 | 6/2005 |
| WO | WO-2005/095403 A2 | 10/2005 |
| WO | WO-2005/113581 A1 | 12/2005 |
| WO | WO-2006/000085 A1 | 1/2006 |
| WO | WO-2006/007700 A1 | 1/2006 |
| WO | WO-2006/007708 A1 | 1/2006 |
| WO | WO-2006/026352 A1 | 3/2006 |
| WO | WO-2006086381 A2 | 8/2006 |
| WO | WO-2006/119061 A2 | 11/2006 |
| WO | WO-2006/122188 A2 | 11/2006 |
| WO | WO-2006/130607 A2 | 12/2006 |
| WO | WO-2006/130666 A2 | 12/2006 |
| WO | WO-2007/009227 A1 | 1/2007 |
| WO | WO-2007005838 A2 | 1/2007 |
| WO | WO-2007/016441 A1 | 2/2007 |
| WO | WO-2007015787 A1 | 2/2007 |
| WO | WO-2007015855 A1 | 2/2007 |
| WO | WO-2007044893 A2 | 4/2007 |
| WO | WO-2007044933 A1 | 4/2007 |
| WO | WO-2007/089618 A2 | 8/2007 |
| WO | WO-2007/131966 A1 | 11/2007 |
| WO | WO-2008/005511 A2 | 1/2008 |
| WO | WO-2008/051477 A2 | 5/2008 |
| WO | WO-2008/057208 A2 | 5/2008 |
| WO | WO-2008/057209 A1 | 5/2008 |
| WO | WO-2008/112108 A1 | 9/2008 |
| WO | WO-2009/047264 A1 | 4/2009 |
| WO | WO-2009/082697 A1 | 7/2009 |
| WO | WO-2009/082701 A1 | 7/2009 |
| WO | WO-2011/002807 A1 | 1/2011 |
| WO | WO-2011/002808 A1 | 1/2011 |

OTHER PUBLICATIONS

Huang, J.F. et al., J Viral Hepatitis 13(6): 396-401, 2006.
Hung, C.H. et al., J Viral Hepatitis 13(6): 409-414, 2006.
International Search Report PCT/US08/87725 mailed Feb. 23, 2009.
International Search Report PCT/US08/87736 mailed Feb. 23, 2009.
International Search Report PCT/US10/40473 mailed Aug. 30, 2010.
International Search Report PCT/US10/40474 mailed Aug. 30, 2010.
Lamarre et al., "An NS3 protease inhibitor with antiviral effects in humans infected with hepatitis C virus" Nature 186-189, 314 (2004).
Lin et al., The Journal of Biological Chemistry, vol. 279, No. 17, Issue of Apr. 23, 17508-17514, 2004.
Liverton N. et al., J. Am. Chem. Soc., 130 (14), 4607-4609, 2008.
Llinàs-Brunet et al., "Structure-activity study on a novel series of macrocyclic inhibitors of the hepatitis C virus NS3 protease leading to the discovery of BILN 2061" J. Med. Chem. 47:1605-1608 (2004).
Lohmann V et al., J. Virol., 77:3007-3019, 2003.
McCauley et al., "Bismacrocyclic Inhibitors of Hepatitis C NS3/4a Protease" Angew. Chem. Int. Ed. 47:1-5 (2008).
McCauley, J.A. et al., Angew. Chem. Int. Ed., 47, 9104-7, 2008.
Moradpour, D. et al., Eur. J. Gastroenterol. Hepatol., 11, 1199-1202, 1999.
Ontoria, et al., J. Med. Chem., 47, 6443-6446, 2004.
Perni, R. B. et al., Inhibitors of hepatitis C virus NS3 o 4A protease 2. Warhead SAR and optimization., Bioorganic & Medicinal Chemistry Letters, 14(6):1441-1446 (2004).
Perni, R. B. et al., Inhibitors of hepatitis C virus NS3 o 4A protease. Part 3: P2 proline variants, Bioorganic & Medicinal Chemistry Letters, 14(8):1939-1942 (2004).

(56) References Cited

OTHER PUBLICATIONS

Raboisson et al., "Structure-activity relationship study on a novel series of cyclopentane-containing macrocyclic inhibitors of the hepatitis C virus NS3/4A protease leading to the discovery of TMC435350" *Bioorganic & Medical Chemistry Letters* (2008), 4853-4858.

Ronn et al., "Novel C-terminal Functionalities in Hepatitis C Virus NS3 Protease Inhibitors" The 229th ACS National Meeting, in San Diego, CA, Mar. 13-17, 2005.

Rostovtsev et al., Angew. Chem. Int. Ed., 41, 2596-99, 2002.

Rönn et al., "Evaluation of a diverse set of potential P1 carboxylic acid bioisosteres in hepatitis C virus NS3 protease inhibitors" *Bioorganic & Medical Chemistry* 15 (2007) 4057-4068.

Rönn et al., "Exploration of acyl sulfonamides as carboxylic acid replacements in protease inhibitors of the hepatitis C virus full-length NS3" *Bioorganic & Medical Chemistry* 14 (2006) 544-559.

Rönn, Digital Comprehensive Summaries of Uppsala Dissertations from the Faculty of Pharmacy 53, "Design and Synthesis of Inhibitors Targeting the Hepatitis C Virus NS3 Protease", 2007, 1-80.

Seiwert et al., "Preclinical characteristics of the hepatitis C virus NS3/4A protease inhibitor ITMN-191 (R7227)" *Antimicrob Agents Chemother.* 52(12):4432-4441 (2008).

Simmonds et al., Hepatology, vol. 42, No. 4, 962-973, 2005.

Sun et al., Bioconjugate Chem., 17, 52-57, 2006.

Supplementary European Search Report for Application No. EP 08864666 mailed Apr. 17, 2012.

Supplementary European Search Report for Application No. EP 08865122 mailed Apr. 17, 2012.

Walker, M.A. et al., DDT 4: 518-29, 1999.

Weiland, O., FEMS Microbiol. Rev. 14: 279-88, 1994.

Yin, Z. et al., Peptide inhibitors of dengue virus NS3 protease. Part 1: Warhead, Bioorganic & Medicinal Chemistry Letters, 16(1):36-39 (2006).

Written Opinion for PCT/US2008/087725, 7 pages (Feb. 23, 2009).

Written Opinion for PCT/US2008/087736, 7 pages (Feb. 23, 2009).

Written Opinion for PCT/US2010/040473, 5 pages (Aug. 30, 2010).

Written Opinion for PCT/US2010/040474, 4 pages (Aug. 30, 2010).

U.S. Appl. No. 14/293,444, filed Jun. 2, 2014, Niu et al.

U.S. Appl. No. 14/639,228, filed Mar. 5, 2015, Niu et al.

U.S. Appl. No. 15/202,501, Jul. 5, 2016, Niu et al.

FIG. 7

Compound I-11 Contacted with HCV A156T

HCV R156T w/ I-11

23216.73{r59}
24210.34{r8}
24506.73{r146}
25328.09{r406}
25527.05{r206}
25763.06{r15}
26317.64{r10}
28338.61{r122}

Mass/Charge

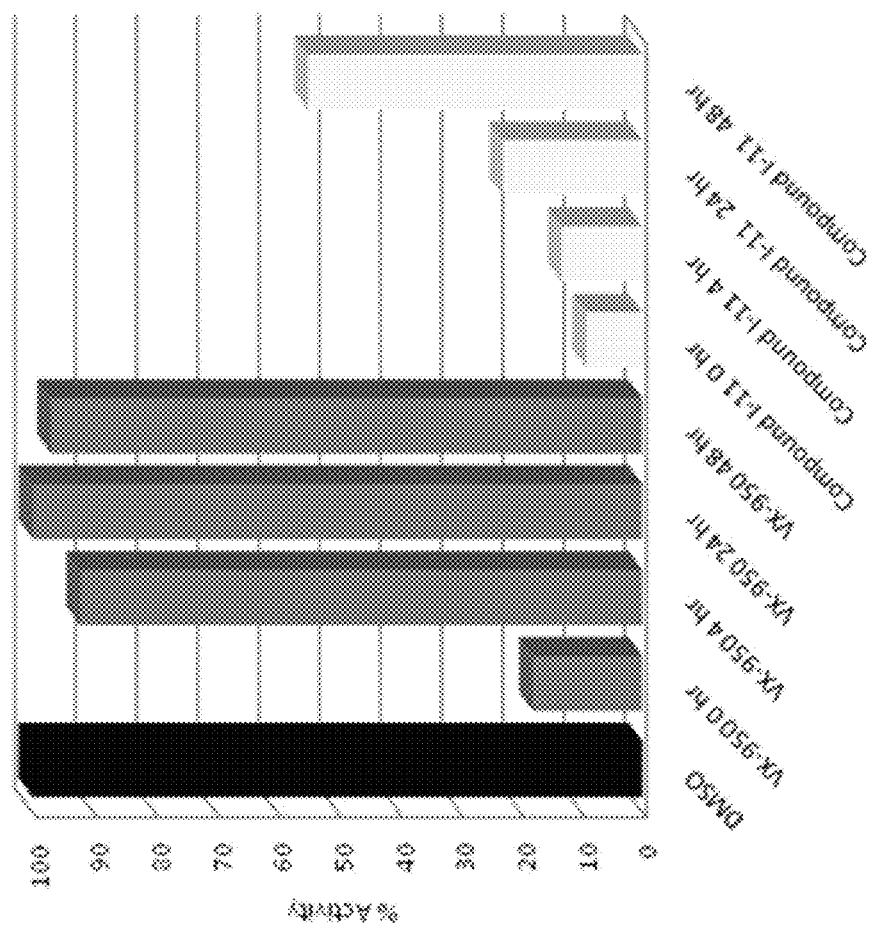

Washout Experiment in WT Replicon Cells

SEQUENCE LISTING

<160> NUMBER OF SEQ ID NOS: 77

<210> SEQ ID NO 1
<211> LENGTH: 20
<212> TYPE: PRT
<213> ORGANISM: Hepatitis C virus

<400> SEQUENCE: 1

Gly His Ala Val Gly Leu Phe Arg Ala Ala Val Cys Thr Arg Gly Val
1               5                   10                  15

Ala Lys Ala Val
            20

<210> SEQ ID NO 2
<211> LENGTH: 20
<212> TYPE: PRT
<213> ORGANISM: Hepatitis C virus

<400> SEQUENCE: 2

Gly His Ala Val Gly Ile Phe Arg Ala Ala Val Cys Thr Arg Gly Val
1               5                   10                  15

Ala Lys Ala Val
            20

<210> SEQ ID NO 3
<211> LENGTH: 20
<212> TYPE: PRT
<213> ORGANISM: Hepatitis C virus

<400> SEQUENCE: 3

Gly His Ala Val Gly Ile Phe Arg Ala Ala Val Cys Thr Arg Gly Val
1               5                   10                  15

Ala Lys Ala Val
            20

<210> SEQ ID NO 4
<211> LENGTH: 20
<212> TYPE: PRT
<213> ORGANISM: Hepatitis C virus

<400> SEQUENCE: 4

Gly His Ala Val Gly Leu Phe Arg Ala Ala Val Cys Thr Arg Gly Val
1               5                   10                  15

Ala Lys Ala Val
            20

<210> SEQ ID NO 5
<211> LENGTH: 20
<212> TYPE: PRT
<213> ORGANISM: Hepatitis C virus

<400> SEQUENCE: 5

Gly His Ala Val Gly Ile Phe Arg Ala Ala Val Cys Thr Arg Gly Val
1               5                   10                  15

Ala Lys Ala Val
            20

<210> SEQ ID NO 6
<211> LENGTH: 20
<212> TYPE: PRT
<213> ORGANISM: Hepatitis C virus

<400> SEQUENCE: 6

```
Gly His Val Val Gly Ile Phe Arg Ala Ala Val Cys Thr Arg Gly Val
1               5                   10                  15

Ala Lys Ala Val
            20

<210> SEQ ID NO 7
<211> LENGTH: 20
<212> TYPE: PRT
<213> ORGANISM: Hepatitis C virus

<400> SEQUENCE: 7

Gly His Ala Val Gly Ile Phe Arg Ala Ala Val Cys Thr Arg Gly Val
1               5                   10                  15

Ala Lys Ala Val
            20

<210> SEQ ID NO 8
<211> LENGTH: 20
<212> TYPE: PRT
<213> ORGANISM: Hepatitis C virus

<400> SEQUENCE: 8

Gly His Ala Val Gly Ile Phe Arg Ala Ala Val Cys Thr Arg Gly Val
1               5                   10                  15

Ala Lys Ala Val
            20

<210> SEQ ID NO 9
<211> LENGTH: 20
<212> TYPE: PRT
<213> ORGANISM: Hepatitis C virus

<400> SEQUENCE: 9

Gly His Val Ala Gly Ile Phe Arg Ala Ala Val Cys Thr Arg Gly Val
1               5                   10                  15

Ala Lys Ala Val
            20

<210> SEQ ID NO 10
<211> LENGTH: 20
<212> TYPE: PRT
<213> ORGANISM: Hepatitis C virus

<400> SEQUENCE: 10

Gly His Ala Val Gly Ile Phe Arg Ala Ala Val Cys Ser Arg Gly Val
1               5                   10                  15

Ala Lys Ser Ile
            20

<210> SEQ ID NO 11
<211> LENGTH: 20
<212> TYPE: PRT
<213> ORGANISM: Hepatitis C virus

<400> SEQUENCE: 11

Gly His Ala Val Gly Ile Phe Arg Ala Ala Val Cys Ser Arg Gly Val
1               5                   10                  15

Ala Lys Ser Ile
            20

<210> SEQ ID NO 12
```

-continued

```
<211> LENGTH: 20
<212> TYPE: PRT
<213> ORGANISM: Hepatitis C virus

<400> SEQUENCE: 12

Gly His Ala Val Gly Ile Phe Arg Ala Ala Val Cys Ser Arg Gly Val
1               5                   10                  15

Ala Lys Ser Ile
            20

<210> SEQ ID NO 13
<211> LENGTH: 20
<212> TYPE: PRT
<213> ORGANISM: Hepatitis C virus

<400> SEQUENCE: 13

Gly His Ala Val Gly Leu Phe Arg Ala Ala Val Cys Ala Arg Gly Val
1               5                   10                  15

Ala Lys Ser Ile
            20

<210> SEQ ID NO 14
<211> LENGTH: 20
<212> TYPE: PRT
<213> ORGANISM: Hepatitis C virus

<400> SEQUENCE: 14

Gly His Ala Val Gly Leu Phe Arg Ala Ala Val Cys Ala Arg Gly Val
1               5                   10                  15

Ala Lys Ser Ile
            20

<210> SEQ ID NO 15
<211> LENGTH: 20
<212> TYPE: PRT
<213> ORGANISM: Hepatitis C virus

<400> SEQUENCE: 15

Gly His Ala Val Gly Ile Phe Arg Ala Ala Val Cys Ser Arg Gly Val
1               5                   10                  15

Ala Lys Ser Ile
            20

<210> SEQ ID NO 16
<211> LENGTH: 20
<212> TYPE: PRT
<213> ORGANISM: Hepatitis C virus

<400> SEQUENCE: 16

Ala His Ala Val Gly Ile Phe Arg Ala Ala Val Cys Ser Arg Gly Val
1               5                   10                  15

Ala Lys Ser Ile
            20

<210> SEQ ID NO 17
<211> LENGTH: 20
<212> TYPE: PRT
<213> ORGANISM: Hepatitis C virus

<400> SEQUENCE: 17

Gly His Ala Val Gly Ile Phe Arg Ala Ala Ile Cys Thr Arg Gly Ala
1               5                   10                  15
```

Ala Lys Ser Ile
            20

<210> SEQ ID NO 18
<211> LENGTH: 20
<212> TYPE: PRT
<213> ORGANISM: Hepatitis C virus

<400> SEQUENCE: 18

Gly His Val Ala Gly Ile Phe Arg Ala Ala Val Cys Thr Arg Gly Val
1               5                   10                  15

Ala Lys Ala Leu
            20

<210> SEQ ID NO 19
<211> LENGTH: 20
<212> TYPE: PRT
<213> ORGANISM: Hepatitis C virus

<400> SEQUENCE: 19

Gly His Val Ala Gly Ile Phe Arg Ala Ala Val Cys Thr Arg Gly Val
1               5                   10                  15

Ala Lys Ala Leu
            20

<210> SEQ ID NO 20
<211> LENGTH: 20
<212> TYPE: PRT
<213> ORGANISM: Hepatitis C virus

<400> SEQUENCE: 20

Gly His Val Ala Gly Ile Phe Arg Ala Ala Val Cys Thr Arg Gly Val
1               5                   10                  15

Ala Lys Ala Leu
            20

<210> SEQ ID NO 21
<211> LENGTH: 20
<212> TYPE: PRT
<213> ORGANISM: Hepatitis C virus

<400> SEQUENCE: 21

Gly His Val Met Gly Ile Phe Ile Ala Val Val Cys Thr Arg Gly Val
1               5                   10                  15

Ala Lys Ala Leu
            20

<210> SEQ ID NO 22
<211> LENGTH: 20
<212> TYPE: PRT
<213> ORGANISM: Hepatitis C virus

<400> SEQUENCE: 22

Gly His Val Val Gly Ile Phe Arg Ala Ala Val Cys Thr Arg Gly Val
1               5                   10                  15

Ala Lys Ala Leu
            20

<210> SEQ ID NO 23
<211> LENGTH: 20
<212> TYPE: PRT
<213> ORGANISM: Hepatitis C virus

```
<400> SEQUENCE: 23

Gly His Val Ala Gly Ile Phe Arg Ala Ala Val Cys Thr Arg Gly Val
1               5                   10                  15

Ala Lys Ala Leu
            20

<210> SEQ ID NO 24
<211> LENGTH: 20
<212> TYPE: PRT
<213> ORGANISM: Hepatitis C virus

<400> SEQUENCE: 24

Gly His Ala Ala Gly Ile Phe Arg Ala Ala Val Cys Thr Arg Gly Val
1               5                   10                  15

Ala Lys Ala Val
            20

<210> SEQ ID NO 25
<211> LENGTH: 20
<212> TYPE: PRT
<213> ORGANISM: Hepatitis C virus

<400> SEQUENCE: 25

Gly His Ala Ala Gly Leu Phe Arg Ala Ala Val Cys Thr Arg Gly Val
1               5                   10                  15

Ala Lys Ala Val
            20

<210> SEQ ID NO 26
<211> LENGTH: 20
<212> TYPE: PRT
<213> ORGANISM: Hepatitis C virus

<400> SEQUENCE: 26

Gly His Ala Ala Gly Leu Phe Arg Ala Ala Val Cys Thr Arg Gly Val
1               5                   10                  15

Ala Lys Ala Val
            20

<210> SEQ ID NO 27
<211> LENGTH: 20
<212> TYPE: PRT
<213> ORGANISM: Hepatitis C virus

<400> SEQUENCE: 27

Gly His Ala Ala Gly Ile Phe Arg Ala Ala Val Cys Thr Arg Gly Val
1               5                   10                  15

Ala Lys Ala Val
            20

<210> SEQ ID NO 28
<211> LENGTH: 20
<212> TYPE: PRT
<213> ORGANISM: Hepatitis C virus

<400> SEQUENCE: 28

Gly His Ala Ala Gly Ile Phe Arg Ala Ala Val Cys Thr Arg Gly Val
1               5                   10                  15

Ala Lys Thr Val
            20
```

```
<210> SEQ ID NO 29
<211> LENGTH: 20
<212> TYPE: PRT
<213> ORGANISM: Hepatitis C virus

<400> SEQUENCE: 29

Gly His Ala Val Gly Ile Phe Arg Ala Ala Val Cys Thr Arg Gly Val
1               5                   10                  15

Ala Lys Ala Val
            20

<210> SEQ ID NO 30
<211> LENGTH: 20
<212> TYPE: PRT
<213> ORGANISM: Hepatitis C virus

<400> SEQUENCE: 30

Gly His Ala Val Gly Ile Phe Arg Ala Ala Val Cys Thr Arg Gly Val
1               5                   10                  15

Ala Lys Ala Val
            20

<210> SEQ ID NO 31
<211> LENGTH: 20
<212> TYPE: PRT
<213> ORGANISM: Hepatitis C virus

<400> SEQUENCE: 31

Gly His Val Val Gly Val Phe Arg Ala Ala Val Cys Thr Arg Gly Val
1               5                   10                  15

Ala Lys Ala Leu
            20

<210> SEQ ID NO 32
<211> LENGTH: 20
<212> TYPE: PRT
<213> ORGANISM: Hepatitis C virus

<400> SEQUENCE: 32

Gly His Val Val Gly Val Phe Arg Ala Ala Val Cys Thr Arg Gly Val
1               5                   10                  15

Ala Lys Ala Leu
            20

<210> SEQ ID NO 33
<211> LENGTH: 20
<212> TYPE: PRT
<213> ORGANISM: Hepatitis C virus

<400> SEQUENCE: 33

Gly His Val Val Gly Leu Phe Arg Ala Ala Val Cys Thr Arg Gly Val
1               5                   10                  15

Ala Lys Ser Leu
            20

<210> SEQ ID NO 34
<211> LENGTH: 20
<212> TYPE: PRT
<213> ORGANISM: Hepatitis C virus

<400> SEQUENCE: 34

Gly His Val Val Gly Leu Phe Arg Ala Ala Val Cys Thr Arg Gly Val
1               5                   10                  15
```

```
<210> SEQ ID NO 35
<211> LENGTH: 20
<212> TYPE: PRT
<213> ORGANISM: Hepatitis C virus

<400> SEQUENCE: 35

Gly His Val Val Gly Leu Phe Arg Ala Ala Val Cys Thr Arg Gly Val
1               5                   10                  15
Ala Lys Ser Leu
            20

<210> SEQ ID NO 36
<211> LENGTH: 20
<212> TYPE: PRT
<213> ORGANISM: Hepatitis C virus

<400> SEQUENCE: 36

Gly His Val Val Gly Leu Phe Arg Ala Ala Val Cys Thr Arg Gly Val
1               5                   10                  15
Ala Lys Ala Leu
            20

<210> SEQ ID NO 37
<211> LENGTH: 20
<212> TYPE: PRT
<213> ORGANISM: Hepatitis C virus

<400> SEQUENCE: 37

Gly His Val Val Gly Leu Phe Arg Ala Ala Val Cys Thr Arg Gly Val
1               5                   10                  15
Ala Lys Ala Leu
            20

<210> SEQ ID NO 38
<211> LENGTH: 20
<212> TYPE: PRT
<213> ORGANISM: Hepatitis C virus

<400> SEQUENCE: 38

Asp His Val Val Gly Leu Phe Arg Ala Ala Val Cys Thr Arg Gly Val
1               5                   10                  15
Ala Lys Ala Leu
            20

<210> SEQ ID NO 39
<211> LENGTH: 20
<212> TYPE: PRT
<213> ORGANISM: Hepatitis C virus

<400> SEQUENCE: 39

Gly His Val Val Gly Leu Phe Arg Ala Ala Val Cys Thr Arg Gly Val
1               5                   10                  15
Ala Lys Ala Ile
            20

<210> SEQ ID NO 40
<211> LENGTH: 20
<212> TYPE: PRT
<213> ORGANISM: Hepatitis C virus
```

```
<400> SEQUENCE: 40

Gly His Ala Val Gly Ile Phe Arg Ala Ala Val Cys Thr Arg Gly Val
1               5                   10                  15

Ala Lys Ala Ile
            20

<210> SEQ ID NO 41
<211> LENGTH: 20
<212> TYPE: PRT
<213> ORGANISM: Hepatitis C virus

<400> SEQUENCE: 41

Gly His Ala Val Gly Ile Phe Arg Ala Ala Val Cys Thr Arg Gly Val
1               5                   10                  15

Ala Lys Ala Ile
            20

<210> SEQ ID NO 42
<211> LENGTH: 20
<212> TYPE: PRT
<213> ORGANISM: Hepatitis C virus

<400> SEQUENCE: 42

Gly His Val Val Gly Leu Phe Arg Ala Ala Val Cys Thr Arg Gly Val
1               5                   10                  15

Ala Lys Ala Leu
            20

<210> SEQ ID NO 43
<211> LENGTH: 20
<212> TYPE: PRT
<213> ORGANISM: Hepatitis C virus

<400> SEQUENCE: 43

Gly His Val Val Gly Leu Phe Arg Ala Ala Val Cys Thr Arg Gly Val
1               5                   10                  15

Ala Lys Ala Leu
            20

<210> SEQ ID NO 44
<211> LENGTH: 20
<212> TYPE: PRT
<213> ORGANISM: Hepatitis C virus

<400> SEQUENCE: 44

Gly His Val Ala Gly Ile Phe Arg Ala Ala Val Cys Thr Arg Gly Val
1               5                   10                  15

Ala Lys Ser Leu
            20

<210> SEQ ID NO 45
<211> LENGTH: 20
<212> TYPE: PRT
<213> ORGANISM: Hepatitis C virus

<400> SEQUENCE: 45

Gly His Val Ala Gly Ile Phe Arg Ala Ala Val Cys Thr Arg Gly Val
1               5                   10                  15

Ala Lys Ser Leu
            20
```

```
<210> SEQ ID NO 46
<211> LENGTH: 20
<212> TYPE: PRT
<213> ORGANISM: Hepatitis C virus

<400> SEQUENCE: 46

Gly His Val Ala Gly Ile Phe Arg Ala Ala Val Cys Thr Arg Gly Val
1               5                   10                  15

Ala Lys Ser Leu
            20

<210> SEQ ID NO 47
<211> LENGTH: 20
<212> TYPE: PRT
<213> ORGANISM: Hepatitis C virus

<400> SEQUENCE: 47

Gly His Val Ala Gly Ile Phe Arg Ala Ala Val Cys Thr Arg Gly Val
1               5                   10                  15

Ala Lys Ser Leu
            20

<210> SEQ ID NO 48
<211> LENGTH: 20
<212> TYPE: PRT
<213> ORGANISM: Hepatitis C virus

<400> SEQUENCE: 48

Gly His Val Ala Gly Ile Phe Arg Ala Ala Val Cys Thr Arg Gly Val
1               5                   10                  15

Ala Lys Ser Leu
            20

<210> SEQ ID NO 49
<211> LENGTH: 20
<212> TYPE: PRT
<213> ORGANISM: Hepatitis C virus

<400> SEQUENCE: 49

Gly His Val Ala Gly Ile Phe Arg Ala Ala Val Cys Thr Arg Gly Val
1               5                   10                  15

Ala Lys Ser Leu
            20

<210> SEQ ID NO 50
<211> LENGTH: 20
<212> TYPE: PRT
<213> ORGANISM: Hepatitis C virus

<400> SEQUENCE: 50

Gly His Val Ala Gly Ile Phe Arg Ala Ala Val Cys Thr Arg Gly Val
1               5                   10                  15

Ala Lys Ser Leu
            20

<210> SEQ ID NO 51
<211> LENGTH: 20
<212> TYPE: PRT
<213> ORGANISM: Hepatitis C virus

<400> SEQUENCE: 51

Gly His Val Ala Gly Ile Phe Arg Ala Ala Val Cys Thr Arg Gly Val
```

```
                 1               5                  10                 15

Ala Lys Ser Leu
            20

<210> SEQ ID NO 52
<211> LENGTH: 20
<212> TYPE: PRT
<213> ORGANISM: Hepatitis C virus

<400> SEQUENCE: 52

Gly His Ala Val Gly Val Phe Arg Ala Ala Val Cys Thr Arg Gly Val
1               5                   10                  15

Ala Lys Ser Leu
            20

<210> SEQ ID NO 53
<211> LENGTH: 20
<212> TYPE: PRT
<213> ORGANISM: Hepatitis C virus

<400> SEQUENCE: 53

Gly His Ala Val Gly Val Phe Arg Ala Ala Val Cys Thr Arg Gly Val
1               5                   10                  15

Ala Lys Ser Leu
            20

<210> SEQ ID NO 54
<211> LENGTH: 20
<212> TYPE: PRT
<213> ORGANISM: Hepatitis C virus

<400> SEQUENCE: 54

Gly His Val Val Gly Ile Phe Arg Ala Ala Val Cys Thr Arg Gly Val
1               5                   10                  15

Ala Lys Ser Leu
            20

<210> SEQ ID NO 55
<211> LENGTH: 20
<212> TYPE: PRT
<213> ORGANISM: Hepatitis C virus

<400> SEQUENCE: 55

Gly His Val Val Gly Ile Phe Arg Ala Ala Val Cys Thr Arg Gly Val
1               5                   10                  15

Ala Lys Ser Leu
            20

<210> SEQ ID NO 56
<211> LENGTH: 20
<212> TYPE: PRT
<213> ORGANISM: Hepatitis C virus

<400> SEQUENCE: 56

Gly His Ala Val Gly Leu Phe Arg Ala Ala Val Cys Thr Arg Gly Val
1               5                   10                  15

Ala Lys Ala Ile
            20

<210> SEQ ID NO 57
<211> LENGTH: 20
<212> TYPE: PRT
```

<213> ORGANISM: Hepatitis C virus

<400> SEQUENCE: 57

Gly His Val Val Gly Leu Phe Arg Ala Ala Val Cys Thr Arg Gly Val
1               5                   10                  15

Ala Lys Ala Ile
            20

<210> SEQ ID NO 58
<211> LENGTH: 20
<212> TYPE: PRT
<213> ORGANISM: Hepatitis C virus

<400> SEQUENCE: 58

Gly His Ala Val Gly Leu Phe Arg Ala Ala Val Cys Thr Arg Gly Val
1               5                   10                  15

Ala Lys Ala Ile
            20

<210> SEQ ID NO 59
<211> LENGTH: 20
<212> TYPE: PRT
<213> ORGANISM: Hepatitis C virus

<400> SEQUENCE: 59

Gly His Val Val Gly Leu Phe Arg Ala Ala Val Cys Thr Arg Gly Val
1               5                   10                  15

Ala Lys Ala Ile
            20

<210> SEQ ID NO 60
<211> LENGTH: 20
<212> TYPE: PRT
<213> ORGANISM: Hepatitis C virus

<400> SEQUENCE: 60

Gly His Val Val Gly Leu Phe Arg Ala Ala Val Cys Thr Arg Gly Val
1               5                   10                  15

Ala Lys Ala Ile
            20

<210> SEQ ID NO 61
<211> LENGTH: 20
<212> TYPE: PRT
<213> ORGANISM: Hepatitis C virus

<400> SEQUENCE: 61

Gly His Val Val Gly Leu Phe Arg Ala Ala Val Cys Thr Arg Gly Val
1               5                   10                  15

Ala Lys Ala Ile
            20

<210> SEQ ID NO 62
<211> LENGTH: 20
<212> TYPE: PRT
<213> ORGANISM: Hepatitis C virus

<400> SEQUENCE: 62

Ser His Cys Val Gly Ile Phe Arg Ala Ala Val Cys Thr Arg Gly Val
1               5                   10                  15

Ala Lys Ala Val
            20

-continued

<210> SEQ ID NO 63
<211> LENGTH: 21
<212> TYPE: DNA
<213> ORGANISM: Artificial sequence
<220> FEATURE:
<223> OTHER INFORMATION: Synthetic; designed from HCV protease NS3

<400> SEQUENCE: 63
acgcagaaag cgtctagcca t                                              21

<210> SEQ ID NO 64
<211> LENGTH: 19
<212> TYPE: DNA
<213> ORGANISM: Artificial sequence
<220> FEATURE:
<223> OTHER INFORMATION: Synthetic; designed from HCV protease NS3

<400> SEQUENCE: 64
tactcaccgg ttccgcaga                                                 19

<210> SEQ ID NO 65
<211> LENGTH: 23
<212> TYPE: DNA
<213> ORGANISM: Artificial sequence
<220> FEATURE:
<223> OTHER INFORMATION: Synthetic; designed from HCV protease NS3
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (23)..(23)
<223> OTHER INFORMATION: Carboxytetramethylrhodamine

<400> SEQUENCE: 65
cctggaggct gcacgacact cat                                            23

<210> SEQ ID NO 66
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 66
gctgtgggca tctttcggtc tgccgtgtgc acccgaggg                           39

<210> SEQ ID NO 67
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 67
ccctcgggtg cacacggcag accgaaagat gcccacagc                           39

<210> SEQ ID NO 68
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 68
gctgtgggca tctttcggac tgccgtgtgc acccgaggg                                   39

<210> SEQ ID NO 69
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 69
ccctcgggtg cacacggcag tccgaaagat gcccacagc                                   39

<210> SEQ ID NO 70
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 70
ggggttgcga aggcggtggc ctttgtaccc gtcgagtct                                   39

<210> SEQ ID NO 71
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 71
agactcgacg ggtacaaagg ccaccgcctt cgcaacccc                                   39

<210> SEQ ID NO 72
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 72
ggggttgcga aggcggtggt ctttgtaccc gtcgagtct                                   39

<210> SEQ ID NO 73
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 73
agactcgacg ggtacaaaga ccaccgcctt cgcaacccc                                   39

<210> SEQ ID NO 74
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 74
atctttcggg ctgccgtgag cacccgaggg gttgcgaag                                   39

<210> SEQ ID NO 75
<211> LENGTH: 39
<212> TYPE: DNA
<213> ORGANISM: Artificial sequence

```
<220> FEATURE:
<223> OTHER INFORMATION: Synthetic; designed from HCV protease NS3

<400> SEQUENCE: 75
cttcgcaacc cctcgggtgc tcacggcagc ccgaaagat                              39

<210> SEQ ID NO 76
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 76
cacgctgtgg gcatctttaa ggctgccgtg tgcacccga                              39

<210> SEQ ID NO 77
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 77
tcgggtgcac acggcagcct taaagatgcc cacagcgtg                              39
```

HCV PROTEASE INHIBITORS AND USES THEREOF

CROSS-REFERENCE TO RELATED APPLICATIONS

The present invention is divisional of U.S. Ser. No. 12/339,770, filed Dec. 19, 2008, now U.S. Pat. No. 8,778,877, which claims priority to U.S. provisional application Ser. No. 61/016,110, filed Dec. 21, 2007, U.S. provisional application Ser. No. 61/016,473, filed Dec. 23, 2007, U.S. provisional application Ser. No. 61/075,001, filed Jun. 23, 2008, and U.S. provisional application Ser. No. 61/098,675, filed Sep. 19, 2008, the entirety of each of which is hereby incorporated by reference.

TECHNICAL FIELD OF THE INVENTION

The present invention relates to compounds useful as inhibitors of HCV protease. The invention also provides pharmaceutically acceptable compositions comprising compounds of the present invention and methods of using said compositions in the treatment of various disorders.

BACKGROUND OF THE INVENTION

It is estimated that over 170 million people worldwide are infected with the Hepatitis C virus (HCV). With an estimated human sero-prevalence of 3% globally, HCV is the major cause for most cases of non-A, non-B hepatitis, (Alberti, A. et al., J. Hepatology 31, (Suppl. 1): 17-24, 1999). While the symptoms of acute hepatitis subside in some patients, at least 85% of HCV infections become chronic, and 20% of those infected develop liver cirrhosis. There is less than a 50% survival rate at four years post cirrhosis diagnosis. Chronic HCV infection is also associated with increased incidence of hepatocellular carcinoma.

HCV is a positive-stranded RNA virus whose genome encodes a polyprotein of approximately 3000 amino acids. This precursor protein is processed into at least 10 viral structural and nonstructural proteins: C, E1, E2, p7, NS2, NS3, NS4A, NS4B, NS5A, and NS5B (Blight, K. J., et al., Antiviral Ther. 3, Suppl. 3: 71-81, 1998). HCV nonstructural (NS) proteins are derived by proteolytic cleavage of the polyprotein and are presumed to provide the essential catalytic machinery for viral replication.

NS3 is an approximately 68 Kda protein, and has both an N-terminal serine protease domain and an RNA-dependent ATPase domain at its C-terminus. It has been shown that the NS4A protein serves as a co-factor for the serine protease activity of NS3. NS3 functions as a proteolytic enzyme that cleaves sites liberating other nonstructural proteins necessary for HCV replication and is a viable therapeutic target for antiviral chemotherapy.

No vaccines are available for HCV, and the established therapy of interferon treatment is effective in only 15-20% of patients (Weiland, O., FEMS Microbiol. Rev. 14: 279-88, 1994), and has significant side effects (Walker, M. A., et al., DDT 4: 518-29, 1999; Moradpour, D., et al., Eur. J. Gastroenterol. Hepatol. 11: 1199-1202, 1999). While the current standard of care, pegylated interferon α in combination with ribavirin, is more efficacious and appears to decrease hepatocellular carcinoma in patients with HCV-related cirrhosis (Hung, C. H., et al., J Viral Hepatitis 13(6): 409-414, 2006), this treatment has also been shown to produce side effects such as thyroid dysfunction (Huang, J. F., et al., J Viral Hepatitis 13(6): 396-401, 2006).

The poor prognosis for patients suffering from HCV infection and the current lack of effective, approved treatments, highlights the overwhelming need for new inhibitors of HCV NS3 protease.

SUMMARY OF THE INVENTION

It has now been found that compounds of this invention, and pharmaceutically acceptable compositions thereof, are effective as inhibitors of HCV protease. Such compounds have the general formula I:

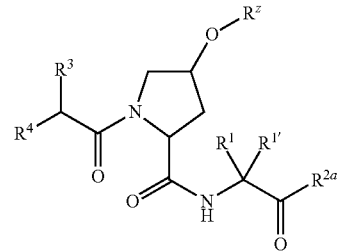

or a pharmaceutically acceptable salt thereof, wherein $R^1$, $R^{1'}$, $R^{2a}$, $R^3$, $R^4$ and $R^z$ are as defined herein.

Compounds of the present invention, and pharmaceutically acceptable compositions thereof, are useful for treating a variety of diseases, disorders or conditions, associated with HCV. Such diseases, disorders, or conditions include those described herein.

Compounds provided by this invention are also useful for the study of HCV protease in biological and pathological phenomena; the study of intracellular signal transduction pathways mediated by HCV protease; and the comparative evaluation of new HCV protease inhibitors.

BRIEF DESCRIPTION OF THE DRAWINGS

FIG. 7 depicts a mass spectroscopic analysis of HCV NS3/4A mutant A156T protease in the presence of test compound I-11.

FIG. 9 and 9a depict that an irreversible covalent inhibitor (compound I-11) of NS3 protease demonstrates prolonged inhibition of NS3 protease activity in the wild-type replicon cells, as measured by self-cleavage, after the compounds are removed.

DETAILED DESCRIPTION OF CERTAIN EMBODIMENTS

Figure 1:
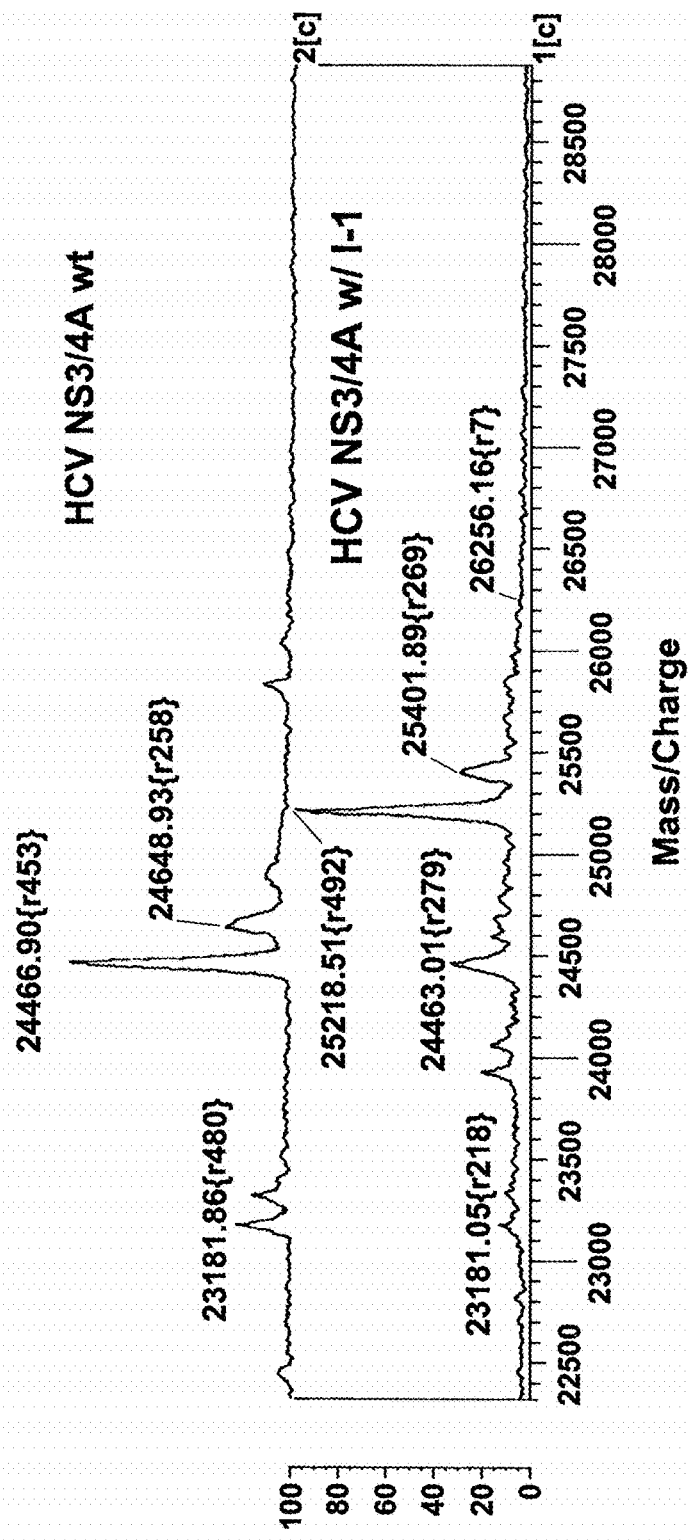
FIG. 1 depicts a mass spectroscopic analysis of HCV NS3/4A wild-type protease in the presence of test compound I-1.

1. General Description of Compounds of the Invention:

In certain embodiments, the present invention provides a compound of formula I:

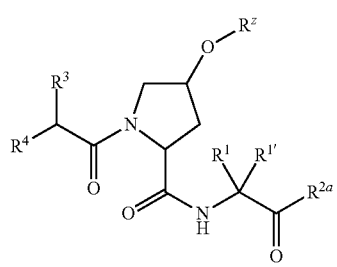

I or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{2a}$ is —OH or —NHSO$_2$R$^2$;

$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:

two R on the same nitrogen atom are taken together with the nitrogen to form a 4-7 membered heterocyclic ring having 1-2 heteroatoms independently selected from nitrogen, oxygen, or sulfur;

$R^3$ is a warhead group, or:

$R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group; or $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group;

$R^4$ is H, —NHC(O)R$^5$, —NHC(O)OR$^6$,

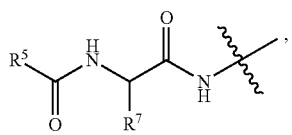

or a natural or unnatural amino acid side-chain group;

each $R^5$ is independently —N(R)$_2$ or an optionally substituted group selected from $C_{1-6}$ aliphatic, a bridged bicy-clic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

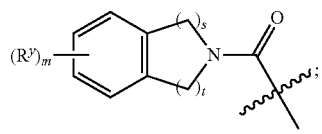

or $R^4$ and $R^z$ are taken together with their intervening atoms to form an optionally substituted, saturated or unsaturated 16-22 membered ring having 2-6 heteroatoms independently selected from nitrogen, oxygen, or sulfur;

each occurrence of $R^y$ is independently selected from halogen, —OR°, —CN, —NO$_2$, —N(R°)$_2$, or optionally substituted $C_{1-4}$ aliphatic; and m is an integer from 0 to 4, inclusive;

s is an integer from 0 to 4, inclusive;

t is an integer from 0 to 4, inclusive;

wherein the sum of s and t is non-zero.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms.

In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

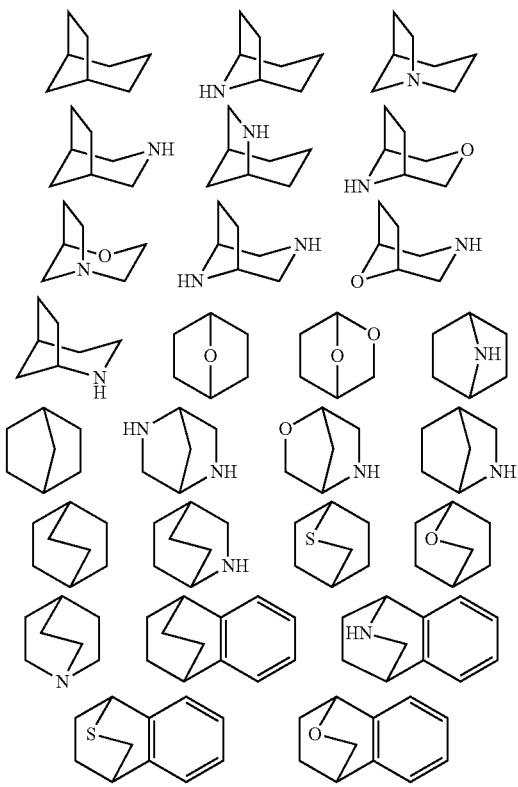

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

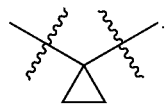

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the phrase "natural amino acid side-chain group" refers to the side-chain group of any of the 20 amino acids naturally occuring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to the side-chain group of amino acids not included in the list of 20 amino acids naturally occuring in proteins, as described above. Such amino acids include the D-isomer of any of the 20 naturally occuring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\bullet$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^3$, of a provided compound comprises one or more deuterium atoms.

As used herein, the term "irreversible" or "irreversible inhibitor" refers to an inhibitor (i.e. a compound) that is able to be covalently bonded to HCV protease in a substantially non-reversible manner. That is, whereas a reversible inhibitor is able to bind to (but is generally unable to form a covalent bond with) HCV protease, and therefore can become dissociated from the HCV protease an irreversible inhibitor will remain substantially bound to HCV protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to HCV protease once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with HCV protease, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein.

As used herein, the term "inhibitor" is defined as a compound that binds to and/or inhibits HCV protease with measurable affinity. In certain embodiments, an inhibitor has an $IC_{50}$ and/or binding constant of less about 50 µM, less than about 1 µM, less than about 500 nM, less than about 100 nM, less than about 10 nM, or less than about 1 nM.

A compound of the present invention may be tethered to a detectable moiety. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in HCV protease activity between a sample comprising a compound of the present invention, or composition thereof, and HCV protease, and an equivalent sample comprising HCV protease, in the absence of said compound, or composition thereof.

3. Description of Exemplary Compounds:

In certain embodiments, the present invention provides a compound of formula I:

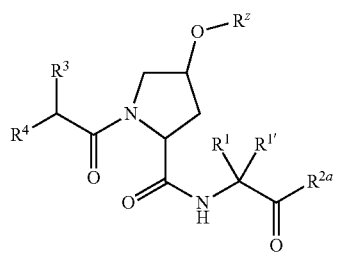

I or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{2a}$ is —OH or —$NHSO_2R^2$;

$R^2$ is —$N(R)_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:
  two R on the same nitrogen atom are taken together with the nitrogen to form a 4-7 membered heterocyclic ring having 1-2 heteroatoms independently selected from nitrogen, oxygen, or sulfur;

$R^3$ is -L-Y, wherein:
  L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—;

Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, $NO_2$, halogen, CN, a suitable leaving group, or a $C_{1-6}$ aliphatic optionally substituted with oxo, halogen, $NO_2$, or CN, wherein:
  Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO₂—, —N(R)C(O)—, —C(O)N(R)—, —N(R)SO₂—, or —SO₂N(R)—; and
  Z is hydrogen or $C_{1-6}$ aliphatic optionally substituted with oxo, halogen, $NO_2$, or CN; or $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group;

$R^4$ is H, —$NHC(O)R^5$, —$NHC(O)OR^6$,

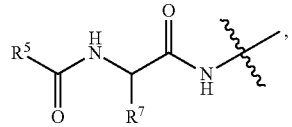

or a natural or unnatural amino acid side-chain group;

each $R^5$ is independently —$N(R)_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

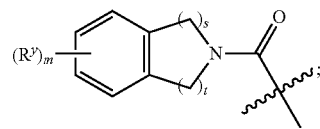

or $R^4$ and $R^z$ are taken together with their intervening atoms to form an optionally substituted, saturated or unsaturated 16-22 membered ring having 2-6 heteroatoms independently selected from nitrogen, oxygen, or sulfur;

each occurrence of $R^y$ is independently selected from halogen, —OR°, —CN, —NO$_2$, —N(R°)$_2$, or optionally substituted $C_{1-4}$ aliphatic; and m is an integer from 0 to 4, inclusive;
s is an integer from 0 to 4, inclusive;
t is an integer from 0 to 4, inclusive;
wherein the sum of s and t is non-zero.

In certain embodiments, L is a covalent bond.

In certain embodiments, L is a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, L is a bivalent $C_{1-8}$ saturated or unsaturated, straight or branched, hydrocarbon chain. In certain embodiments, L is —CH$_2$—.

In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, —O—, —N(R)—, or —C(O)—.

In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-, wherein each R is independently hydrogen or optionally substituted $C_{1-6}$ aliphatic.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)-cyclopropylene-.

As defined generally above, Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, $NO_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and, Z is hydrogen or $C_{1-6}$ aliphatic optionally substituted with oxo, halogen, $NO_2$, or CN.

In certain embodiments, Y is hydrogen.

In certain embodiments, Y is $C_{1-6}$ aliphatic optionally substituted with oxo, halogen, $NO_2$, or CN. In some embodiments, Y is $C_{2-6}$ alkenyl optionally substituted with oxo, halogen, $NO_2$, or CN. In other embodiments, Y is $C_{2-6}$ alkynyl optionally substituted with oxo, halogen, $NO_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, $NO_2$, or CN. Such Y groups include —$CH_2$F, —$CH_2$Cl, —$CH_2$CN, and —$CH_2NO_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

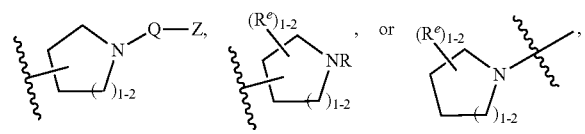

wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

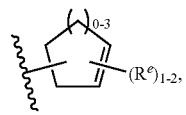

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

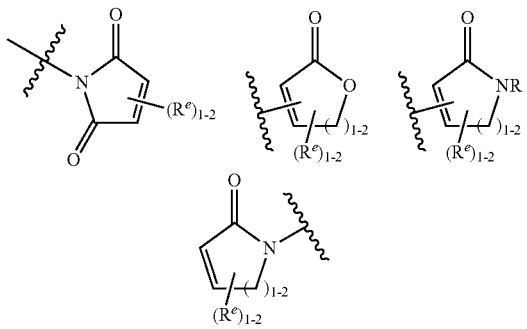

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

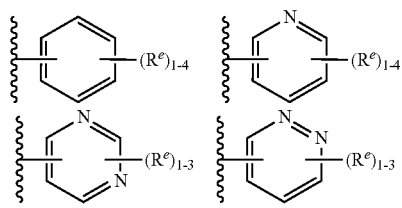

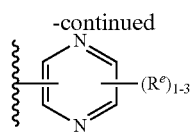

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

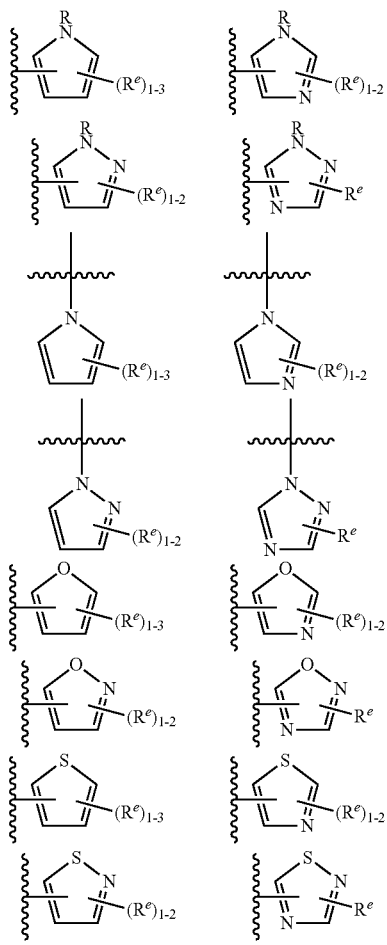

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH=$CH_2$ or —C(O)CH=$CH_2$.

In certain embodiments, each $R^e$ is independently selected from oxo, $NO_2$, CN, fluoro, chloro, —NHC(O)CH=$CH_2$, —C(O)CH=$CH_2$, —$CH_2$CH=$CH_2$, —C≡CH, —C(O)OCH$_2$Cl, —C(O)OCH$_2$F, —C(O)OCH$_2$CN, —C(O)CH$_2$Cl, —C(O)CH$_2$F, —C(O)CH$_2$CN, or —CH$_2$C(O)CH$_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:
(a) L is a bivalent $C_{2-8}$ straight or branched, hydrocarbon chain wherein L has at least one double bond and one or two additional methylene units of L are optionally and independently replaced by —NRC(O)—, —C(O)

NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or C$_{1-6}$ aliphatic optionally substituted with oxo, halogen, NO$_2$, or CN; or (b) L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (c) L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (d) L is a bivalent C$_{2-8}$ straight or branched, hydrocarbon chain wherein L has at least one double bond and at least one methylene unit of L is replaced by —C(O)—; and Y is hydrogen or C$_{1-6}$ aliphatic optionally substituted with oxo, halogen, NO$_2$, or CN; or (e) L is a bivalent C$_{2-8}$ straight or branched, hydrocarbon chain wherein L has at least one double bond and at least one methylene unit of L is replaced by —OC(O)—; and Y is hydrogen or C$_{1-6}$ aliphatic optionally substituted with oxo, halogen, NO$_2$, or CN; or (f) L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-; wherein R is H or optionally substituted C$_{1-6}$ aliphatic; and Y is hydrogen or C$_{1-6}$ aliphatic optionally substituted with oxo, halogen, NO$_2$, or CN; or (g) L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-; and Y is hydrogen or C$_{1-6}$ aliphatic optionally substituted with oxo, halogen, NO$_2$, or CN; or (h) L is a bivalent C$_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (i) L is a bivalent C$_{2-8}$ straight or branched, hydrocarbon chain wherein L has at least one triple bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, or —C(O)O—, and Y is hydrogen or C$_{1-6}$ aliphatic optionally substituted with oxo, halogen, NO$_2$, or CN; or (j) L is —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—; and Y is hydrogen or C$_{1-6}$ aliphatic optionally substituted with oxo, halogen, NO$_2$, or CN; or (k) L is a bivalent C$_{2-8}$ straight or branched, hydrocarbon chain wherein one methylene unit of L is replaced by cyclopropylene and one or two additional methylene units of L are independently replaced by —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen or C$_{1-6}$ aliphatic optionally substituted with oxo, halogen, NO$_2$, or CN; or (l) L is a covalent bond and Y is selected from:
(i) C$_{1-6}$ alkyl substituted with oxo, halogen, NO$_2$, or CN;
(ii) C$_{2-6}$ alkenyl optionally substituted with oxo, halogen, NO$_2$, or CN; or
(iii) C$_{2-6}$ alkynyl optionally substituted with oxo, halogen, NO$_2$, or CN; or
(iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or
(v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or
(vi)

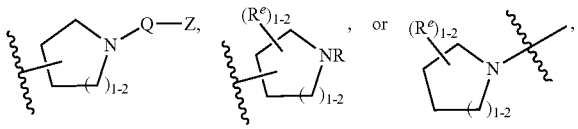

wherein each R, Q, Z, and R$^e$ is as defined above and described herein; or
(vii) a saturated 3-6 membered carbocyclic ring, wherein said ring is substituted with 1-4 R$^e$ groups, wherein each R$^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or
(ix) a partially unsaturated 3-6 membered carbocyclic ring, wherein said ring is substituted with 1-4 R$^e$ groups, wherein each R$^e$ is as defined above and described herein; or (x)

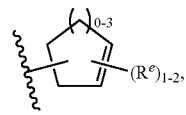

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

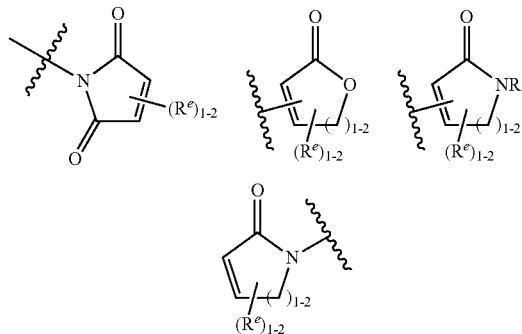

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

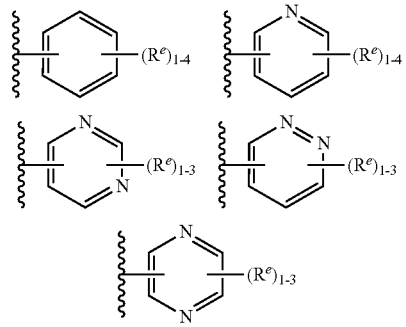

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

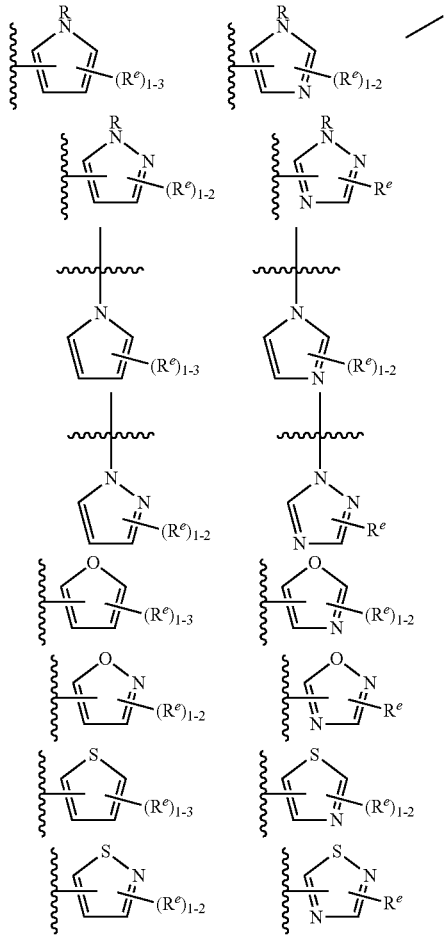

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

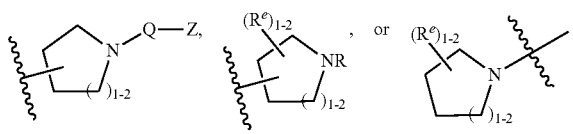

wherein each R, Q, Z, and Re is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

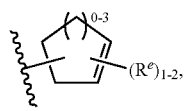

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

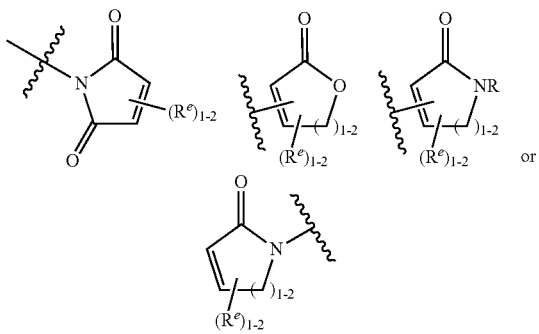

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

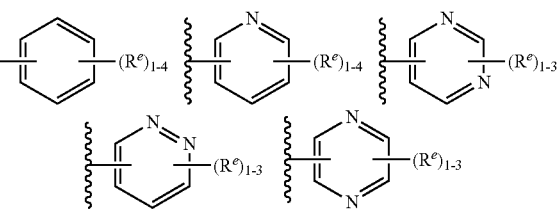

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

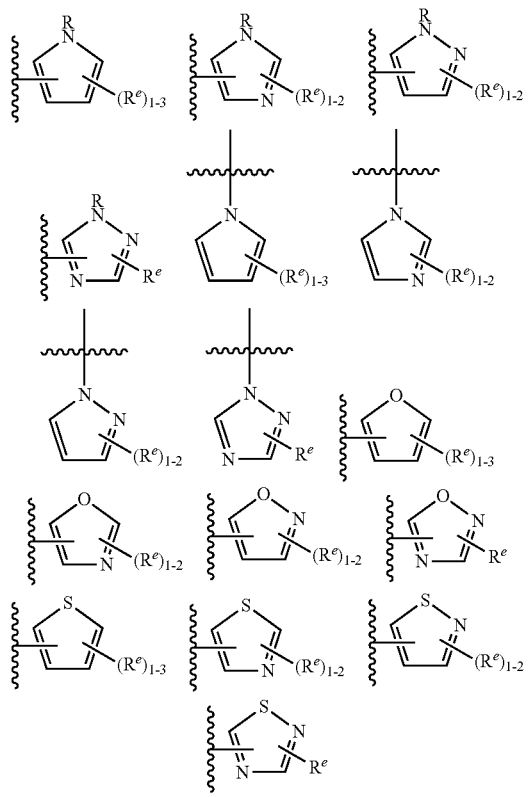

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

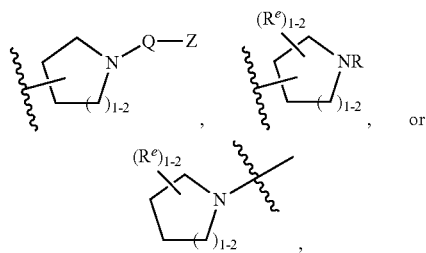

wherein each R, Q, Z, and Re is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

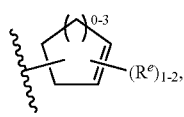

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

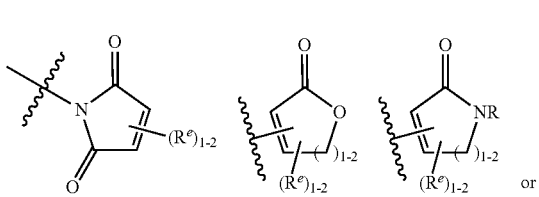

-continued

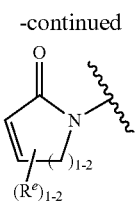

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

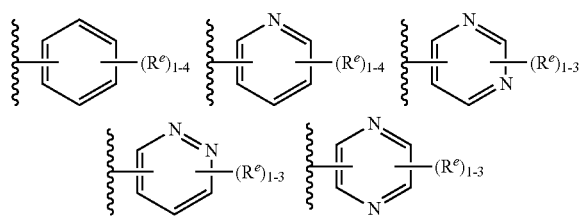

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

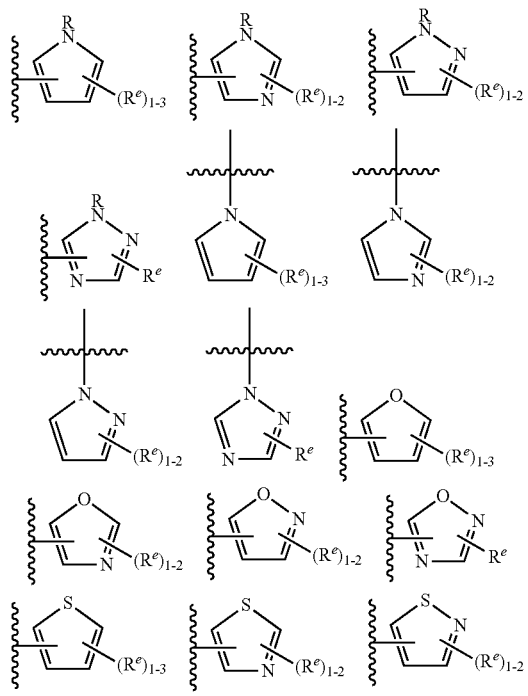

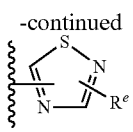

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each Re is as defined above and described herein; or (vi)

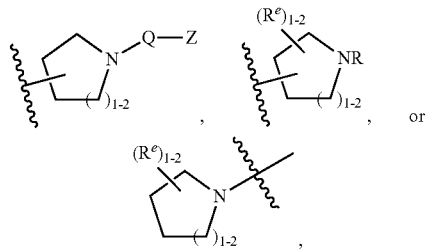

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

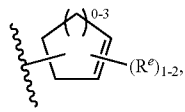

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

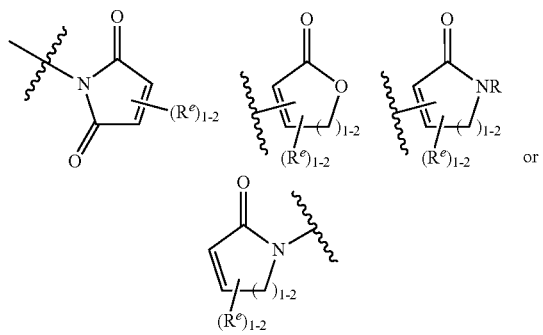

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

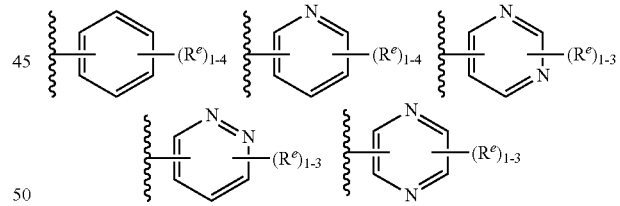

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

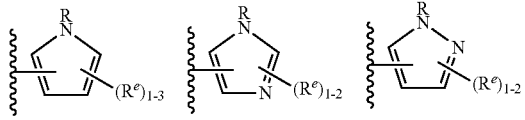

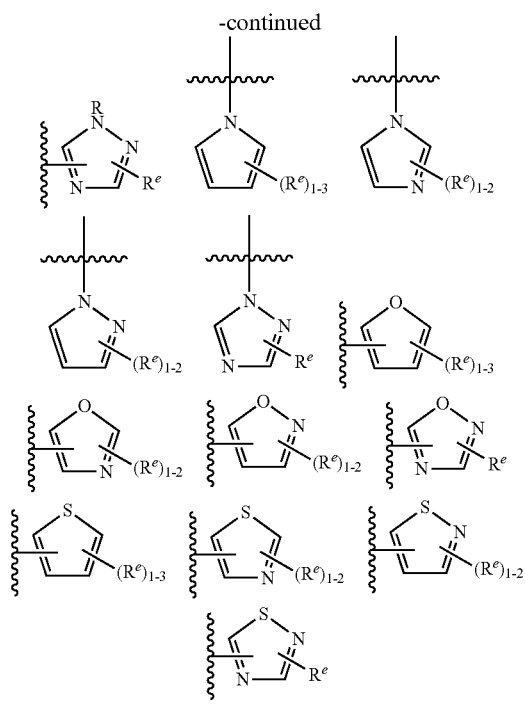

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—; and Y is selected from:

(i) $C_{1-6}$ alkyl substituted with oxo, halogen, NO$_2$, or CN; or
(ii) $C_{2-6}$ alkenyl optionally substituted with oxo, halogen, NO$_2$, or CN; or
(iii) $C_{2-6}$ alkynyl optionally substituted with oxo, halogen, NO$_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or
(vi)

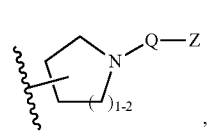 , 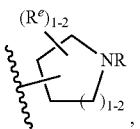 , or

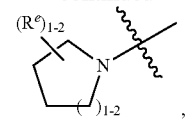

wherein each R, Q, Z, and Re is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or
(x)

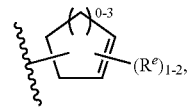

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

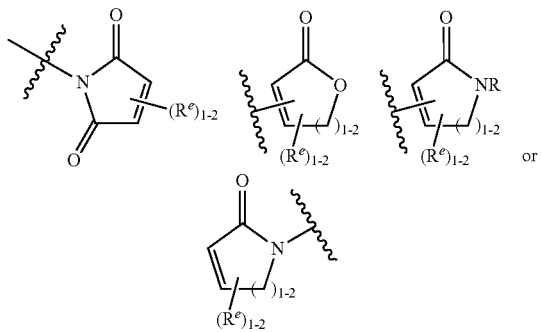

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or
(xiv)

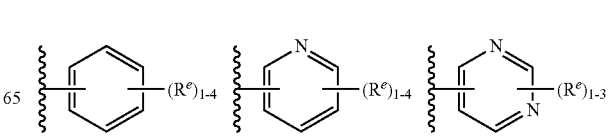

-continued

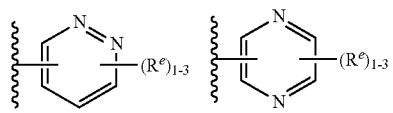

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

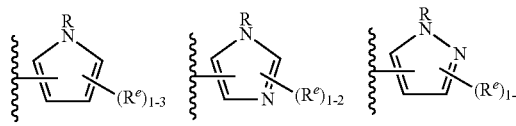

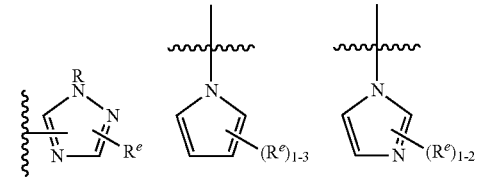

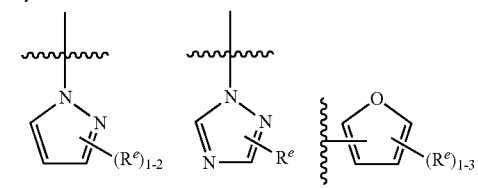

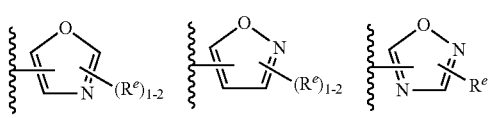

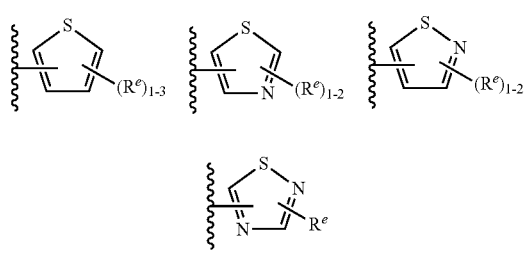

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group of formula I is selected from those set forth in Table 1, below, wherein each wavy line indicates the point of attachment to the rest of the molecule.

TABLE 1

Exemplary Y Groups of Formula I:

| | |
|---|---|
| 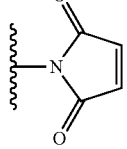 | a |
| 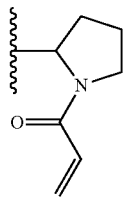 [SMILES: *C1CCCN1C(=O)C=C] | b |
| 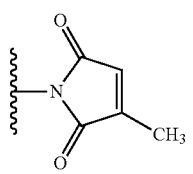 [SMILES: *N1C(=O)C=C(C)C1=O] | c |
| 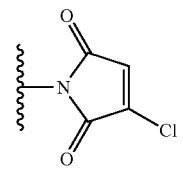 | d |
| 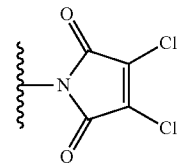 [SMILES: *N1C(=O)C(Cl)=C(Cl)C1=O] | e |
| 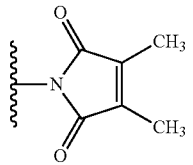 [SMILES: *N1C(=O)C(C)=C(C)C1=O] | f |
| 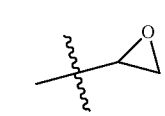 [SMILES: *C1CO1] | g |
| 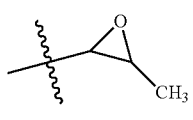 [SMILES: *C1OC1C] | h |
| 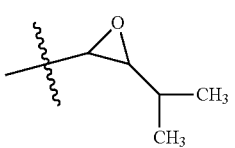 | i |

TABLE 1-continued
Exemplary Y Groups of Formula I:
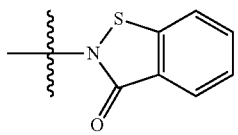 [SMILES: *n1sc2ccccc2c1=O] j
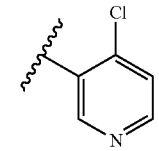 k
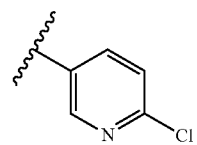 [SMILES: *c1ccc(Cl)nc1] l
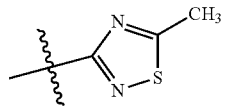 [SMILES: *c1nsc(C)n1] m
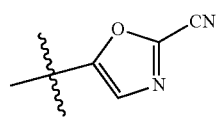 n
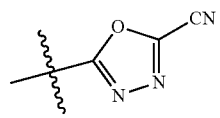 [SMILES: *c1nnc(C#N)o1] o
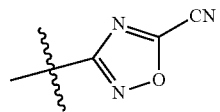 [SMILES: *c1noc(C#N)n1] p
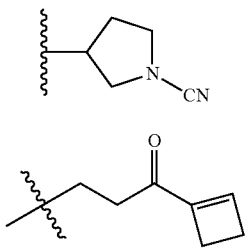 q
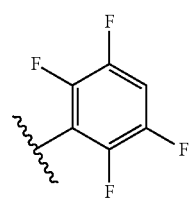 r
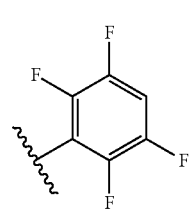 s
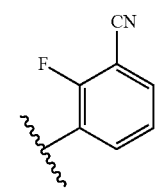 [SMILES: *c1cccc(C#N)c1F] t
TABLE 1-continued
Exemplary Y Groups of Formula I:
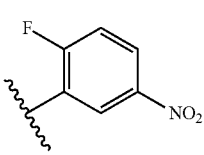 [SMILES: *c1cc([N+](=O)[O-])ccc1F] u
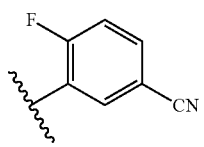 [SMILES: *c1cc(C#N)ccc1F] v
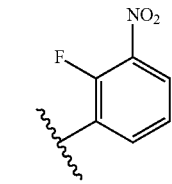 [SMILES: *c1cccc([N+](=O)[O-])c1F] w
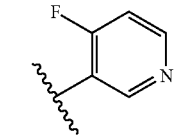 [SMILES: *c1cnccc1F] x
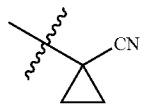 [SMILES: *C1(C#N)CC1] y
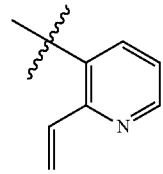 [SMILES: *c1cccnc1C=C] z
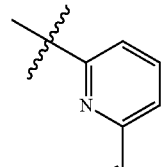 aa
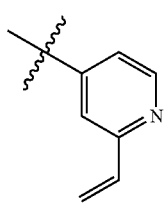 [SMILES: *c1ccnc(C=C)c1] bb
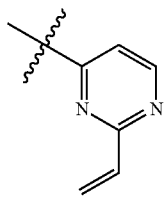 cc TABLE 1-continued
Exemplary Y Groups of Formula I:
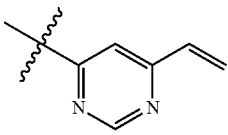 dd
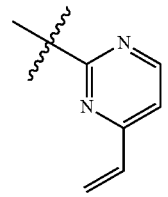 [SMILES: *c1nccc(C=C)n1] ee
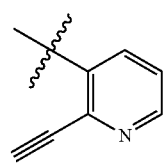 [SMILES: *c1cccnc1C#C] ff
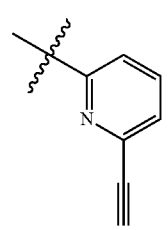 gg
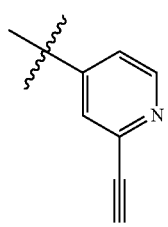 [SMILES: *c1ccnc(C#C)c1] hh
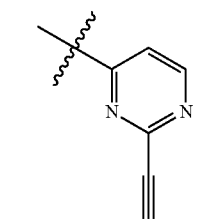 [SMILES: *c1ccnc(C#C)n1] ii
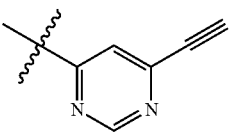 [SMILES: *c1cc(C#C)ncn1] jj
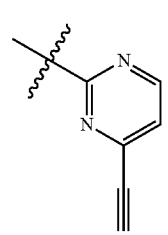 [SMILES: *c1nccc(C#C)n1] kk
TABLE 1-continued
Exemplary Y Groups of Formula I:
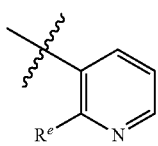 ll
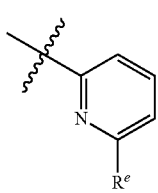 mm
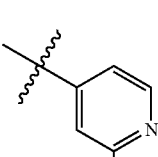 nn
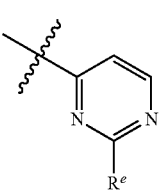 oo
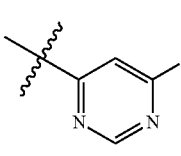 pp
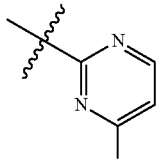 qq
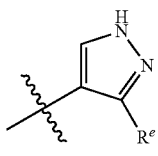 rr
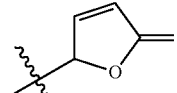 ss
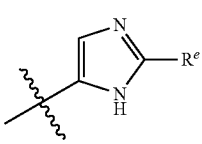 tt TABLE 1-continued
Exemplary Y Groups of Formula I:
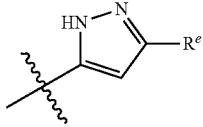 uu
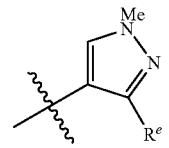 vv
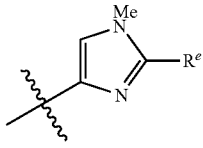 ww
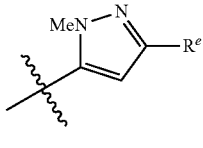 xx
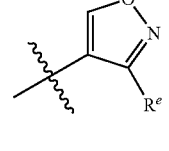 yy
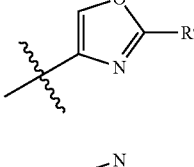 zz
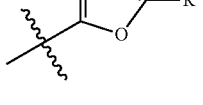 aaa
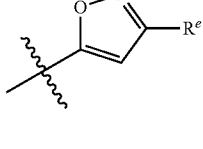 bbb
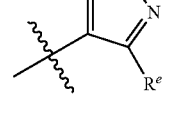 ccc
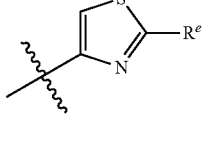 ddd
TABLE 1-continued
Exemplary Y Groups of Formula I:
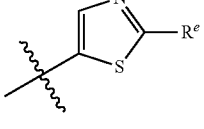 eee
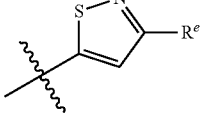 fff
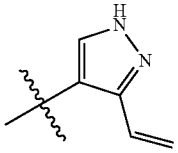 [SMILES: *c1c[nH]nc1C=C] ggg
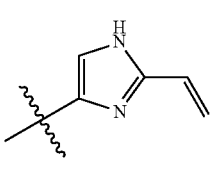 [SMILES: *c1c[nH]c(C=C)n1] hhh
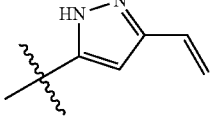 iii
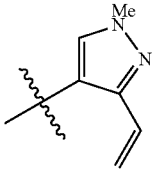 [SMILES: *c1cn(C)nc1C=C] jjj
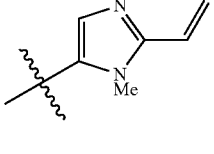 [SMILES: *c1cnc(C=C)n1C] kkk
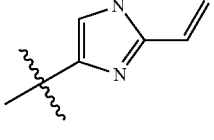 lll
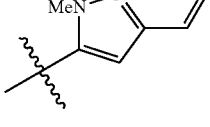 mmm
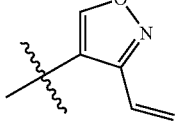 nnn TABLE 1-continued
Exemplary Y Groups of Formula I:
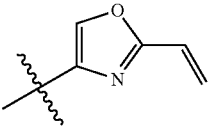 [SMILES: *c1coc(C=C)n1] ooo
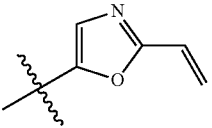 [SMILES: *c1cnc(C=C)o1] ppp
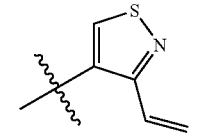 qqq
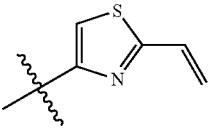 [SMILES: *c1csc(C=C)n1] rrr
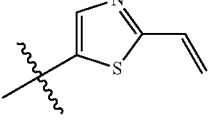 sss
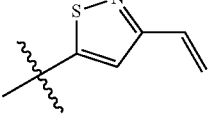 ttt
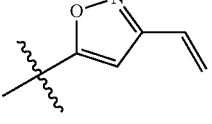 uuu
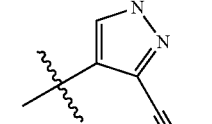 vvv
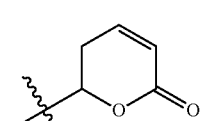 qqq
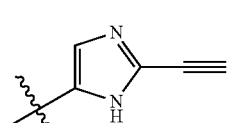 www
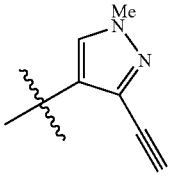 [SMILES: *c1cn(C)nc1C#C] xxx
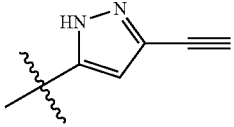 [SMILES: *c1cc(C#C)n[nH]1] yyy
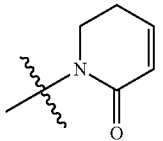 [SMILES: *N1CCC=CC1=O] zzz
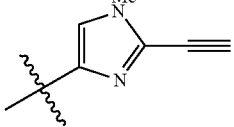 aaaa
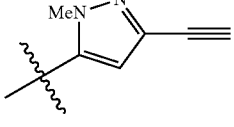 bbbb
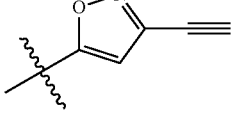 cccc
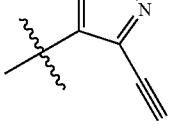 dddd
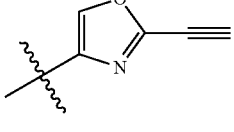 eeee
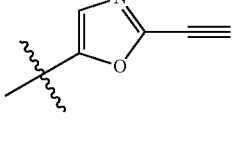 ffff
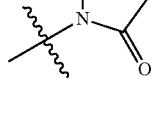 gggg TABLE 1-continued
Exemplary Y Groups of Formula I:
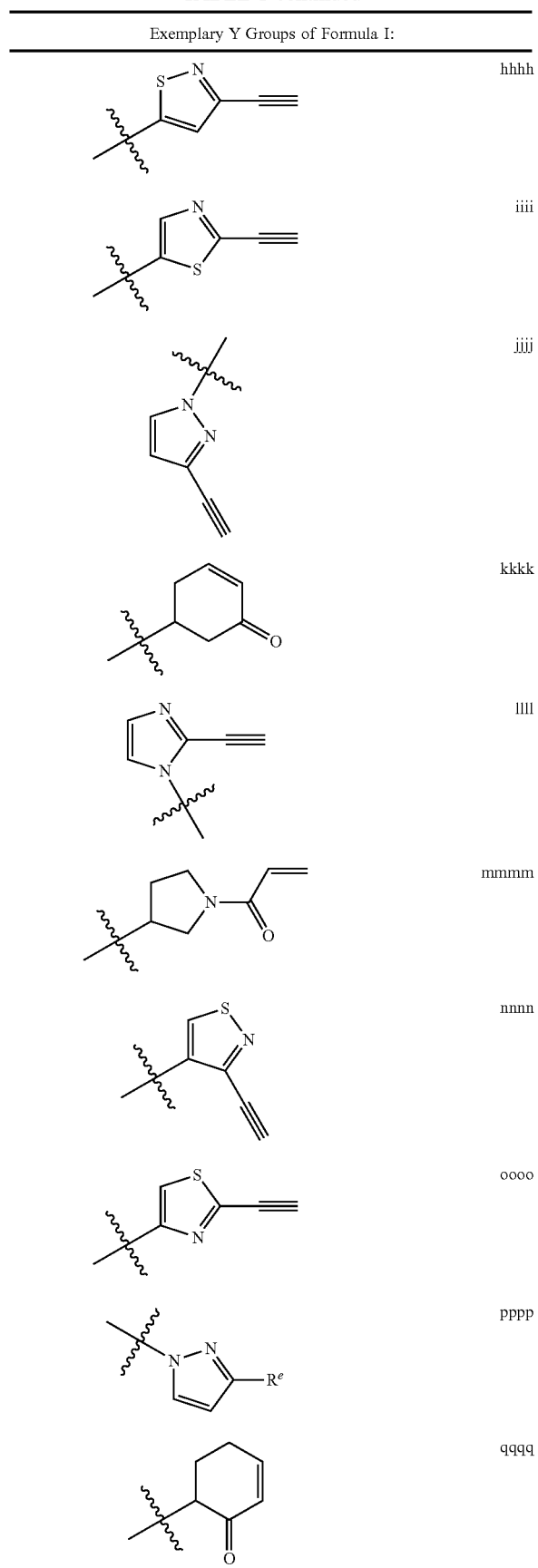
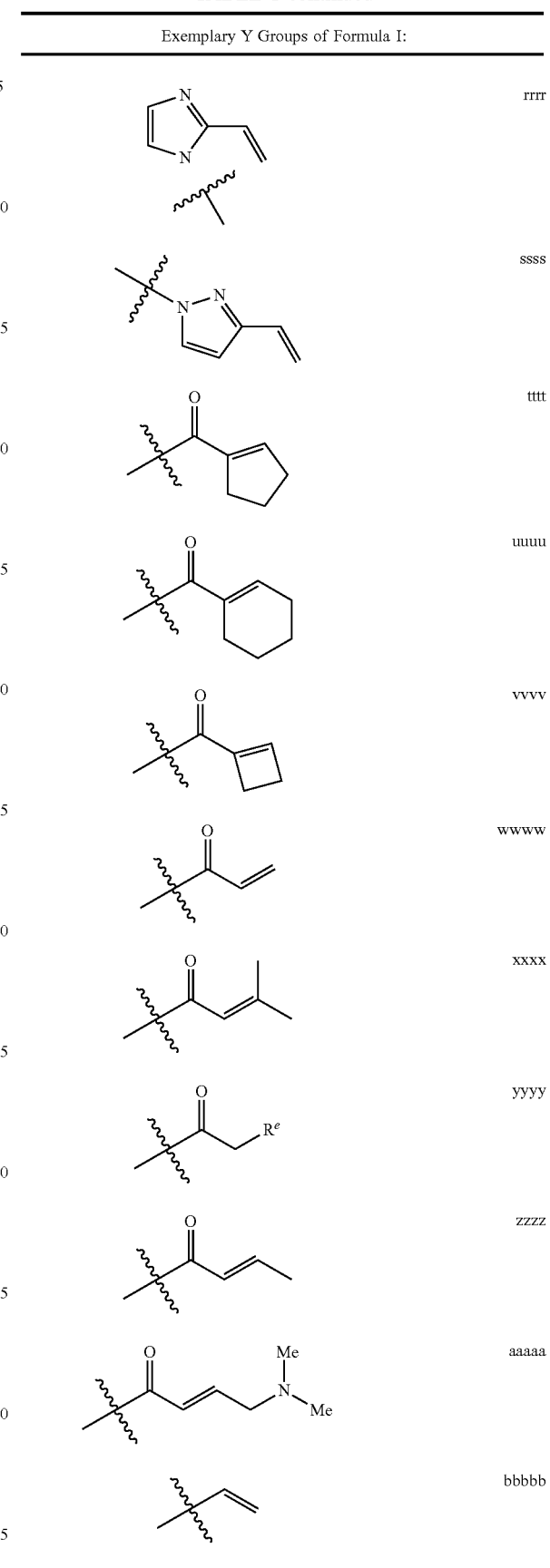

TABLE 1-continued

Exemplary Y Groups of Formula I:

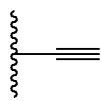  ccccc

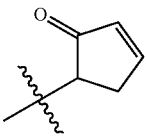 [SMILES: *C1CC=CC1=O]  ddddd wherein each $R^e$ is independently a suitable leaving group, $NO_2$, CN, or oxo.

In certain embodiments, the $R^3$ group of formula I is selected from those set forth in Table 2, below, wherein each wavy line indicates the point of attachment to the rest of the molecule.

TABLE 2

Exemplary $R^3$ Groups:

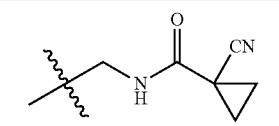 [SMILES: *CNC(=O)C1(C#N)CC1]  a

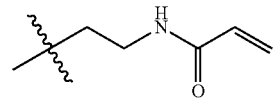 [SMILES: *CCNC(=O)C=C]  b

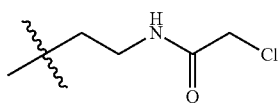 [SMILES: *CCNC(=O)CCl]  c

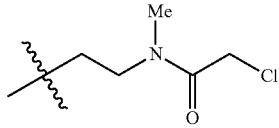 [SMILES: *CCN(C)C(=O)CCl]  d

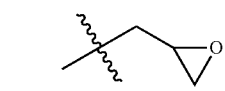 [SMILES: *CC1CO1]  e

  f

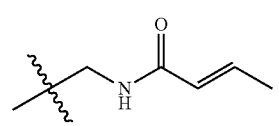 [SMILES: *CNC(=O)/C=C/C]  g

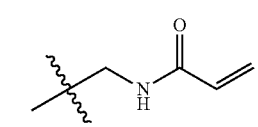 [SMILES: *CNC(=O)C=C]  h

TABLE 2-continued

Exemplary $R^3$ Groups:

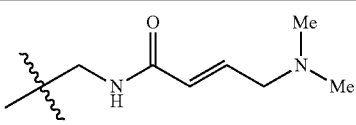 [SMILES: *CNC(=O)/C=C/CN(C)C]  i

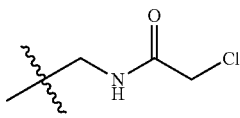 [SMILES: *CNC(=O)CCl]  j

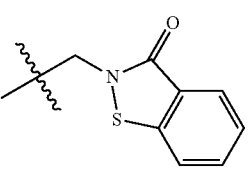 [SMILES: *Cn1sc2ccccc2c1=O]  k

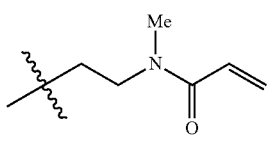 [SMILES: *CCN(C)C(=O)C=C]  l

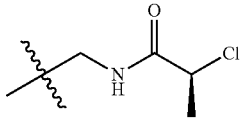 [SMILES: *CNC(=O)[C@H](C)Cl]  m

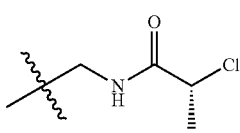 [SMILES: *CNC(=O)[C@@H](C)Cl]  n

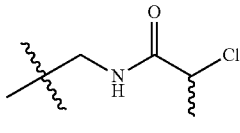 [SMILES: *CNC(=O)C(C)Cl]  o

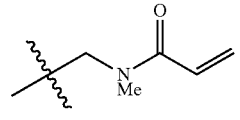 [SMILES: *CN(C)C(=O)C=C]  p

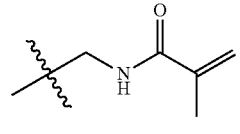  q

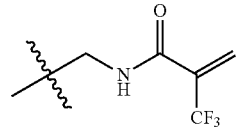  r

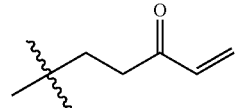 [SMILES: *CCC(=O)C=C]  s

TABLE 2-continued

Exemplary R³ Groups:

| | |
|---|---|
| (structure) | t |
| (structure) | u |
| (structure) | v |
| (structure) | w |
| (structure) | x |
| (structure) | y |
| (structure) | z |
| (structure) | aa |
| (structure) | bb |
| (structure) | cc |
| (structure) | dd |
| (structure) | ee |
| (structure) | ff |
| (structure) | gg |
| (structure) | hh |
| (structure) | ii |
| (structure) | jj |
| (structure) | kk |
| (structure) | ll |
| (structure) | mm |

TABLE 2-continued
Exemplary R³ Groups:
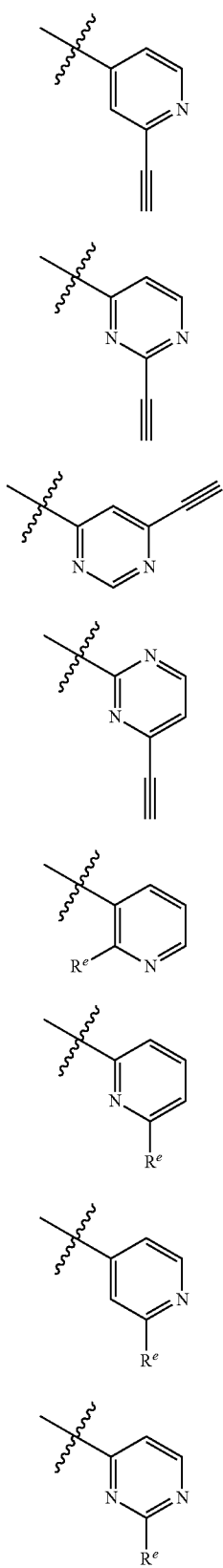
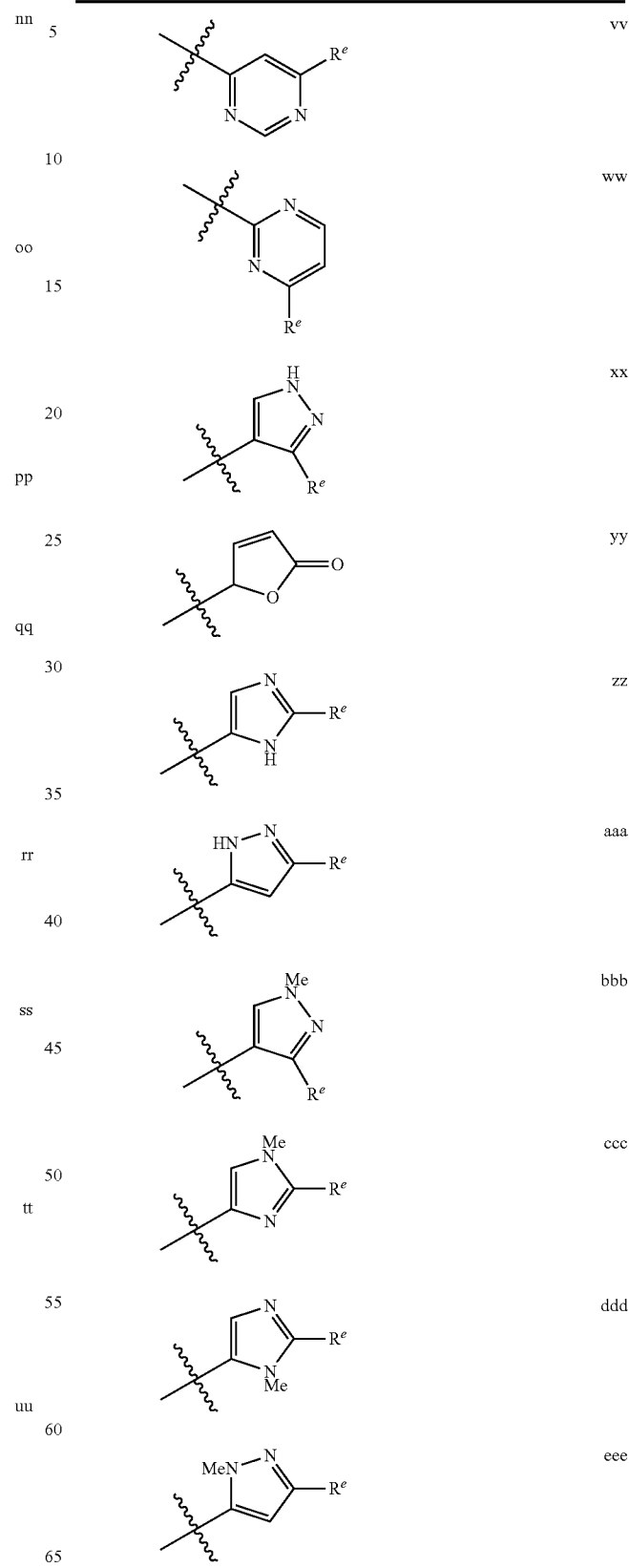

TABLE 2-continued

Exemplary R³ Groups:

TABLE 2-continued
Exemplary R³ Groups:
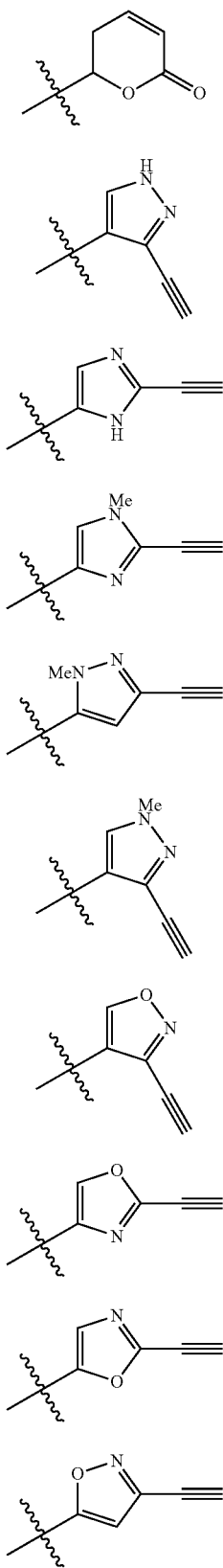
aaaa
bbbb
cccc
dddd
eeee
ffff
gggg
hhhh
iiii
jjjj
TABLE 2-continued
Exemplary R³ Groups:
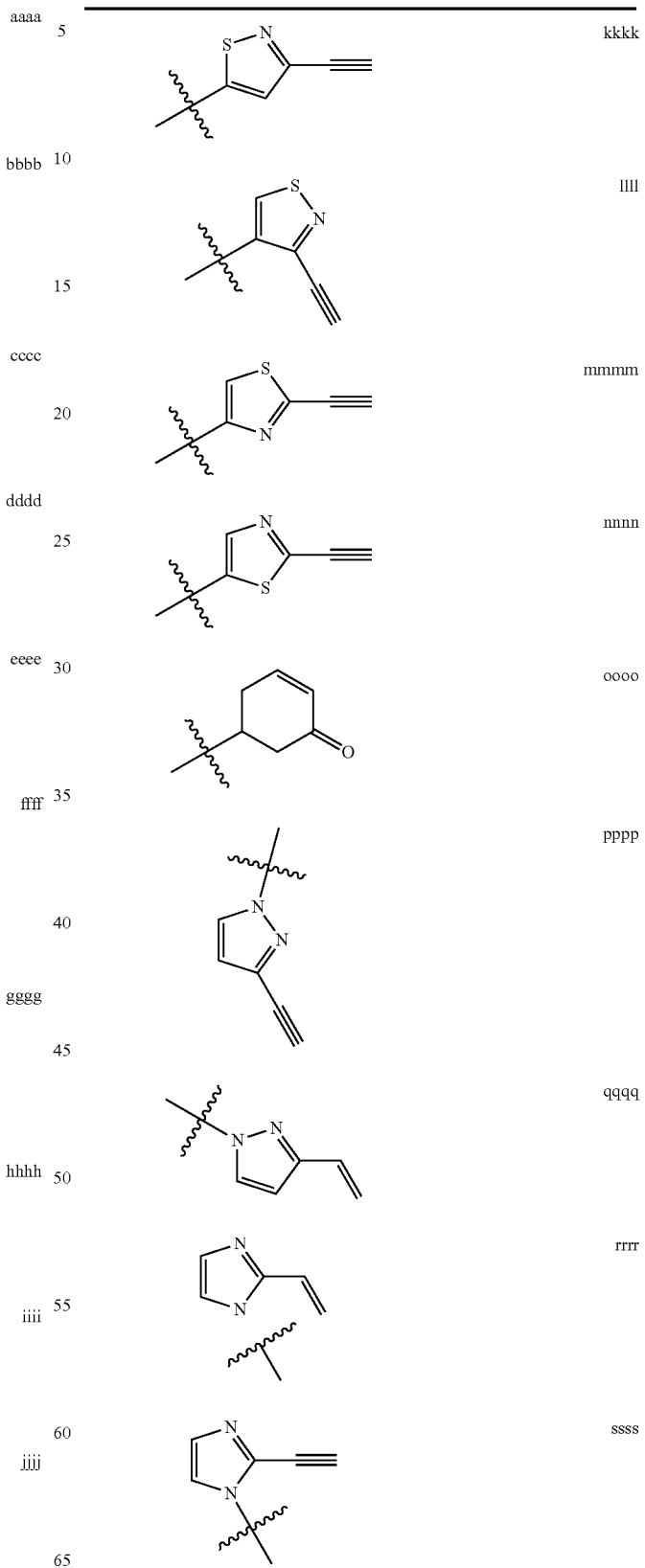
kkkk
llll
mmmm
nnnn
oooo
pppp
qqqq
rrrr
ssss

TABLE 2-continued
Exemplary R³ Groups:
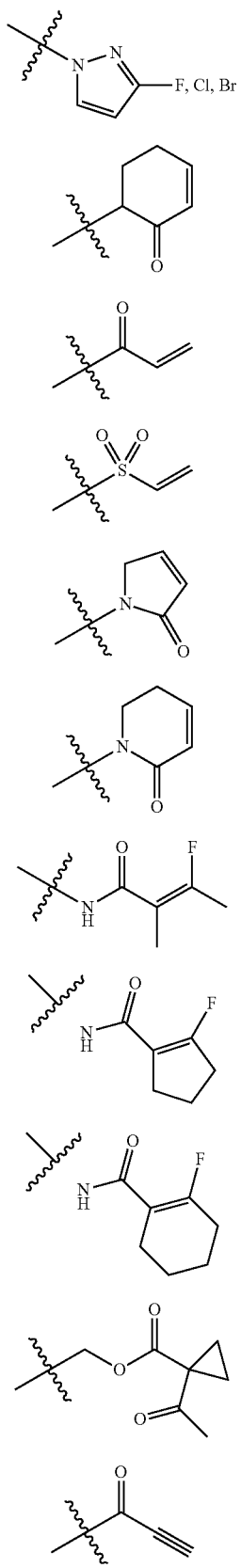
tttt
uuuu
vvvv
wwww
xxxx
yyyy
zzzz
aaaaa
bbbbb
ccccc
ddddd
TABLE 2-continued
Exemplary R³ Groups:
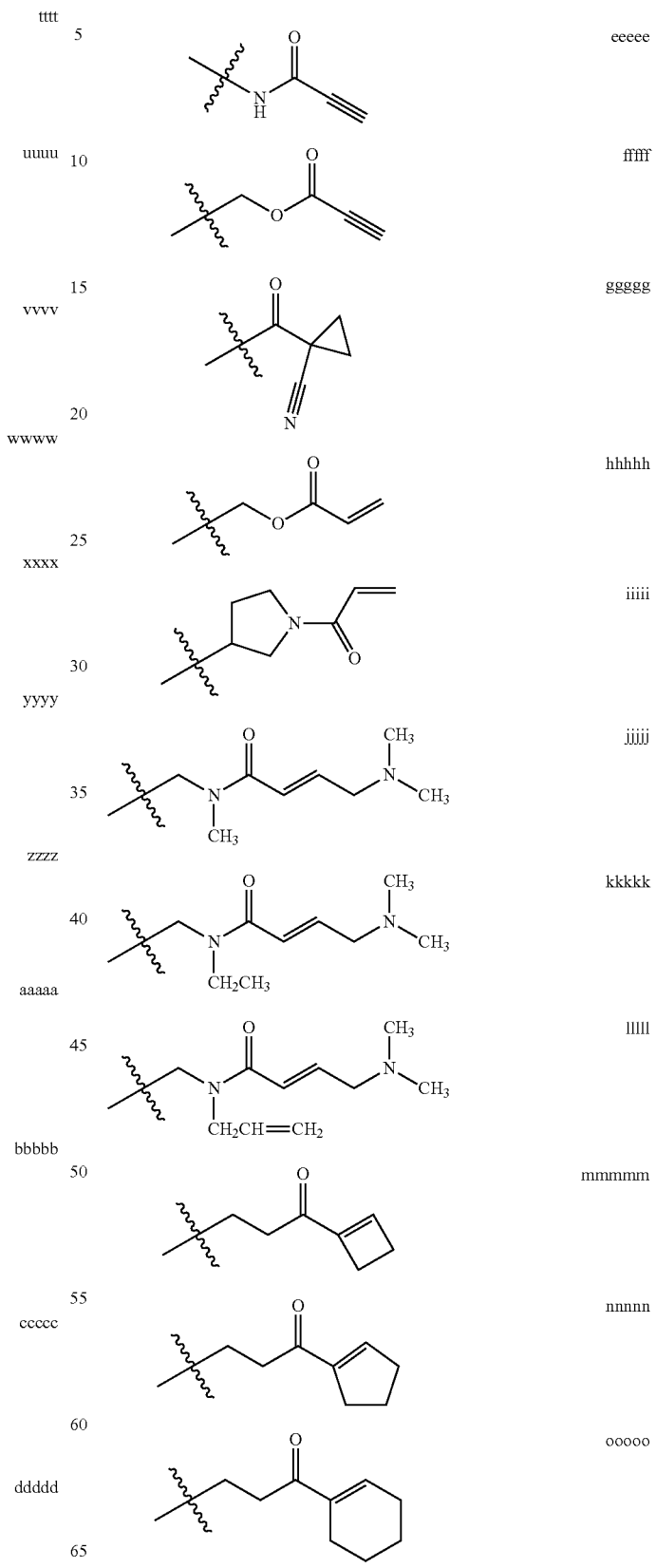
eeeee
fffff
ggggg
hhhhh
iiiii
jjjjj
kkkkk
lllll
mmmmm
nnnnn
ooooo

TABLE 2-continued

Exemplary R³ Groups:

| Structure | Label |
|---|---|
| tert-butyl acrylate ester | ppppp |
| tert-butyl crotonate ester | qqqqq |
| (E)-5-(dimethylamino)pent-3-en-2-one | rrrrr |
| tert-butyl (E)-4-(dimethylamino)but-2-enoate | sssss |
| acrylamide | ttttt |
| (E)-4-(dimethylamino)but-2-enamide | uuuuu |
| vinyl ketone | vvvvv |
| vinyl sulfone | wwwww |
| chloromethyl ketone | xxxxx |
| ethynyl sulfoxide | yyyyy |
| vinyl sulfoxide | zzzzz |
| cyanomethyl ketone | aaaaaa |
| fluoromethyl ketone | bbbbbb |
| vinyl sulfonamide | cccccc |
| 3-methylbut-2-en-1-one | dddddd |
| acetoxymethyl ketone (Ac) | eeeeee |
| pent-1-en-3-one | fffff |
| pent-1-yn-3-one | gggggg |
| 5-methylhex-4-en-3-one | hhhhhh |
| 2-vinylimidazol-1-ylmethyl | iiiiii |
| acrylate ester (CH₂O-acrylate) | jjjjjj |
| vinyl acrylate ester | kkkkkk |
| 5-methylhex-4-en-3-one isomer | llllll |
| 1-acetoxyprop-2-yl ketone | mmmmmm |

TABLE 2-continued

Exemplary R³ Groups:

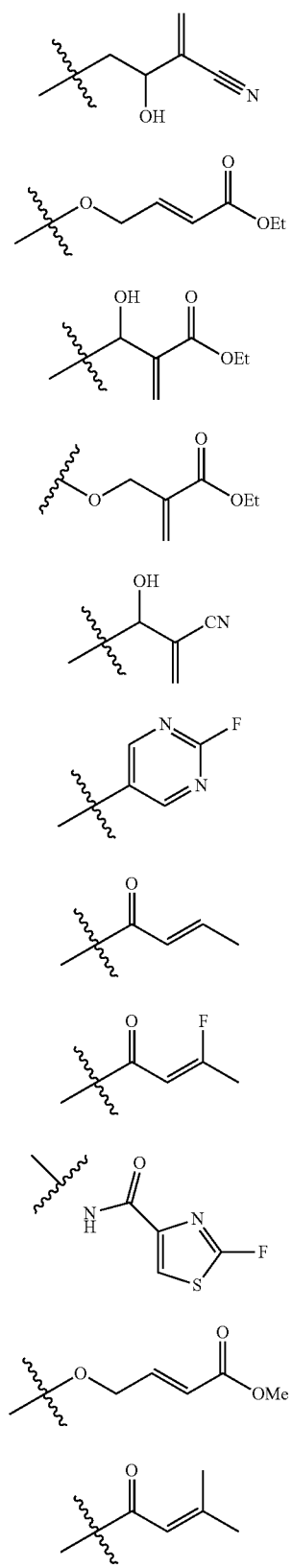

nnnnnn oooooo ppppp qqqqqq rrrrrr ssssss tttttt uuuuuu vvvvvv wwwwww xxxxxx

TABLE 2-continued

Exemplary R³ Groups:

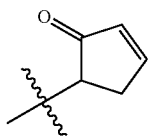 [SMILES: *C1CC=CC1=O]

yyyyyy wherein each $R^e$ is independently a suitable leaving group, $NO_2$, CN, or oxo.

In certain embodiments, the $R^1$ and $R^{1'}$ groups of formula I are independently hydrogen or optionally substituted $C_{1-6}$ aliphatic. In some embodiments, $R^1$ is hydrogen and $R^{1'}$ is $C_{1-4}$ aliphatic. In other embodiments, $R^1$ is hydrogen and $R^{1'}$ is n-propyl.

In certain embodiments, the $R^1$ and $R^{1'}$ groups of formula I are taken together to form an optionally substituted 3-7 membered carbocyclic ring. In some embodiments, the $R^1$ and $R^{1'}$ groups of formula I are taken together to form an optionally substituted cyclopropyl ring. In some embodiments, the $R^1$ and $R^{1'}$ groups of formula I are taken together to form a cyclopropyl ring substituted with ethyl or vinyl.

In some embodiments, $R^4$ is H, —NHC(O)R⁵, —NHC(O)OR⁶,

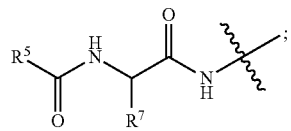

or or $R^4$ and $R^z$ are taken together with their intervening atoms to form an optionally substituted, saturated or unsaturated 16-22 membered ring having 2-6 heteroatoms independently selected from nitrogen, oxygen, or sulfur.

In certain embodiments, the $R^4$ group of formula I is —NHC(O)R⁵. In some embodiments, the $R^4$ group of formula I is —NHC(O)OR⁶. In other embodiments, the $R^4$ group of formula I is

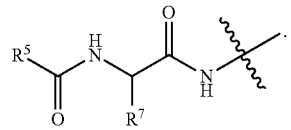

In certain embodiments, the $R^4$ group of formula I is hydrogen.

In some embodiments, when $R^4$ is —NHC(O)R⁵, R⁵ is $C_{1-6}$ aliphatic or an optionally substituted group selected from a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In some embodiments, when $R^4$ is —NHC(O)OR⁶, R⁶ is $C_{1-6}$ aliphatic or an optionally substituted group selected from a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In some embodiments, the $R^4$ group of formula I is an amino acid side-chain group. In some embodiments, the $R^4$ group of formula I is an unnatural amino acid side-chain group. In some embodiments, the $R^4$ group of formula I is an aliphatic unnatural amino acid side-chain group. In some embodiments, the $R^4$ group of formula I is an unnatural amino acid side-chain group of alanine substituted with one, two, or three $R°$ groups, wherein each $R°$ is as defined above. In some embodiments, the $R^4$ group of formula I is a natural amino acid side-chain group.

In certain embodiments, the $R^4$ group of formula I is the natural amino acid side-chain group of alanine (i.e., $R^4$ is methyl). In some embodiments, the $R^4$ group of formula I is the natural amino acid side-chain group of D-alanine. In some embodiments, the $R^4$ group of formula I is the natural amino acid side-chain group of L-alanine.

In other embodiments, the $R^4$ group of formula I is the natural amino acid side-chain group of valine. In some embodiments, the $R^4$ group of formula I is the natural amino acid side-chain group of D-valine. In some embodiments, the $R^4$ group of formula I is the natural amino acid side-chain group of L-valine.

In some embodiments, the $R^4$ group of formula I consists of a mixture of amino acid side-chain groups in both the D- and L-configuration. Such $R^4$ groups are referred to herein as "D,L-mixed amino acid side-chain groups." In some embodiments, the ratio of D- to L-amino acid side-chain groups is selected from any of 6:1, 5:1, 4:1, 3:1, 2:1, 1:1, 1:2, 1:3, 1:4; 1:5, and 1:6. Thus, in certain embodiments, the $R^4$ group of formula I is a D,L-mixed alanine side-chain group. In other embodiments, the $R^4$ group of formula I is a D,L-mixed valine side-chain group.

While not wishing to be bound by any particular theory, it is believed that for compounds of formula I, having an amino acid side-chain group in the D-configuration is useful in allowing a compound to adopt an orientation conducive to binding HCV protease.

In certain embodiments, the $R^5$ and $R^7$ groups of formula I are independently optionally substituted groups selected from optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur. In some embodiments, $R^5$ is an optionally substituted 5-10 membered heteroaryl having 1-4 heteroatoms independently selected from nitrogen, oxygen, or sulfur, and $R^7$ is an optionally substituted $C_{1-6}$ aliphatic group. In some embodiments, $R^5$ is

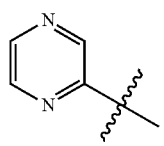 [SMILES: *c1cnccn1]

and $R^7$ is cyclohexyl.

In certain embodiments, $R^4$ is —NHC(O)$R^5$, wherein $R^5$ is independently —N(R)$_2$ or an optionally substituted group selected from $C_{1-6}$ aliphatic. In some embodiments, $R^5$ is —N(R)$_2$ and each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur. In some embodiments, $R^5$ is —N(R)$_2$ and each R is independently hydrogen or t-butyl.

In certain embodiments, the $R^5$ group of formula I is an optionally substituted 5-10 membered heteroaryl ring having 1-4 heteroatoms independently selected from nitrogen, oxygen, or sulfur. In some embodiments, $R^5$ is an optionally substituted 6 membered heteroaryl ring having 1-2 nitrogens. In certain embodiments, $R^5$ is piperazinyl.

In certain embodiments, the $R^7$ group of formula I is an optionally substituted $C_{1-6}$ aliphatic group. In some embodiments, $R^7$ is a branched $C_{1-5}$ alkyl group. In other embodiments, $R^7$ is cyclopentyl or cyclohexyl.

In certain embodiments, $R^z$ is

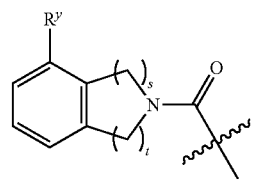

In certain embodiments, $R^z$ is

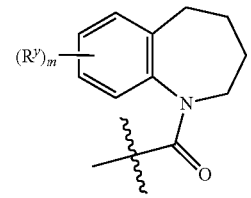

In certain embodiments, $R^z$ is

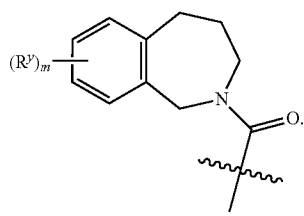

In certain embodiments, $R^z$ is

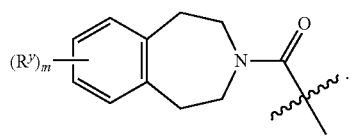

In certain embodiments, $R^z$ is

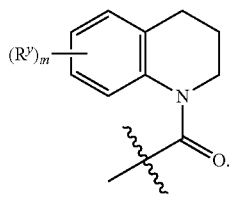

In certain embodiments, $R^z$ is

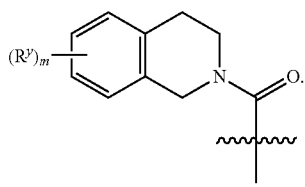

In certain embodiments, $R^z$ is

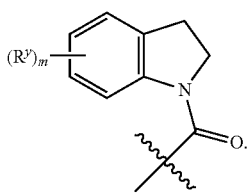

In certain embodiments, $R^z$ is

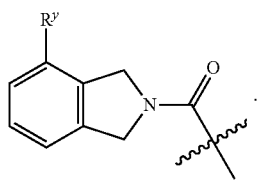

In certain embodiments, $R^z$ is

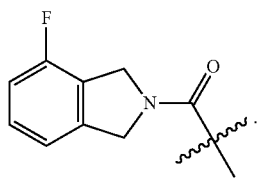 [SMILES: *C(=O)N1Cc2cccc(F)c2C1]

In some embodiments, $R^y$ is halogen. In other embodiments, $R^y$ is $C_{1-4}$ aliphatic. In certain embodiments, $R^y$ is fluoro. In certain embodiments, $R^y$ is chloro. In certain embodiments, $R^y$ is bromo. In certain embodiments, $R^y$ is iodo. In other embodiments, $R^y$ is vinyl.

In some embodiments, m is an integer between 1 and 3, inclusive. In some embodiments, m is 1. In some embodiments, m is 2. In some embodiments, m is 3.

In some embodiments, s is an integer between 1 and 3, inclusive. In some embodiments, s is 0. In some embodiments, s is 1. In some embodiments, s is 2. In some embodiments, s is 3. In some embodiments, s is 4.

In some embodiments, t is an integer between 1 and 3, inclusive. In some embodiments, t is 0. In some embodiments, t is 1. In some embodiments, t is 2. In some embodiments, t is 3. In some embodiments, t is 4.

In certain embodiments, the $R^{2a}$ group of formula I is —OH. In other embodiments, the $R^{2a}$ group of formula I is —NHSO$_2$R$^2$, wherein $R^2$ is as defined above and described herein. Thus, the present invention provides a compound of formula I-a or I-b:

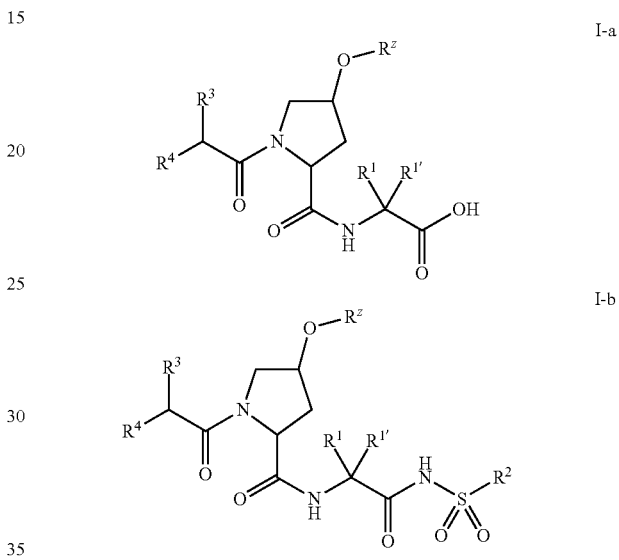

or a pharmaceutically acceptable salt thereof, wherein each of $R^1$, $R^{1'}$, $R^2$, $R^3$, $R^4$, and $R^z$ is as defined above for formula I and described in classes and subclasses above and herein.

In certain embodiments, the $R^2$ group of formula I-b is —N(R)$_2$. In other embodiments, the $R^2$ group of formula I-b is an optionally substituted group selected from $C_{3-7}$ cycloalkyl, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur. In certain embodiments, $R^2$ is $C_{3-7}$ cycloalkyl or 6-10 membered aryl. In some embodiments, $R^2$ is optionally substituted 6-10 membered aryl. In some embodiments, $R^2$ is phenyl. In certain embodiments, $R^2$ is cyclopropyl.

In certain embodiments, $R^2$ is selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the $R^3$ group of formula I is a warhead group. In some embodiments, the $R^3$ and $R^1$ groups of formula I are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group. In some embodiments, $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group.

As defined generally above, the ring formed by the $R^3$ and $R^1$ groups of formula I comprises a warhead group. As used herein, the phrase "comprises a warhead group" means that the ring formed by $R^3$ and $R^1$ is either substituted with a warhead group or has such a warhead group incorporated within the ring. For example, the ring formed by $R^3$ and $R^1$ may be substituted with an -L-Y warhead group, wherein such groups are as described herein. Alternatively, the ring formed by $R^3$ and $R^1$ has the appropriate features of a warhead group incorporated within the ring. For example, the ring formed by $R^3$ and $R^1$ may include one or more units of unsaturation and optional substituents and/or heteroatoms which, in combination, result in a moiety that is capable of covalently modifying HCV protease in accordance with the present invention. In certain embodiments, the ring formed by $R^3$ and $R^1$ is optionally substituted at the α-, β-, or γ-position with respect to the carbon to which $R^4$ is attached.

It will be appreciated that when $R^3$ and $R^1$ are taken together with their intervening atoms to form an optionally substituted saturated or unsaturated 12-18 membered ring having 2-6 heteroatoms independently selected from nitrogen oxygen, or sulfur, such compounds include those wherein $R^3$ and a ring formed by $R^1$ and $R^{1'}$ are taken together.

Exemplary compounds of formula I wherein $R^3$ and a ring formed by $R^1$ and $R^{1'}$ are taken together include those of formula I-c-1, I-c-2, I-c-3, I-c-4, I-c-5-, and I-c-6:

I-c-1

I-c-2

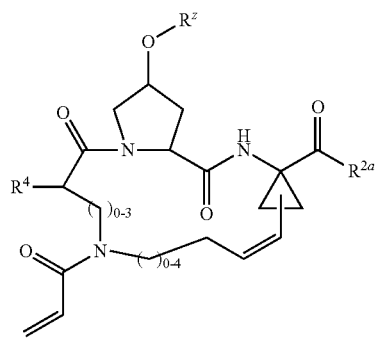

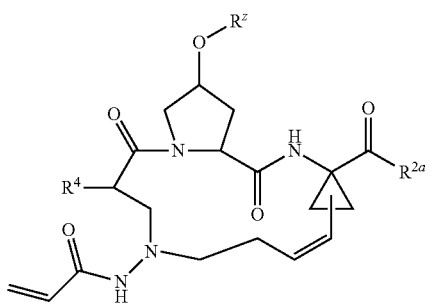

I-c-3

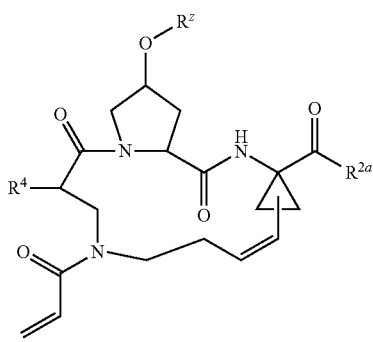

I-c-4

I-c-5

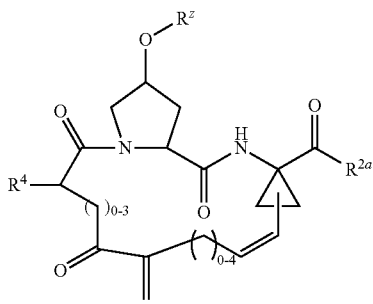

I-c-6

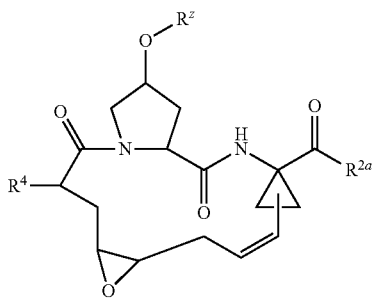

or a pharmaceutically acceptable salt thereof, wherein each of $R^z$, R4, and $R^z$ is as defined above and described in classes and subclasses herein. It will be appreciated that, although formulae I-c-1, I-c-2, I-c-3, I-c-4, I-c-5, and I-c-6 depict a cyclopropyl ring formed by $R^1$ and $R^{1'}$, this group is depicted for the purposes of exemplification and therefore other $R^1$ and $R^{1'}$ groups, as described herein, are contemplated.

Exemplary such compounds include those set forth in Table 3, infra.

While compounds of formulae I-c-1, I-c-2, I-c-3, I-c-4, I-c-5, and I-c-6 are depicted as having (Z)-double bond stereochemistry in the macrocyclic ring, it will be understood that, in certain embodiments, compounds of formulae I-c-1, I-c-2, I-c-3, I-c-4, I-c-5, and I-c-6 may be provided having (E)-double bond stereochemistry in the macrocyclic ring. In some embodiments, mixtures of both stereoisomers are provided. In other embodiments, compounds of formulae I-c-1, I-c-2, I-c-3, I-c-4, I-c-5, and I-c-6 may be treated under suitable conditions to saturate the double bond.

In certain embodiments, $R^1$ and $R^{1'}$ are taken together to form an optionally substituted 3-7 membered carbocyclic ring. In some embodiments, such compounds are of formula I-d:

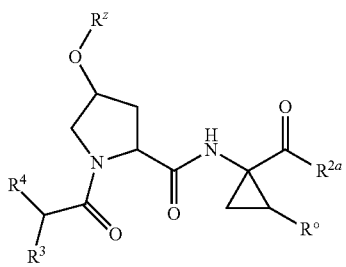

I-d or a pharmaceutically acceptable salt thereof, wherein each $R^{2a}$, $R^3$, $R^4$, $R^z$, and $R^\circ$ is as defined in formula I and described in classes and subclasses above and herein.

In some embodiments, $R^\circ$ is an optionally substituted group selected from $C_{1-6}$ aliphatic. In some embodiments, $R^\circ$ is ethyl. In other embodiments, $R^\circ$ is vinyl.

Exemplary $R^3$ groups of formula I-d include those described above and herein, as well as those depicted in Table 3, below.

In certain embodiments, $R^4$ and $R^z$ are taken together with their intervening atoms to form an optionally substituted, saturated or unsaturated 16-22 membered ring having 2-6 heteroatoms independently selected from nitrogen, oxygen, or sulfur. In some embodiments, $R^4$ and $R^z$ are taken together with their intervening atoms to form an optionally substituted, unsaturated 18-22 membered ring having 3-5 heteroatoms independently selected from nitrogen, oxygen, or sulfur. In some embodiments, the ring formed by $R^4$ and $R^z$ is substituted with one or more $R^m$ groups, wherein each occurrence of $R^m$ is independently halogen, —OR°; —CN; —SCN; —SR°; —SOR°; —SO$_2$R°; —NO$_2$; —N(R°)$_2$; —NHC(O)R°, or an optionally substituted group selected from the group consisting of $C_{1-6}$ aliphatic and $C_{3-7}$ cycloalkyl. In certain embodiments, the present invention provides compounds of formula I-e or I-f:

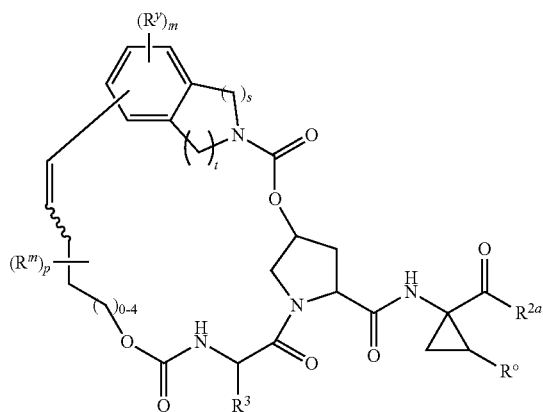

I-e

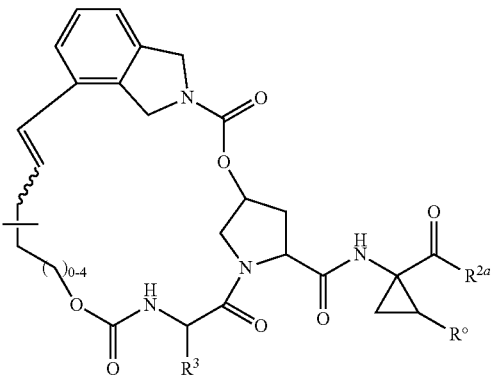

I-f or a pharmaceutically acceptable salt thereof, wherein each of m, s, t, $R^{2a}$, $R^3$, $R^y$, and $R^\circ$ is as defined in formula I and described in classes and subclasses above and herein;
p is an integer from 1 to 6, inclusive; and
each occurrence of $R^m$ is independently halogen, —OR°; —CN; —N(R°)$_2$; or an optionally substituted group selected from the group consisting of $C_{1-6}$ aliphatic and $C_{3-7}$ cycloalkyl.

In some embodiments, p is 1. In some embodiments, p is 2.

In certain embodiments, $R^m$ is $C_{1-6}$ aliphatic. In some embodiments, $R^m$ is methyl.

In some embodiments, $R^\circ$ is an optionally substituted group selected from $C_{1-6}$ aliphatic. In some embodiments, $R^\circ$ is ethyl. In other embodiments, $R^\circ$ is vinyl.

Exemplary $R^3$ groups of formulae I-e and I-f include those described herein and depicted in Table 3, below.

While compounds of formulae I-e and I-f are depicted as having either (Z) or (E) double bond stereochemistry in the macrocyclic ring, it will be understood that, in certain embodiments, compounds of formulae I-e and I-f may be provided having (E)-double bond stereochemistry in the macrocyclic ring. In certain embodiments, compounds of formulae I-e and I-f may be provided having (Z)-double bond stereochemistry in the macrocyclic ring. In some embodiments, mixtures of both stereoisomers are provided. In other embodiments, compounds of formulae I-e and I-f may be treated under suitable conditions to saturate the double bond, thereby forming a compound of formula I-g or I-h:

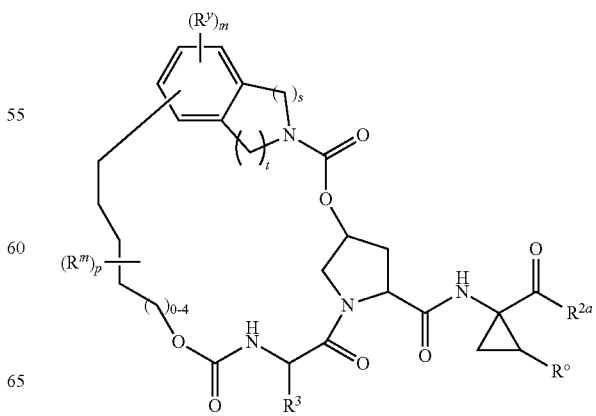

I-g

-continued

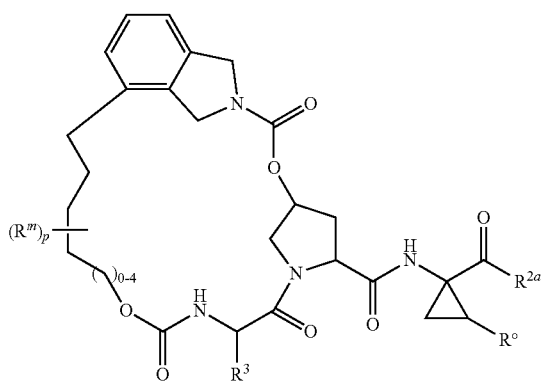

I-h or a pharmaceutically acceptable salt thereof.

In certain embodiments, $R^4$ and $R^z$ are taken together as described above, and $R^3$ and a ring formed by $R^1$ and $R^{1'}$ are taken together as described above, to form novel bimacrocyclic compounds. In certain embodiments, the ring formed by $R^4$ and $R^z$ is substituted with one or more $R^m$ groups as described above for formulae I-e and I-f. In some embodiments, the macrocyclic ring formed by $R^3$ and a ring formed by $R^1$ and $R^{1'}$ is substituted with an -L-Y warhead group to provide a compound of formula I-j or I-k:

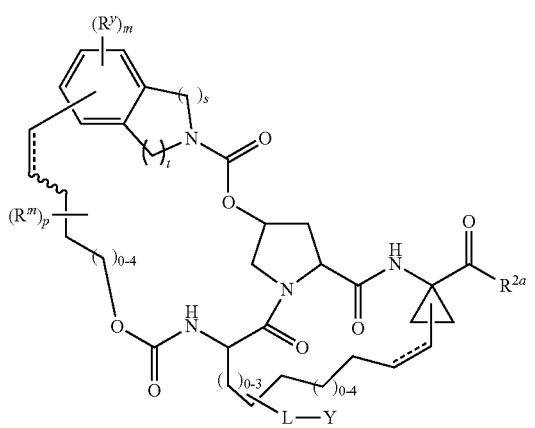

I-j

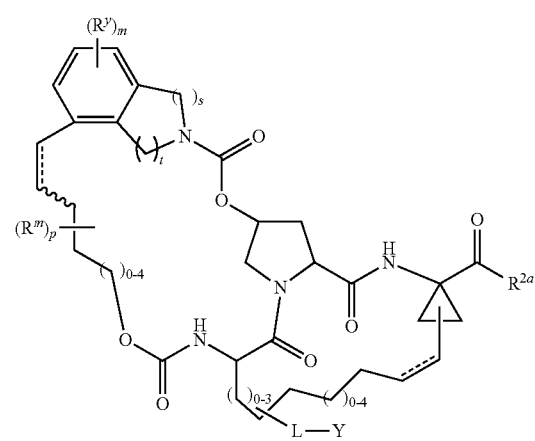

I-k or a pharmaceutically acceptable salt thereof; wherein each --- independently represents a single or double bond. Methods of preparing such compounds, in addition to those described herein for the synthesis of other macrocycles and compounds incorporating a warhead, include those described by McCauley, J. A. et al., *Angew. Chem. Int. Ed.*, 2008, 47, pp. 9104-7.

In some embodiments, a methylene unit of the macrocyclic ring formed by $R^3$ and a ring formed by $R^1$ and $R^{1'}$ is replaced by an L-Y moiety to provide a compound of formula I-m or I-n:

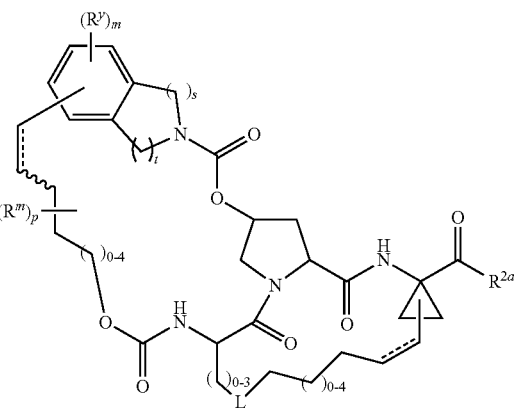

I-m

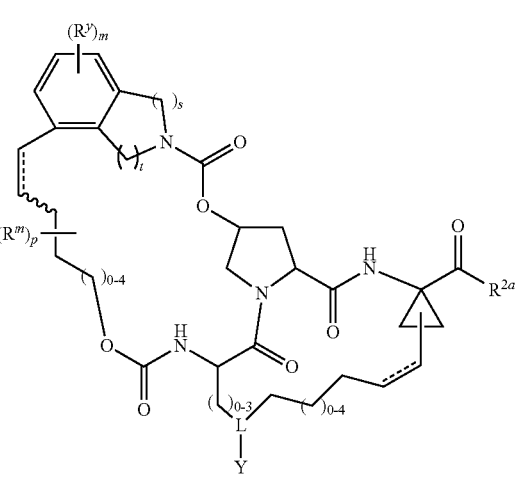

I-n or a pharmaceutically acceptable salt thereof; wherein each --- independently represents a single or double bond.

As described above and herein, in certain embodiments, the R⁴ group for compounds of formula I is hydrogen. In certain embodiments, the present invention provides a compound of formula II-a or II-b:

II-a

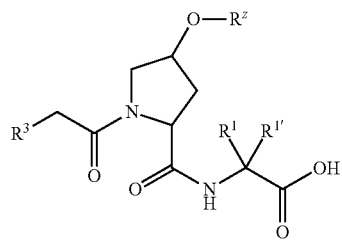

II-b

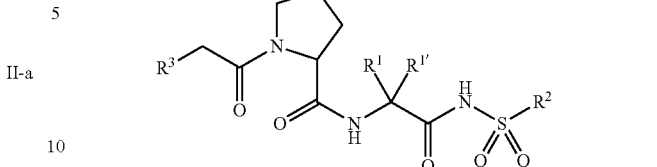

wherein each of the R¹, R¹', R², R³, and R$^z$ groups is as defined for formula I above and described in classes and subclasses herein.

Exemplary compounds of formula I are set forth in Table 3 below.

TABLE 3

Exemplary Compounds of Formula I

I-1

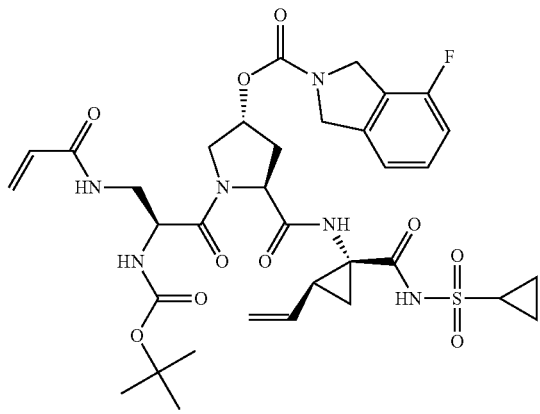 [SMILES: C=CC(=O)NC[C@H](NC(=O)OC(C)(C)C)C(=O)N1C[C@H](OC(=O)N2Cc3cccc(F)c3C2)C[C@H]1C(=O)N[C@]1(C(=O)NS(=O)(=O)C2CC2)C[C@H]1C=C]

I-2

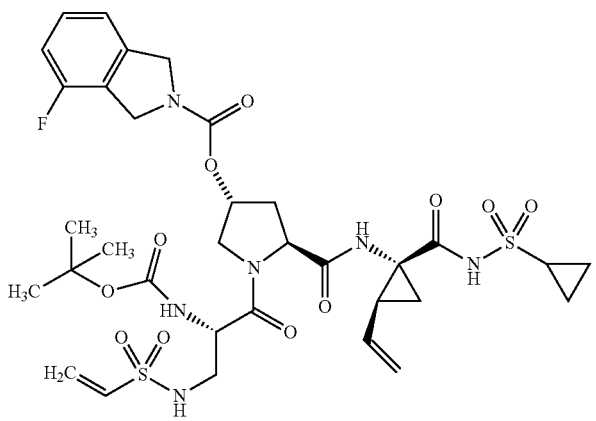 [SMILES: C=C[C@@H]1C[C@]1(NC(=O)[C@@H]1C[C@@H](OC(=O)N2Cc3cccc(F)c3C2)CN1C(=O)[C@H](CNS(=O)(=O)C=C)NC(=O)OC(C)(C)C)C(=O)NS(=O)(=O)C1CC1]

TABLE 3-continued
Exemplary Compounds of Formula I
I-3
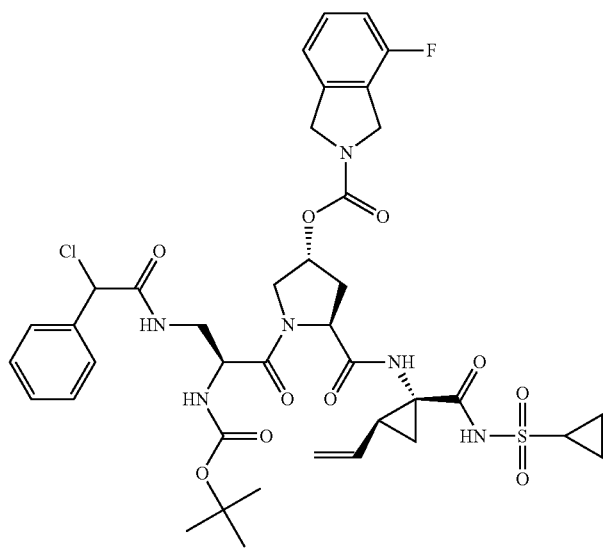 [SMILES: C=C[C@@H]1C[C@]1(NC(=O)[C@@H]1C[C@@H](OC(=O)N2Cc3cccc(F)c3C2)CN1C(=O)[C@H](CNC(=O)C(Cl)c1ccccc1)NC(=O)OC(C)(C)C)C(=O)NS(=O)(=O)C1CC1]
I-4
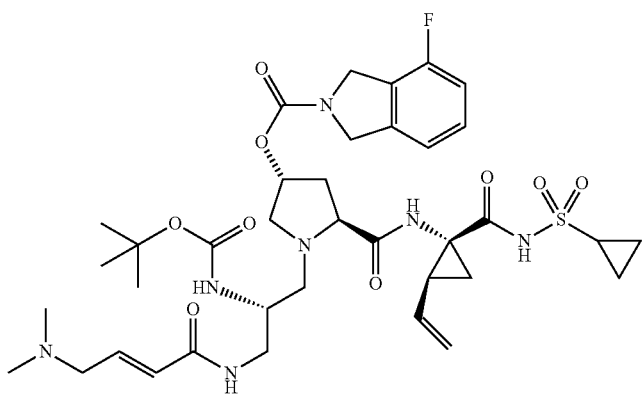
I-5
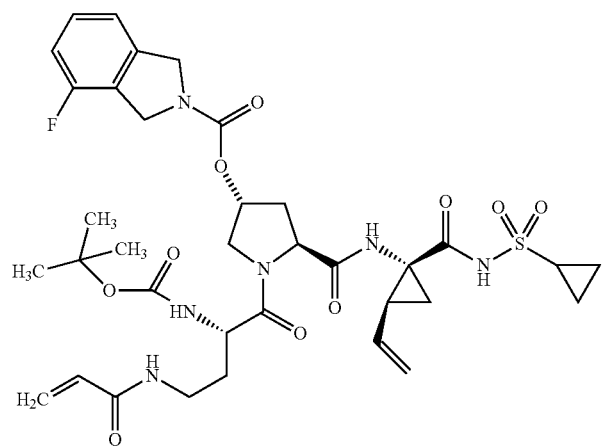

TABLE 3-continued
Exemplary Compounds of Formula I
I-6
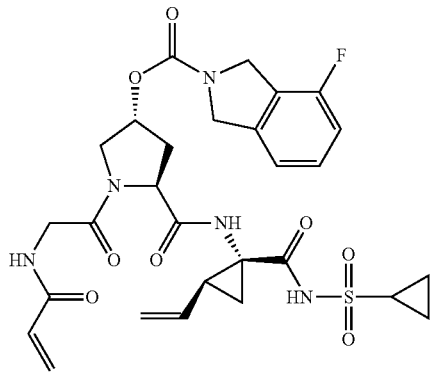 [SMILES: C=CC(=O)NCC(=O)N1C[C@H](OC(=O)N2Cc3cccc(F)c3C2)C[C@H]1C(=O)N[C@]1(C(=O)NS(=O)(=O)C2CC2)C[C@H]1C=C]
I-7
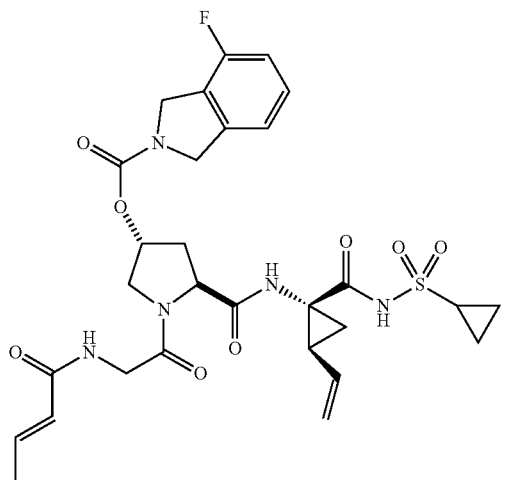
I-8
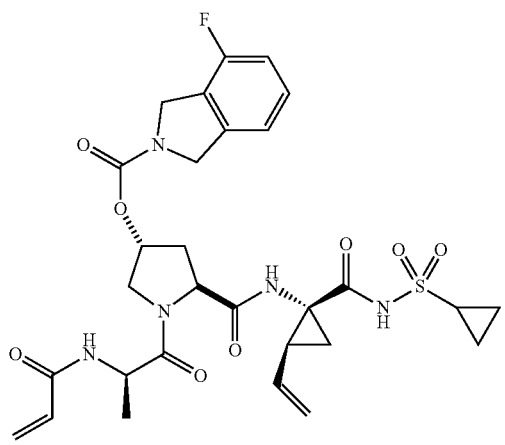

TABLE 3-continued
Exemplary Compounds of Formula I
I-9
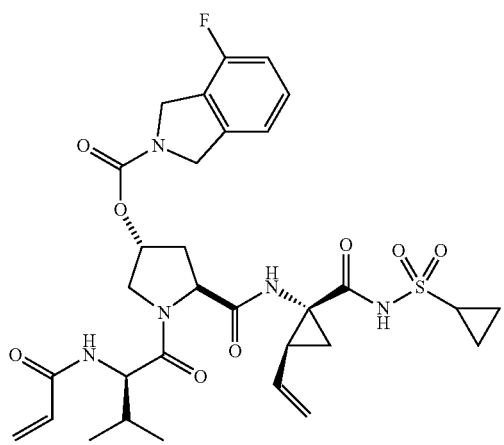
I-10
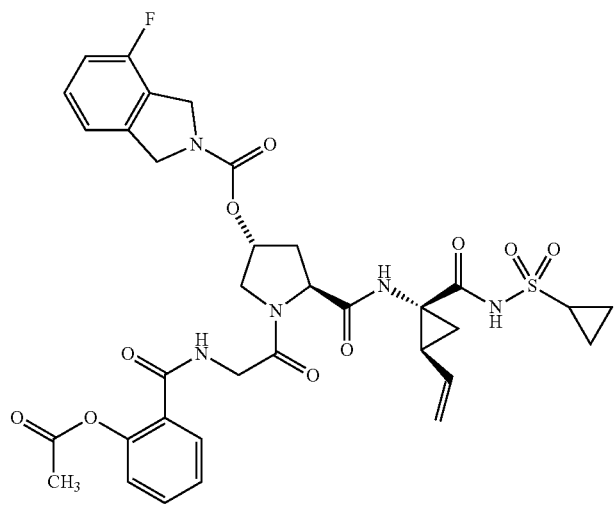
I-11
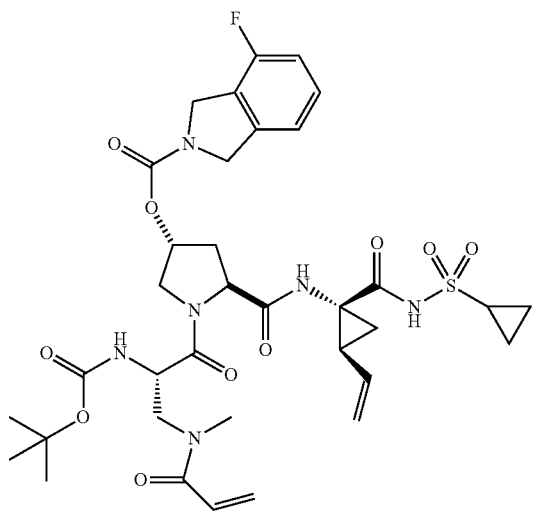

US 9,676,785 B2
TABLE 3-continued
Exemplary Compounds of Formula I
I-12
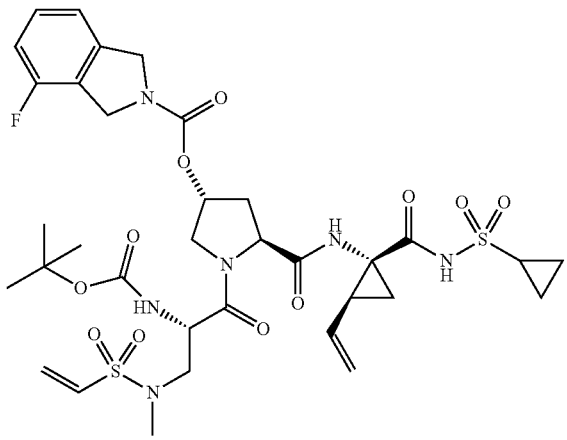
I-13
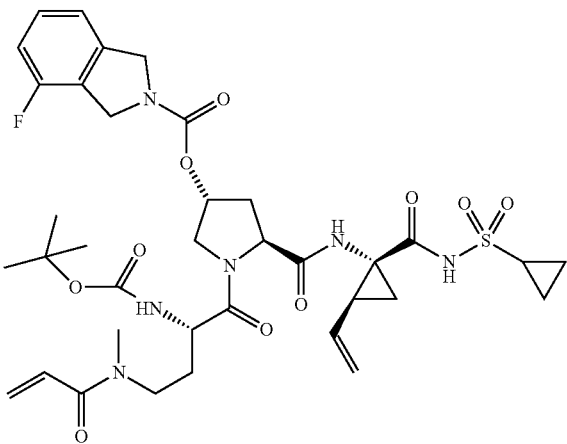
I-14
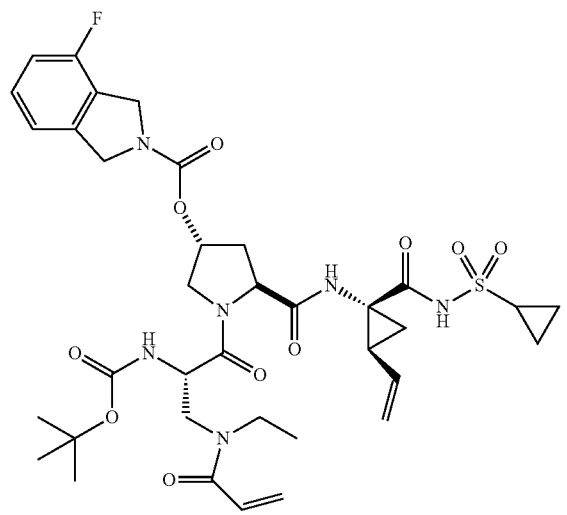

TABLE 3-continued
Exemplary Compounds of Formula I
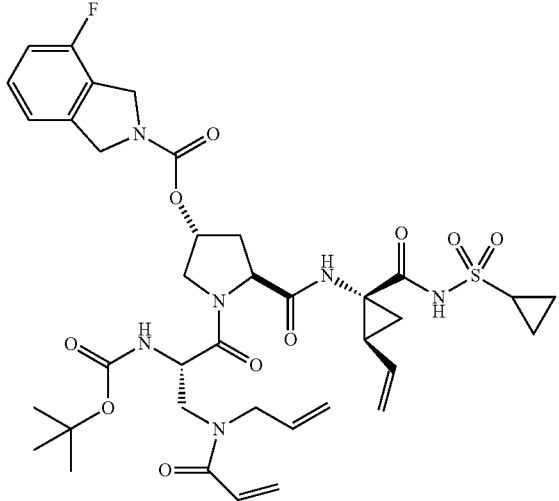
I-15
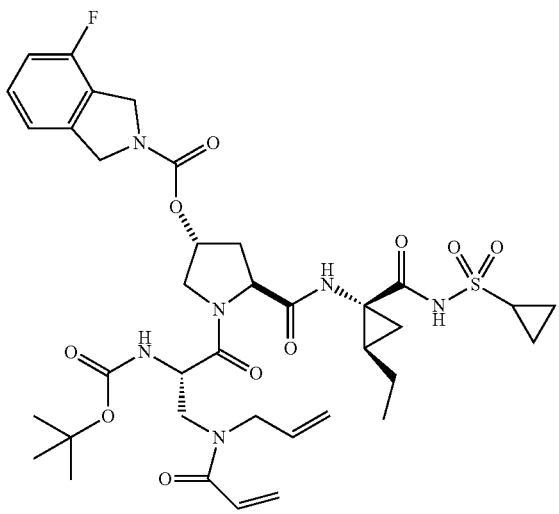
I-16
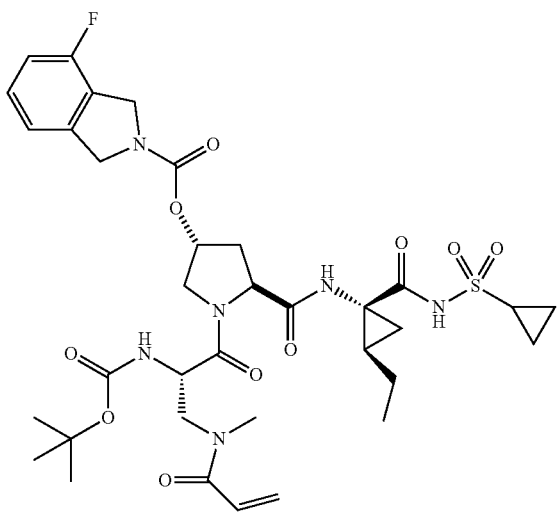
I-17

TABLE 3-continued
Exemplary Compounds of Formula I
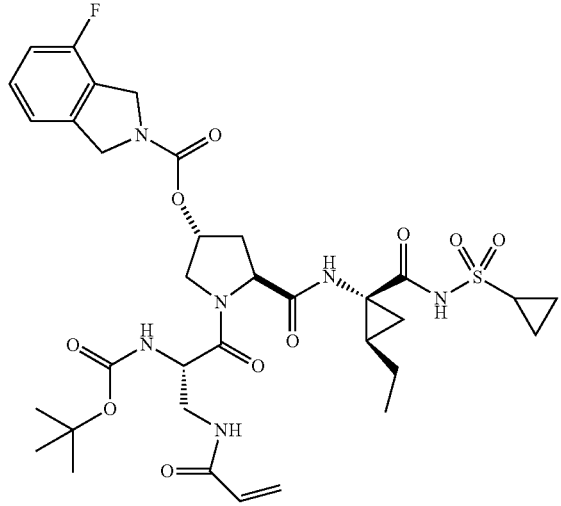
I-18
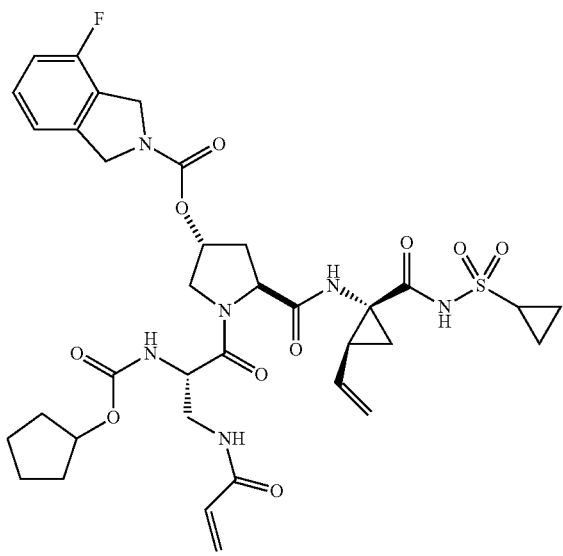
I-19
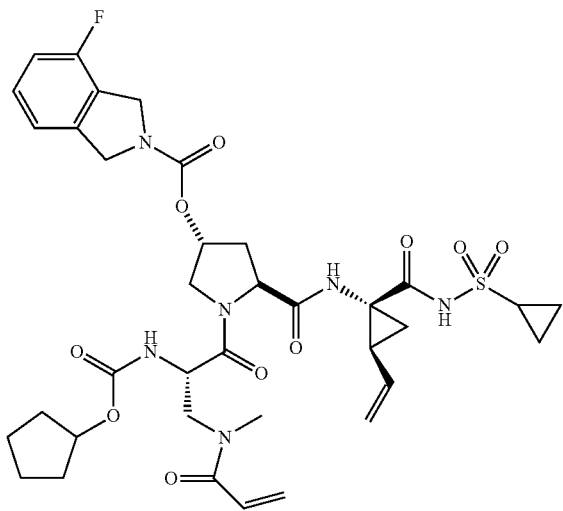
I-20

TABLE 3-continued
Exemplary Compounds of Formula I
I-21
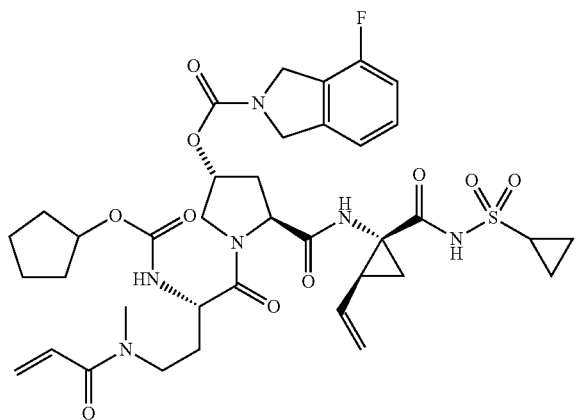 [SMILES: C=CC(=O)N(C)CC[C@H](NC(=O)OC1CCCC1)C(=O)N1C[C@H](OC(=O)N2Cc3cccc(F)c3C2)C[C@H]1C(=O)N[C@]1(C(=O)NS(=O)(=O)C2CC2)C[C@H]1C=C]
I-22
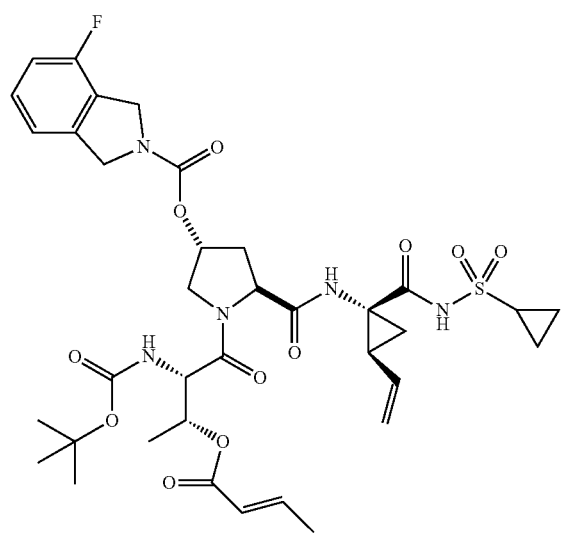
I-23
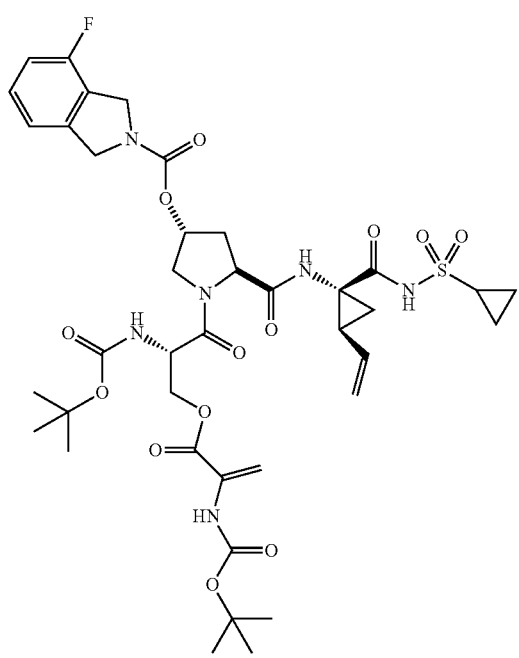

TABLE 3-continued
Exemplary Compounds of Formula I
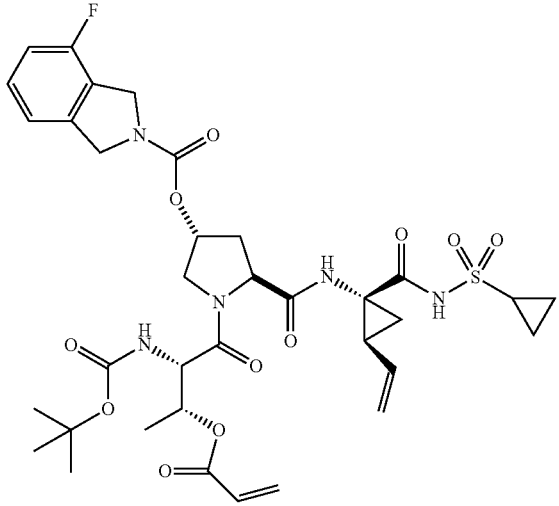
I-24
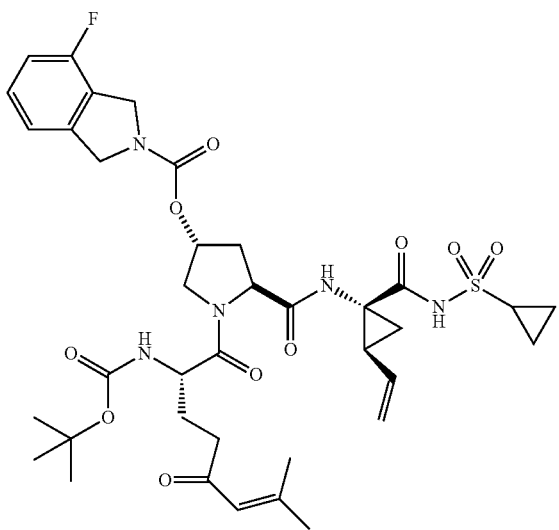
I-25
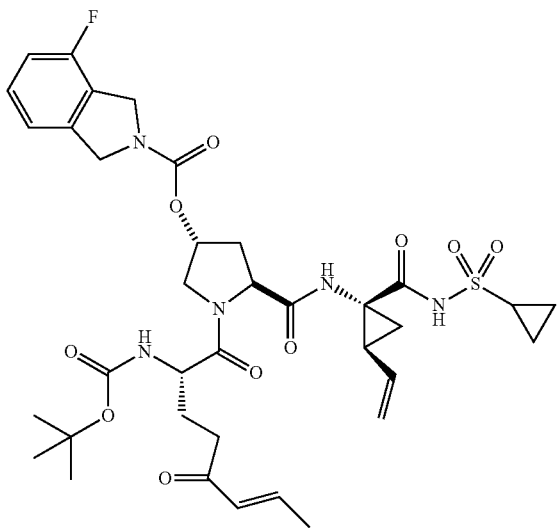
I-26

TABLE 3-continued
Exemplary Compounds of Formula I
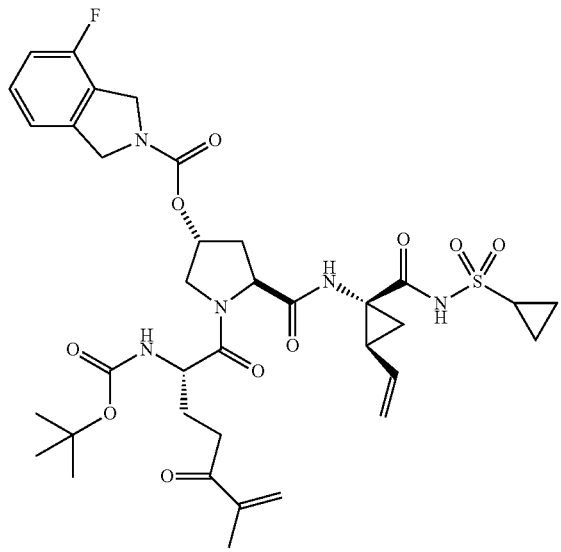
I-27
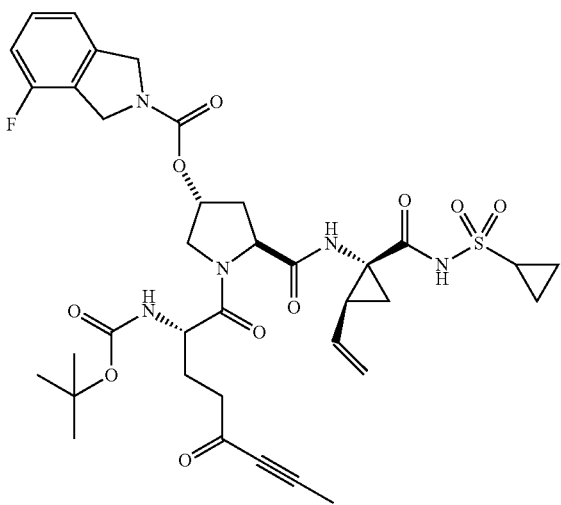
I-28
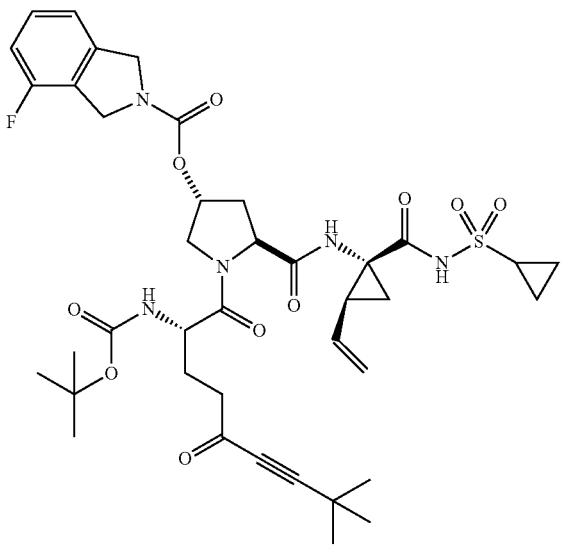
I-29

TABLE 3-continued
Exemplary Compounds of Formula I
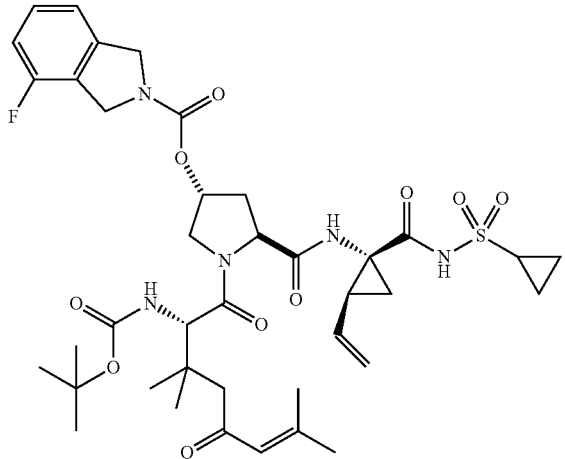
I-30
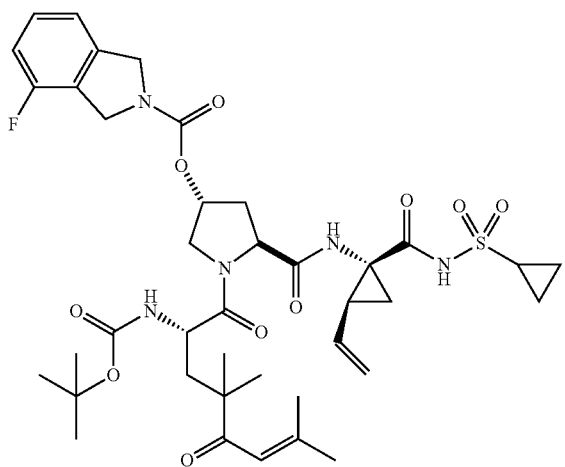
I-31
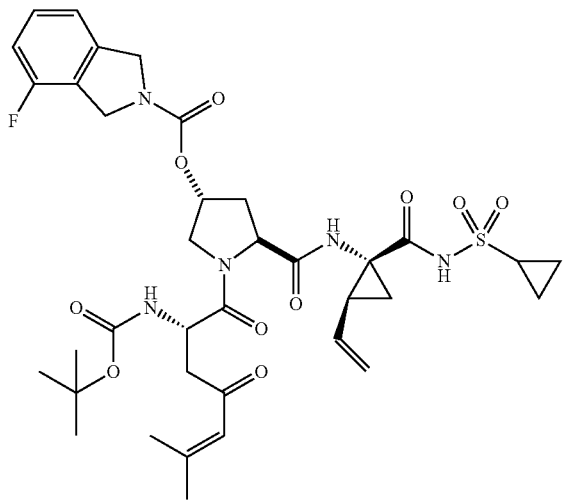
I-32

TABLE 3-continued
Exemplary Compounds of Formula I
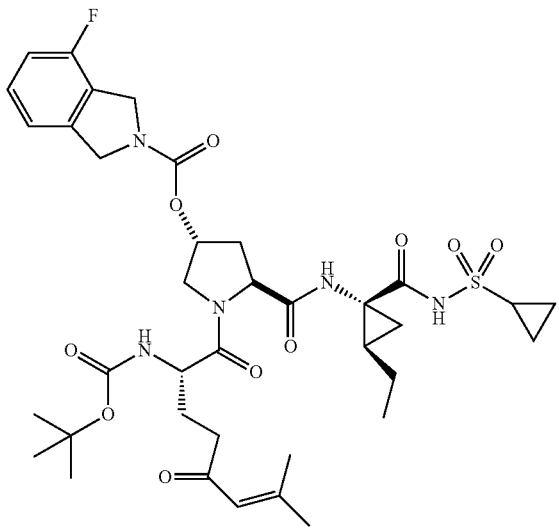
I-33
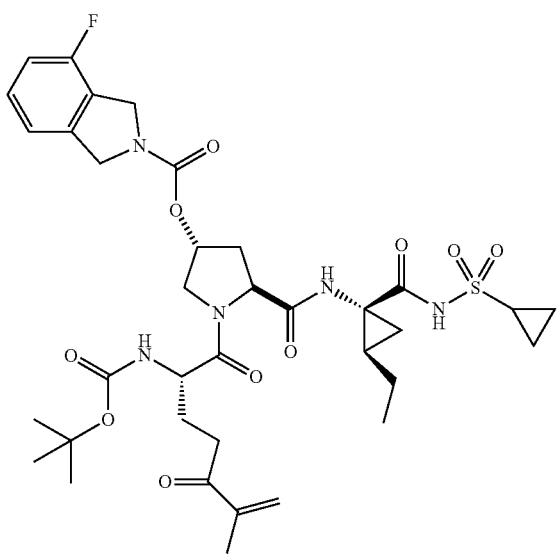
I-34
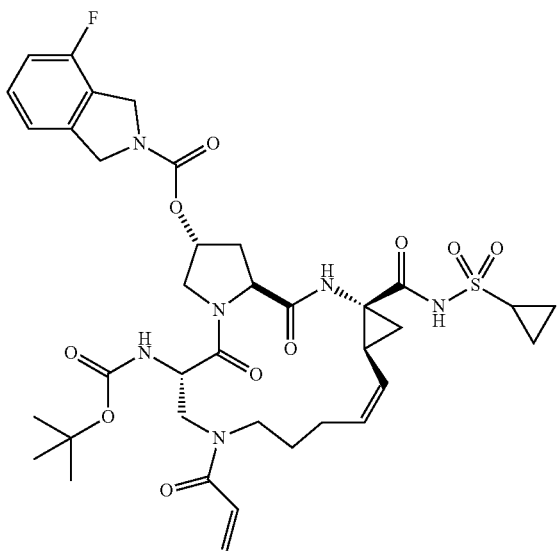
I-35

US 9,676,785 B2
TABLE 3-continued
Exemplary Compounds of Formula I
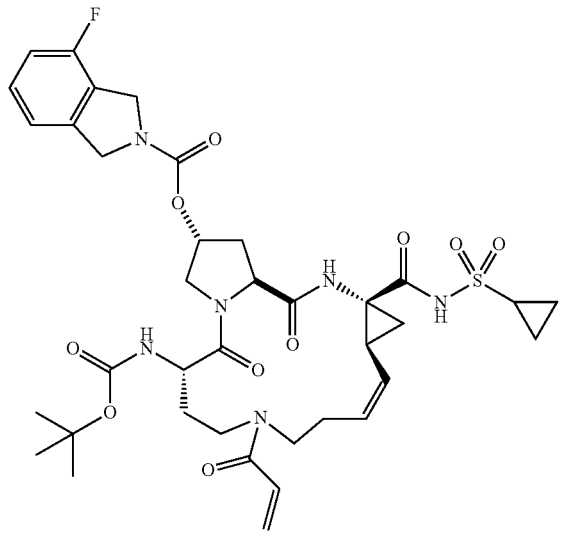
I-36
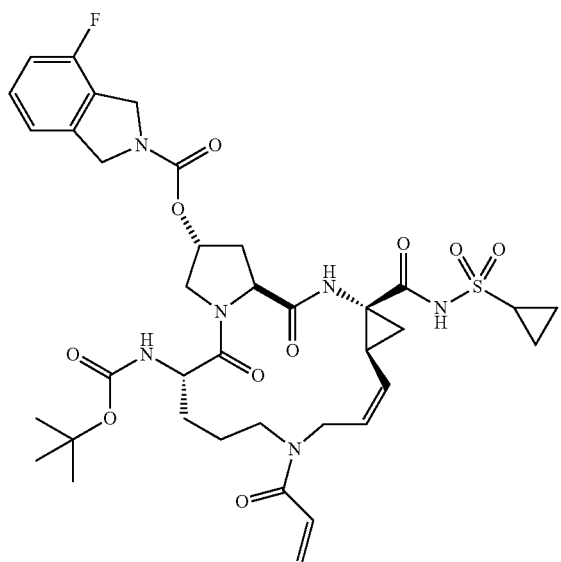
I-37
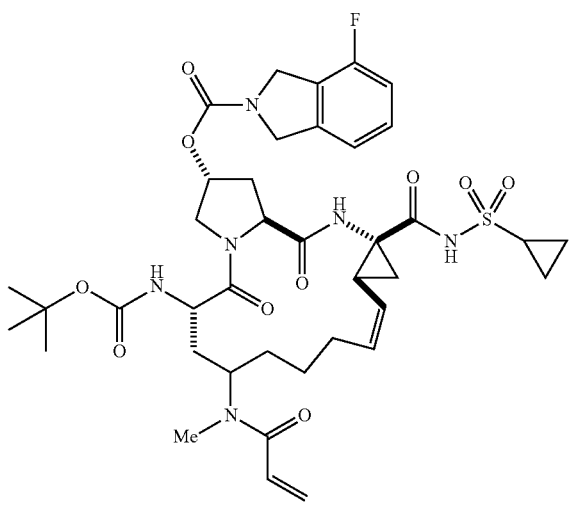
I-38

TABLE 3-continued
Exemplary Compounds of Formula I
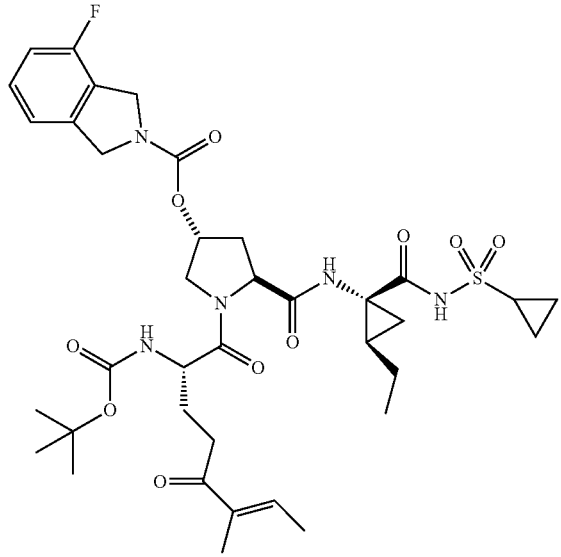
I-39
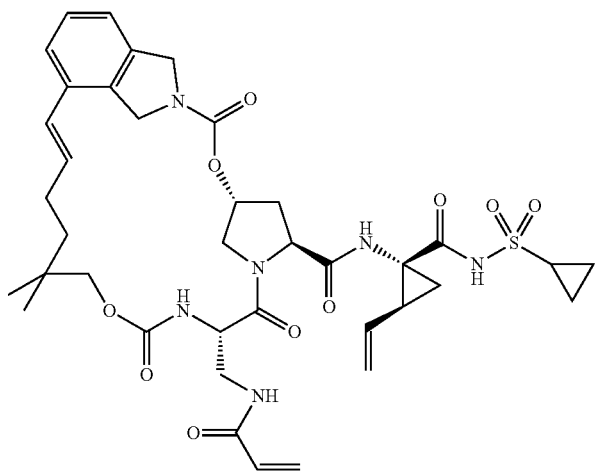 [SMILES: C=CC(=O)NC[C@@H]1NC(=O)OCC(C)(C)CC/C=C/c2cccc3c2CN(C3)C(=O)O[C@@H]2C[C@@H](C(=O)N[C@]3(C(=O)NS(=O)(=O)C4CC4)C[C@H]3C=C)N(C2)C1=O]
I-40
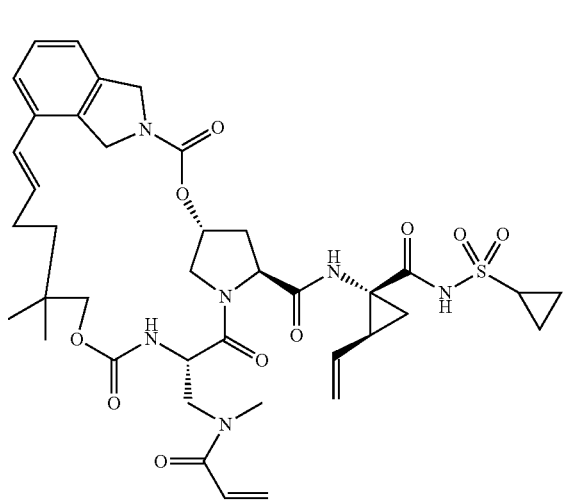 [SMILES: C=CC(=O)N(C)C[C@@H]1NC(=O)OCC(C)(C)CC/C=C/c2cccc3c2CN(C3)C(=O)O[C@@H]2C[C@@H](C(=O)N[C@]3(C(=O)NS(=O)(=O)C4CC4)C[C@H]3C=C)N(C2)C1=O]
I-41

TABLE 3-continued
Exemplary Compounds of Formula I
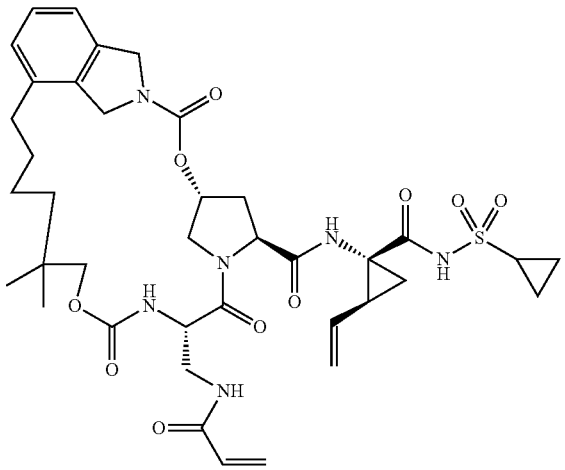 [SMILES: C=CC(=O)NC[C@@H]1NC(=O)OCC(C)(C)CCCCc2cccc3c2CN(C3)C(=O)O[C@@H]2C[C@@H](C(=O)N[C@]3(C(=O)NS(=O)(=O)C4CC4)C[C@H]3C=C)N(C2)C1=O]
I-42
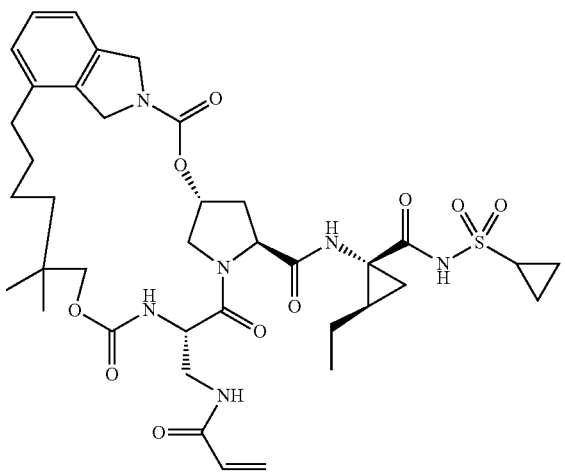 [SMILES: C=CC(=O)NC[C@@H]1NC(=O)OCC(C)(C)CCCCc2cccc3c2CN(C3)C(=O)O[C@@H]2C[C@@H](C(=O)N[C@]3(C(=O)NS(=O)(=O)C4CC4)C[C@H]3CC)N(C2)C1=O]
I-43
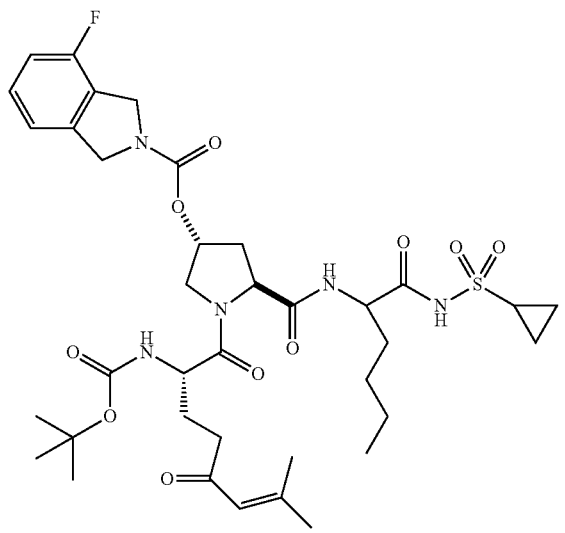
I-44

TABLE 3-continued
Exemplary Compounds of Formula I
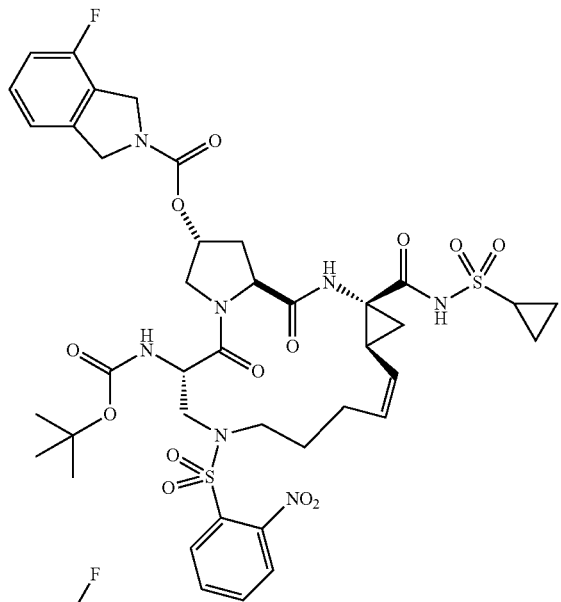
I-45
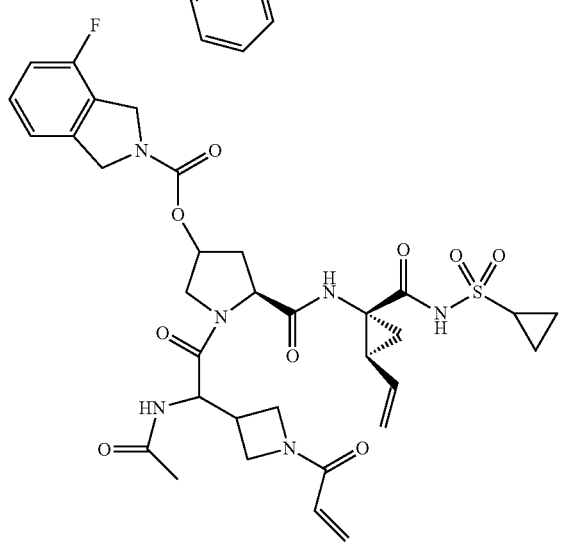
I-46
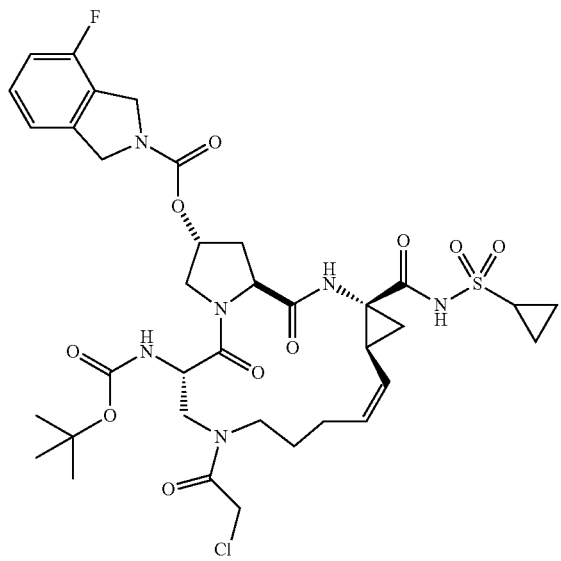
I-47

TABLE 3-continued
Exemplary Compounds of Formula I
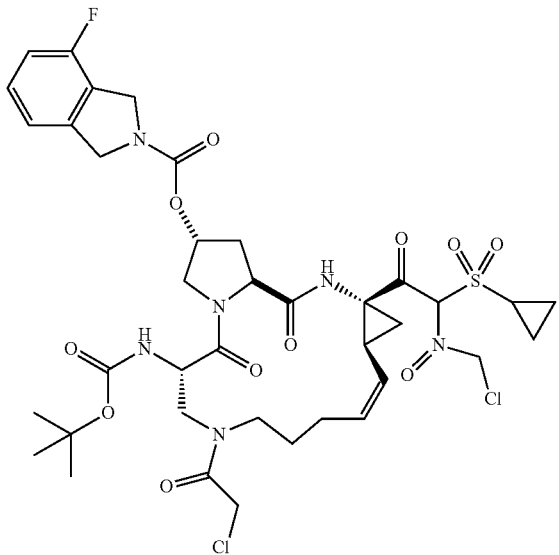
I-48
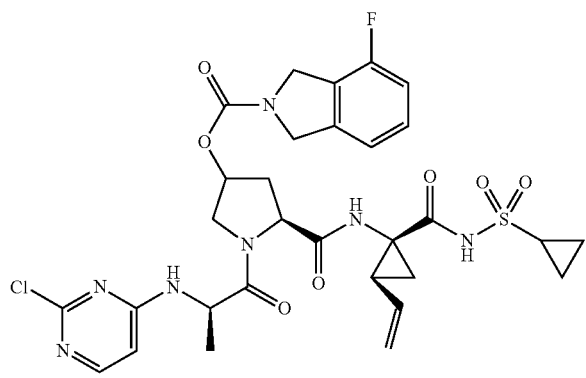 [SMILES: C=C[C@@H]1C[C@]1(NC(=O)[C@@H]1CC(OC(=O)N2Cc3cccc(F)c3C2)CN1C(=O)[C@@H](C)Nc1ccnc(Cl)n1)C(=O)NS(=O)(=O)C1CC1]
I-49
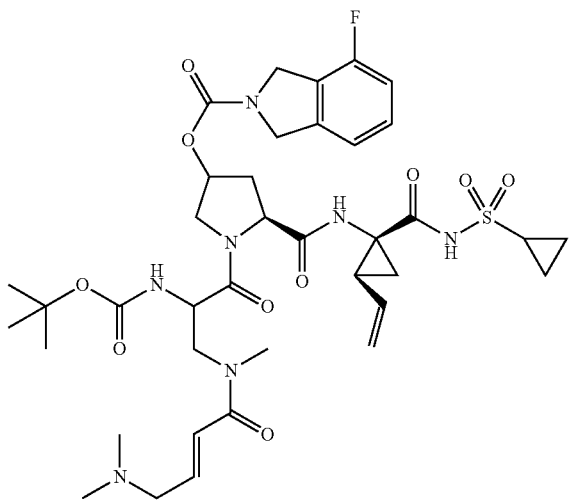 [SMILES: C=C[C@@H]1C[C@]1(NC(=O)[C@@H]1CC(OC(=O)N2Cc3cccc(F)c3C2)CN1C(=O)C(CN(C)C(=O)/C=C/CN(C)C)NC(=O)OC(C)(C)C)C(=O)NS(=O)(=O)C1CC1]
I-50

TABLE 3-continued
Exemplary Compounds of Formula I
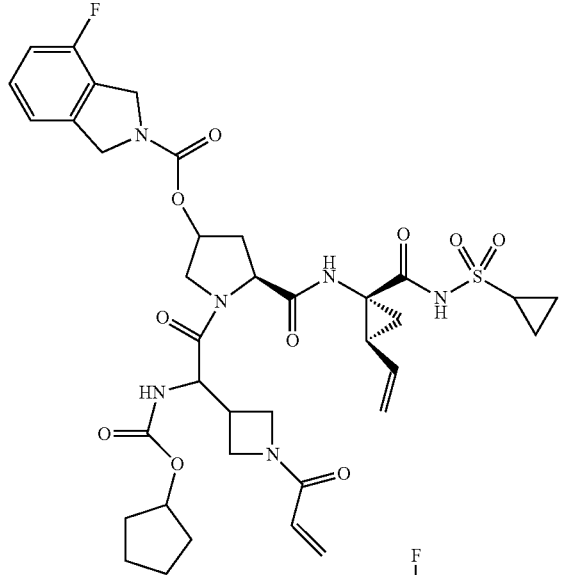 [SMILES: C=CC(=O)N1CC(C(NC(=O)OC2CCCC2)C(=O)N2CC(OC(=O)N3Cc4cccc(F)c4C3)C[C@H]2C(=O)N[C@]2(C(=O)NS(=O)(=O)C3CC3)C[C@H]2C=C)C1]
I-51
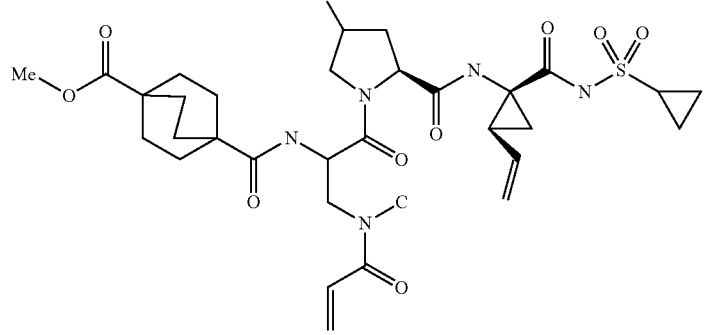
I-52
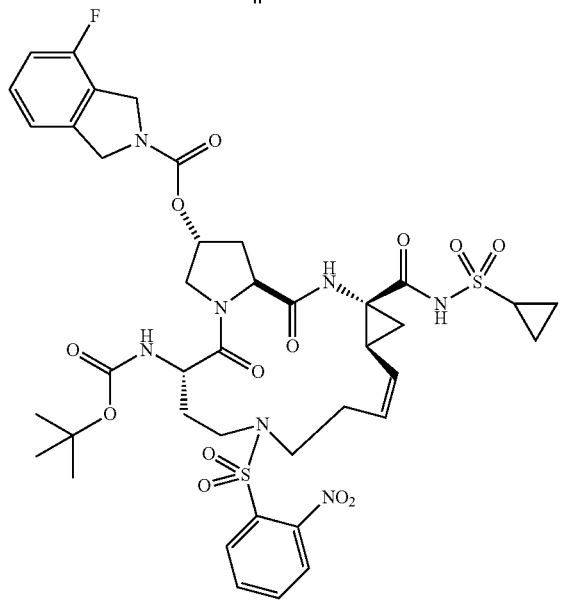
I-53

TABLE 3-continued
Exemplary Compounds of Formula I
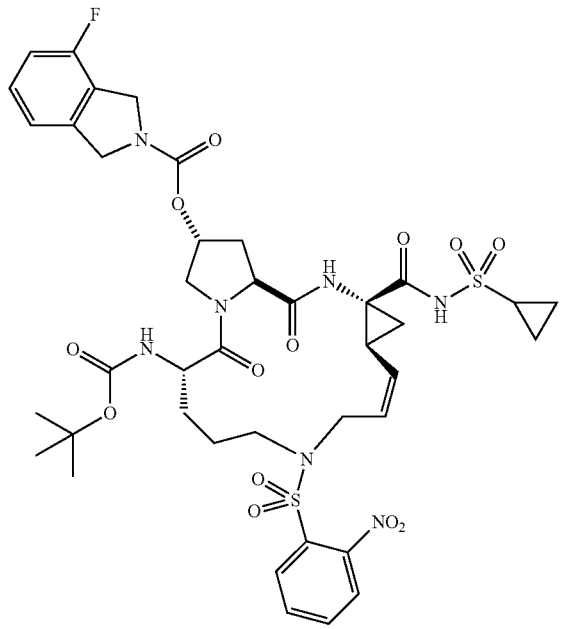
I-54
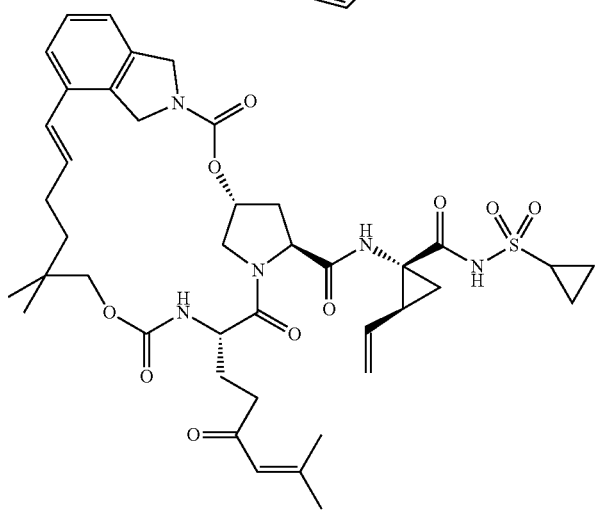
I-55
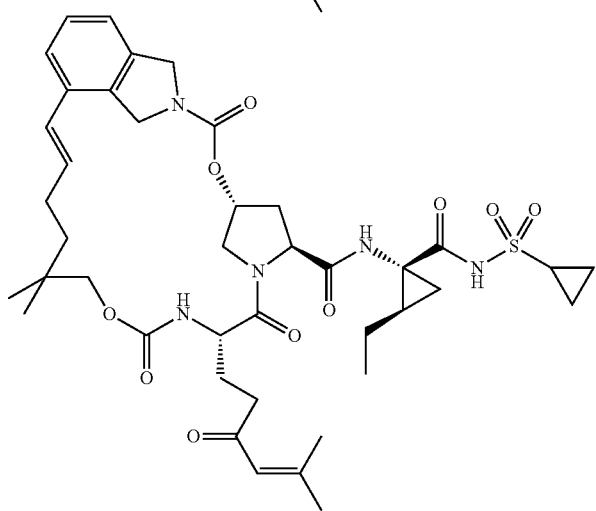
I-56

TABLE 3-continued
Exemplary Compounds of Formula I
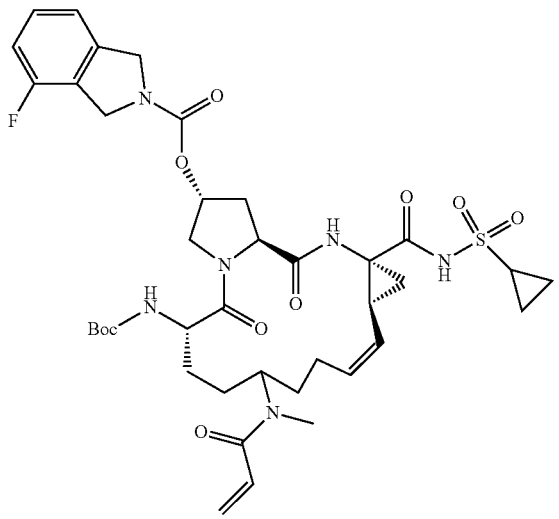 [SMILES: C=CC(=O)N(C)C1CC/C=C\[C@@H]2C[C@@]2(C(=O)NS(=O)(=O)C2CC2)NC(=O)[C@@H]2C[C@@H](OC(=O)N3Cc4cccc(F)c4C3)CN2C(=O)[C@@H](NC(=O)OC(C)(C)C)CC1]
I-57
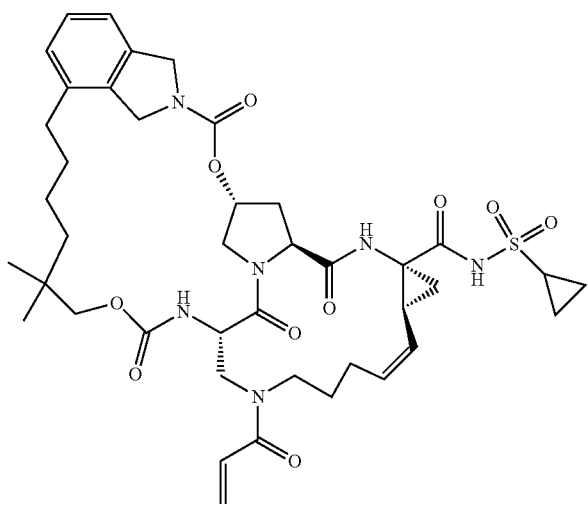 [SMILES: C=CC(=O)N1CCC/C=C\[C@@H]2C[C@@]2(C(=O)NS(=O)(=O)C2CC2)NC(=O)[C@@H]2C[C@@H]3CN2C(=O)[C@H](C1)NC(=O)OCC(C)(C)CCCCc1cccc2c1CN(C2)C(=O)O3]
I-58
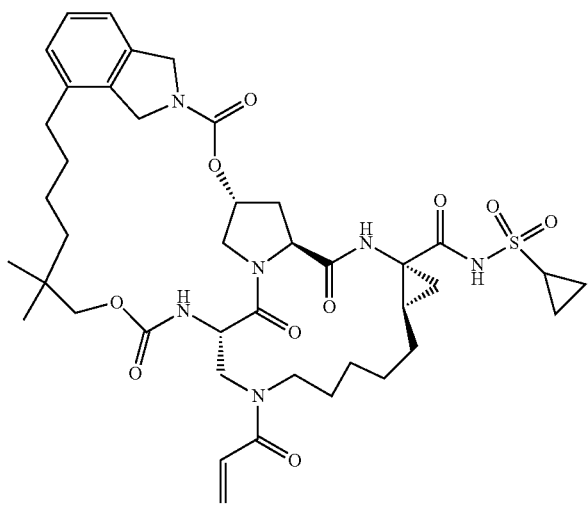 [SMILES: C=CC(=O)N1CCCCC[C@@H]2C[C@@]2(C(=O)NS(=O)(=O)C2CC2)NC(=O)[C@@H]2C[C@@H]3CN2C(=O)[C@H](C1)NC(=O)OCC(C)(C)CCCCc1cccc2c1CN(C2)C(=O)O3]
I-59

TABLE 3-continued
Exemplary Compounds of Formula I
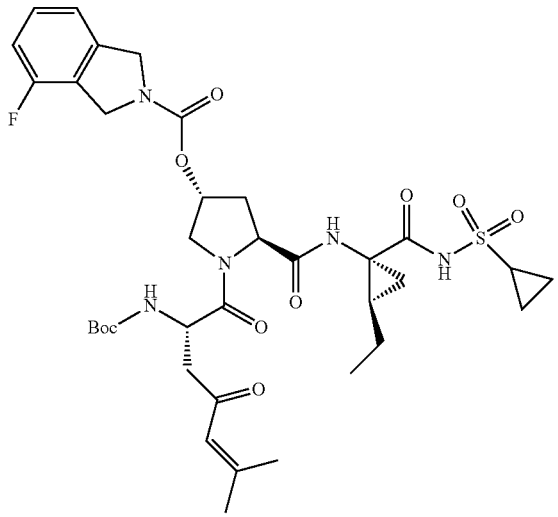 [SMILES: CC[C@@H]1C[C@]1(NC(=O)[C@@H]1C[C@@H](OC(=O)N2Cc3cccc(F)c3C2)CN1C(=O)[C@H](CC(=O)C=C(C)C)NC(=O)OC(C)(C)C)C(=O)NS(=O)(=O)C1CC1]
I-60
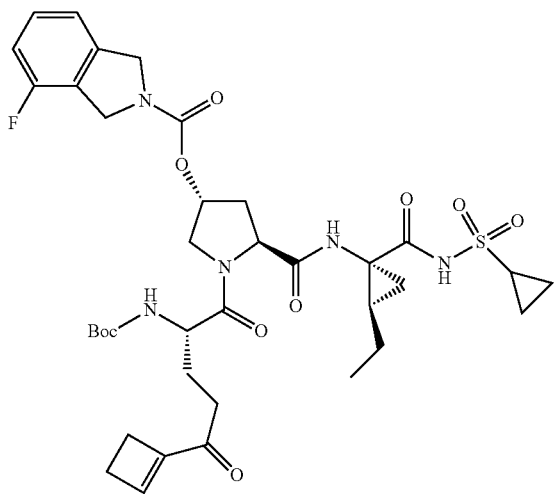 [SMILES: CC[C@@H]1C[C@]1(NC(=O)[C@@H]1C[C@@H](OC(=O)N2Cc3cccc(F)c3C2)CN1C(=O)[C@H](CCC(=O)C1=CCC1)NC(=O)OC(C)(C)C)C(=O)NS(=O)(=O)C1CC1]
I-61
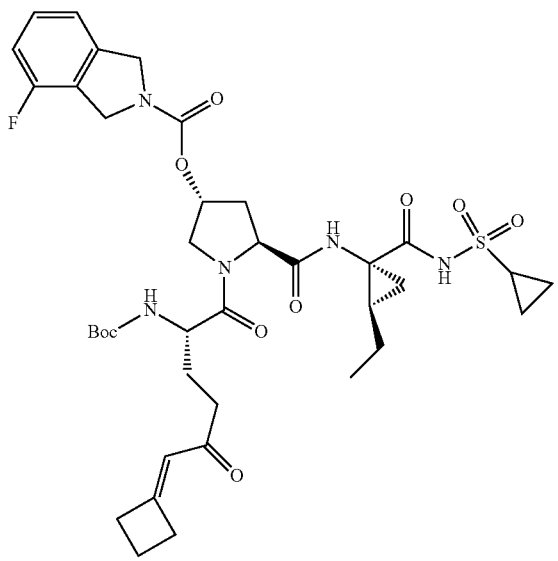 [SMILES: CC[C@@H]1C[C@]1(NC(=O)[C@@H]1C[C@@H](OC(=O)N2Cc3cccc(F)c3C2)CN1C(=O)[C@H](CCC(=O)C=C1CCC1)NC(=O)OC(C)(C)C)C(=O)NS(=O)(=O)C1CC1]
I-62

TABLE 3-continued
Exemplary Compounds of Formula I
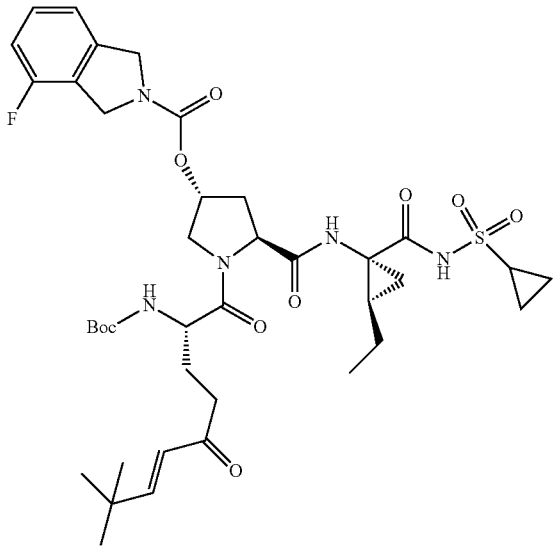 [SMILES: CC[C@@H]1C[C@]1(NC(=O)[C@@H]1C[C@@H](OC(=O)N2Cc3cccc(F)c3C2)CN1C(=O)[C@H](CCC(=O)/C=C/C(C)(C)C)NC(=O)OC(C)(C)C)C(=O)NS(=O)(=O)C1CC1]
I-63
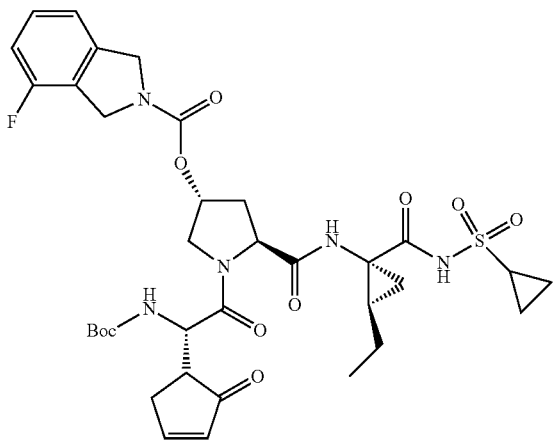 [SMILES: CC[C@@H]1C[C@]1(NC(=O)[C@@H]1C[C@@H](OC(=O)N2Cc3cccc(F)c3C2)CN1C(=O)[C@@H](NC(=O)OC(C)(C)C)C1CC=CC1=O)C(=O)NS(=O)(=O)C1CC1]
I-64
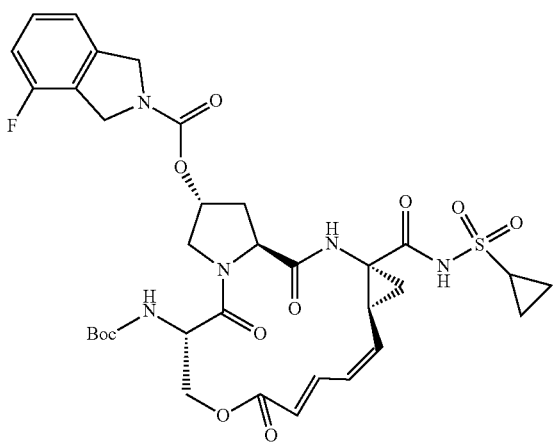 [SMILES: CC(C)(C)OC(=O)N[C@H]1COC(=O)/C=C/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O]
I-65

TABLE 3-continued

Exemplary Compounds of Formula I

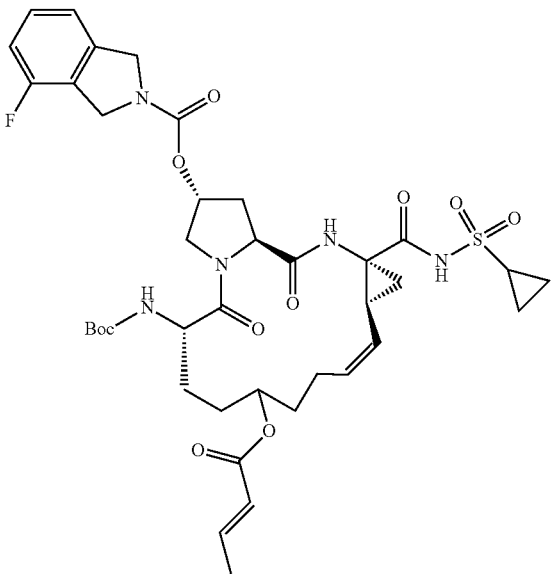 [SMILES: C/C=C/C(=O)OC1CC/C=C\[C@@H]2C[C@@]2(C(=O)NS(=O)(=O)C2CC2)NC(=O)[C@@H]2C[C@@H](OC(=O)N3Cc4cccc(F)c4C3)CN2C(=O)[C@@H](NC(=O)OC(C)(C)C)CC1]

I-66

In certain embodiments, the present invention provides any compound depicted in Table 3, above, or a pharmaceutically acceptable salt thereof.

As defined generally above, $R^3$ is a warhead group. Without wishing to be bound by any particular theory, it is believed that such $R^3$ groups, i.e. warhead groups, are particularly suitable for covalently binding to a key cysteine residue in the binding domain of HCV protease. One of ordinary skill in the art will appreciate that HCV protease, and mutants thereof, have a cysteine residue in the binding domain. In certain embodiments, compounds of the present invention have a warhead group characterized in that inventive compounds may target the C159 cysteine residue of HCV protease.

Thus, in some embodiments, $R^3$ is characterized in that the -L-Y moiety is capable of covalently binding to a cysteine residue thereby irreversibly inhibiting the enzyme. In certain embodiments, the cysteine residue is Cys159 of HCV protease, or a mutant thereof, where the provided residue numbering is in accordance with Uniprot (code Q91RS4).

One of ordinary skill in the art will recognize that a variety of warhead groups, as defined herein, are suitable for such covalent bonding. Such $R^3$ groups include, but are not limited to, those described herein and depicted in Table 3, supra. This phenomenon may be determined by performing mass spectroscopic experiments using the protocol described in detail in Examples 17 through 21, infra.

According to another aspect, the present invention provides a conjugate comprising HCV protease, or a mutant thereof, covalently bonded to an inhibitor at Cys159. In some embodiments, the inhibitor is covalently bonded via a linker moiety.

In certain embodiments, the present invention provides a conjugate of the formula Cys159-linker-inhibitor moiety. One of ordinary skill in the art will recognize that the "linker" group corresponds to an -L-Y warhead group as described herein. Accordingly, in certain embodiments, the linker group is as defined for -L-Y was defined above and described in classes and subclasses herein. It will be appreciated, however, that the linker group is bivalent and, therefore, the corresponding -L-Y group is also intended to be bivalent resulting from the reaction of the warhead with the Cys 159 of HCV protease, or a mutant thereof.

In certain embodiments, the inhibitor moiety is a compound of formula A:

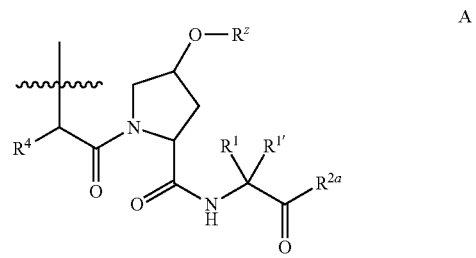

A wherein each of the $R^1$, $R^{1'}$, $R^{2a}$, $R^4$, and $R^z$ groups of formula A is as defined for formula I above and described in classes and subclasses herein. Thus, in certain embodiments, the present invention provides a conjugate of the formula:

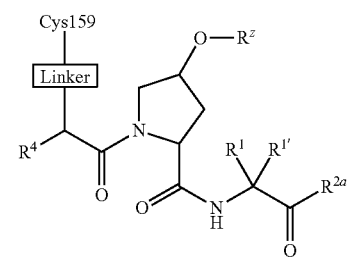

wherein each of the $R^1$, $R^{1'}$, $R^{2a}$, $R^4$, and $R^z$ groups of the conjugate is as defined for formula I above and described in classes and subclasses herein.

In some embodiments, $R^3$ is characterized in that the -L-Y moiety is capable of covalently binding to a cysteine residue thereby irreversibly inhibiting the enzyme. In certain embodiments, the cysteine residue is Cys16 of HCV protease, or a mutant thereof, where the provided residue numbering is in accordance with Uniprot (code Q91RS4).

According to another aspect, the present invention provides a conjugate comprising HCV protease, or a mutant thereof, covalently bonded to an inhibitor at Cys16. In some embodiments, the inhibitor is covalently bonded via a linker moiety.

In certain embodiments, the present invention provides a conjugate of the formula Cys 16-linker-inhibitor moiety. One of ordinary skill in the art will recognize that the "linker" group corresponds to an -L-Y warhead group as described herein. Accordingly, in certain embodiments, the linker group is as defined for -L-Y was defined above and described in classes and subclasses herein. It will be appreciated, however, that the linker group is bivalent and, therefore, the corresponding -L-Y group is also intended to be bivalent resulting from the reaction of the warhead with the Cys16 of HCV protease, or a mutant thereof.

In certain embodiments, the inhibitor moiety is a compound of formula A-1:

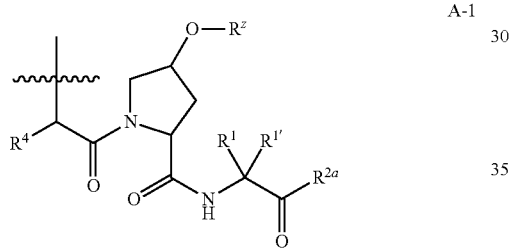

wherein each of the $R^1$, $R^{1'}$, $R^{2a}$, $R^4$, and $R^z$ groups of formula A-1 is as defined for formula I above and described in classes and subclasses herein. Thus, in certain embodiments, the present invention provides a conjugate of the formula:

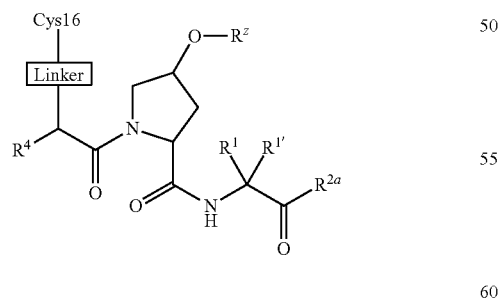

wherein each of the $R^1$, $R^{1'}$, $R^{2a}$, $R^4$, and $R^z$ groups of the conjugate is as defined for formula I above and described in classes and subclasses herein.

General Methods of Providing the Present Compounds

In certain embodiments, the present compounds are generally prepared according to Scheme 1 set forth below:

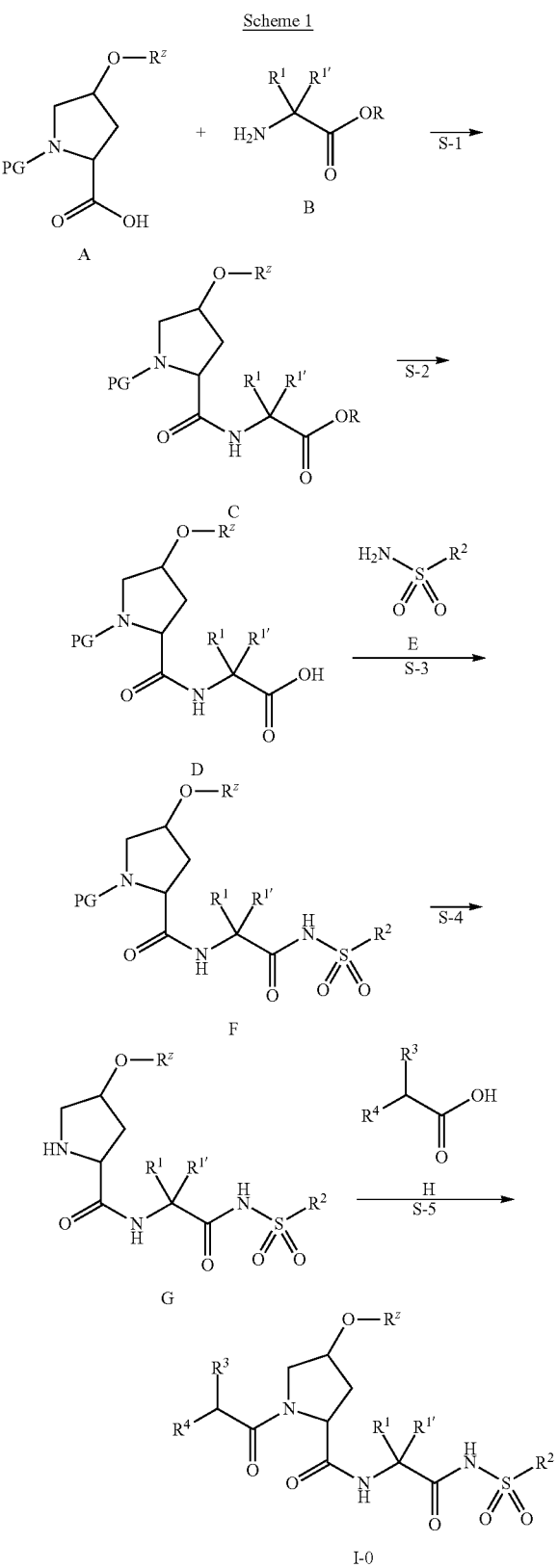

In one aspect, the present invention provides methods for preparing compounds of formula I, according to the steps depicted in Scheme 1 above wherein each variable is as defined and described herein and each PG is a suitable protecting group. At step S-1, an N-protected (e.g. Boc) proline derivative of formula A is condensed with an alpha-aminoester of formula B using peptide coupling conditions to give a dipeptide of formula C. Suitable peptide coupling conditions are well known in the art and include those described in detail in PCT publication number WO2002094822 (U.S. Pat. No. 6,825,347), the entirety of which is hereby incorporated by reference. Unless otherwise indicated, said conditions are referenced as suitable peptide coupling conditions throughout this application.

At step S-2, the ester group is hydrolyzed with a suitable base and subsequently neutralized to give a dipeptide of formula D. Suitable bases include, but are not limited to, alkaline metals, alkaline earth metal hydroxides, and combinations thereof. In some embodiments, the base is lithium hydroxide.

At step S-3, a dipeptide of formula D is coupled with a sulfonamide of formula E using suitable peptide coupling conditions to give an acylsulfonamide of formula F.

At step S-4, cleavage of the protective group (e.g. Boc removal) from a dipeptide of formula F gives an amine of formula G. In certain embodiments, cleavage of the Boc group is achieved by contacting a compound of formula F with a mineral or organic acid in a halogenated hydrocarbon solvent. In some embodiments, In some embodiments, the acid is trifluoroacetic acid and the solvent is dichloromethane.

At step S-5, an amine of formula G is coupled with an carboxylic acid of formula H using suitable peptide coupling conditions to give an intermediate compound of formula I-0.

Intermediate compound of formula I-0 is converted to compounds of formula I in steps which are described as examples herein.

As defined generally above, the PG group of formulae A, C, D, and F is a suitable amino protecting group. Suitable amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like.

In other embodiments, the present compounds are generally prepared according to Scheme 2 set forth below.

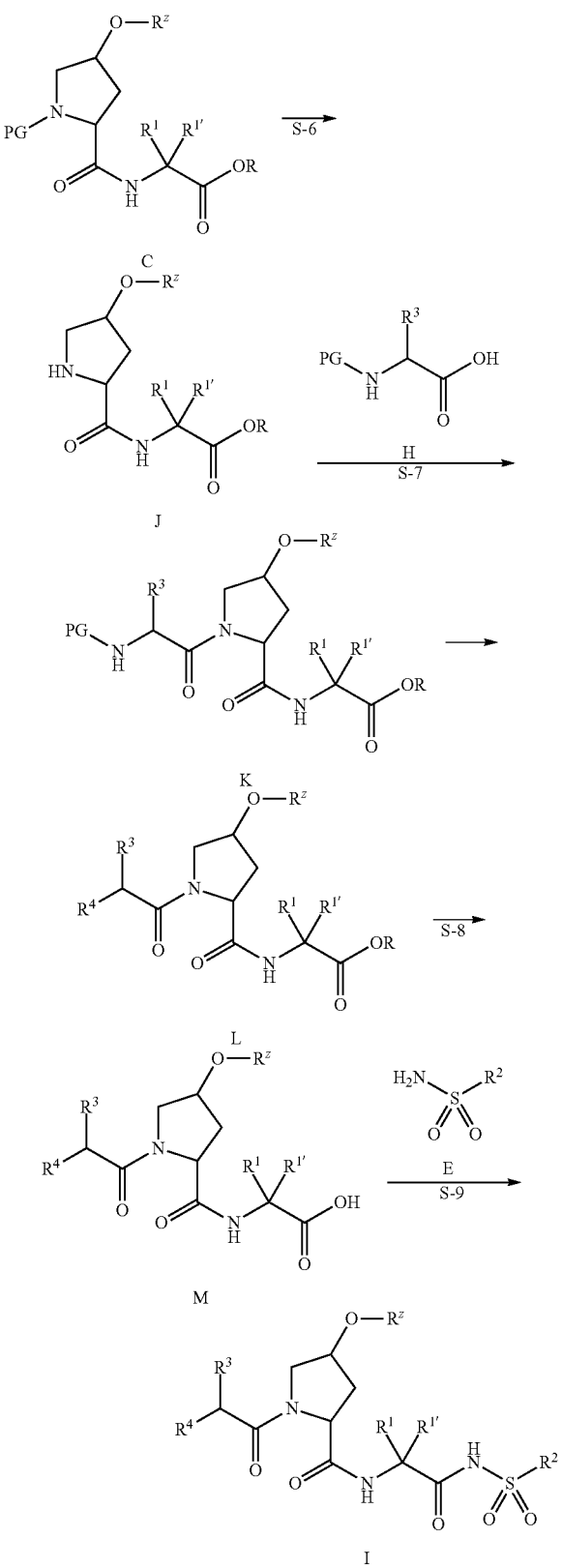

Scheme 2

In one aspect, the present invention provides methods for preparing compounds of formula I, according to the steps depicted in Scheme 1 above. At step S-6, removal of the Boc group from a dipeptide of formula C is achieved under acid-catalyzed conditions to give a dipeptide ester of formula J.

At step S-7, a dipeptide ester of formula J is condensed with a functionalized amino acid of formula H using suitable peptide coupling conditions to give a tripeptide ester of formula K which is further converted to a tripeptide ester of formula L in steps which are described as examples herein.

At step S-8, the ester group on a compound of formula L is hydrolyzed with a suitable base and subsequently neutralized to give a tripeptide of formula M. Suitable bases include, but are not limited to, alkaline metals, alkaline earth metal hydroxides, and combinations thereof. In some embodiments, the base is lithium hydroxide.

At step S-9, a tripeptide of formula M is condensed with a sulfonamide of formula E using suitable peptide coupling conditions to give compounds of formula I.

The PG group of formulae C, H, and K is a suitable amino protecting group as described above.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit HCV protease, or a mutant thereof, in a biological sample or in a patient. In certain embodiments, the amount of compound in compositions of this invention is such that is effective to measurably inhibit HCV protease, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of HCV protease, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of HCV protease activity and/or the activity of a mutant thereof. Thus, provided compounds are useful for treating non-A, non-B hepatitis, including hepatitis C.

HCV is an extremely variable virus that forms polymorphic swarms of variants within the host. Worldwide, six different genotypes have now been defined (Simmonds et al., Hepatology, Vol. 42, No. 4, 2005). These genotypes have been further classified into more closely related, genetically distinct subtypes. Comparative sequence portions, known as consensus sequences, are set forth in Table 3a, below. HCV genotypes and subtypes are distributed differently in different parts of the world, and certain genotypes predominate in certain areas. Genotypes 1-3 are widely distributed throughout the world. Subtype 1a is prevalent in North and South America, Europe, and Australia. Subtype 1b is common in North America and Europe, and is also found in parts of Asia. Genotype 2 is present in most developed countries, but is less common than genotype 1 (http://www.hcvadvocate.org/hepatitis/factsheets_pdf/genotype_FS.pdf). Other genotypes are prevalent in ex-US patient populations and are therefore important targets.

Notably, a cysteine located at amino acid position 159 in genotype 1b is conserved in all genotypes and subtypes of HCV NS3 sequenced to date, although the amino acid position may be different in other genotypes and subtypes. Targeting this cysteine residue with irreversible inhibitors should enable the development of agents which are effective against multiple HCV genotypes.

As described herein, the present invention provides irreversible inhibitors of one or more HCV protease genotypes, and variants thereof. Such compounds, comprising a warhead group designated as $R^3$, include those of formulae I, I-a, I-b, I-c-1, I-c-2, I-c-3, I-c-4, I-c-5, I-c-6, I-d, I-e, I-f, I-g, I-h, II-a, and II-b, as described herein. In some embodiments, $R^3$ is characterized in that the -L-Y moiety is capable of covalently binding to a cysteine residue thereby irreversibly inhibiting the enzyme. Without wishing to be bound by any particular theory, it is believed that such $R^3$ groups, i.e. warhead groups, are particularly suitable for covalently binding to a key cysteine residue in the binding domain of one or more HCV protease genotypes or variants thereof. In some embodiments, one or more genotypes inhibited by compounds of the present invention include 1a, 1b, 2a, and 3a. In certain embodiments, one or more such variants include A156T, A156S, D168V, D168A, and R155K.

One of ordinary skill in the art will appreciate that HCV protease genotypes and variants thereof have one or more cysteine residues near the binding domain. Without wishing to be bound by any particular theory, it is believed that proximity of a warhead group to the cysteine of interest facilitates covalent modification of that cysteine by the warhead group. In some embodiments, the cysteine residue of interest is Cys159 of HCV protease subtype 1b, or a variant thereof, where the provided residue numbering is in accordance with Uniprot (code Q91RS4). Cysteine residues of other HCV protease genotypes and subtypes suitable for covalent modification by irreversible inhibitors of the present invention include those summarized in Table 3a, below, where the bold and underlined "<u>C</u>" refers to a cysteine residue conserved at an equivalent position to Cys159 of HCV protease subtype 1b.

TABLE 3a

| HCV geno-type/sub-type | Representative Sequence Portion[a] | Patient ID | Sequence Identifier |
|---|---|---|---|
| 1a | GHAVGLFRAAV<u>C</u>TRGVAKAV | _.H77.NC_004102 | SEQ ID NO: 1 |
| 1a | GHAVGIFRAAV<u>C</u>TRGVAKAV | CH.BID-V271.EU482858 | SEQ ID NO: 2 |

TABLE 3a-continued

| HCV genotype/subtype | Representative Sequence Portion[a] | Patient ID | Sequence Identifier |
|---|---|---|---|
| 1a | GHAVGIFRAAVC TRGVAKAV | DE.BID-V25.EU482831 | SEQ ID NO: 3 |
| 1a | GHAVGLFRAAVC TRGVAKAV | US.H77-H21.AF011753 | SEQ ID NO: 4 |
| 1b | GHAVGIFRAAVC TRGVAKAV | AU.HCV-A.AJ000009 | SEQ ID NO: 5 |
| 1b | GHVVGIFRAAVC TRGVAKAV | CH.BID-V272.EU482859 | SEQ ID NO: 6 |
| 1b | GHAVGIFRAAVC TRGVAKAV | JP.HCV-BK.M58335 | SEQ ID NO: 7 |
| 1c | GHAVGIFRAAVC TRGVAKAV | ID.HC-G9.D14853 | SEQ ID NO: 8 |
| 1c | GHVAGIFRAAVC TRGVAKAV | IN.AY051292.AY051292 | SEQ ID NO: 9 |
| 2a | GHAVGIFRAAVC SRGVAKSI | JP.AY746460.AY746460 | SEQ ID NO: 10 |
| 2a | GHAVGIFRAAVC SRGVAKSI | JP.JCH-6.AB047645 | SEQ ID NO: 11 |
| 2a | GHAVGIFRAAVC SRGVAKSI | _.G2AK1.AF169003 | SEQ ID NO: 12 |
| 2b | GHAVGLFRAAVC ARGVAKSI | JP.HC-J8.D10988 | SEQ ID NO: 13 |
| 2b | GHAVGLFRAAVC ARGVAKSI | JP.MD2b1-2.AY232731 | SEQ ID NO: 14 |
| 2c | GHAVGIFRAAVC SRGVAKSI | _.BEBE1.D50409 | SEQ ID NO: 15 |
| 2i | AHAVGIFRAAVC SRGVAKSI | VN.D54.DQ155561 | SEQ ID NO: 16 |
| 2k | GHAVGIFRAAIC TRGAAKSI | MD.VAT96.AB031663 | SEQ ID NO: 17 |
| 3a | GHVAGIFRAAVC TRGVAKAL | CH.452.DQ437509 | SEQ ID NO: 18 |
| 3a | GHVAGIFRAAVC TRGVAKAL | DE.HCVCENS1.X76918 | SEQ ID NO: 19 |
| 3a | GHVAGIFRAAVC TRGVAKAL | ID.ps23.EU315121 | SEQ ID NO: 20 |
| 3b | GHVMGIFIAVVC TRGVAKAL | IN.RG416.DQ284965 | SEQ ID NO: 21 |
| 3b | GHVVGIFRAAVC TRGVAKAL | JP.HCV-Tr.D49374 | SEQ ID NO: 22 |
| 3k | GHVAGIFRAAVC TRGVAKAL | ID.JK049.D63821 | SEQ ID NO: 23 |
| 4a | GHAAGIFRAAVC TRGVAKAV | EG.Eg9.DQ988077 | SEQ ID NO: 24 |
| 4a | GHAAGLFRAAVC TRGVAKAV | _.01-09.DQ418782 | SEQ ID NO: 25 |
| 4a | GHAAGLFRAAVC TRGVAKAV | _.F753.DQ418787 | SEQ ID NO: 26 |
| 4d | GHAAGIFRAAVC TRGVAKAV | _.03-18.DQ418786 | SEQ ID NO: 27 |
| 4d | GHAAGIFRAAVC TRGVAKTV | _.24.DQ516083 | SEQ ID NO: 28 |
| 4f | GHAVGIFRAAVC TRGVAKAV | FR.IFBT84.EF589160 | SEQ ID NO: 29 |
| 4f | GHAVGIFRAAVC TRGVAKAV | FR.IFBT88.EF589161 | SEQ ID NO: 30 |
| 5a | GHVVGVFRAAVC TRGVAKAL | GB.EUH1480.Y13184 | SEQ ID NO: 31 |
| 5a | GHVVGVFRAAVC TRGVAKAL | ZA.SA13.AF064490 | SEQ ID NO: 32 |
| 6a | GHVVGLFRAAVC TRGVAKSL | HK.6a74.DQ480524 | SEQ ID NO: 33 |
| 6a | GHVVGLFRAAVC TRGVAKSL | HK.6a77.DQ480512 | SEQ ID NO: 34 |
| 6a | GHVVGLFRAAVCT TRGVAKSL | HK.EUHK2.Y12083 | SEQ ID NO: 35 |
| 6b | GHVVGLFRAAVC TRGVAKAL | _.Th580.NC_009827 | SEQ ID NO: 36 |
| 6c | GHVVGLFRAAVC TRGVAKAL | TH.Th846.EF424629 | SEQ ID NO: 37 |
| 6d | DHVVGLFRAAVC TRGVAKAL | VN.VN235.D84263 | SEQ ID NO: 38 |
| 6e | GHVVGLFRAAVC TRGVAKAI | CN.GX004.DQ314805 | SEQ ID NO: 39 |
| 6f | GHAVGIFRAAVC TRGVAKAI | TH.C-0044.DQ835760 | SEQ ID NO: 40 |
| 6f | GHAVGIFRAAVC TRGVAKAI | TH.C-0046.DQ835764 | SEQ ID NO: 41 |
| 6g | GHVVGLFRAAVC TRGVAKAL | HK.HK6554.DQ314806 | SEQ ID NO: 42 |
| 6g | GHVVGLFRAAVC TRGVAKAL | IDJK046.D63822 | SEQ ID NO: 43 |
| 6h | GHVAGIFRAAVC TRGVAKSL | VN.VN004.D84265 | SEQ ID NO: 44 |
| 6i | GHVAGIFRAAVC TRGVAKSL | TH.C-0159.DQ835762 | SEQ ID NO: 45 |
| 6j | GHVAGIFRAAVC TRGVAKSL | TH.C-0667.DQ835761 | SEQ ID NO: 46 |
| 6j | GHVAGIFRAAVC TRGVAKSL | TH.Th553.DQ835769 | SEQ ID NO: 47 |
| 6k | GHVAGIFRAAVC TRGVAKSL | CN.KM41.DQ278893 | SEQ ID NO: 48 |
| 6k | GHVAGIFRAAVC TRGVAKSL | CN.KM45.DQ278891 | SEQ ID NO: 49 |
| 6k | GHVAGIFRAAVC TRGVAKSL | VN.VN405.D84264 | SEQ ID NO: 50 |

TABLE 3a-continued

| HCV geno-type/ sub-type | Representa-tive Sequence Portion[a] | Patient ID | Sequence Identifier |
|---|---|---|---|
| 6l | GHVAGIFRAAVC TRGVAKSL | US.537796.EF424628 | SEQ ID NO: 51 |
| 6m | GHAVGVFRAAVC TRGVAKSL | TH.C-0185.DQ835765 | SEQ ID NO: 52 |
| 6m | GHAVGVFRAAVC TRGVAKSL | TH.C-0208.DQ835763 | SEQ ID NO: 53 |
| 6n | GHVVGIFRAAVC TRGVAKSL | CN.KM42.DQ278894 | SEQ ID NO: 54 |
| 6n | GHVVGIFRAAVC TRGVAKSL | TH.D86/93.DQ835768 | SEQ ID NO: 55 |
| 6o | GHAVGLFRAAVC TRGVAKAI | CA.QC227.EF424627 | SEQ ID NO: 56 |
| 6p | GHVVGLFRAAVC TRGVAKAI | CA.QC216.EF424626 | SEQ ID NO: 57 |
| 6q | GHAVGLFRAAVC TRGVAKAI | CA.QC99.EF424625 | SEQ ID NO: 58 |
| 6t | GHVVGLFRAAVC TRGVAKAI | VN.TV241.EF632069 | SEQ ID NO: 59 |
| 6t | GHVVGLFRAAVC TRGVAKAI | VN.TV249.EF632070 | SEQ ID NO: 60 |
| 6t | GHVVGLFRAAVC TRGVAKAI | VN.VT21.EF632071 | SEQ ID NO: 61 |
| 7a | SHCVGIFRAAVC TRGVAKAV | CA.QC69.EF108306 | SEQ ID NO: 62 |

[a]It will be appreciated by one of ordinary skill in the art that every virus is prone to mutation and subject to polymorphisms, and any genotype consensus sequences described herein are representative of a given genotype or subtype. Such representative consensus sequences are available at http://hcv.lanl-.gov/content/sequence/NEWALIGN/align.html.

Drug resistance is emerging as a significant challenge for targeted therapies. For example, drug resistance has been reported for HCV protease inhibitors in development. Such compounds include BILN 2061 and VX-950, developed by Boehringer Ingelheim and Vertex Pharmaceuticals, respectively. The structures of BILN 2061 and VX-950 are depicted below.

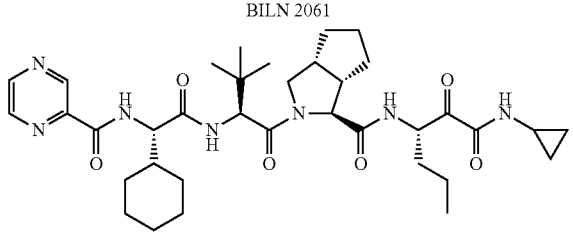

In fact, a recent article published by Vertex Pharmaceuticals, entitled, "In Vitro Resistance Studies of Hepatitis C Virus Serine Protease," squarely addresses the problem of mutant resistance observed with VX-950 and BILN 2061. See Lin et al., The Journal of Biological Chemistry, Vol. 279, No. 17, Issue of April 23, pp. 17508-17514, 2004. This article concludes that "future hepatitis C therapy involving small molecule inhibitors of HCV enzymes might require multidrug combination, as in the case of the current HIV treatments." See page 17513, last paragraph.

Resistance to specific antiviral drugs is a major factor limiting the efficacy of therapies against many retroviruses or RNA viruses. The error-prone nature of these viruses allows for the development of mutations that afford resistance to currently available drugs or drugs undergoing clinical testing. The resistance problem is a critical hurdle faced in drug development of new HCV-specific inhibitors to treat HCV patients.

A recent in vitro resistance study using two HCV NS3·4A protease inhibitors, VX-950 and BILN 2061, found that resistance mutations selected against either inhibitor resulted in a significant reduction in susceptibility to the inhibitor itself. However, the primary resistance mutations against BILN 2061 were fully susceptible to VX-950, and the major resistance mutation against VX-950 remained sensitive to BILN 2061 (Lin et al., Jour. Biol. Chem. 279(17): 17508-14, 2004).

It has been surprisingly found that provided compounds inhibit at least five HCV protease mutants, including A156T, A156S, D168V, and D168A and R155K. This stands in contrast to other known HCV protease inhibitors (e.g., VX-950 and BILN 2061) which inhibit only two mutants each. In fact, no drug described in the prior art has been shown to be an effective inhibitor of all known HCV protease mutants. For example, and as set forth in Tables 4a and 4b below, where the BILN 2061 and VX-950 data are as reported by Lin et al. and elsewhere in the HCV literature, and the data for compound I-3 was obtained according to methods set forth in the Examples, infra. Without wishing to be bound by any particular theory, it is believed that compounds of the present invention may be effective inhibitors of drug resistant forms of HCV protease. While Table 4b shows compound I-3 activity against four reference HCV variants (A156T, A156S, D168V, and D168A), the ensuing examples will describe other provided compounds of the invention that are active against these variants as well as a fifth (R155K) variant.

TABLE 4a

Comparative $K_i$ Values (nM)[a]

|  | BILN 2061 | VX-950 |
|---|---|---|
| WT | 19 | 100 |
| A156T | >1200 | 9900 |
| A156S | 112 | 2900 |
| D168V | >1200 | 43 |
| D168A | >1200 | 150 |

[a]Wild-type data were obtained from cell-based assays, and mutant data were obtained from biochemical assays. See Lin et al. and protocols described herein.

TABLE 4b

Comparative $IC_{50}$ Values (nM)[a]

|  | BILN 2061 | VX-950 | Compound I-1 |
|---|---|---|---|
| WT | 4 | 402 | 0.66 |
| A156T | — | — | 3 |
| A156S | 7 | 4650 | 2 |
| D168V | 5090 | 163 | 2 |
| D168A | 1860 | 193 | 8 |

[a]Wild-type data were obtained from cell-based assays, and mutant data were obtained from biochemical assays. See Lin et al. and protocols described herein.

Without wishing to be bound by any particular theory, it is believed that a compound of formula I is more effective at inhibiting HCV protease, or a mutant thereof, as compared to a corresponding compound of formula I wherein the $R^3$ moiety of formula I is instead a non-warhead group, such as straight alkyl (e.g., unsubstituted alkyl), branched alkyl, cycloalkyl, or alkenyl. For example, a compound of formula I can be more effective at inhibition of HCV protease, or a mutant thereof, as compared to a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

A compound of formula I, as disclosed above, can be more potent with respect to an $IC_{50}$ against HCV protease, or a mutant such as A156T, A156S, D168V, D168A, or other mutants such as those disclosed herein, than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. Such comparative potency of a compound of formula I as compared to a corresponding compound of formula I wherein the $R^3$ moiety of formula I is instead a non-warhead moiety, can be determined by standard time-dependent assay methods, such as those described in detail in the Examples section, infra. In certain embodiments, a compound of formula I is measurably more potent than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. In some embodiments, a compound of formula I is measurably more potent, wherein such potency is observed after about 1 minute, about 2 minutes, about 5 minutes, about 10 minutes, about 20 minutes, about 30 minutes, about 1 hour, about 2 hours, about 3 hours, about 4 hours, about 8 hours, about 12 hours, about 16 hours, about 24 hours, or about 48 hours, than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. In some embodiments, a compound of formula I is any of about 1.5 times, about 2 times, about 5 times, about 10 times, about 20 times, about 25 times, about 50 times, about 100 times, or even about 1000 times more potent than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

As used herein, the term "clinical drug resistance" refers to the loss of susceptibility of a drug target to drug treatment as a consequence of mutations in the drug target As used herein, the term "resistance" refers to changes in the wild-type nucleic acid sequence coding a target protein, and/or the protein sequence of the target, which changes decrease or abolish the inhibitory effect of the inhibitor on the target protein.

Examples of proteases that are inhibited by the compounds and compositions described herein and against which the methods described herein are useful include NS3, NS3·4A, or a mutant thereof.

The activity of a compound utilized in this invention as an inhibitor of NS3, NS3·4A, or a mutant thereof, may be assayed in vitro, in vivo or in a cell line. In vitro assays include assays that determine inhibition of either the serine protease activity and/or the subsequent functional consequences, or ATPase activity of activated NS3, NS3·4A, or a mutant thereof. Alternate in vitro assays quantitate the ability of the inhibitor to bind to NS3 or NS3·4A. Inhibitor binding may be measured by radiolabelling the inhibitor prior to binding, isolating the inhibitor/NS3 or inhibitor/NS3·4A complex and determining the amount of radiolabel bound. Alternatively, inhibitor binding may be determined by running a competition experiment where new inhibitors are incubated with NS3 or NS3·4A bound to known radioligands. Detailed conditions for assaying a compound utilized in this invention as an inhibitor of NS3 or NS3·4A, or a mutant thereof, are set forth in the Examples below.

Serine proteases are a large family of proteolytic enzymes that cleave peptide bonds in proteins. The serine protease family includes the digestive enzymes chymotrypsin, trypsin, and elastase, and proteases involved in blood clotting. Serine proteases possess a characteristic "catalytic triad" comprising serine, aspartic acid, and histidine, that together function to activate serine to form a covalent bond with the enzyme substrate, thereby hydrolyzing a peptide bond. In addition to those stated above, serine proteases participate in a variety of functions including immunity and inflammation.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms.

For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a provided composition is administered to a patient in need thereof once daily. Without wishing to be bound by any particular theory, it is believed that prolonged duration of action of an irreversible inhibitor of HCV NS3 protease is particularly advantageous for once daily administration to a patient in need thereof for the treatment of a disorder associated with HCV NS3 protease. In certain embodiments, a provided composition is administered to a patient in need thereof at least once daily. In other embodiments, a provided composition is administered to a patient in need thereof twice daily, three times daily, or four times daily.

Compounds of formula I, for example, generally provide prolonged duration of action when administered to a patient as compared to a corresponding compound of formula I wherein the $R^3$ moiety of formula I is instead a non-warhead moiety such as straight alkyl (e.g., unsubstituted alkyl), branched alkyl, cycloalkyl, or alkenyl. For example, a compound of formula I can provide prolonged duration of action when administered to a patient as compared to a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting serine protease activity in a biological sample comprising the step of contacting said biological sample with a compound of this invention, or a composition comprising said compound.

According to another embodiment, the invention relates to a method of inhibiting HCV protease, or a mutant thereof, activity in a biological sample comprising the step of contacting said biological sample with a compound of this invention, or a composition comprising said compound. In certain embodiments, the invention relates to a method of irreversibly inhibiting HCV protease, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of HCV protease, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting HCV protease, or a mutant thereof, activity in a patient comprising the step of administering to said patient a compound of the present invention, or a composition comprising said compound.

According to another embodiment, the invention relates to a method of inhibiting HCV protease, or a mutant thereof, activity in a patient comprising the step of administering to said patient a compound of the present invention, or a composition comprising said compound. According to certain embodiments, the invention relates to a method of irreversibly inhibiting HCV protease, or a mutant thereof, activity in a patient comprising the step of administering to said patient a compound of the present invention, or a composition comprising said compound. In other embodiments, the present invention provides a method for treating a disorder mediated by HCV protease, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of HCV protease, or a variant thereof. In some embodiments, a provided compound, or composition thereof, is administered in combination with another antiviral agent. Such antiviral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors, e.g. BILN 2061 and VX-950); inhibitors of other targets in the HCV life cycle, including helicase and polymerase inhibitors; inhibitors of internal ribosome entry; broad-spectrum viral inhibitors, such as IMPDH inhibitors (e.g., mycophenolic acid and derivatives thereof); or combinations of any of the above.

In certain embodiments, a combination of 2 or more antiviral agents may be administered. In certain embodiments, a combination of 3 or more antiviral agents may be administered. In some embodiments, the antiviral agents are selected from ribavirin or interferon. In other embodiments, the antiviral agent is α-interferon.

Other examples of agents the inhibitors of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples, below, correspond to compound numbers set forth in Table 3, supra.

Example 1

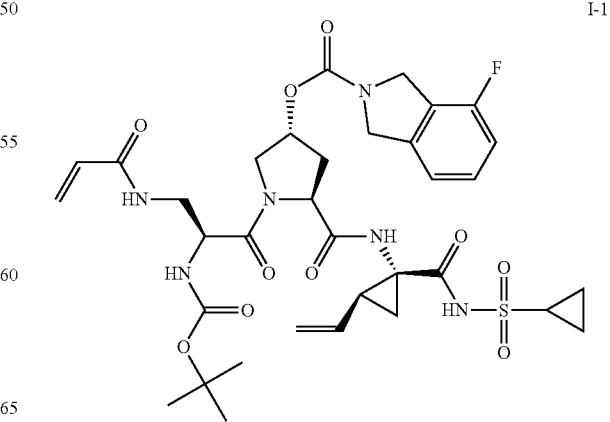

I-1

The title compound was prepared according to the steps and intermediates as described below.

Step 1a: Intermediate 1a

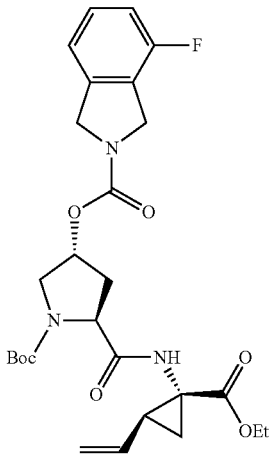 [SMILES: C=C[C@@H]1C[C@]1(NC(=O)[C@@H]1C[C@@H](OC(=O)N2Cc3cccc(F)c3C2)CN1C(=O)OC(C)(C)C)C(=O)OCC]

To a solution of (1R,2S)-1-amino-2-vinylcyclopropane carboxylic acid ethyl ester toluenesulfonic acid (0.33 g, 1.0 mmol) and (2S,4R)-1-(tert-butoxycarbonyl)-4-(4-fluoroisoindoline-2-carbonyloxy)pyrrolidine-2-carboxylic acid (0.4 g, 1.0 mmol) in 10 mL of acetonitrile was added HATU (0.44 g, 1.2 mmol) and then DIEA (0.46 mL, 2.5 mmol) under stirring. The mixture was stirred at r.t. for two hours. After the complete consumption of starting materials, the reaction mixture was evaporated. The residue was dissolved in 30 mL ethyl acetate and washed with water and brine twice and dried over Na$_2$SO$_4$. After removal of solvent, the crude product was subject to chromatography on silica gel (hexane:EtOAc=1:1). 0.35 g of the title compound was obtained: MS m/z: 532.0 (M+H+).

Step 1b: Intermediate 1b

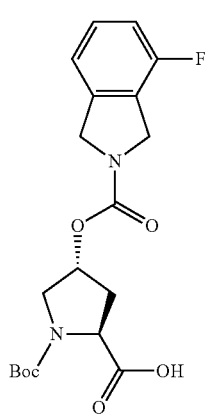 [SMILES: CC(C)(C)OC(=O)N1C[C@H](OC(=O)N2Cc3cccc(F)c3C2)C[C@H]1C(=O)O]

To a solution of the product of step 1a (0.35 g, 0.66 mmol) in 5 mL of THF/MeOH (1:1) was added 1N LiOH aqueous solution (2 mL, 2.0 mmol). After stirring at r.t. for 10 hours, the reaction mixture was neutralized with 1.0 N HCl. The organic solvents were evaporated under vacuum, and the remaining aqueous phase was acidified to pH ~3 using 1.0 N HCl and was extracted with EtOAc. The organic layer was washed with brine, and was dried over anhydrous magnesium sulfate. After removal of solvent, 0.3 g of the title compound was obtained: MS m/z: 526.2 (M+H$^+$).

Step 1: Intermediate 1c

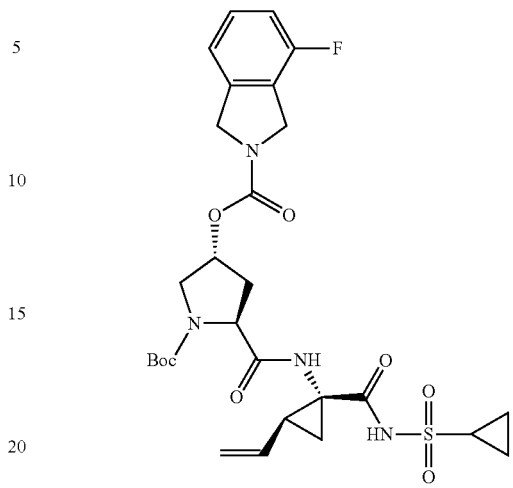

To a solution of the product of step1b (0.30 g, 0.6 mmol) in 10 mL of DCM was added CDI (0.16 g, 1.0 mmol) and the resulting solution was stirred at 40° C. for 1 hour. cyclopropylsulfonamide (0.18 g, 1.5 mmol) and DBU (0.16 g, 1.0 mmol) were added to the reaction mixture. The mixture was stirred at 40° C. for additional 10 hours. The solvent was then removed and the residue was diluted with EtOAc and was washed with aqueous NaOAc buffer (pH~5, 2×10 mL), NaHCO$_3$ solution and brine. After drying over Na$_2$SO$_4$ and removal of solvent, the residue was subjected to chromatography on silica gel using hexane/EtOAc (1:1~1:2). A total of 0.30 g of the title compound was obtained: R$_f$ 0.1 (EtOAc:hexane=1:1), MS m/z: 605.0 (M−1).

Step 1: Intermediate 1d

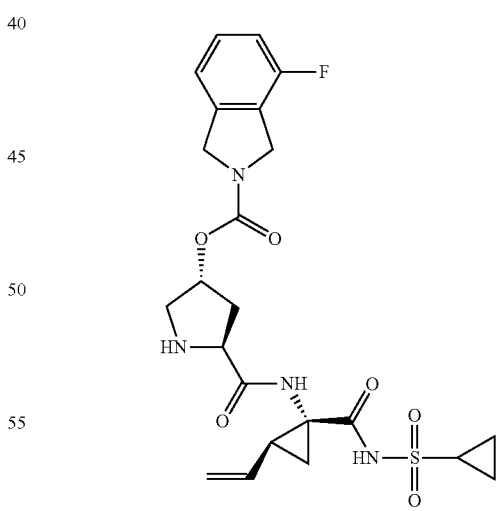

The product from step 1c (0.25 g, 0.41 mmol) was dissolved in 4 N HCl in dioxane. The mixture was stirred at r.t. for 1 hour. After removal of solvents, a 10-mL portion of DCM was poured in followed by evaporation to dryness. This process of DCM addition followed by evaporation was repeated four times to give a residue solid which was used directly for the next step: MS m/z: 507.0 (M+H$^+$).

Step 1e: Intermediate 1e

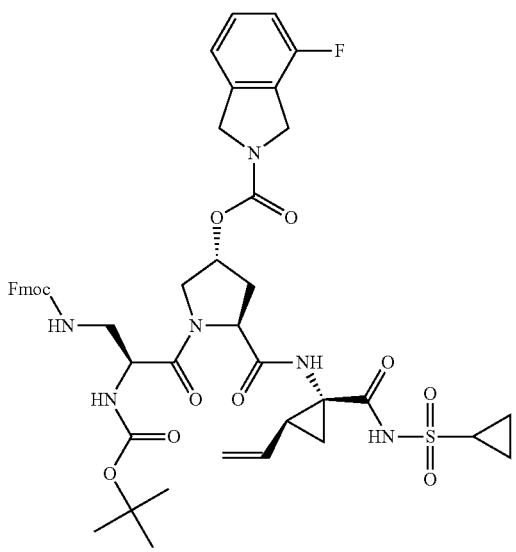

To a solution of the product of step 1d (0.16 g, 0.28 mmol) and N-Boc-3-(Fmoc)amino-L-alanine (0.15 g, 0.35 mmol) in 5.0 mL of DMF was added HATU (125 mg, 0.33 mmol) and DIEA (130 mg, 1.0 mmol) at r.t. under stirring. TLC analysis indicated completion of the coupling reaction had occurred after one hour. A 20-mL portion of EtOAc was poured in and the mixture was washed with a buffer (pH~4, AcONa/AcOH), NaHCO₃ and brine, and was dried over MgSO₄. After removal of solvent, the crude oil product was subject to chromatography on silica gel (eluents: EtOAc/hexane). A total of 0.14 g of the title compound was obtained.

Step 1f: Intermediate 1f

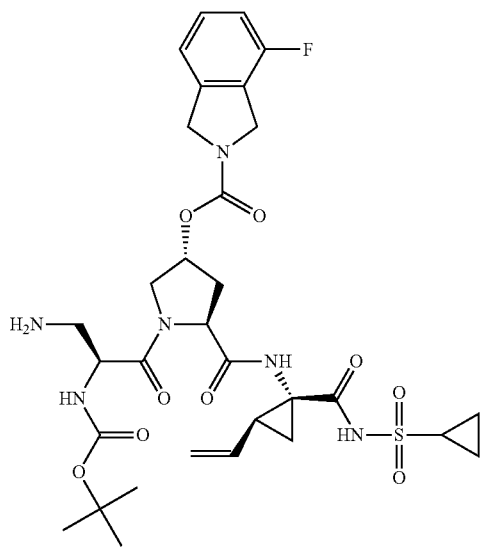 [SMILES: C=C[C@@H]1C[C@]1(NC(=O)[C@@H]1C[C@@H](OC(=O)N2Cc3cccc(F)c3C2)CN1C(=O)[C@H](CN)NC(=O)OC(C)(C)C)C(=O)NS(=O)(=O)C1CC1]

A solution of 0.10 g of the product of step 1e in 1 mL of DMF with 12% piperidine was stirred for 1.5 hours at r.t. and then was evaporated to dryness under high vacuum. The residue was triturated with hexane/ether (4:1) to yield 70 mg of the title compound.

Step 1g: Compound (I-1)

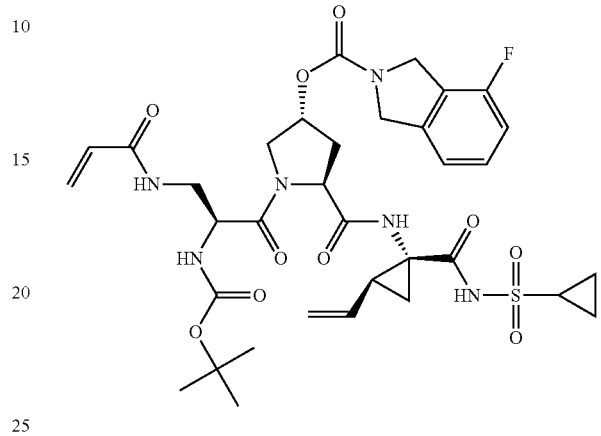

(3R,5S)-1-((S)-3-acrylamido-2-(tert-butoxycarbonylamino)propanoyl)-5-(((1R,2S)-1-(cyclopropylsulfonylcarbamoyl)-2-vinylcyclopropylcarbamoyl)pyrrolidin-3-yl 4-fluoroisoindoline-2-carboxylate: Acryloyl chloride (10 uL, 0.12 mmol) was added dropwise at 0° C. to a stirred solution of 55 mg (0.08 mmol) of the product from step 1f in 3 mL of DCM containing 3 equiv. of triethylamine. The reaction mixture was stirred at r.t. for 1.5 hrs and then was diluted with 10 mL of DCM. The resulting solution was washed twice with brine and was dried over magnesium sulfate. Removal of solvent afforded the crude product, which was purified by chromatography on silica gel eluting first with hexane/EtOAc (1:3~1:5) and then with DCM-methanol (50:1~25:1)). A total of 27 mg of the title compound was obtained: R$_f$ 0.4 (EA:MeOH=10:1); MS m/z: 746.9 (M+H⁺).

In similar fashion using the product of Intermediate 1f the following compounds were prepared:

I-2

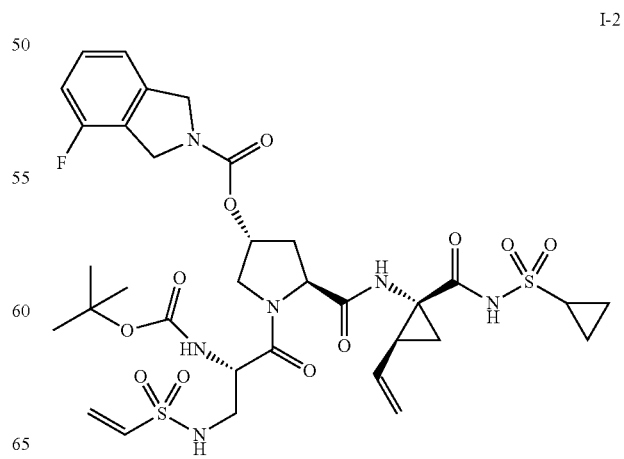

(3R,5S)-1-((S)-2-(tert-butoxycarbonylamino)-3-(vinylsulfonamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate Rf: 0.50 (EtOAc/MeOH 10:1); MS m/z: 805.3 (M+H$^+$).

(3R,5S)-1-((S)-2-(tert-butoxycarbonylamino)-3-((E)-4-(dimethylamino)but-2-enamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.35 (DCM/MeOH 9:1); MS m/z: 804.3 (M+H$^+$).

In similar fashion using the product of Intermediate 1d and (S)-4-(Fmocamino)-2-(tert-butoxycarbonylamino)butanoic acid, the following compound was prepared:

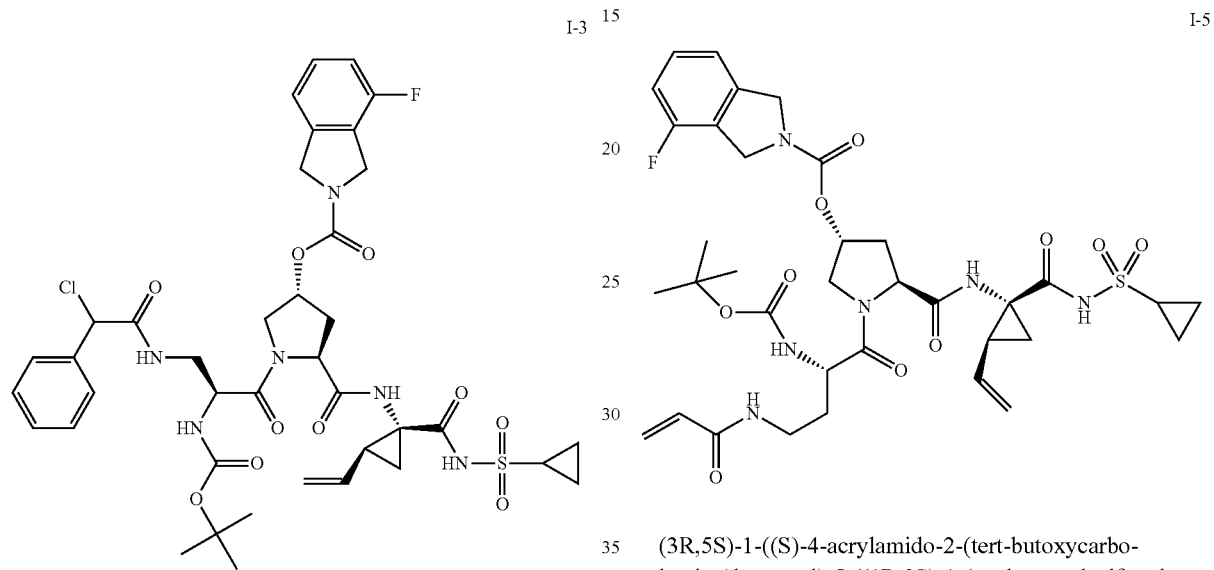

(3R,5S)-1-((2S)-2-(tert-butoxycarbonylamino)-3-(2-chloro-2-phenylacetamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.50 (DCM/MeOH 95:5); MS m/z: 845.2 (M+H$^+$).

(3R,5S)-1-((S)-4-acrylamido-2-(tert-butoxycarbonylamino)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.40 (EtOAc/MeOH 10:1); MS m/z: 761.3 (M+H$^+$).

Example 2

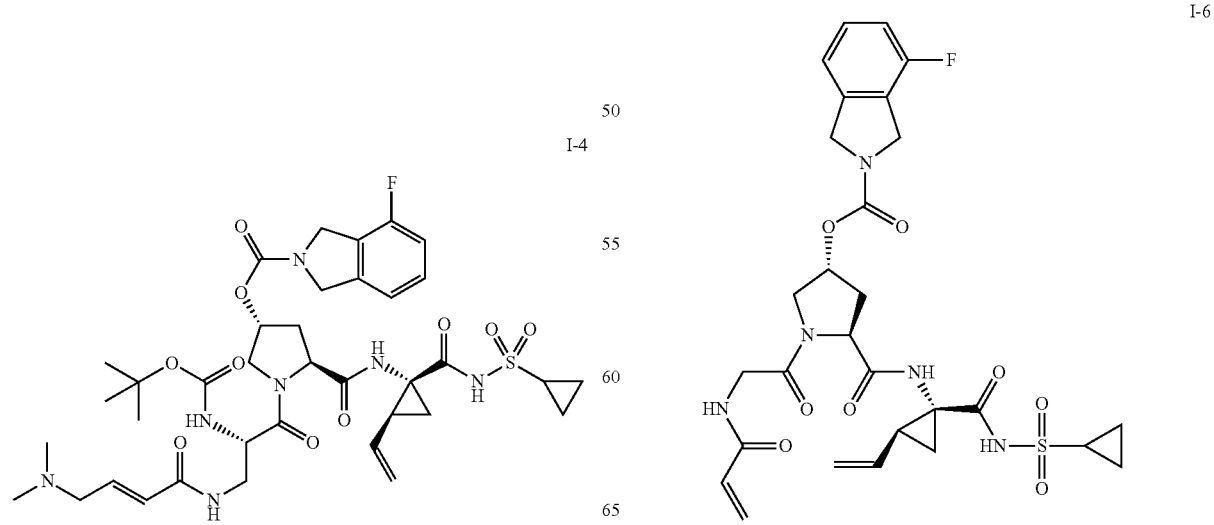

The title compound was prepared according to the steps and intermediates as described below.

Step 2a: Intermediate 2a

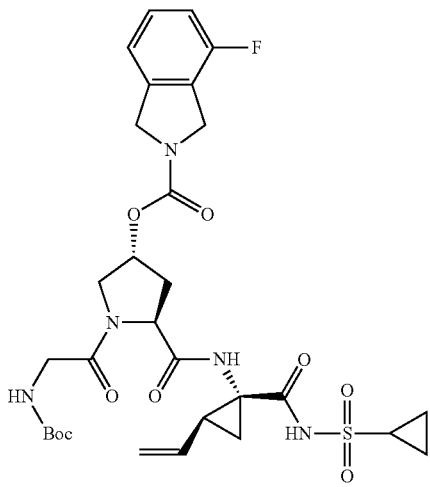 [SMILES: C=C[C@@H]1C[C@]1(NC(=O)[C@@H]1C[C@@H](OC(=O)N2Cc3cccc(F)c3C2)CN1C(=O)CNC(=O)OC(C)(C)C)C(=O)NS(=O)(=O)C1CC1]

To a solution of the product of step 1d from Example 1 (0.12 g, 0.22 mmol) and N-Boc-glycine (0.054 g, 0.31 mmol) in 4.0 mL of acetonitrile was added HATU (133 mg, 0.35 mmol) and DIEA (0.12 mL, 0.66 mmol) at r.t. under stirring. The reaction mixture was stirred for 2 h. LC-MS and TLC analysis indicated completion of the coupling reaction. A 20-mL of EtOAc was poured in and the mixture was washed with a buffer (pH~4, AcONa/AcOH), NaHCO$_3$ and brine, and was dried over Na$_2$SO$_4$. After removal of solvent, the crude product was subject to chromatography on silica gel (eluents: EtOAc/hexane). A total of 0.10 g of the title compound was obtained: R$_f$ 0.2 (EtOAc); MS m/z: 664.0 (M+H$^+$).

Step 2b: Intermediate 2b

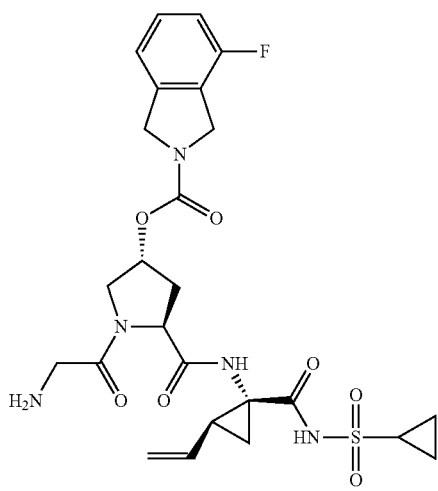 [SMILES: C=C[C@@H]1C[C@]1(NC(=O)[C@@H]1C[C@@H](OC(=O)N2Cc3cccc(F)c3C2)CN1C(=O)CN)C(=O)NS(=O)(=O)C1CC1]

The product from step 2a (0.10 g, 0.15 mmol) was dissolved in 2 mL of 4 N HCl in dixoxane and the reaction was stirred for 1 hour at RT. After removal of solvents, a 3-mL portion of DCM was poured in followed by evaporation to dryness. This process of DCM addition followed by evaporation was repeated three times to give the title compound Intermediate 2b as its HCl salt (0.10 g). MS m/z: 564.0 (M+H$^+$).

Step 2c

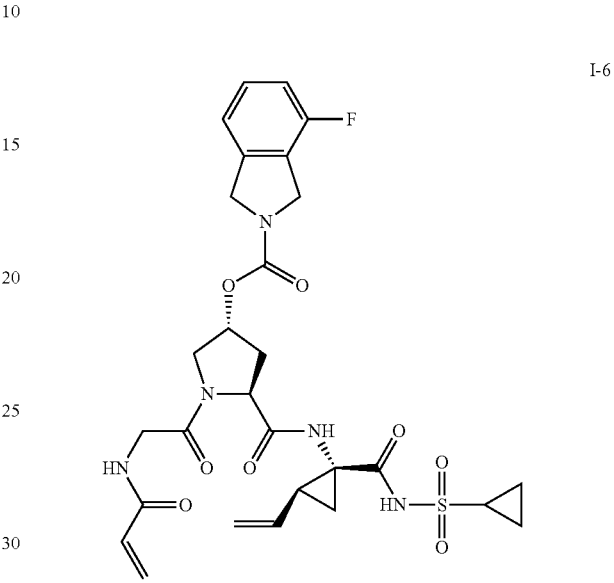

I-6

(3R,5S)-1-(2-acrylamidoacetyl)-5-((1R,2S)-1-(cyclopropylsulfonylcarbamoyl)-2-vinylcyclopropylcarbamoyl)pyrrolidin-3-yl 4-fluoroisoindoline-2-carboxylate: The title compound was made by coupling Intermediate 2b and acrylic acid using HATU following the coupling reactions described for Intermediate 2a. A total of 50 mg of the title compound was obtained: R$_f$ 0.1 (EtOAc); MS m/z: 617.9 (M+H$^+$).

Following the procedures described in Example 2, the following compounds were made similarly:

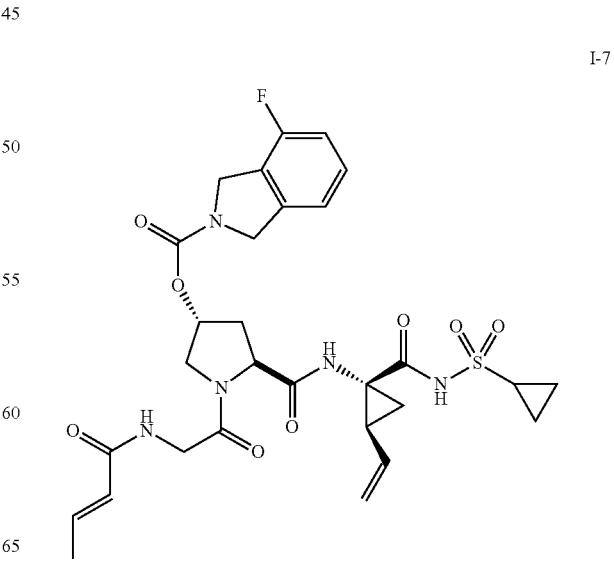

I-7

(3R,5S)-1-(2-(E)-but-2-enamidoacetyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 632.0 (M+H⁺).

I-8

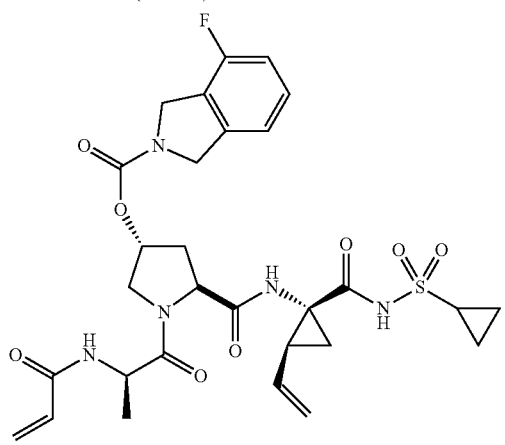

(3R,5S)-1-((R)-2-acrylamidopropanoyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 632.1 (M+H⁺).

I-9

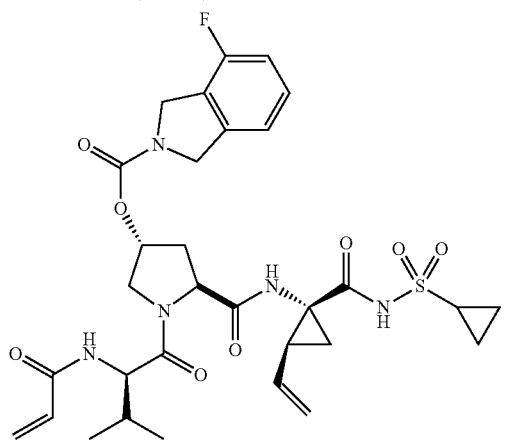

(3R,5S)-1-((R)-2-acrylamido-3-methylbutanoyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 660.2 (M+H⁺).

I-10

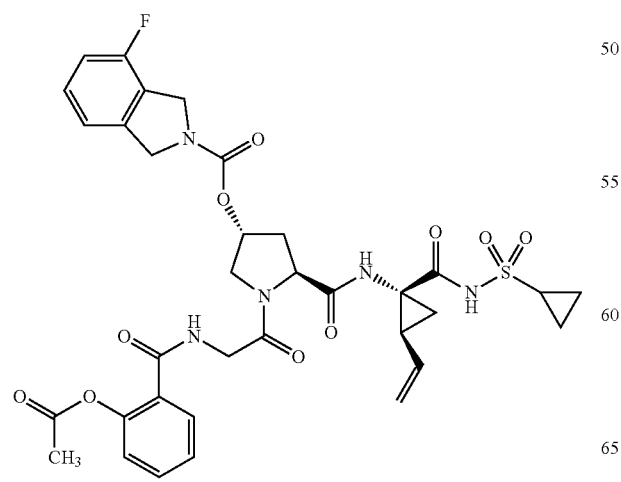

(3R,5S)-1-(2-(2-acetoxybenzamido)acetyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 724.0 (M+H⁺).

I-49

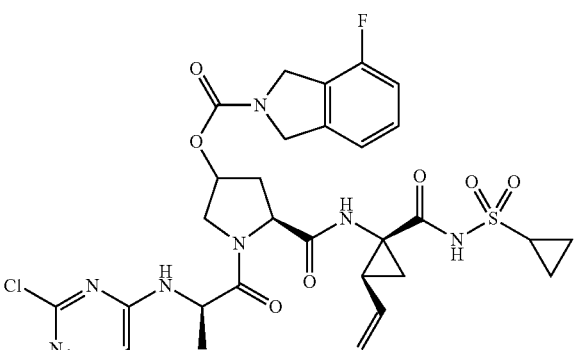

(5S)-1-((R)-2-(2-chloropyrimidin-4-ylamino)propanoyl)-5-((1R,2S)-1-(cyclopropylsulfonylcarbamoyl)-2-vinylcyclopropylcarbamoyl)pyrrolidin-3-yl-4-fluoroisoindoline-2-carboxylate: Rf: 0.35 (DCM/MeOH 95:5), MS m/z: 690.3 (M+H⁺).

Following the procedures described in Example 2, the following compounds were made similarly:

I-46

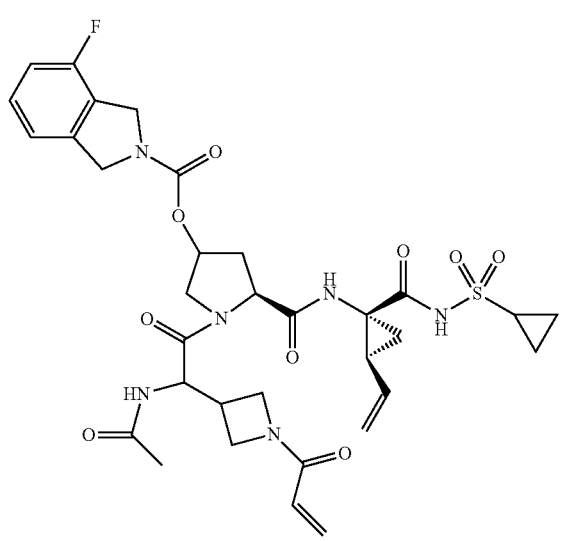

(5S)-1-(2-acetamido-2-(1-acryloylazetidin-3-yl)acetyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 715.2 (M+H+).

I-51

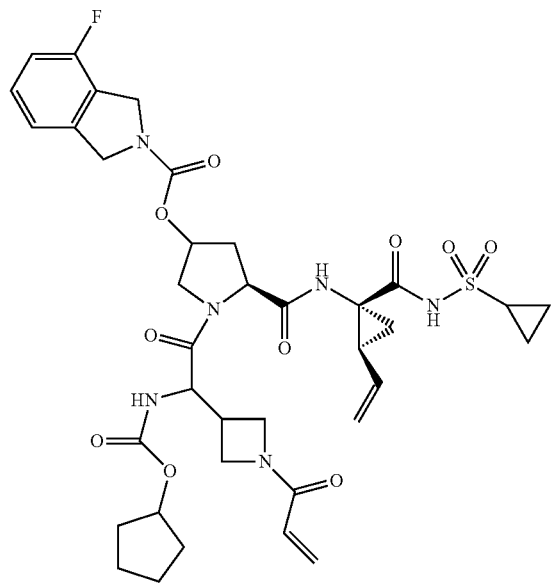

(5S)-1-(2-(1-acryloylazetidin-3-yl)-2-(cyclopentyloxycarbonylamino)acetyl)-5-((1R,2S)-1-(cyclopropylsulfonylcarbamoyl)-2-vinylcyclopropylcarbamoyl)pyrrolidin-3-yl-4-fluoroisoindoline-2-carboxylate: MS m/z: 785.2 (M+H+).

Example 3

I-11

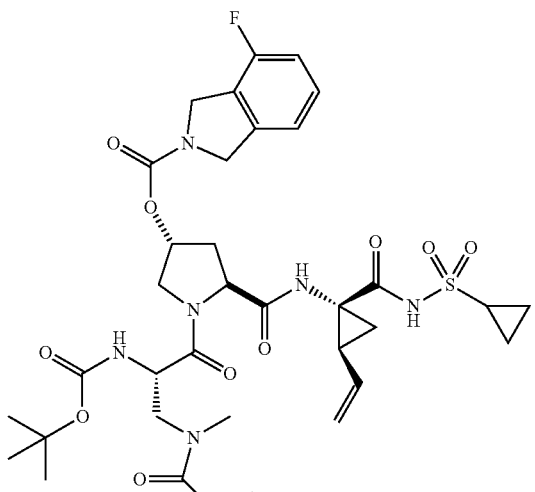

The title compound was prepared according to the steps and intermediates as described below.

Step 3a: Intermediate 3a

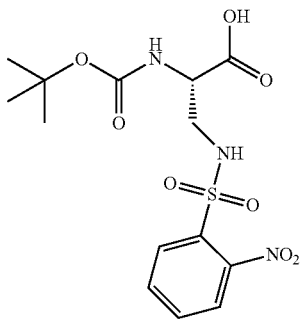 [SMILES: CC(C)(C)OC(=O)N[C@@H](CNS(=O)(=O)c1ccccc1[N+](=O)[O-])C(=O)O]

To a solution of (S)-3-amino-2-(tert-butoxycarbonylamino)propanoic acid (2.04 g, 10 mmol), TEA (4.5 mL, 30 mmol) in 50 mL CH$_2$Cl$_2$ was added nitrobenzenesulfonyl chloride (2.9 g, 13.0 mmol) at RT. The mixture was stirred for 10 hours at RT. The solvent was removed under vacuum followed by the addition of 100 mL EtOAc. The organic layer was washed with 1 N HCl (to pH 3), water and brine. The organic layer was dried over Na$_2$SO$_4$, filtered and the solvent was removed to afford the crude Intermediate 3a (4.0 g).

Step 3b: Intermediate 3b

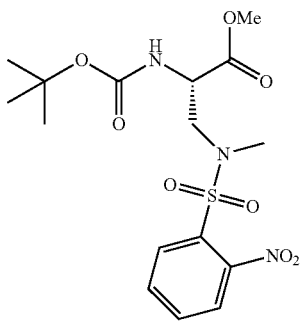 [SMILES: COC(=O)[C@H](CN(C)S(=O)(=O)c1ccccc1[N+](=O)[O-])NC(=O)OC(C)(C)C]

The crude Intermediate 3a (2.0 g), K$_2$CO$_3$ (1.5, 4 equiv.) were dissolved in 10 mL DMF. MeI (0.8 mL, 4 eqiv.) was added to the reaction at RT. The resulting mixture was stirred for 20 hours. The DMF was mostly removed under vacuum and 100 mL EtOAc was added and the mixture was washed with water and brine. The organic layer was dried over Na$_2$SO$_4$. After removal of solvent, the crude product was subject to a short silica gel column (eluents: EtOAc/hexane) to produce 1.62 g of the Intermediate 3b. MS m/z: 439.9 (M+Na$^+$).

Step 3c: Intermediate 3c

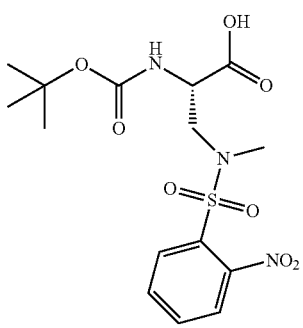 [SMILES: CN(C[C@H](NC(=O)OC(C)(C)C)C(=O)O)S(=O)(=O)c1ccccc1[N+](=O)[O-]]

To a solution of Intermediate 3b (1.6 g, 3.8 mmol) in 10 mL of THF/MeOH (1:1) was added 1 N LiOH aqueous solution (5.8 mL, 5.8 mmol). After stirring at r.t. for 10 hours, the reaction mixture was neutralized with 1.0 N HCl. The organic solvent was evaporated under vacuum, and the remaining aqueous phase was acidified to pH-3 using 1.0 N HCl and was extracted with EtOAc. The organic layer was washed with brine, and was dried over anhydrous sodium sulfate. After removal of solvent, 1.5 g of Intermediate 3c was obtained. MS m/z: 402.0 (M-1, negative mode).

Step 3d: Intermediate 3d

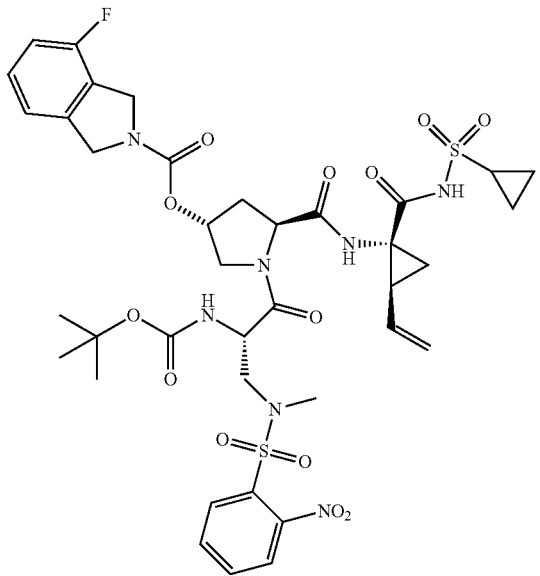

To a solution of Intermediate 1d (0.12 g, 0.20 mmol) and Intermediate 3c (0.12 g, 0.3 mmol) in 5.0 mL of anhydrous acetonitrile was added HATU (0.11 g, 0.3 mmol) and DIEA (0.14 mL, 0.9 mmol) at r.t. under stirring. TLC analysis and LC-MS indicated completion of the coupling reaction after one hour. A 20-mL portion of EtOAc was poured in and the mixture was washed with a buffer (pH-4, AcONa/AcOH), NaHCO$_3$ and brine. The organic layer was dried over Na$_2$SO$_4$. After removal of solvent, the crude product was subject to chromatography on silica gel (eluents: EtOAc/hexane). A total of 0.10 g of Intermediate 3d was obtained: R$_f$ 0.1 (EtOAc); MS m/z: 891.8 (M+H$^+$).

Step 3e: Intermediate 3e

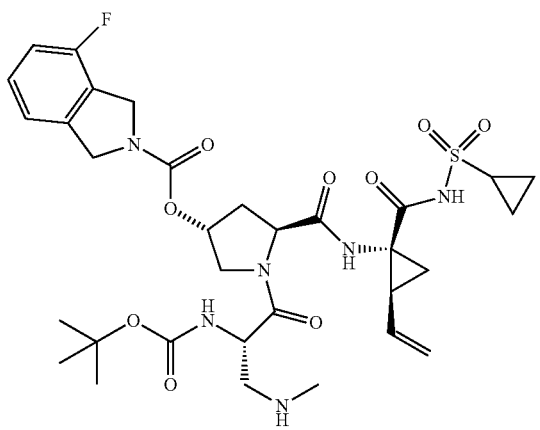

To a solution of Intermediate 3d (0.10 g, 0.11 mmol) in 3 mL DMF was added phenylthiol (30 mg, 0.26 mmol) and K$_2$CO$_3$ (40 mg, 0.3 mmol). The resulting mixture was stirred for 20 hours at RT. 30 mL EtOAc was added and the mixture was washed with water and brine and water. The organic layer was dried over Na$_2$SO$_4$. After removal of solvent, the crude product was subject to chromatography on silica gel (eluents: EtOAc/hexane) to produce 0.1 g of crude Intermediate 3e. MS m/z: 706.9 (M+H+).

Step 3f: Compound I-11

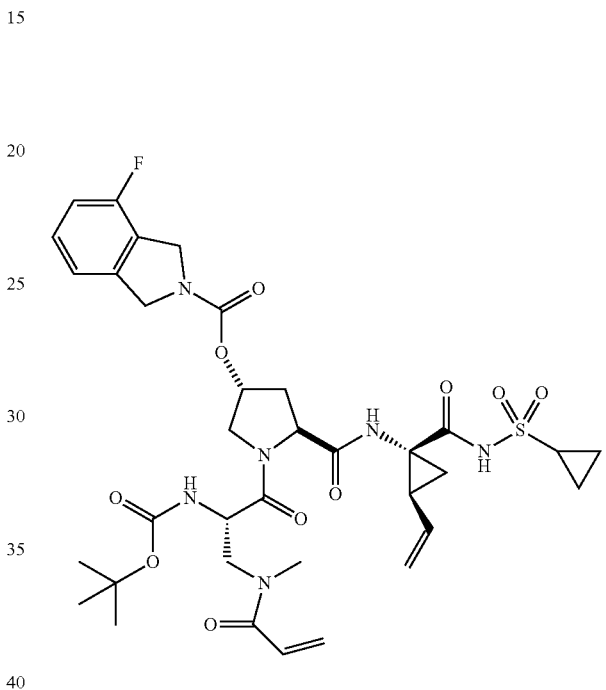

(3R,5S)-1-((S)-2-(tert-butoxycarbonylamino)-3-(N-methylacrylamido)propanoyl)-5-(((1R,2S)-1-(cyclopropyl-sulfonylcarbamoyl)-2-vinylcyclopropylcarbamoyl)pyrrolidin-3-yl 4-fluoroisoindoline-2-carboxylate (I-11) Acryloyl chloride (9 uL, 0.11 mmol) was added dropwise at 0 OC to a stirred solution of 0.1 g (0.1 mmol) of the product from step 3e in 3 mL of DCM containing 0.04 mL (0.3 mmol) of triethylamine. The reaction mixture was stirred at r.t. for 1.5 hrs and then was diluted with 10 mL of DCM. The resulting solution was washed twice with brine and was dried over magnesium sulfate. Removal of solvent afforded the crude product, which was purified by chromatography on silica gel eluting first with hexane/EtOAc (1:3~1:5) and then with EtOAc. A total of 20 mg of the title compound was obtained:

R$_f$ 0.15 (EtOAc); MS m/z: 760.9 (M+H$^+$). $^1$HNMR (CD$_3$OD, 400 MHz) δ 7.32 (m, 1H), 7.13-6.98 (m, 2H), 6.75 (m, 1H), 6.23 (dd, 1H, J=2.3, 16.5 Hz), 5.73 (m, 2H), 5.45-5.29 (m, 2H), 5.12 (dd, 1H, J=1.4, 10.0 Hz), 4.72 (s, 4H), 4.45 (m, 1H), 4.25-4.09 (m, 1H), 3.91 (m, 1H), 3.75-3.50 (m, 1H), 3.15 (s, 3H), 2.96 (m, 1H), 2.42 (m, 1H), 2.25 (m, 2H), 1.87 (m, 1H), 1.45-0.85 (m, 14H).

In similar fashion using the Intermediate 3e, 2-chloroethanesulfonyl chloride, and triethyl amine, the following compound was prepared:

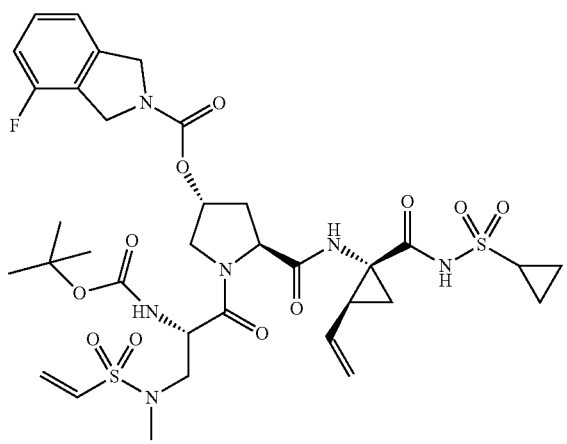

I-12

(3R,5S)-1-((S)-2-(tert-butoxycarbonylamino)-3-(N-methylvinylsulfonamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.55 (DCM/MeOH 95:5); MS m/z: 797.3 (M+H$^+$).

In similar fashion, using (S)-4-(Fmocamino)-2-(tert-butoxycarbonylamino)butanoic acid in step 3a in the place of (S)-3-amino-2-(tert-butoxycarbonylamino)propanoic acid, the following compound was prepared:

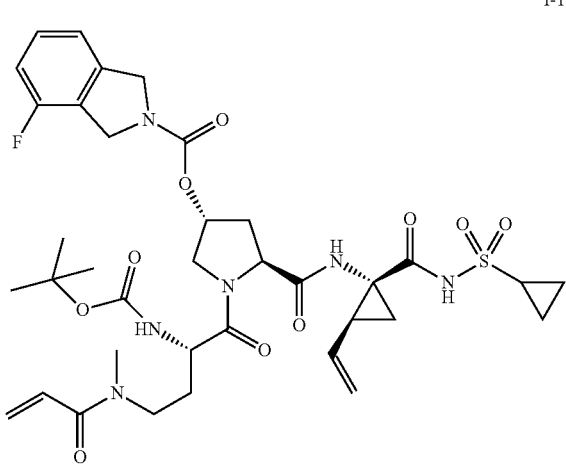

I-13

(3R,5S)-1-((S)-2-(tert-butoxycarbonylamino)-4-(N-methylacrylamido)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.45 (DCM/MeOH 95:5); MS m/z: 775.3 (M+H$^+$).

In similar fashion, following the procedures described in Example 3, compound I-14 can be made by using ethyl iodide in step 3b in place of methyl iodide:

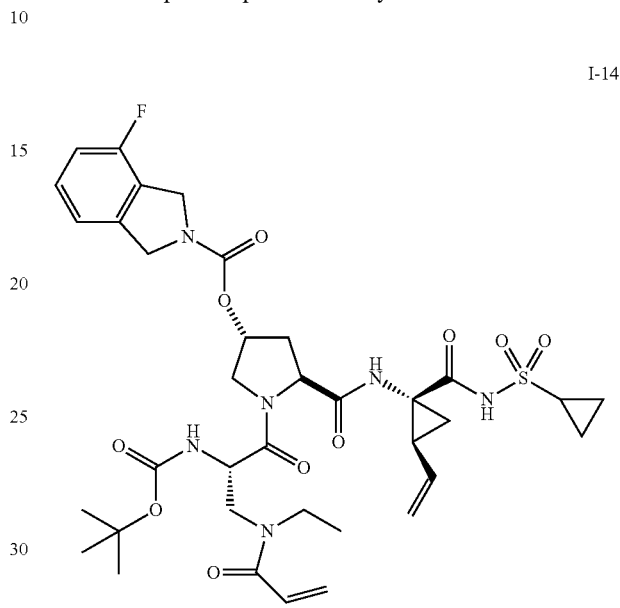

I-14

(3R,5S)-1-((S)-2-(tert-butoxycarbonylamino)-3-(N-ethylacrylamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate Compound I-15 was made by following the procedures described in Example 3, using allyl bromide in step 3b in place of methyl iodide.

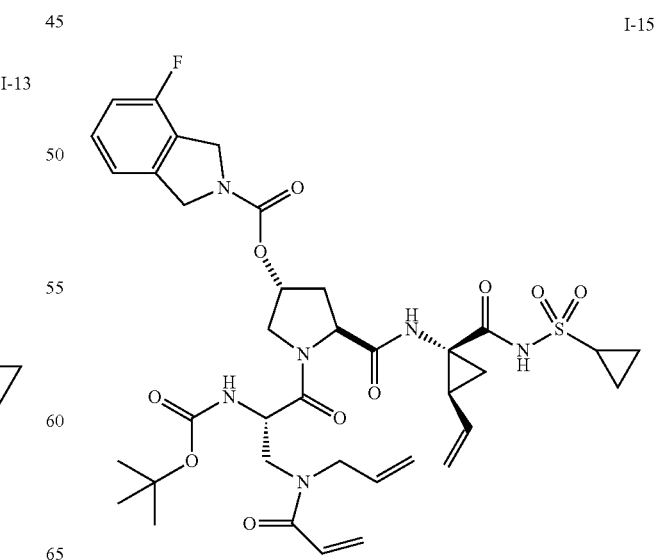

I-15

153

(3R,5S)-1-((S)-3-(N-allylacrylamido)-2-(tert-butoxycarbonylamino)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.58 (DCM/MeOH 95:5); MS m/z: 787.3 (M+H⁺).

The following compounds can be made by starting with the (1R,2S)-1-amino-2-ethylcyclopropane carboxylic acid ethyl ester in step 1a and following the appropriate procedures described in Example 3:

154

(3R,5S)-1-((S)-2-(tert-butoxycarbonylamino)-3-(N-methylacrylamido)propanoyl)-5-((1R,2R)-1-(cyclopropylsulfonylcarbamoyl)-2-ethylcyclopropylcarbamoyl)pyrrolidin-3-yl 4-fluoroisoindoline-2-carboxylate

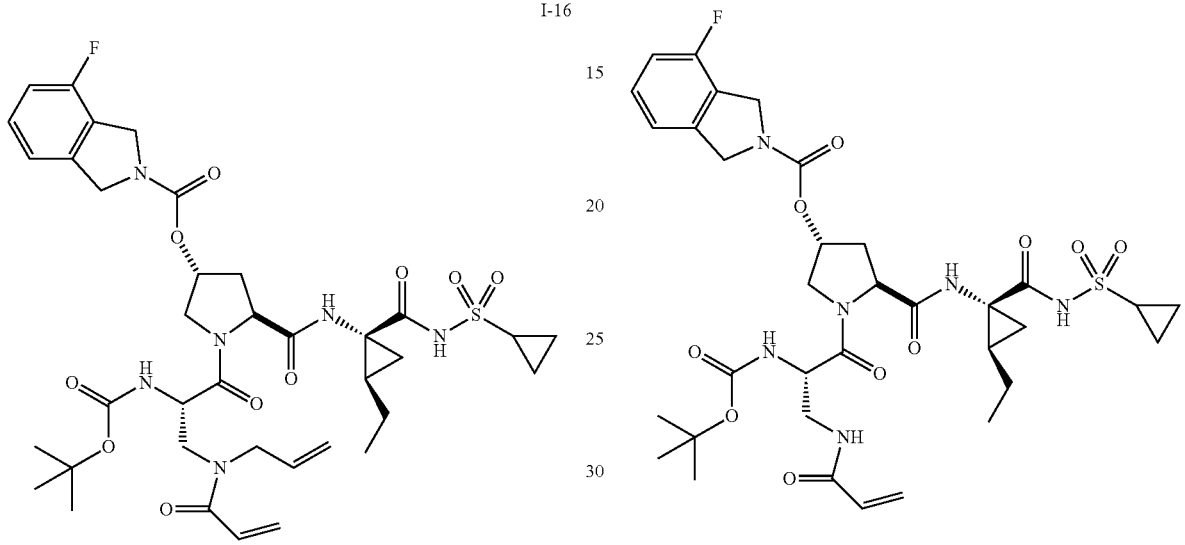

I-16

I-18

(3R,5S)-1-((S)-3-(N-allylacrylamido)-2-(tert-butoxycarbonylamino)propanoyl)-5-((1R,2R)-1-(cyclopropylsulfonylcarbamoyl)-2-ethylcyclopropylcarbamoyl)pyrrolidin-3-yl 4-fluoroisoindoline-2-carboxylate (3R,5S)-1-((S)-3-acrylamido-2-(tert-butoxycarbonylamino)propanoyl)-5-((1R,2R)-1-(cyclopropylsulfonylcarbamoyl)-2-ethylcyclopropylcarbamoyl)pyrrolidin-3-yl 4-fluoroisoindoline-2-carboxylate In similar fashion, the following compound was prepared:

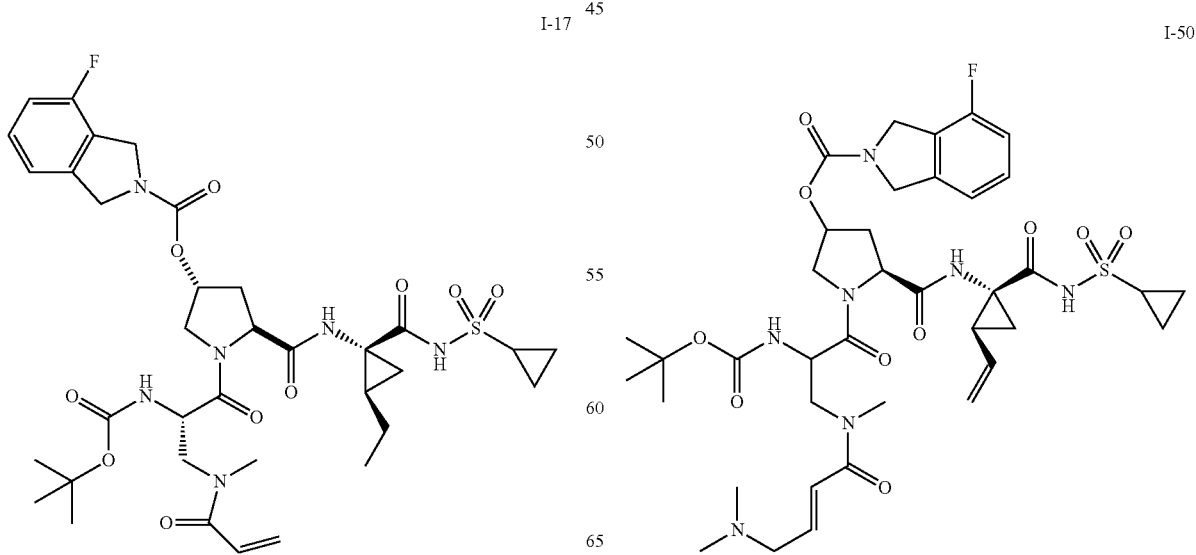

I-17

I-50

(5S)-1-(2-(tert-butoxycarbonylamino)-3-((E)-4-(dimethylamino)-N-methylbut-2-enamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.45 (DCM/MeOH 95:5); MS m/z: 818.5 (M+H$^+$).

Example 4

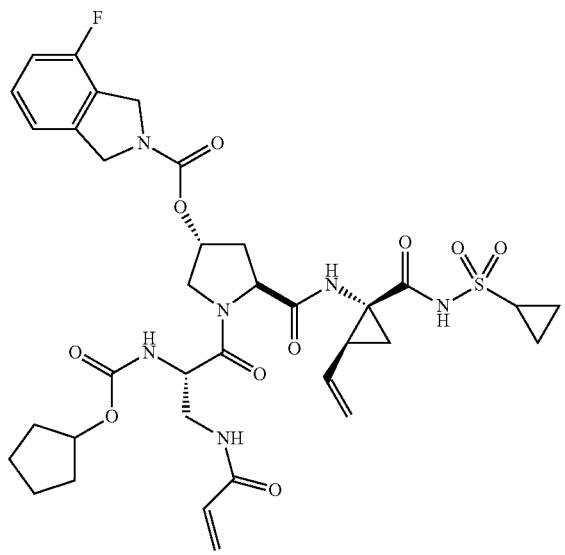

I-19

The title compound was prepared according to the steps and intermediates as described below.

Step 4a: Intermediate 4a

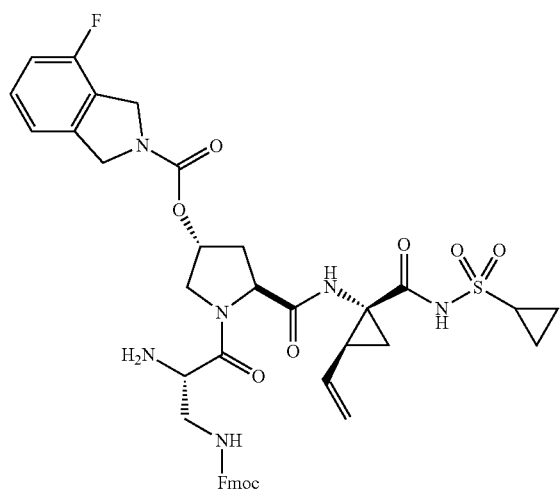

The Intermediate 1e from step 1e was treated with 4 N HCl according to the procedure described in step 1d to afford the Intermediate 4a as its HCl salt. MS m/z: 815.2 (M+H$^+$).

Step 4b: Intermediate 4b

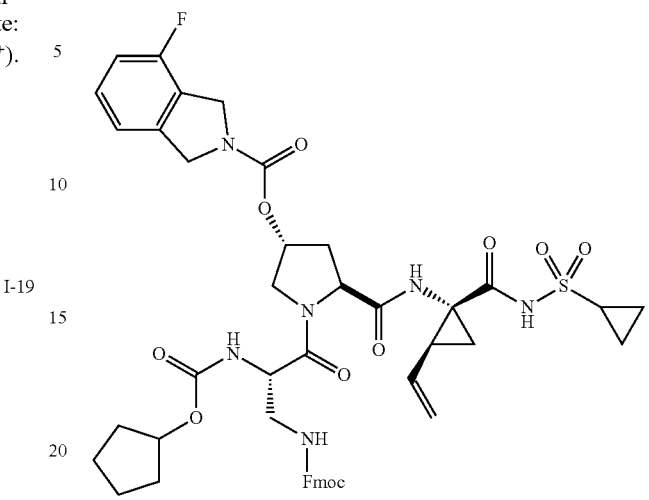

Cyclopentylchloroformate (1.5 equiv.) was added dropwise at 0° C. to a stirred solution of Intermediate 4a (1 equiv.) from step 4a in DCM containing 3 equiv. of triethylamine. The reaction mixture was stirred at r.t. for 1.5 hrs and then was diluted with 10 mL of DCM. The resulting solution was washed twice with brine and was dried over magnesium sulfate. Removal of solvent afforded the crude product, which was purified by chromatography on silica gel eluting first with hexane/EtOAc (1:3~1:5) and then with EtOAc to afford the title compound (60-90%): MS m/z: 925.2 (M−1).

Step 4c: Compound I-19

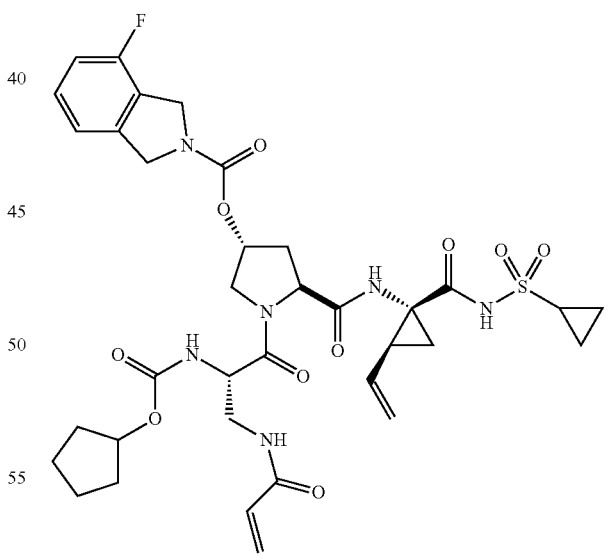

(3R,5S)-1-((S)-3-acrylamido-2-(cyclopentyloxycarbonylamino)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: The title compound was prepared from Intermediate 4b according to the procedures described in step 1f and step 1g. MS m/z: 759.0 (M+H$^+$).

Starting from the appropriate intermediates, in similar fashion, the following compounds were prepared:

I-20

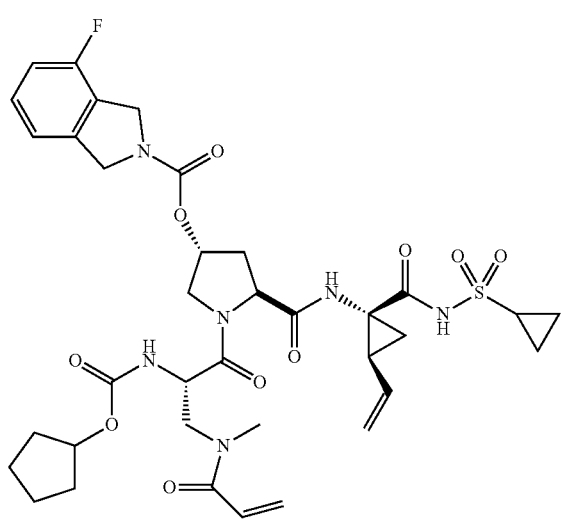 [SMILES: C=CC(=O)N(C)C[C@H](NC(=O)OC(C)(C)C)C(=O)N1C[C@H](OC(=O)N2Cc3cccc(F)c3C2)C[C@H]1C(=O)N[C@]1(C(=O)NS(=O)(=O)C2CC2)C[C@H]1C=C]

(3R,5S)-1-((S)-2-(cyclopentyloxycarbonylamino)-3-(N-methylacrylamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.4 (EtOAc/MeOH 20:1); MS m/z: 773.2 (M+H⁺).

I-21

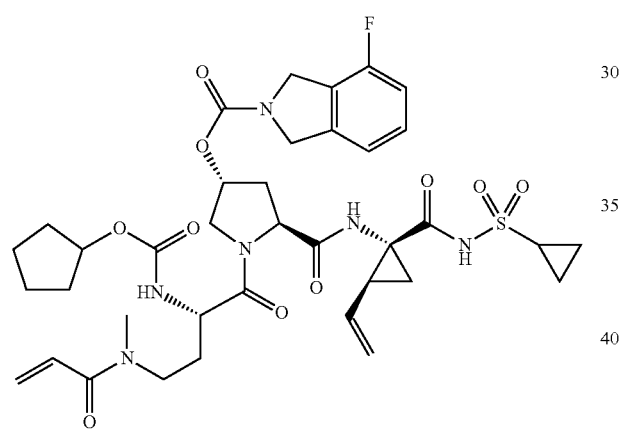

(3R,5S)-1-((S)-2-(cyclopentyloxycarbonylamino)-4-(N-methylacrylamido)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.4 (EtOAc/MeOH 20:1); MS m/z: 787.3 (M+H⁺).

I-52

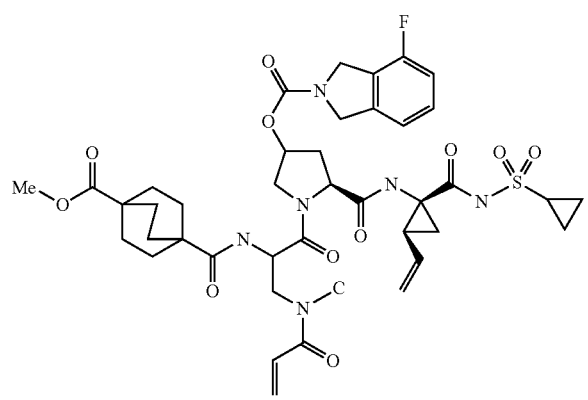

(5S)-5-((1R,2S)-1-(cyclopropylsulfonylcarbamoyl)-2-vinylcyclopropylcarbamoyl)-1-(2-(4-(methoxycarbonyl)bicyclo[2.2.2]octane-1-carboxamido)-3-(N-methylacrylamido)propanoyl)pyrrolidin-3-yl 4-fluoroisoindoline-2-carboxylate:

Rf: 0.45 (EtOAc/MeOH 10:1); MS m/z: 855.3 (M+H⁺).

Example 5

I-22

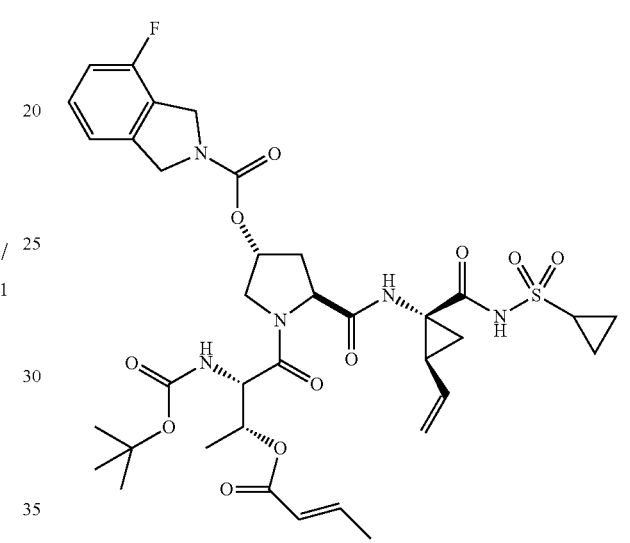

The title compound was prepared according to the steps and intermediates as described below:

Step 5a: Intermediate 5a

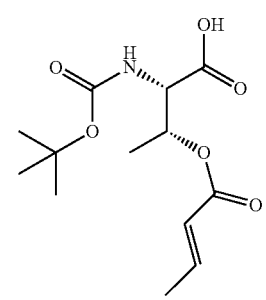 [SMILES: C/C=C/C(=O)O[C@H](C)[C@H](NC(=O)OC(C)(C)C)C(=O)O]

To a solution of Boc-L-Threonine (0.44 g 2.0 mmol) in 10.0 mL of DCM was added crotyl chloride (0.32 g, 3.0 mmol) at RT followed by the addition of catalytic amount of DMAP and TEA (1.0 mL, 6 mmol). The reaction mixture was stirred for 10 h at RT. Aqueous NaHCO₃ solution (10 mL) was added to quench the reaction. After 2 hours, 1 N HCl aqueous solution was added slowly to pH ~3. The DCM layer was collected and the aqueous was extracted by DCM (2×10 mL). The organic layer was dried over Na₂SO₄, filterd and the solvent was removed to provide the crude product.

Step 5b: I-22

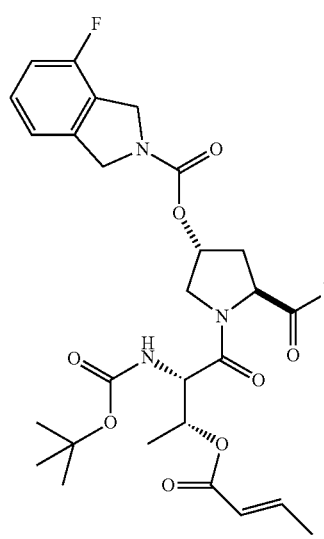

(3R,5S)-1-((2S,3R)-3-((E)-but-2-enoyloxy)-2-(tert-butoxycarbonylamino)butanoyl)-5-((1R,2S)-1-(cyclopropylsulfonylcarbamoyl)-2-vinylcyclopropylcarbamoyl)pyrrolidin-3-yl-4-fluoroisoindoline-2-carboxylate: The title compound was made by coupling Intermediate 1d from Example 1 and Intermediate 5a using HATU following the coupling reactions described for Intermediate 1e in Example 1. A total of 90 mg of the title compound was obtained from 109 mg of Intermediate 1d: R$_f$ 0.5 (EtOAc); MS m/z: 774.3 (M+H$^+$).

Starting from the Intermediate 1d, by coupling with the appropriate intermediates, in similar fashion, the following compounds were prepared:

I-23

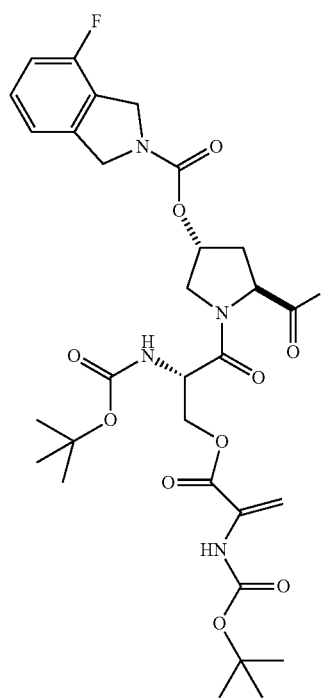

(3R,5S)-1-((S)-2-(tert-butoxycarbonylamino)-3-(2-(tert-butoxycarbonylamino)acryloyloxy)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: MS m/z: 862.2 (M−1).

I-24

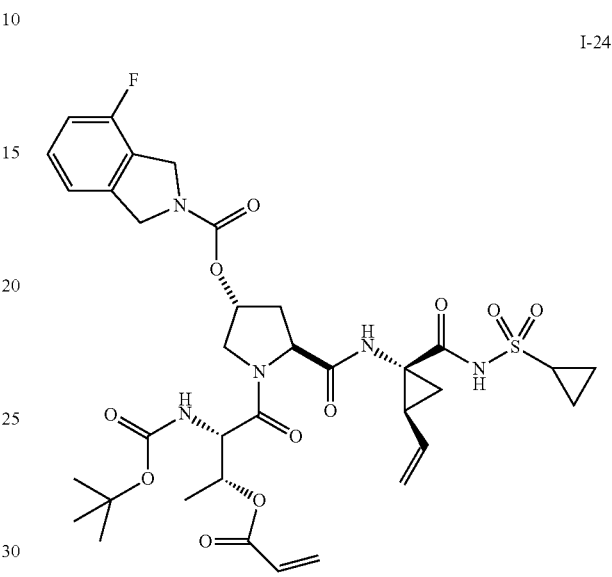

(3R,5S)-1-((2S,3R)-3-(acryloyloxy)-2-(tert-butoxycarbonylamino)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: Rf: 0.4 (EtOAc); MS m/z: 760.1 (M−1).

Example 6

Compound I-25

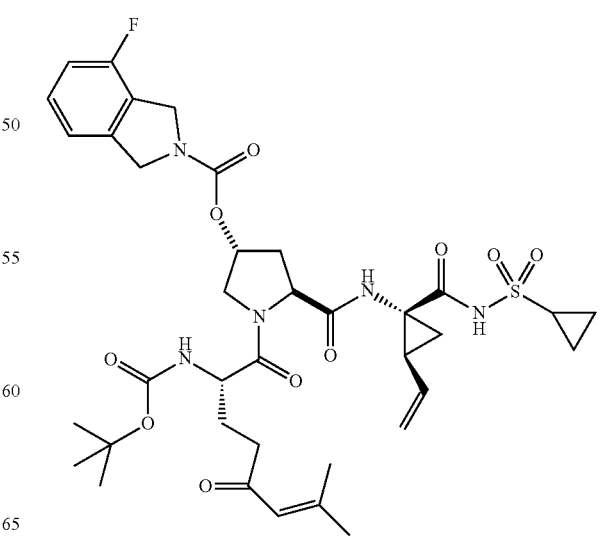

(I-25): The title compound was prepared according to the steps and intermediates as described below:

Step 6a: Intermediate 6a

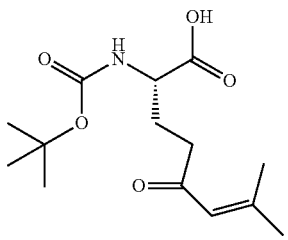 [SMILES: CC(C)=CC(=O)CC[C@H](NC(=O)OC(C)(C)C)C(=O)O]

To a solution of N-Boc-pyroglutamic acid (0.23 g 1.0 mmol) in 10.0 mL of anhydrous THF was added 2-methyl-prop-1-enyl)magnesium bromide (0.5 M in THF, 5 mL, 2.5 mmol) at −78° C. slowly. The reaction mixture was stirred for 1 h at −78° C. 1 N HCl (2.5 mL) aqueous solution was added and the mixture was slowly warmed up to RT. The pH was adjusted to ~3-4 by 1 N HCl. The THF was then removed under vacuum and the remaining aqueous was extracted by DCM (3×15 mL). The organic layer was dried over Na₂SO₄, filterd and the solvent was removed to provide the crude product.

Step 6b: I-25

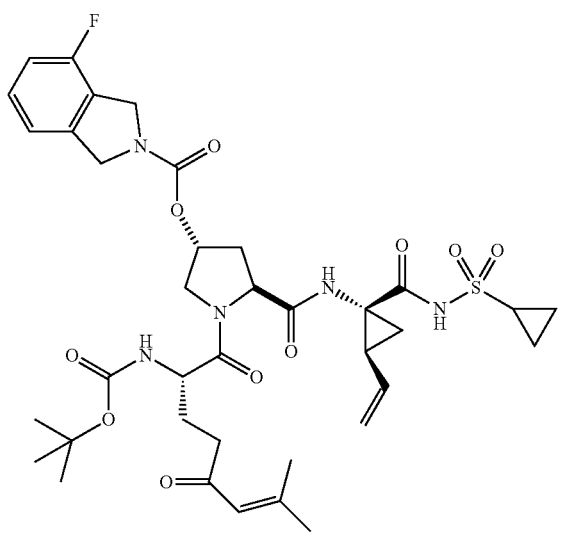

(3R,5S)-1-((S)-2-(tert-butoxycarbonylamino)-7-methyl-5-oxooct-6-enoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: The title compound was made by coupling Intermediate 1d from Example 1 and Intermediate 6a using HATU following the coupling reactions described for Intermediate 1e in Example 1. A total of 80 mg of the title compound was obtained from 108 mg of Intermediate 1d: $R_f$ 0.3 (EtOAc); MS m/z: 774.1 (M+H⁺).
¹HNMR (CD₃OD, 400 MHz) δ 7.31 (dd, 1H, J=13.3, 7.4 Hz), 7.13-6.98 (m, 2H), 6.18 (s, 1H), 5.74 (m, 1H), 5.38 (s, 1H), 5.32 (d, 1H, J=17.0 Hz), 5.12 (d, 1H, J=10.1 Hz), 4.72 (s, 4H), 4.48 (dd, 1H, J=17.0, 9.16 Hz), 4.29 (m, 2H), 3.89 (m, 1H), 2.93 (m, 1H), 2.60-2.35 (m, 2H), 2.22 (m, 2H), 2.10 (s, 3H), 2.02-1.75 (br, 1H), 1.88 (s, 3H), 1.46-0.80 (m, 14H).

¹³C NMR (CD₃OD, 100 MHz):
δ 201.8, 175.3, 174.5, 170.6, 157.7, 156.9, 155.6, 141.1, 134.2, 131.2, 124.8, 119.9, 119.7, 118.6, 115.0, 114.8, 80.3, 76.1, 61.0, 55.0, 54.9, 54.8, 53.5, 53.3, 52.7, 50.3, 50.1, 42.6, 40.3, 35.7, 35.4, 32.1, 28.7, 28.5, 27.7, 26.9, 24.0, 20.9, 6.74, 6.47.

Starting from the Intermediate 1d, by coupling with the appropriate intermediates made similarly as described in Step 6a, the following compounds were prepared:

I-26

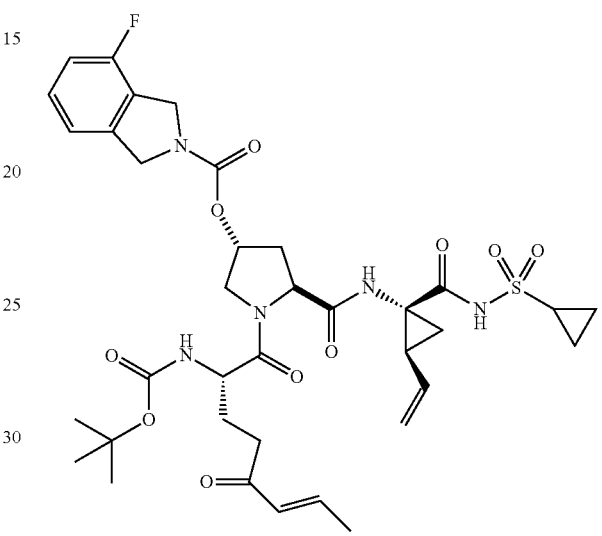

(3R,5S)-1-((S,E)-2-(tert-butoxycarbonylamino)-5-oxooct-6-enoyl)-5-((1R,2S)-1-(cyclopropylsulfonylcarbamoyl)-2-vinylcyclopropylcarbamoyl)pyrrolidin-3-yl-4-fluoroisoindoline-2-carboxylate: A total of 80 mg of the title compound was obtained from 150 mg of Intermediate 1d: $R_f$ 0.3 (EtOAc); MS m/z: 760.3 (M+H⁺).

I-27

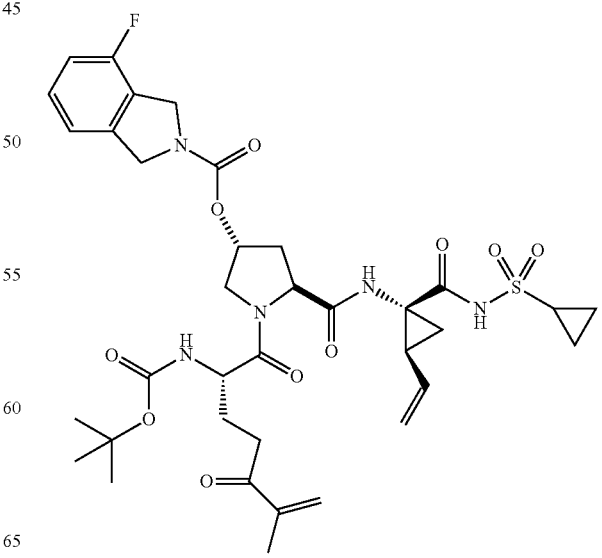

(3R,5S)-1-((S)-2-(tert-butoxycarbonylamino)-6-methyl-5-oxohept-6-enoyl)-5-((1R,2S)-1-(cyclopropylsulfonylcarbamoyl)-2-vinylcyclopropylcarbamoyl)pyrrolidin-3-yl 4-fluoroisoindoline-2-carboxylate: A total of 80 mg of the title compound was obtained from 150 mg of Intermediate 1d: $R_f$ 0.4 (EtOAc); MS m/z: 782.2 (M+Na$^+$). $^1$HNMR (CD$_3$OD, 400 MHz) δ 7.31 (dd, 1H, J=13.3, 7.4 Hz), 7.09 (dd, 1H, J=33, 7.4 Hz), 7.0 (m, 1H), 6.12 (s, 1H), 5.82 (s, 1H), 5.74 (m, 1H), 5.39 (s, 1H), 5.31 (dd, 1H, J=1.4, 17.0 Hz), 5.12 (dd, 1H, J=10.1, 1.4 Hz), 4.73 (m, 4H), 4.48 (m, 1H), 4.32 (m, 2H), 3.90 (m, 1H), 2.91 (m, 1H), 2.42 (m, 1H), 2.22 (m, 2H), 2.01 (m, 1H), 1.90-1.85 (m, 2H), 1.84 (s, 3H), 1.40-1.02 (m, 14H).

I-39

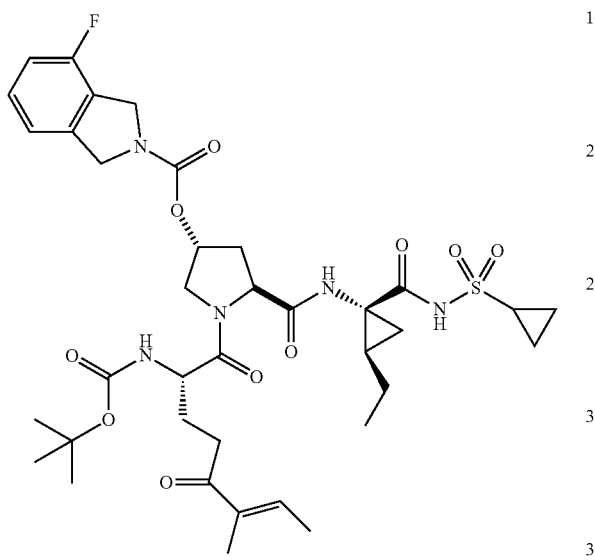

(3R,5S)-1-((S,E)-2-(tert-butoxycarbonylamino)-6-methyl-5-oxooct-6-enoyl)-5-((1R,2R)-1-(cyclopropylsulfonylcarbamoyl)-2-ethylcyclopropylcarbamoyl)pyrrolidin-3-yl 4-fluoroisoindoline-2-carboxylate: A total of 50 mg of the title compound was obtained from 150 mg of Intermediate 1d: $R_f$ 0.5 (EtOAc); MS m/z: 796.2 (M+Na$^+$).

Starting from the Intermediate 1d, the following compounds are prepared by coupling with the appropriate intermediates made similarly as described in Step 6a:

I-28

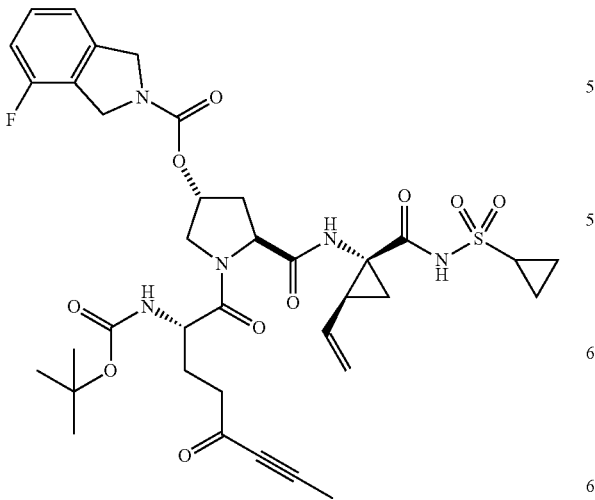

(3R,5S)-1-((S)-2-(tert-butoxycarbonylamino)-5-oxooct-6-ynoyl)-5-((1R,2S)-1-(cyclopropylsulfonylcarbamoyl)-2-vinylcyclopropylcarbamoyl)pyrrolidin-3-yl 4-fluoroisoindoline-2-carboxylate

I-29

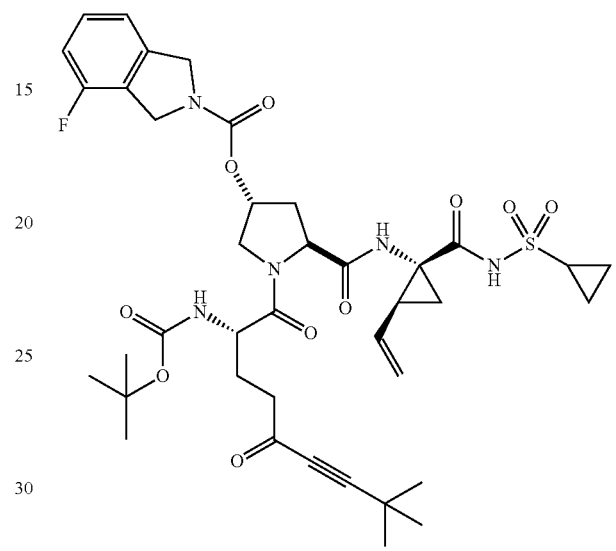

(3R,5S)-1-((S)-2-(tert-butoxycarbonylamino)-8,8-dimethyl-5-oxonon-6-ynoyl)-5-((1R,2S)-1-(cyclopropylsulfonylcarbamoyl)-2-vinylcyclopropylcarbamoyl)pyrrolidin-3-yl 4-fluoroisoindoline-2-carboxylate

I-30

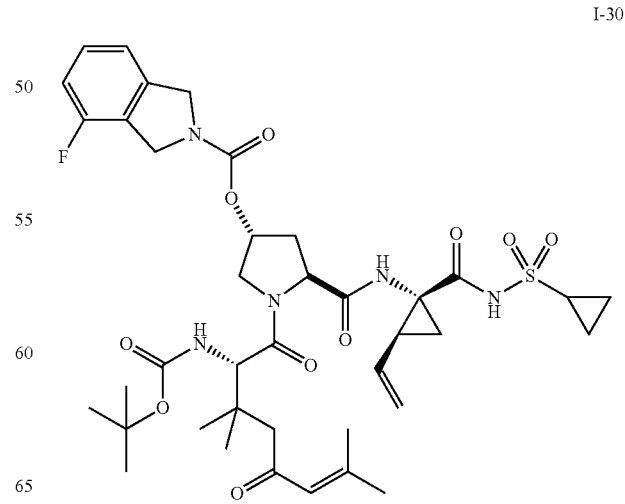

165

(3R,5S)-1-((S)-2-(tert-butoxycarbonylamino)-3,3,7-trimethyl-5-oxooct-6-enoyl)-5-((1R,2S)-1-(cyclopropylsulfonylcarbamoyl)-2-vinylcyclopropylcarbamoyl)pyrrolidin-3-yl 4-fluoroisoindoline-2-carboxylate

166

(3R,5S)-1-((S)-2-(tert-butoxycarbonylamino)-6-methyl-4-oxohept-5-enoyl)-5-((1R,2S)-1-(cyclopropylsulfonylcarbamoyl)-2-vinylcyclopropylcarbamoyl)pyrrolidin-3-yl 4-fluoroisoindoline-2-carboxylate MS m/z: 760.1 (M+H$^+$).

The following compound was made by palladium catalyzed hydrogenation of Intermediate 1d, followed by coupling reaction described in step 6b:

I-31

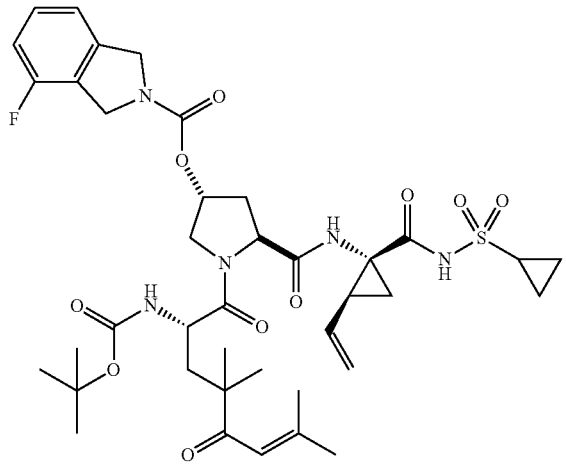

I-33

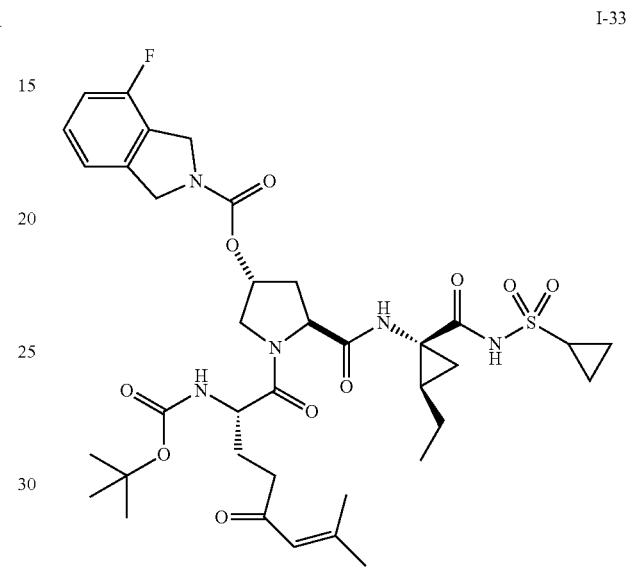

(3R,5S)-1-((S)-2-(tert-butoxycarbonylamino)-4,4,7-trimethyl-5-oxooct-6-enoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (3R,5S)-1-((S)-2-(tert-butoxycarbonylamino)-7-methyl-5-oxooct-6-enoyl)-5-((1R,2R)-1-(cyclopropylsulfonylcarbamoyl)-2-ethylcyclopropylcarbamoyl)pyrrolidin-3-yl 4-fluoroisoindoline-2-carboxylate: A total of 33 mg of the title compound was obtained from 100 mg of Intermediate 1d: R$_f$ 0.5 (EtOAc); MS m/z: 776.2 (M+H$^+$).

In similar fashion, the following compounds are made:

I-32

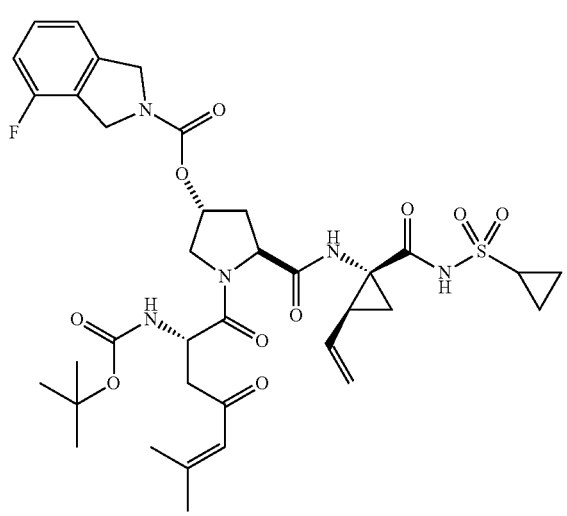

I-34

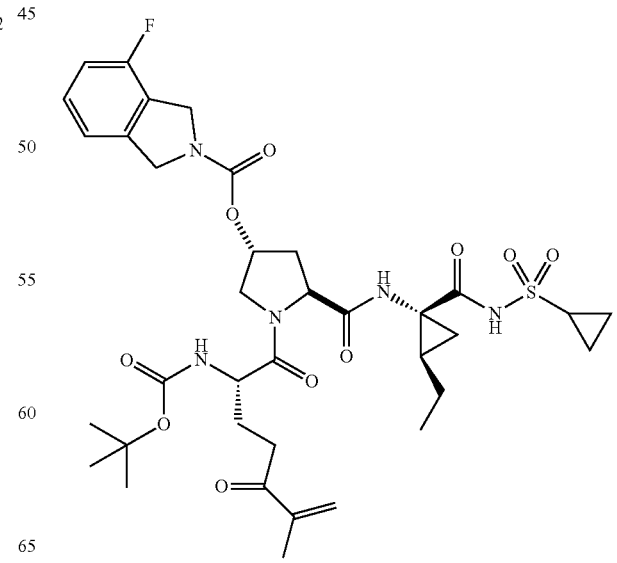

| 167 | 168 |
|---|---|
| (3R,5S)-1-((S)-2-(tert-butoxycarbonylamino)-6-methyl-5-oxohept-6-enoyl)-5-((1R,2R)-1-(cyclopropylsulfonylcarbamoyl)-2-ethylcyclopropylcarbamoyl)pyrrolidin-3-yl 4-fluoroisoindoline-2-carboxylate | (3R,5S)-1-((S)-2-(tert-butoxycarbonylamino)-5-cyclobutenyl-5-oxopentanoyl)-5-((1R,2R)-1-(cyclopropylsulfonylcarbamoyl)-2-ethylcyclopropylcarbamoyl)pyrrolidin-3-yl 4-fluoroisoindoline-2-carboxylate |

I-60

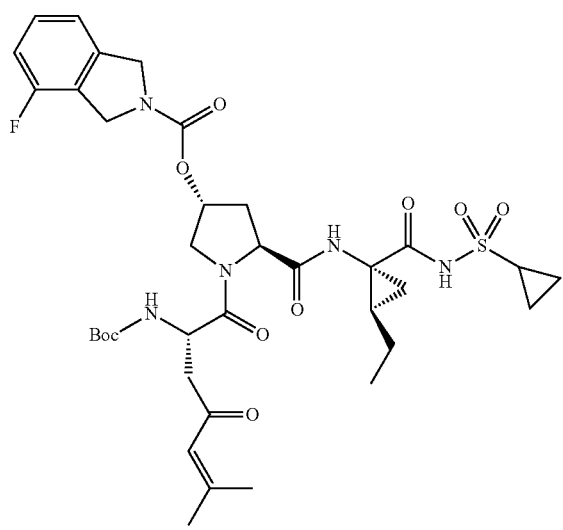

I-62

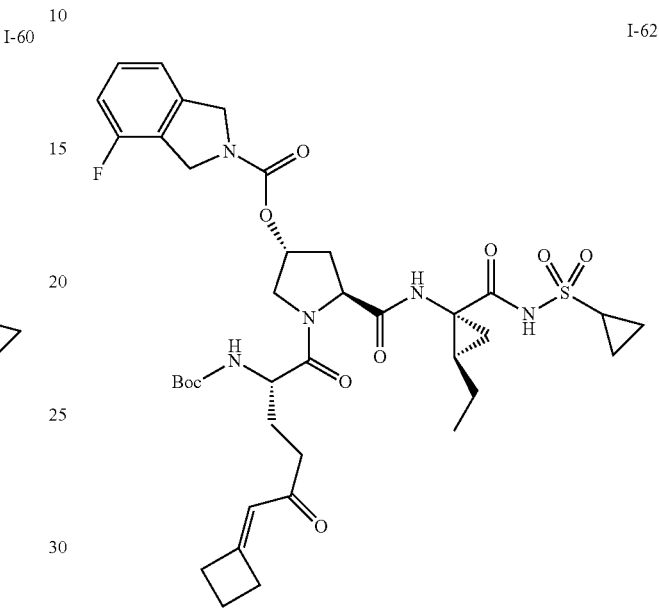

(3R,5S)-1-((S)-2-(tert-butoxycarbonylamino)-6-methyl-4-oxohept-5-enoyl)-5-((1R,2R)-1-(cyclopropylsulfonylcarbamoyl)-2-ethylcyclopropylcarbamoyl)pyrrolidin-3-yl 4-fluoroisoindoline-2-carboxylate (3R,5S)-1-((S)-2-(tert-butoxycarbonylamino)-6-cyclobutylidene-5-oxopentanoyl)-5-((1R,2R)-1-(cyclopropylsulfonylcarbamoyl)-2-ethylcyclopropylcarbamoyl)pyrrolidin-3-yl 4-fluoroisoindoline-2-carboxylate

I-61

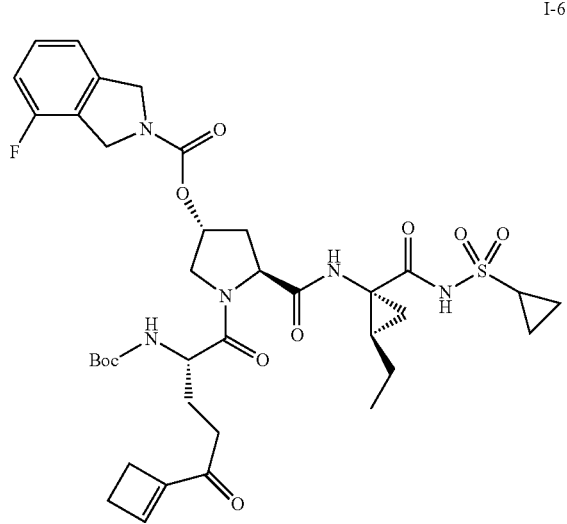 [SMILES: CC[C@@H]1C[C@]1(NC(=O)[C@@H]1C[C@@H](OC(=O)N2Cc3cccc(F)c3C2)CN1C(=O)[C@H](CCC(=O)C1=CCC1)NC(=O)OC(C)(C)C)C(=O)NS(=O)(=O)C1CC1]

I-63

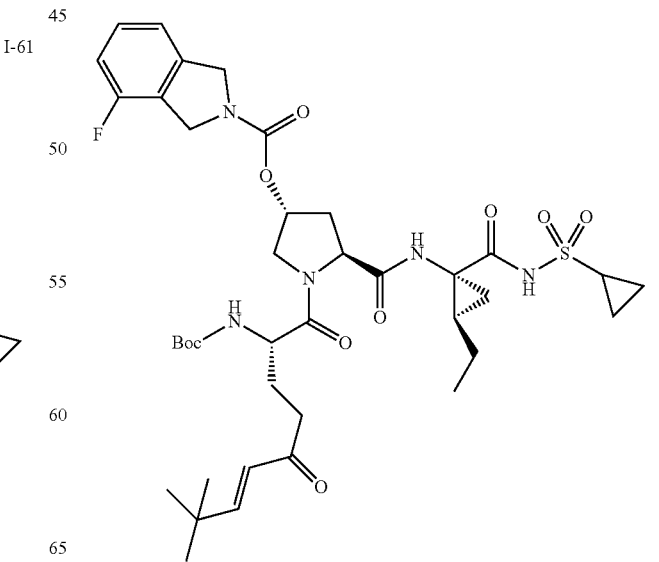

(3R,5S)-1-((S,E)-2-(tert-butoxycarbonylamino)-8,8-dimethyl-5-oxonon-6-enoyl)-5-(((1R,2R)-1-(cyclopropylsulfonylcarbamoyl)-2-ethylcyclopropylcarbamoyl)pyrrolidin-3-yl 4-fluoroisoindoline-2-carboxylate (3R,5S)-1-((S)-2-(tert-butoxycarbonylamino)-7-methyl-5-oxooct-6-enoyl)-5-(1-(cyclopropanesulfonamido)-1-oxohexan-2-ylcarbamoyl)pyrrolidin-3-yl 4-fluoroisoindoline-2-carboxylate: A total of 58 mg of the title compound (I-44) was obtained from 100 mg of Intermediate 1d: $R_f$ 0.5 (EtOAc); MS m/z: 800.2 (M+Na$^+$).

Example 7

I-64

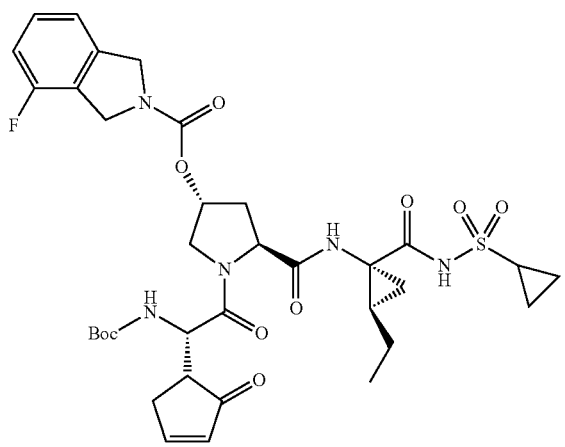

(3R,5S)-1-((S)-2-(tert-butoxycarbonylamino)-2-((S)-2-oxocyclopent-3-enyl)acetyl)-5-(((1R,2R)-1-(cyclopropylsulfonylcarbamoyl)-2-ethylcyclopropylcarbamoyl)pyrrolidin-3-yl 4-fluoroisoindoline-2-carboxylate The following compound was made by prolonged palladium catalyzed hydrogenation (24-48 hours) of Intermediate 1d, followed by coupling reaction described in step 6b:

I-45

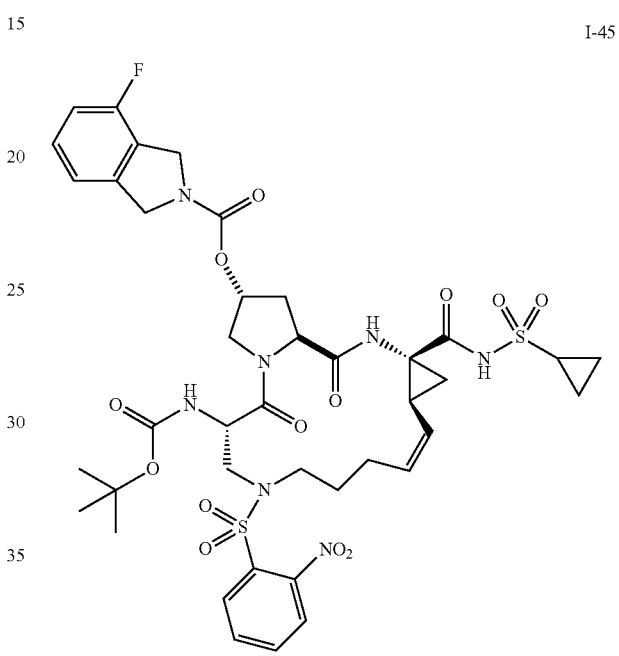

(1aR,3aS,5R,9S,16aS,Z)-11-(o-nitrophenylsulfonyl)-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[n]pyrrolo[2,1-c][1,4,8]triazacyclopentadecin-5-yl-4-fluoroisoindoline-2-carboxylate (I-45): The title compound is prepared according to the steps and intermediates as described below:

Step 7a: Intermediate 7a

I-44

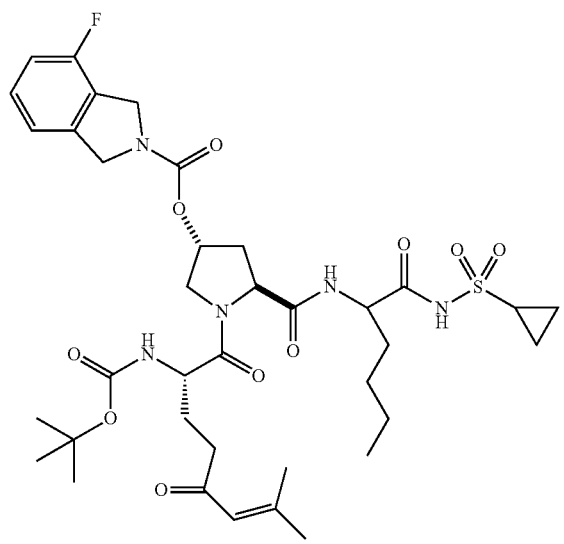

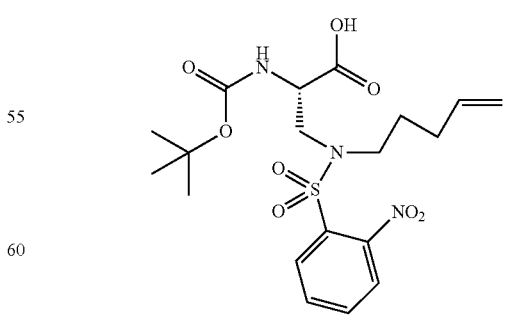

The Intermediate 7a was made following the procedure described for the synthesis of Intermediate 3c by using 5-bromopent-1-ene as the alkylating reagent.

Step 7b: Intermediate 7b

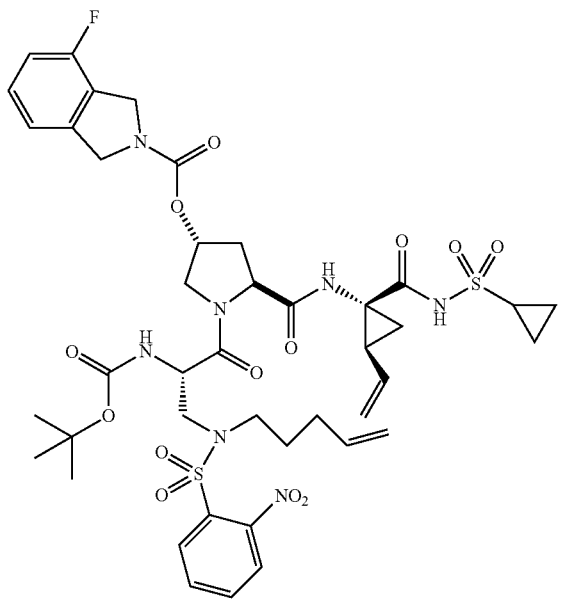

The Intermediate 7b was made by coupling Intermediate 1d from Example 1 and Intermediate 7a using HATU following the coupling reactions described for Intermediate 1e in Example 1. MS: 946.2 (M+1).

Step 7c: Compound I-45

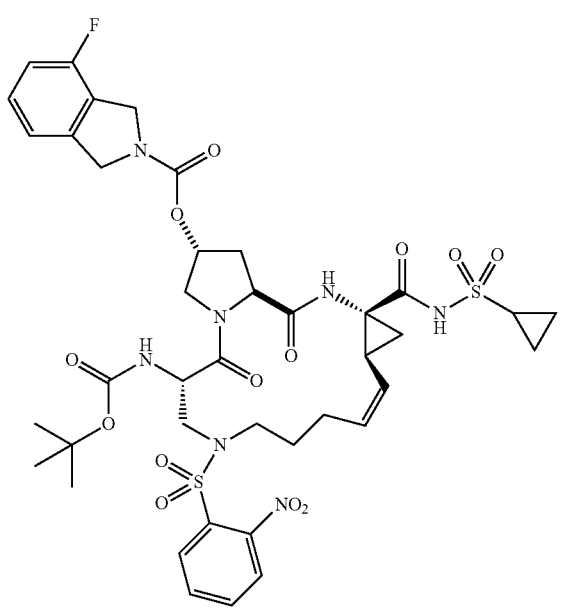

To a solution of 540 mg of Intermediate 7b in 150 mL of anhydrous dichloromethane was added 100 mg 1,3-Bis(2,4,6-trimethylphenyl)-4,5-dihydroimidazol-2-ylidene[2-(i-propoxy)-5-(N,N-dimethylaminosulfonyl)phenyl]methyleneruthenium (II) (Zhan catalyst 1B, RC-303, Zannan Pharma Ltd.) under nitrogen. The resulting mixture was heated at 48° C. overnight. The LC-MS showed complete conversion to the product. Reaction solution was subject to flash column chromatography on silica gel with eluent (heptane/EtOAc v/v 1:1 to pure EtOAc), giving 140 mg of the desired product. MS: 916.3 (ES−).

In similar fashion, by starting with (S)-5-allylamino-2-tert-butoxycarbonylamino-pentanoic acid in step 7a, the following compound was prepared:

I-53

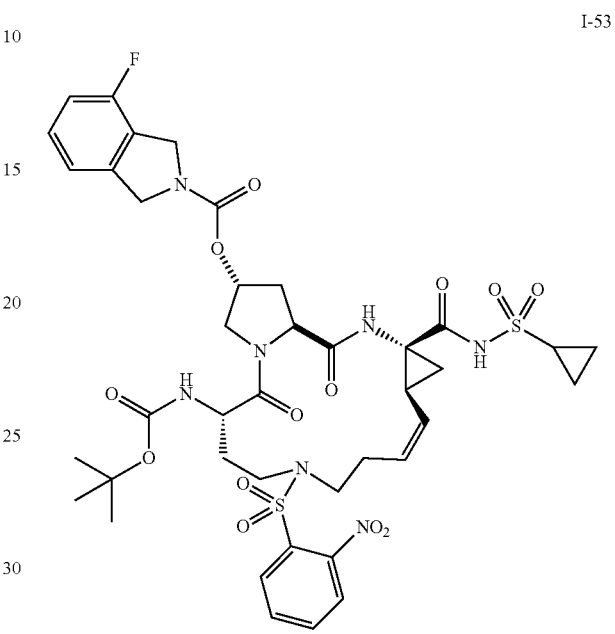

MS: 916.3 (ES−)

In similar fashion, by starting with (S)-4-[But-3-enyl-(2-nitro-benzenesulfonyl)-amino]-2-tert-butoxycarbonylamino-butyric acid in step 7a, the following compound was prepared:

I-54

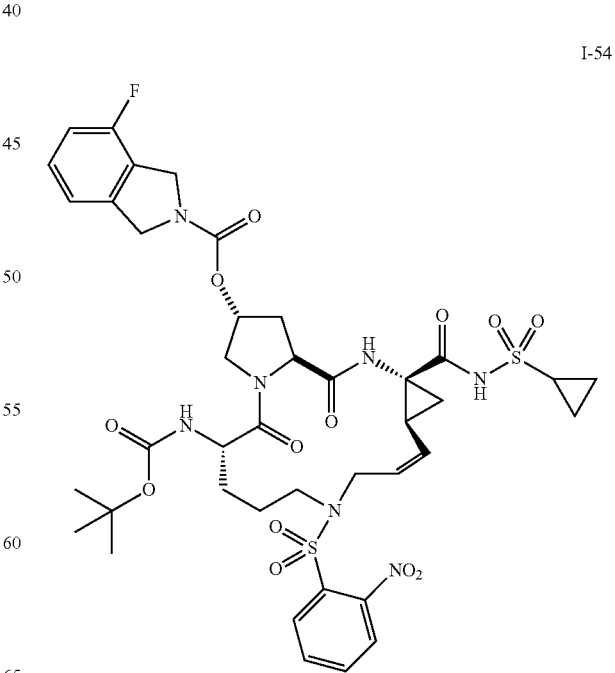

MS: 916.3 (ES−)

Example 8

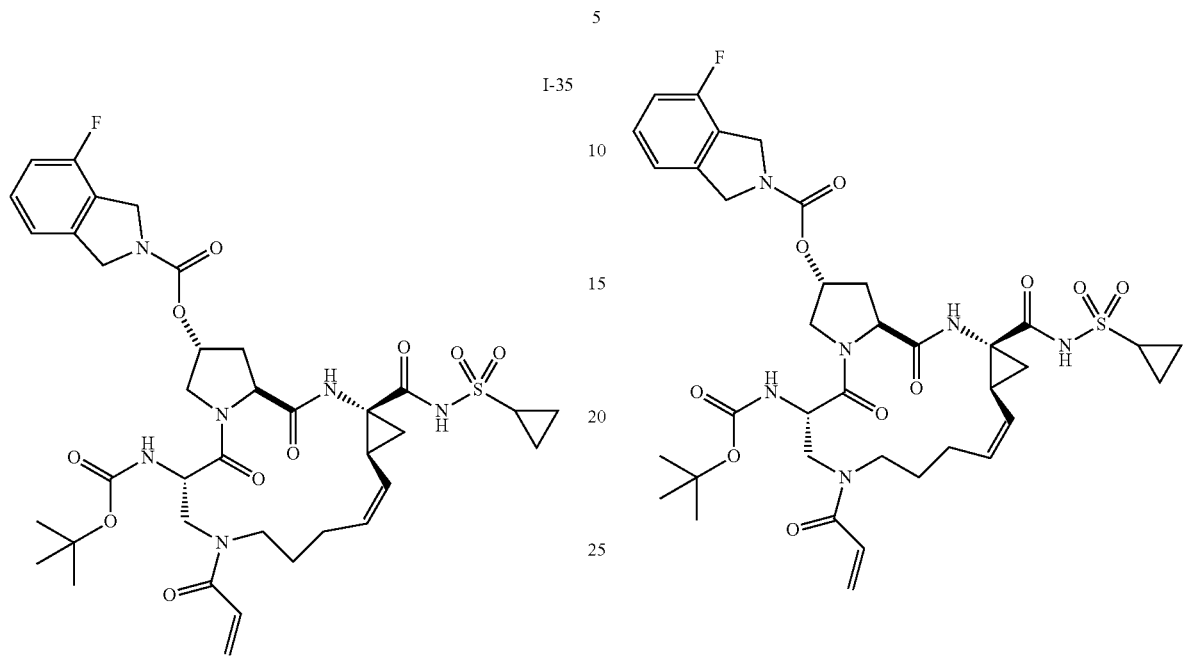

(1aR,3aS,5R,9S,16aS,Z)-11-acryloyl-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[n]pyrrolo[2,1-c][1,4,8]triazacyclopentadecin-5-yl-4-fluoroisoindoline-2-carboxylate (I-35): The title compound was prepared according to the steps and intermediates as described below:

Step 8a: Intermediate 8a:

The Intermediate 8a was made by treating compound I-45 from Example 7 with thiophenol following the procedure described in step 3e. MS: 733.3 (M+1).

Step 8b: Compound I-35:

The title compound was made by treating Intermediate 8a with acryloyl chloride following the procedure described in step 3f. $R_f$ 0.2 (5% MeOH in DCM); MS m/z: 787.3 (M+H$^+$).

In similar fashion, by treating Intermediate 8a with chloroacetyl chloride (1.2 eq), the following compound was prepared:

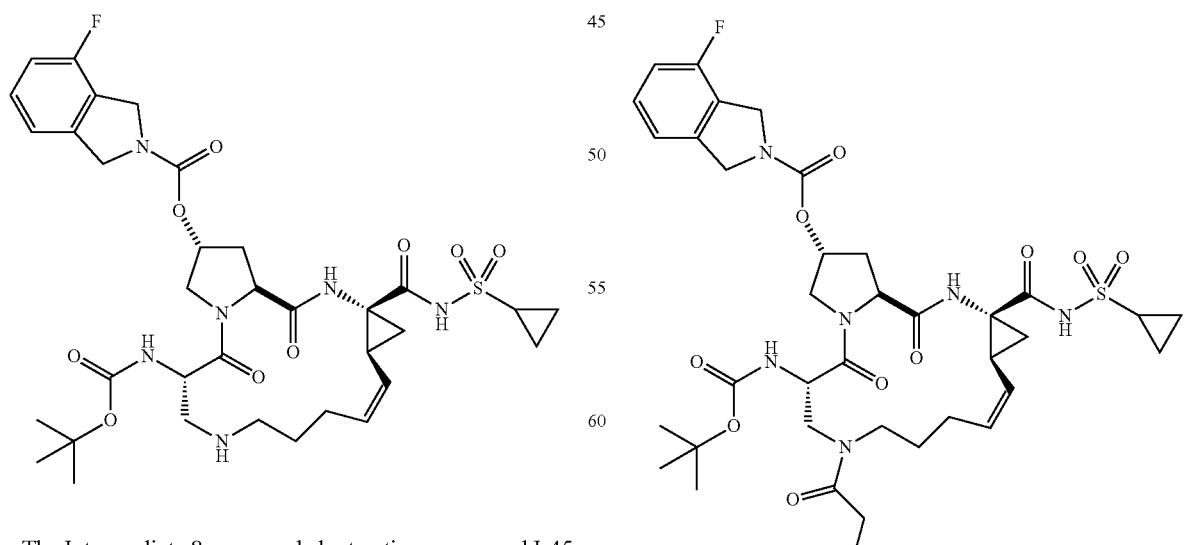

(1aR,3aS,5R,9S,16aS,Z)-11-chloroacetyl-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[n]pyrrolo[2,1-c][1,4,8]triazacyclopentadecin-5-yl-4-fluoroisoindoline-2-carboxylate (I-45)

MS: 831.2 (M+Na⁺).

In similar fashion, by treating Intermediate 8a with Chloroacetyl chloride (3.0 eq), the following compound was prepared:

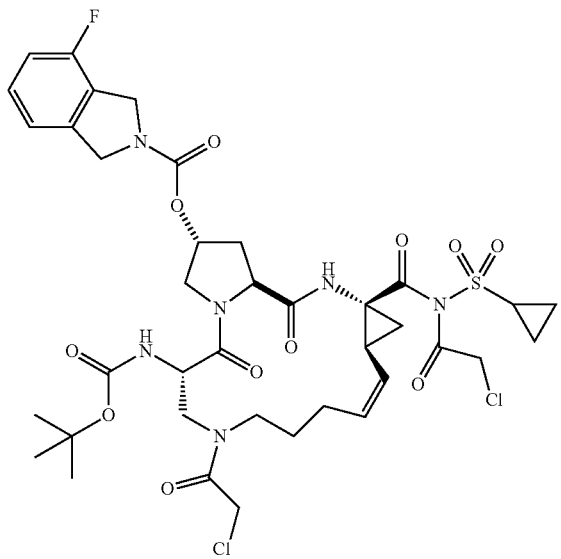

I-48

MS: 907.2 (M+Na⁺).

In similar fashion, by starting with compounds I-53, and I-54 in step 8a, the following compounds were prepared:

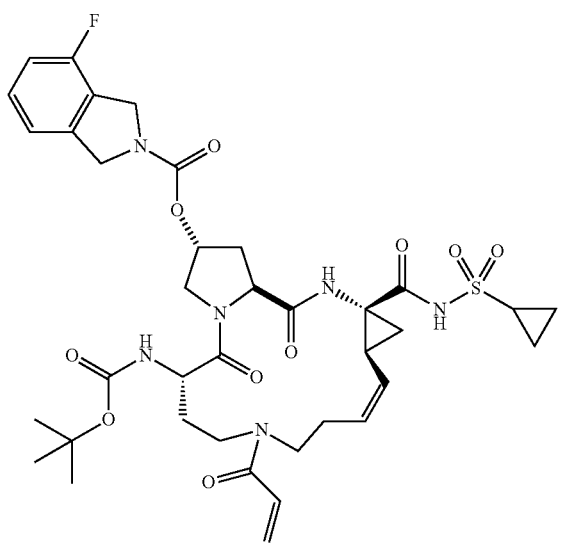

I-36

(1aR,3aS,5R,9S,16aS,Z)-12-acryloyl-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[n]pyrrolo[2,1-c][1,4,9]triazacyclopentadecin-5-yl 4-fluoroisoindoline-2-carboxylate

MS: 785.3 (ES−).

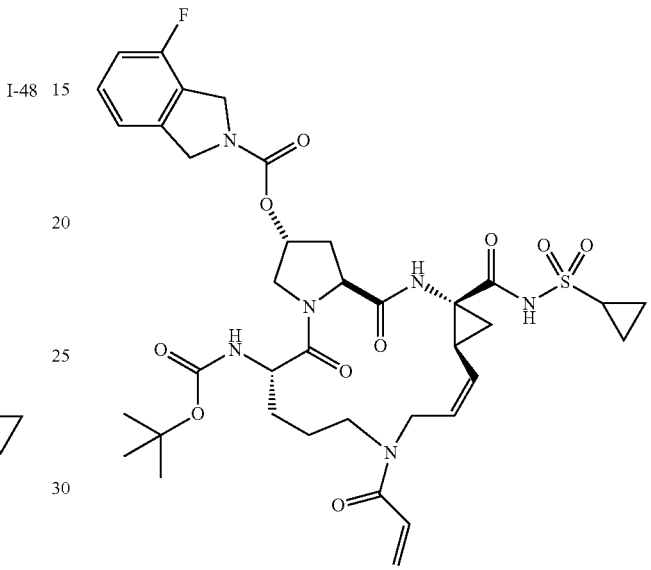

I-37

(1aR,3aS,5R,9S,16aS,Z)-13-acryloyl-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[e]pyrrolo[1,2-a][1,4,10]triazacyclopentadecin-5-yl 4-fluoroisoindoline-2-carboxylate

MS: 787.3 (ES+), 785.3 (ES−).

Example 9 (I-40)

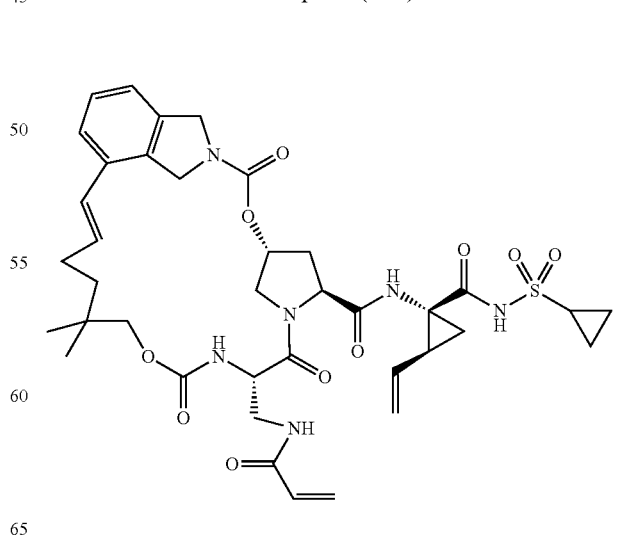

The title compound is prepared according to the steps and intermediates as described in the scheme below:

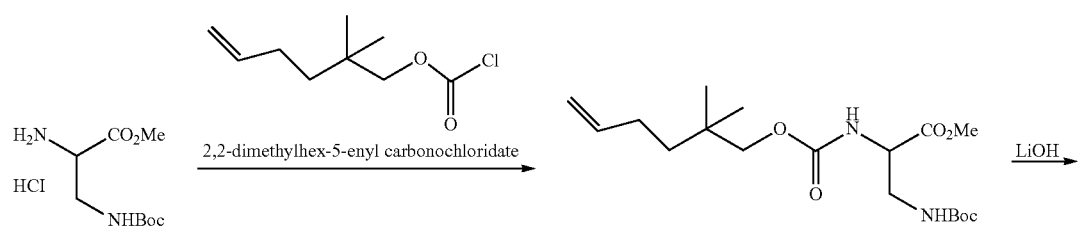
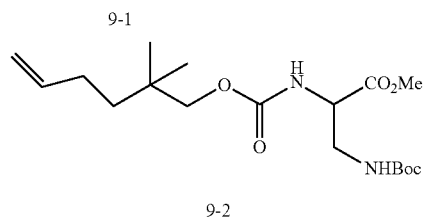
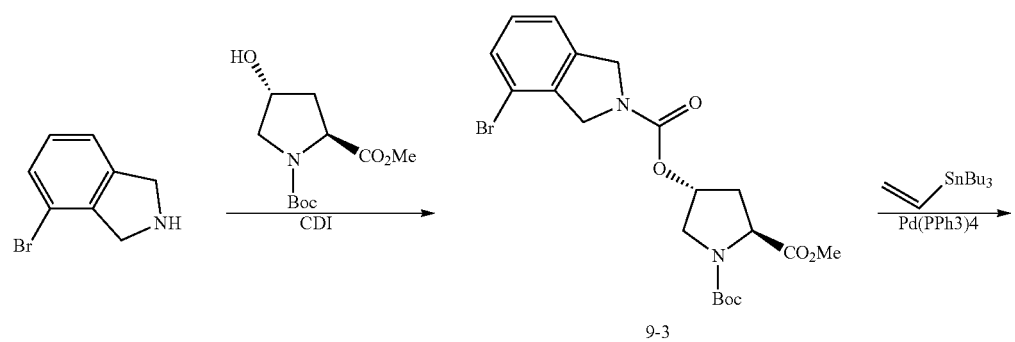
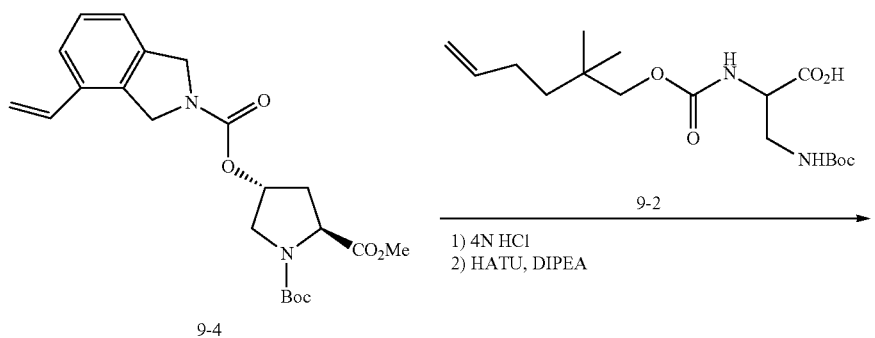
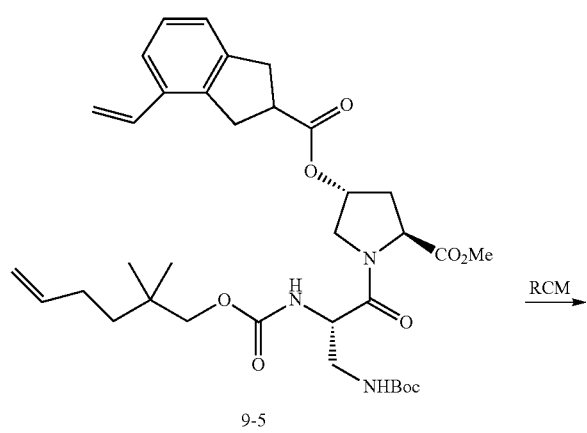

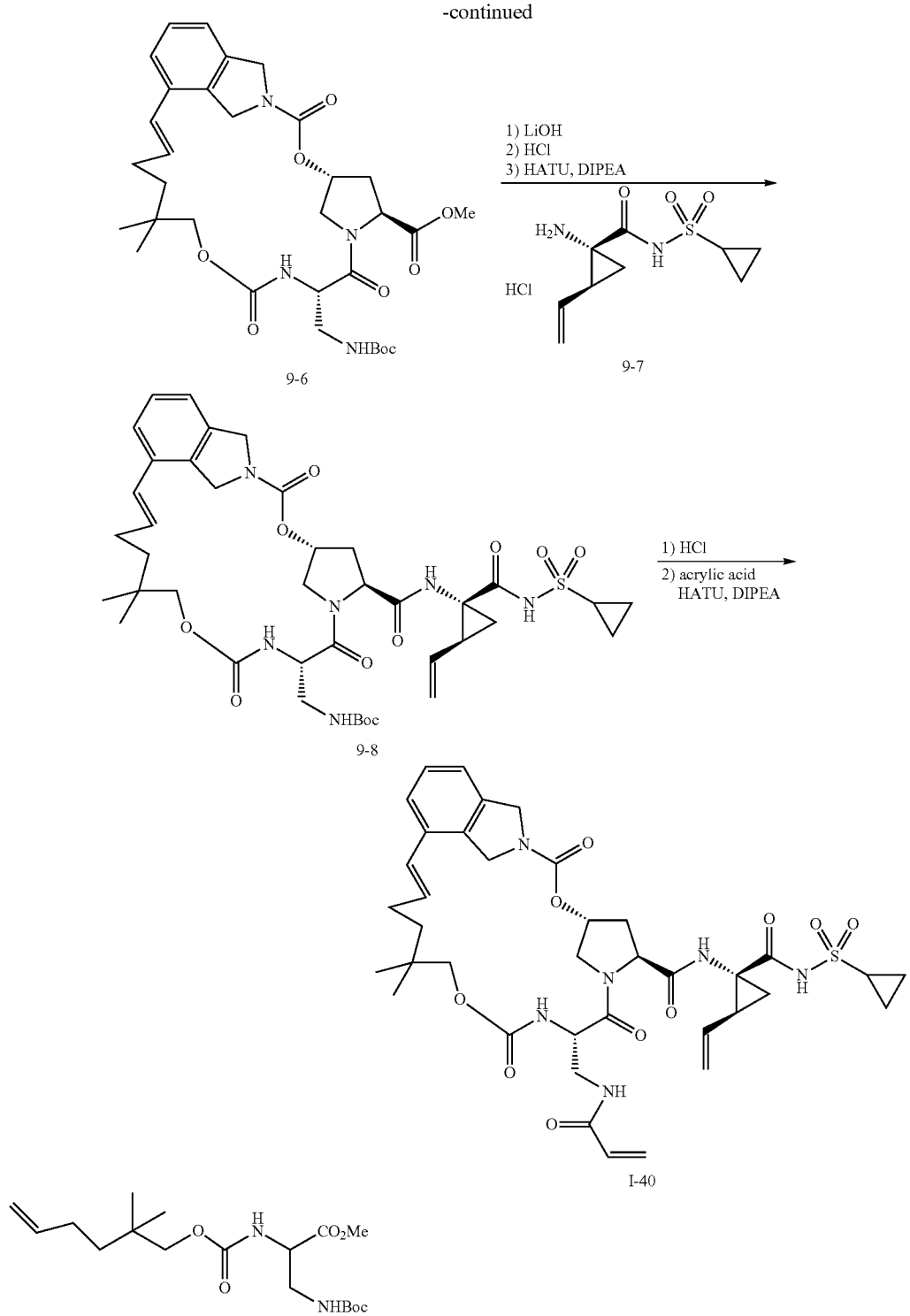

Intermediate 9-1

Methyl 2,2,12,12-tetramethyl-4,9-dioxo-3,10-dioxa-5,8-diazahexadec-15-ene-7-carboxylate (Intermediate 9-1). To a stirring solution of 381 mg of methyl 2-amino-3-(tert-butoxycarbonylamino)propanoate hydrochloride, and 1 mL of Et$_3$N in 10 mL of anhydrous THF, was added 1.5 mmol of 2,2-dimethylhex-5-enyl carbonochloridate. The resulting mixture was stirred at rt overnight, then concentrated. The residue was subject to column chromatography on silica gel with heptanes/EtOAc (v/v 7/1) as eluent, giving 500 mg colorless oil (90%). $^1$HNMR (400 MHz, CDCl$_3$) d 5.82 (m, 1H), 5.64 (br s, 1H), 5.02 (dd, 1H, J=13.2, 1.8 Hz), 4.95 (d, 1H, J=8.2 Hz), 4.83 (br s, 1H), 4.39 (br d, 1H, J=6.0 Hz), 3.83 (br s, 2H), 3.80 (s, 3H), 2.55 (m, 2H), 2.02 (m, 2H), 1.43 (s, 9H), 1.35 (m, 2H), 0.91 (s, 6H).

Intermediate 9-2

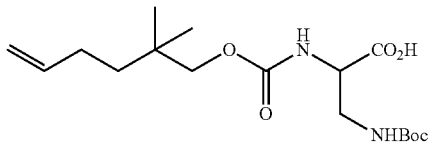 [SMILES: C=CCCC(C)(C)COC(=O)NC(CNC(=O)OC(C)(C)C)C(=O)O]

2,2,12,12-tetramethyl-4,9-dioxo-3,10-dioxa-5,8-diaza-hexadec-15-ene-7-carboxylic acid (Intermediate 9-2). To a stirring mixture of 500 mg of intermediate 8-1 in a mixed solvent of MeOH-THF (5 mL-5 mL), was added 420 mg of LiOH—H$_2$O followed by 5 mL of water. The reaction mixture was stirred at rt for 30 min, then acidified using 12 mL of 1.0 N HCl, and extracted with 60 mL of dichloromethane. The organic layer was washed with brine and dried over MgSO$_4$. After filtration and concentration, 460 mg of sticky oil was obtained as desired product (95%). LC-MS: m/z=357.2 (ES−).

Intermediate 9-3

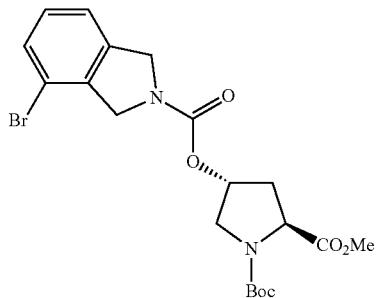 [SMILES: COC(=O)[C@@H]1C[C@@H](OC(=O)N2Cc3cccc(Br)c3C2)CN1C(=O)OC(C)(C)C]

(2S,4R)-1-tert-butyl 2-methyl 4-(4-bromoisoindoline-2-carbonyloxy)pyrrolidine-1,2-dicarboxylate (Intermediate 9-3). To a solution containing 0.5 g of (2S,4R)-1-tert-butyl 2-methyl 4-hydroxypyrrolidine-1,2-dicarboxylate (2 mmol) in 5 mL of N,N-dimethylacetamide, was added 370 mg of carbonyl diimidazole (1.1 equiv.). The reaction was heated at 60° C. for 1 hr, then 400 mg of 4-bromoisoindole (2 mmol) was added. The reaction was continued at 60° C. overnight. After cooling down, the reaction mixture was extracted with 50 mL of EtOAc, and washed with water, brine, and dried over Na$_2$SO$_4$. After filtration and concentration, the residue was purified by flash column chromatography on silica gel using heptanes/EtOAc (v/v 5/2), giving white solid 745 mg (79%). LC-MS: m/z=369.2 (ES+, M+1-Boc).

Intermediate 9-4

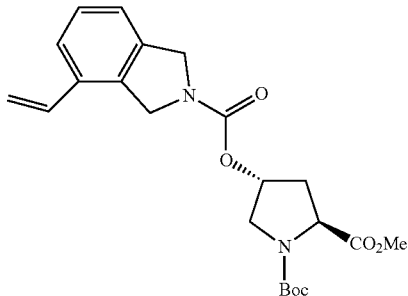 [SMILES: C=Cc1cccc2c1CN(C(=O)O[C@@H]1C[C@@H](C(=O)OC)N(C(=O)OC(C)(C)C)C1)C2]

(2S,4R)-1-tert-butyl 2-methyl 4-(4-vinylisoindoline-2-carbonyloxy)pyrrolidine-1,2-dicarboxylate (Intermediate 9-4). Under Ar, to a solution of 745 mg of intermediate 8-3 (1.58 mmol) in 30 mL of de-gassed toluene, was added 170 mg of palladium tetrakistriphenylphosphine followed by 700 uL of vinyl tributyltin (2.4 mmol). The reaction mixture was heated at 100° C. overnight. After cooling down, the solvent was removed under reduced pressure, and the residue was purified by flash column chromatography on silica gel with heptanes/EtOAc (v/v 9/1-3/1) as eluent, giving white solid 533 mg (81%). LC-MS: m/z=317.2 (ES+, M+1-Boc).

Intermediate 9-5

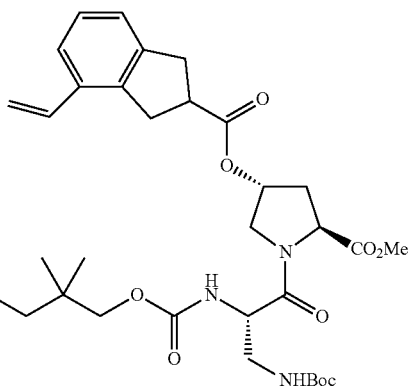

(2S,4R)-methyl 1-((S)-3-(tert-butoxycarbonylamino)-2-((2,2-dimethylhex-5-enyloxy)carbonylamino)propanoyl)-4-(4-vinyl-2,3-dihydro-1H-indene-2-carbonyloxy)pyrrolidine-2-carboxylate (Intermediate 9-5). Intermediate 9-4 was Boc-deprotected using 4 N HCl in dioxane as described in Example 1. 288 mg of this de-Boc intermediate (0.82 mmol) was added to a stirring mixture containing 358 mg of intermediate 9-2 (1.0 mmol), 400 mg of HATU (1.05 mmol), 300 uL of DIPEA in 5 mL of THF. After overnight stirring, the reaction mixture was diluted with 60 mL of EtOAc, and washed with saturated sodium bicarbonate, diluted HCl, and dried over Na$_2$SO$_4$. Concentration and purification by flash column chromatography on silica gel with heptanes/EtOAc (1/1) giving white solid 485 mg (90%). LC-MS: m/z=557.3 (ES+, M+1-Boc).

Intermediate 9-6

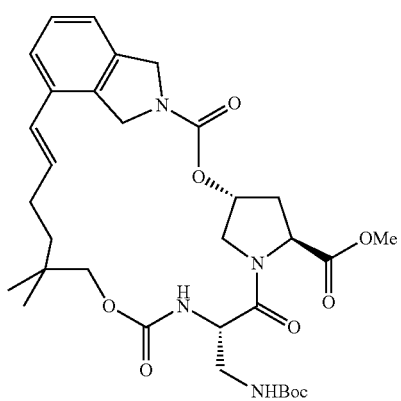 [SMILES: COC(=O)[C@@H]1C[C@@H]2CN1C(=O)[C@H](CNC(=O)OC(C)(C)C)NC(=O)OCC(C)(C)CC/C=C/c1cccc3c1CN(C3)C(=O)O2]

Macrocyclic Intermediate 9-6. Under N$_2$, a diluted solution of 485 mg of intermediate 9-5 and 150 mg Zhan's catalyst 1B were stirred in 100 mL of de-gassed dichloroethane at 50° C. overnight. The reaction mixture was then passed through a short column, then eluted with heptanes/EtOAc (v/v 1/3). The concentrated fraction was then subject to pre-HPLC purification, giving 312 mg of browny solid (70%). LC-MS: m/z=529.2 (ES+, M+1-Boc).

Intermediate 9-8

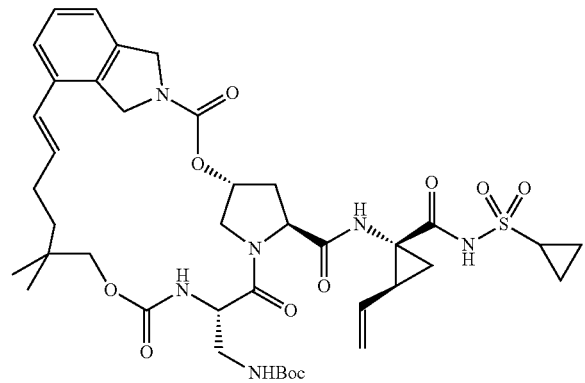 [SMILES: C=C[C@@H]1C[C@]1(NC(=O)[C@@H]1C[C@@H]2CN1C(=O)[C@H](CNC(=O)OC(C)(C)C)NC(=O)OCC(C)(C)CC/C=C/c1cccc3c1CN(C3)C(=O)O2)C(=O)NS(=O)(=O)C1CC1]

Macrocycle Intermediate 9-8. 25 mg of intermediate 9-6 was hydrolyzed in 1 mL of MeOH and 1 mL of THF using 1 mL of 1.0 N LiOH for 1 hr. 1.2 mL of 1.0 N HCl was then added, and the reaction mixture was extracted with 30 mL of dichloromethane. The organic layer was then washed with brine, and dried over MgSO$_4$. After filtration and concentration, the residue was redissolved in 1.5 mL of anhydrous acetonitrile, 25 mg of HATU, 200 uL of DIPEA were then added followed by 13 mg of intermediate 9-7. After stirring at rt for 20 min, the reaction mixture was concentrated and purified directly by prep-HPLC, giving 20 mg yellow solid (61%). LC-MS: m/z=727.2 (ES+, M+1-Boc, 825.2 (ES−).

I-40: To a solution of 20 mg of intermediate 9-8 stirred in 1 L dichloromethane, was added 1.5 mL of 4.0 M HCl in dioxane. After 30 min, the reaction mixture was concentrated. To the residue was added 1.5 mL of acetonitrile, 200 uL of DIPEA, 20 mg of acrylic acid, and 50 mg of HATU. After stirring at rt for 30 min, the reaction mixture was concentrated and purified by prep-HPLC, giving white solid 14.0 mg (68%). LC-MS: m/z=779.3 (ES−), 781.2 (ES+)

In similar fashion, by starting with Intermediate 3c instead of Intermediate 3a, the following compound can be made:

I-41

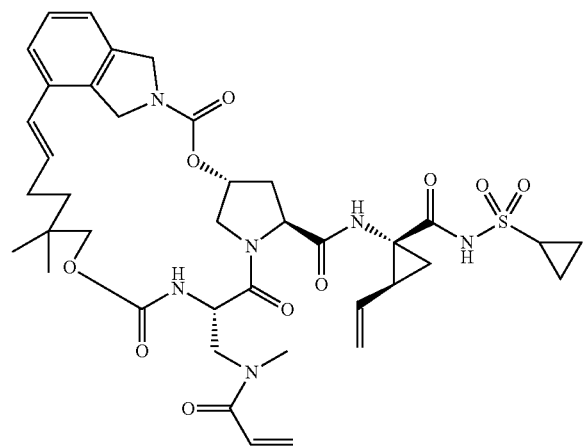

In similar fashion, using the saturated form of Intermediate 9-6, the following compound was made:

I-42

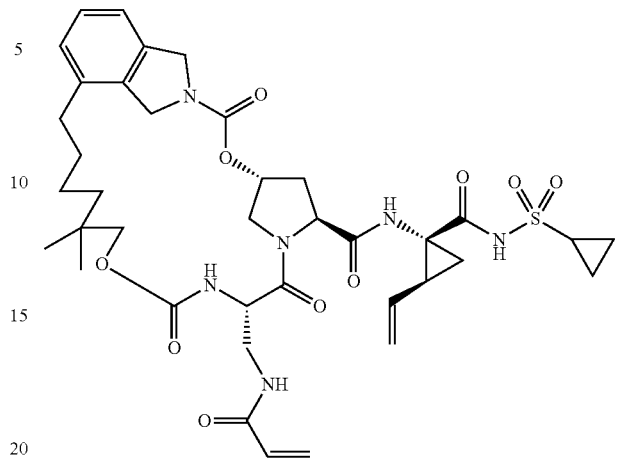

LC-MS: m/z=781.3 (ES−), 783.2 (ES+).

In similar fashion, if both Intermediate 9-7 and Intermediate 9-8 are hydrogenated before coupling, the following compound can be made:

I-43

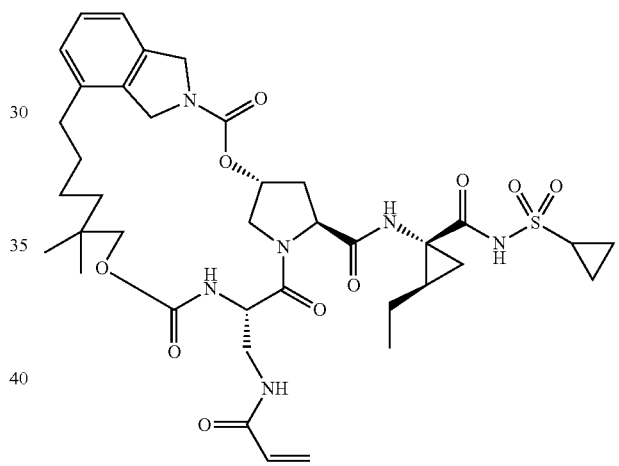

Example 10

I-55

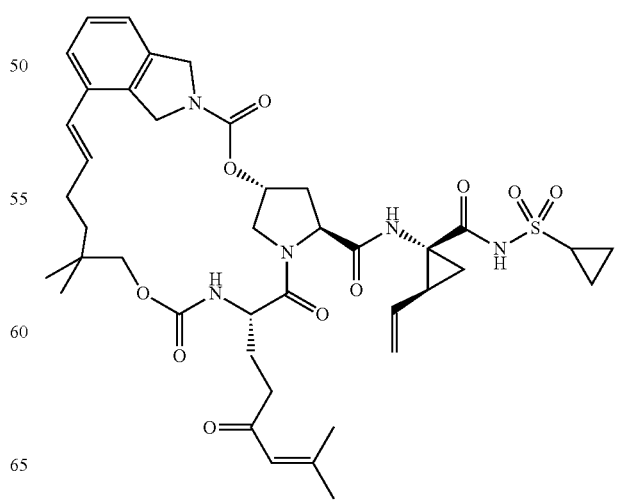

Enone-macrocyclic I-45. The title compound was prepared according to the steps and intermediates as described in the scheme below:
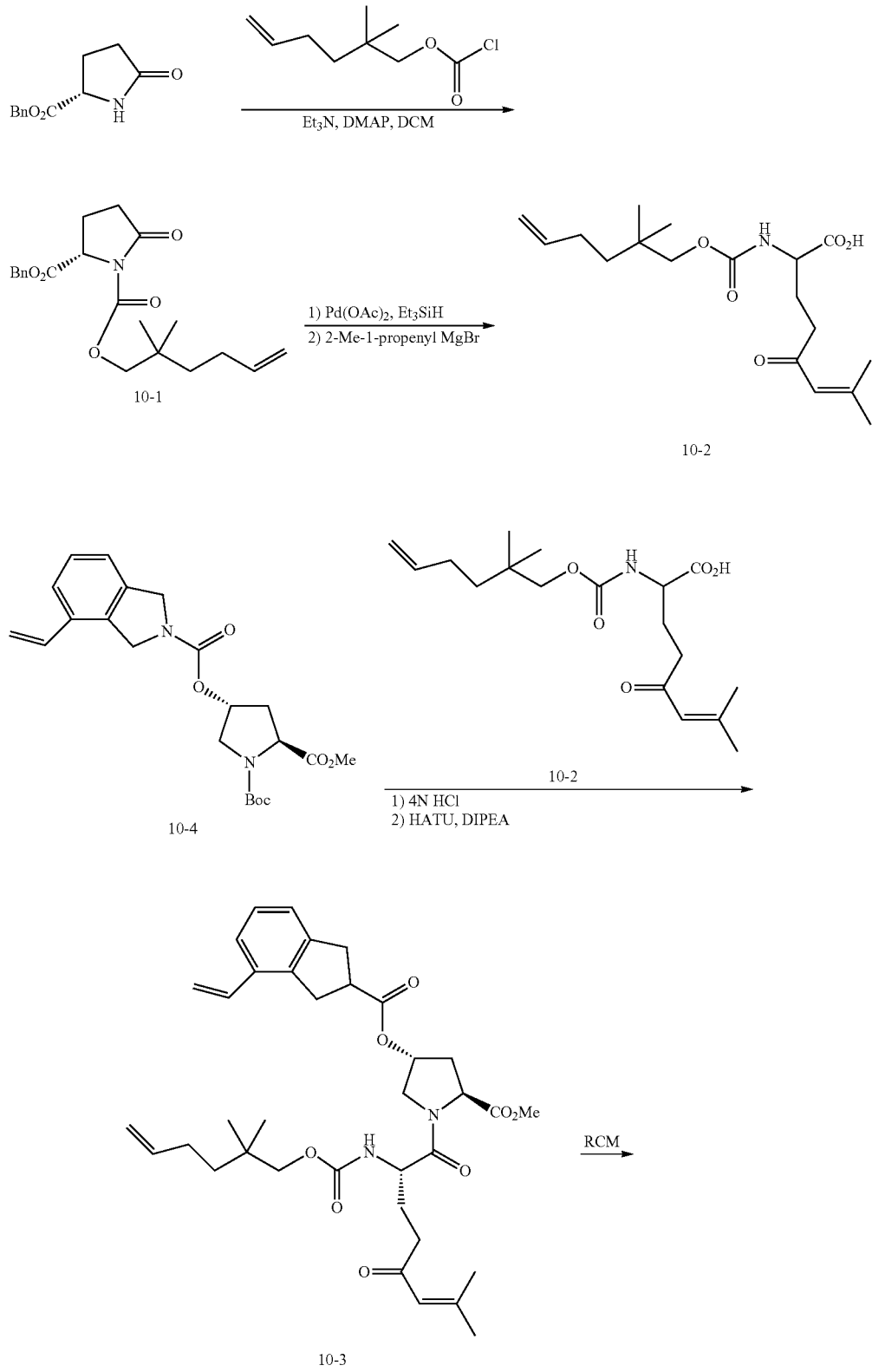

-continued

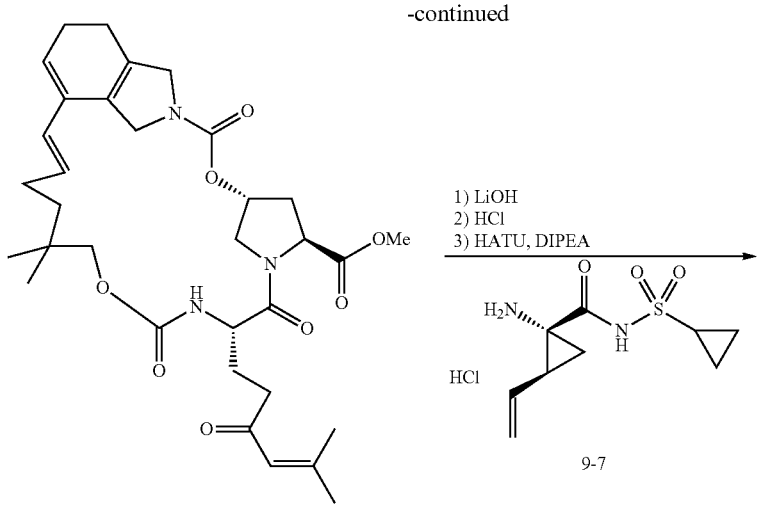

10-4

1) LiOH
2) HCl
3) HATU, DIPEA 9-7

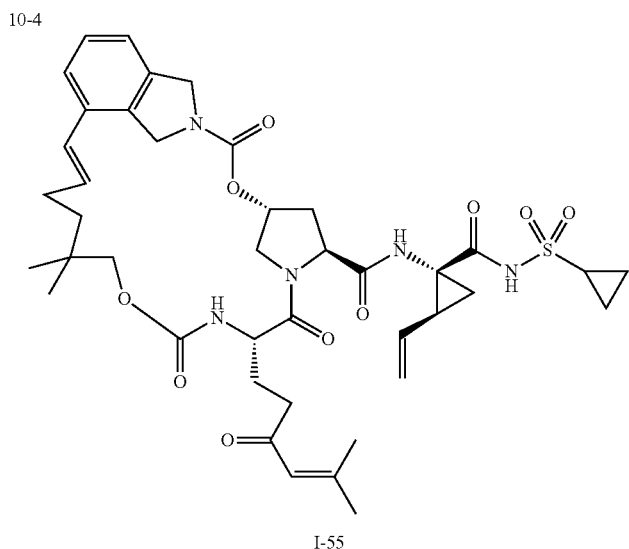

I-55 silica gel using heptane/EtOAc (v/v 4/1-2/1), giving 430 mg of colorless oil as intermediate 10-1 (58%).

Intermediate 10-2

Intermediate 10-1

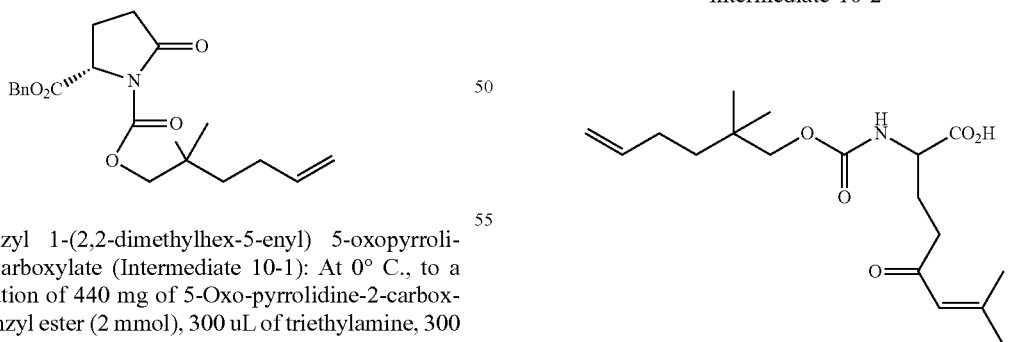

(S)-2-benzyl 1-(2,2-dimethylhex-5-enyl) 5-oxopyrrolidine-1,2-dicarboxylate (Intermediate 10-1): At 0° C., to a stirring solution of 440 mg of 5-Oxo-pyrrolidine-2-carboxylic acid benzyl ester (2 mmol), 300 uL of triethylamine, 300 mg of N,N-dimethylaminopyridine (2.2 mmol) in 7 mL of dichloromethane, was added 2 mmol of 4-pentenyl-1-yl chloroformate. The reaction mixture was then warmed to rt, and stirred 24 hr. After concentration, the resulting residue was dissolved in EtOAc 40 mL, washed with 6 mL of 1.0 N aq. HCl, brine, and dried over anhydrous sodium sulfate. The organic solvent was evaporated under reduced pressure, and the residue was purified by flash chromatography on 2-((2,2-dimethylhex-5-enyloxy)carbonylamino)-7-methyl-5-oxooct-6-enoic acid (Intermediate 10-2). The debenzylation was done with 13 mg of Pd(OAc)$_2$, 24 uL of Et$_3$N, 278 uL of Et$_3$SiH in 2 mL of dichloromethane at rt for 30 min. After filtration, the concentrated residue was subject to Grignard reagent (2.5 equiv) addition at −78° C. for 2 hr.

189

After quenching with diluted acid, the product was extracted with dichloromethane and dried over MgSO$_4$. The concentrated product is desired intermediate 10-2, which was used directly for next step.

Following the general procedures described in Example 9, Intermediate 9-4 was de-Boced with 4 N HCl, then coupled with intermediate 10-2, which produced Intermediate 10-3. Intermediate 10-3 underwent olefin metathesis using either Grubbs catalyst or Zhan's catalyst, to give macrocycle Intermediate 10-4. After basic hydrolysis with LiOH, the acid form of intermediate 10-4 was coupled with Intermediate 9-7, furnishing the title compound I-55. MS: m/e=806.3 (ES$^-$).

In similar fashion, compound I-56 can be prepared when using the saturated form of Intermediate 9-7:

I-56

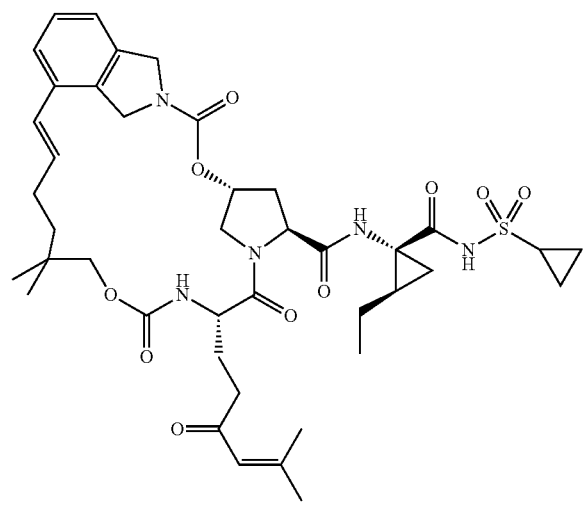

Example 11

Single Chain HCV Protease (Wt) Peptide Expression and Purification

The single-chain proteolytic domain (NS4A$_{21-32}$-GSGS-NS$_{33-631}$) was cloned into pET-14b (Novagen, Madison, Wis.) and transformed into DH10B cells (Invitrogen). The resulting plasmid was transferred into *Escherichia coli* BL21 (Novagen) for protein expression and purification as described previously (1, 2). Briefly, the cultures were grown at 37° C. in LB medium containing 100 µg/mL of ampicillin until the optical density at 600 nm (OD600) reached 1.0 and were induced by addition of isopropyl-β-D-thiogalactopyranoside (IPTG) to 1 mM. After an additional incubation at 18° C. for 20 h, bacteria were harvested by centrifugation at 6,000×g for 10 min and resuspended in a lysis buffer containing 50 mM Na$_3$PO$_4$, pH 8.0, 300 mM NaCl, 5 mM 2-mercaptoethanol, 10% glycerol, 0.5% Igepal CA630, and a protease inhibitor cocktail consisting of 1 mM phenylmethylsulfonyl fluoride, 0.5 µg/mL leupeptin, pepstatin A, and 2 mM benzamidine. Cells were lysed by freezing and thawing, followed by sonication. Cell debris was removed by centrifugation at 12,000×g for 30 min. The supernatant was further clarified by passing through a 0.45-µm filter (Corning) and then loaded onto a HiTrap chelating column charged with NiSO$_4$ (Amersham Pharmacia Biotech). The bound protein was eluted with an imidazole solution in a 100-to-500 mM linear gradient. Selected fractions were run through Ni$^{2+}$ column chromatography and were analyzed on a 10% sodium dodecyl sulfate (SDS)-polyacrylamide gel. The purified protein was resolved by electrophoresis in a 12% SDS-PAGE gel and then transferred onto a nitrocellulose membrane. The protein was analyzed by Western blot analysis using monoclonal antibodies against NS3. Proteins were visualized by using a chemiluminescence kit (Roche) with horseradish peroxidase-conjugated goat anti-mouse antibodies (Pierce) as secondary antibodies. The protein was aliquoted and stored at −80° C.

Example 12

Cloning and Expression of HCV Protease A156S, A156T, D168A, D168V Drug-Resistance Mutants and C159S Variant The mutant DNA fragments of NS4A/NS3 were generated by PCR and cloned into pET expression vector. After transformation into BL21 competent cells, the expression was induced with IPTG for 2 hours. The His-tagged fusion proteins were purified using affinity column followed by size exclusion chromatography.

Example 13

Assay buffer: 2% CHAPS, 50 mM Tris pH 7.5, 50% glycerol, 2 uM M-2235 (Bachem) substrate. In a 50 ul reaction, add 49 ul assay buffer, 1 ul (1U) HCV serine protease (Bioenza). Incubate 20 minutes at room temperature. The plate was read at either 350/460 nm (excitation/emission) on a fluorescent micro-plate reader or monitored at one-minute intervals to achieve the kinetic curve.

The enzyme tolerated 1% DMSO and 2% methanol. In the experiments of testing compounds, the compounds in pure DMSO were diluted 10 times with 20% methanol (10% DMSO and 20% methanol). This compound solution was added to the reaction (not exceeding 10% of the final reaction volume). The final concentration of the organic solvents was: 1% DMSO and 2% methanol.

Example 14

Additional Assay Protocols
Method A:
The compounds were assayed to evaluate the antiviral activity and cytotoxicity of compounds in vitro using HCV RNA replicons. This assay used the cell line ET (luc-ubi-neo/ET), which is a human Huh7 hepatoma cell line that contains an HCV RNA replicon with a stable luciferase (Luc) reporter and three cell culture-adaptive mutations. The HCV RNA levels were directly measured by viral specific TaqMan RT-PCR:

```
Forward primer:
                                        (SEQ ID NO: 63)
ACGCAGAAAGCGTCTAGCCAT Reverse primer:
                                        (SEQ ID NO: 64)
TACTCACCGGTTCCGCAGA Probe:
                                        (SEQ ID NO: 65)
[6-FAM]-CCTGGAGGCTGCACGACACTCAT-[TAMRA]
```

The ET cell line was grown in Dulbecco's modified essential media (DMEM), 10% fetal bovine serum (FBS), 1% penicillin-streptomycin (pen-strep), 1% glutamine, 250 μg/mL G418 in a 5% $CO_2$ incubator at 37° C. All cell culture reagents were obtained from Mediatech (Manassas, Va.). Cells were trypsinized (1% trypsin:EDTA) and plated out at $5 \times 10^3$ cells/well in white 96-well assay plates (Costar) dedicated to cell number (cytotoxicity) or antiviral activity assessments. Drugs were added at six 3-fold concentrations each and the assay was run in DMEM, 5% FBS, 1% pen-strep, 1% glutamine. Human interferon alpha-2b (PBL Biolabs, New Brunswick, N.J.) was included in each run as a positive control compound. Cells were processed 72 hr post drug addition when the cells are still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by CytoTox-1 reagent (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values. $IC_{50}$ values for selected compounds are set forth in Table 5, below.

Method B: HCV Protease Assay Using FRET Methodology

A quantitative, fluorescence resonance energy transfer (FRET)-based methodology was employed to identify HCV NS3/4A protease inhibitors. The assay employed a synthetic FRET peptide, derived from the HCV NS5A/5B cleavage site, with the HCV protease to evaluate the activity of compounds against the protease by monitoring the cleavage activity of the complex. A synthetic peptide which encompasses the NS5A-5B junction (NH2-EDVVCCSMSYK-COOH) was labeled with Dabcyl and Edans at N- and C-termini, respectively (Invitrogen, Carlsbad, Calif.). Fluorescence measurement was used to estimate the $IC_{50}$ value of the test compound. The two fluorophores form a quenching pair and exhibit FRET within the intact peptide. Upon cleavage of the FRET peptide by HCV NS3/4A proteinase complex (100 ng/mL), the fluorescence is recovered and can be continuously monitored at excitation/emission=340/490 nm.

Example 15

HCV Protease FRET Assay for Wild Type and Mutated NS3/4A 1b Enzymes ($IC_{50}$)

The following protocol was used to generate $IC_{50}$ values as depicted for compound 239 in Table 4, above. The protocol is a modified FRET-based assay (v_02) from *In Vitro Resistance Studies of HCV Serine Protease Inhibitors*, 2004, JBC, vol. 279, No. 17, pp17508-17514. Inherent potency of compounds was assessed against A156S, A156T, D168A, and D168V mutants of the HCV NS3/4A 1b protease enzyme as follows:

10× stocks of NS3/4A protease enzyme from Bioenza (Mountain View, Calif.) and 1.13×5-FAM/QXL™ 520 FRET peptide substrate from Anaspec (San Jose, Calif.) were prepared in 50 mM HEPES, pH 7.8, 100 mM NaCl, 5 mM DTT and 20% glycerol. 5 μL of each enzyme were pre-incubated in a Corning (#3573) 384-well, black, non-treated microtiter plate (Corning, N.Y.) for 30 min at 25° C. with a 0.5 μL volume of 50% DMSO and serially diluted compounds prepared in 50% DMSO. Protease reactions were started with the addition of 45 μL of the FRET substrate and monitored for 120 minutes at $\lambda_{ex}487/\lambda_{em}514$ through $Quad^4$ monochromoters in a $Synergy^4$ plate reader from BioTek (Winooski, Vt.). At the conclusion of each assay, progress curves from each well were examined for linear reaction kinetics and fit statistics ($R^2$, absolute sum of squares). Initial velocity (0 minutes to 30+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.). $IC_{50}$ values for selected compounds are set forth in Table 5, below.

Table 5 shows the activity of selected compounds of this invention in the FRET Assay. The compound numbers correspond to the compound numbers in Table 3. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 5

Enzymatic Data for Exemplary Compounds ($IC_{50}$)

| Compound tested | Enzyme/Assay | Inhibition |
|---|---|---|
| (I-1) | WT | A |
|  | HCV A156S | A |
|  | HCV A156T | A |
|  | HCV D168A | A |
|  | HCV D168V | A |
| (I-6) | WT | A |
|  | HCV A156S | A |
|  | HCV A156T | A |
|  | HCV D168A | B |
|  | HCV D168V | B |
| (I-7) | WT | B |
|  | D168A | D |
| (I-11) | WT | A |
|  | D168A | B |

Example 16

HCV Protease FRET Assay for WT and Mutated NS3/4A 1b Enzymes ($IC_{50\_APP}$)

The following protocol was used to generate "apparent" $IC_{50}$ ($IC_{50\_APP}$) values as depicted in Table 6, below. Without wishing to be bound by any particular theory, it is believed that $IC_{50\_APP}$, contrasted with $IC_{50}$ values, may provide a more useful indication of time-dependent inhibition, and are thus more representative of binding affinity. The protocol is a modified FRET-based assay (v_03) developed to evaluate compound potency, rank-order and resistance profiles against wild type and C159S, A156S, A156T, D168A, D168V, R155K mutants of the HCV NS3/4A 1b protease enzyme as follows: 10× stocks of NS3/4A protease enzyme from Bioenza (Mountain View, Calif.) and 1.13×5-FAM/QXL™ 520 FRET peptide substrate from Anaspec (San Jose, Calif.) were prepared in 50 mM Tris-HCl, pH 7.5, 5 mM DTT, 2% CHAPS and 20% glycerol. 5 μL of each enzyme were added to Corning (#3575) 384-well, black, microtiter plates (Corning, N.Y.) after spotting a 0.5 μL volume of 50% DMSO and serially diluted compounds prepared in 50% DMSO. Protease reactions were immediately started after enzyme addition with the addition of 45 μL of the FRET substrate and monitored for 60-90 minutes at $\lambda_{ex}485/\lambda_{em}520$ in a $Synergy^4$ plate reader from BioTek (Winooski, Vt.). At the conclusion of each assay, progress curves from each well were examined for linear reaction kinetics and fit statistics ($R^2$, 95% confidence intervals, absolute sum of squares). Initial velocity (0 minutes to 15+ minutes) from each reaction was determined from the slope of a plot of relative fluorescence units vs time (minutes) and then plotted against inhibitor concentration as a percent of the no inhibitor and no enzyme controls to estimate apparent $IC_{50}$ from log [Inhibitor] vs Response, Variable Slope model in GraphPad Prism from GraphPad Software (San Diego, Calif.).

Table 6 shows the activity of selected compounds of this invention in the FRET Assay. The compound numbers correspond to the compound numbers in Table 3. Compounds having an activity designated as "A" provided an $IC_{50} \leq 10$ nM; compounds having an activity designated as "B" provided an $IC_{50} > 10$ nM and $\leq 100$ nM; compounds having an activity designated as "C" provided an $IC_{50} > 100$ nM and $\leq 1000$ nM; compounds having an activity designated as "D" provided an $IC_{50} > 1000$ nM and $< 10,000$ nM; and compounds having an activity designated as "E" provided an $IC_{50} \geq 10,000$ nM.

TABLE 6

Enzymatic Data for Exemplary Compounds

| Compound tested | Enzyme/Assay | Inhibition |
|---|---|---|
| (I-1) | WT | A |
|  | HCV A156S | A |
|  | HCV A156T | B |
|  | HCV D168A | C |
|  | HCV D168V | B |
|  | Replicon [2] | B |
|  | Replicon [2] | B [1] |
| (I-2) | WT | A |
|  | HCV A156S | A |
|  | HCV A156T | A |
|  | HCV D168A | A |
|  | HCV D168V | A |
|  | Replicon [2] | B |
|  | Replicon [2] | C [1] |
| (I-5) | WT | A |
|  | HCV A156S | A |
|  | HCV A156T | B |
|  | HCV D168A | C |
|  | HCV D168V | B |
|  | Replicon [2] | B |
|  | Replicon [2] | C [1] |
| (I-6) | WT | A |
|  | HCV A156S | A |
|  | HCV A156T | A |
|  | HCV D168A | C |
|  | HCV D168V | C |
|  | Replicon [2] | C |
|  | Replicon [2] | D [1] |
| (I-7) | WT | C |
|  | HCV A156S | C |
|  | HCV A156T | C |
|  | HCV D168A | D |
|  | HCV D168V | D |
| (I-8) | WT | A |
|  | HCV A156S | A |
|  | HCV A156T | A |
|  | HCV D168A | A |
|  | HCV D168V | B |
| (I-9) | WT | A |
|  | HCV A156S | A |
|  | HCV A156T | A |
|  | HCV D168A | B |
|  | HCV D168V | C |
| (I-10) | WT | C |
|  | HCV A156S | C |
|  | HCV A156T | D |
|  | HCV D168A | D |
|  | HCV D168V | D |

TABLE 6-continued

Enzymatic Data for Exemplary Compounds

| Compound tested | Enzyme/Assay | Inhibition |
|---|---|---|
| (I-11) | WT | A |
|  | HCV A156S | A |
|  | HCV A156T | A |
|  | HCV D168A | B |
|  | HCV D168V | B |
|  | HCV R155K | B |
|  | Replicon [2] | A |
|  | Replicon [2] | B [1] |
| (I-13) | WT | A |
|  | HCV A156S | A |
|  | HCV A156T | A |
|  | HCV D168A | C |
|  | HCV D168V | B |
|  | Replicon [2] | B |
|  | Replicon [2] | C [1] |
| (I-19) | WT | A |
|  | HCV A156S | A |
|  | HCV A156T | A |
|  | HCV D168A | B |
|  | HCV D168V | B |
| (I-20) | WT | A |
|  | HCV A156S | A |
|  | HCV A156T | A |
|  | HCV D168A | B |
|  | HCV D168V | B |
|  | Replicon [2] | B |
|  | Replicon [2] | C [1] |
| (I-22) | WT | A |
|  | HCV A156S | A |
|  | HCV A156T | B |
|  | HCV D168A | C |
|  | HCV D168V | C |
|  | HCV R155K | B |
|  | Replicon [2] | B |
|  | Replicon [2] | B [1] |
| (I-23) | WT | A |
|  | HCV A156S | A |
|  | HCV A156T | A |
|  | HCV D168A | A |
|  | HCV D168V | B |
|  | Replicon [2] | B |
|  | Replicon [2] | C [1] |
| (I-24) | WT | A |
|  | HCV A156S | A |
|  | HCV A156T | A |
|  | HCV D168A | A |
|  | HCV D168V | A |
|  | Replicon [2] | B |
|  | Replicon [2] | C [1] |
| (I-25) | WT | A |
|  | HCV A156S | A |
|  | HCV A156T | B |
|  | HCV D168A | C |
|  | HCV D168V | C |
|  | HCV R155K | B |
|  | Replicon [2] | A |
|  | Replicon [2] | B [1] |
| (I-26) | WT | A |
|  | HCV A156S | A |
|  | HCV A156T | A |
|  | HCV D168A | A |
|  | HCV D168V | A |
| (I-27) | WT | A |
|  | HCV A156S | A |
|  | HCV A156T | A |
|  | HCV D168A | A |
|  | HCV D168V | A |
|  | Replicon [2] | B |
|  | Replicon [2] | C [1] |
| (I-32) | WT | A |
|  | HCV A156S | A |
|  | HCV D168A | B |
|  | HCV R155K | B |
|  | HCV C159S | A |
|  | HCV D168V | B |
|  | HCV A156T | A |

TABLE 6-continued

Enzymatic Data for Exemplary Compounds

| Compound tested | Enzyme/Assay | Inhibition |
|---|---|---|
| (I-33) | WT | A |
| | HCV A156S | B |
| | HCV D168A | D |
| | HCV R155K | C |
| (I-35) | WT | A |
| | HCV A156S | A |
| | HCV D168A | B |
| | HCV R155K | B |
| | Replicon | C [3] |
| | Replicon | C [4] |
| (I-36) | WT | A |
| | HCV A156S | A |
| | HCV D168A | A |
| | HCV R155K | A |
| | Replicon | C [3] |
| | Replicon | C [4] |
| (I-37) | WT | A |
| | HCV A156S | A |
| | HCV D168A | B |
| | HCV R155K | B |
| | Replicon | C [3] |
| | Replicon | D [4] |
| (I-39) | WT | A |
| | HCV A156S | A |
| | HCV D168A | C |
| | HCV R155K | B |
| (I-40) | WT | A |
| | HCV A156S | A |
| | HCV D168A | B |
| | HCV R155K | A |
| (I-42) | WT | A |
| | HCV A156S | A |
| | HCV D168A | B |
| | HCV R155K | B |
| (I-44) | WT | A |
| | HCV A156S | B |
| | HCV D168A | D |
| | HCV R155K | D |
| (I-45) | WT | A |
| | HCV A156S | A |
| | HCV D168A | A |
| | HCV R155K | A |
| | Replicon | B [3] |
| | Replicon | C [4] |
| (I-46) | WT | A |
| | HCV A156S | A |
| | HCV D168A | B |
| | HCV R155K | A |
| | Replicon | D [3] |
| | Replicon | D [4] |
| (I-47) | WT | A |
| | HCV A156S | A |
| | HCV D168A | B |
| | HCV R155K | B |
| | Replicon | B [3] |
| | Replicon | C [4] |
| (I-48) | WT | B |
| | HCV A156S | B |
| | HCV D168A | C |
| | HCV R155K | C |
| (I-49) | WT | C |
| | HCV A156S | C |
| | HCV D168A | D |
| | HCV R155K | D |
| | Replicon | D [3] |
| | Replicon | D [4] |
| (I-50) | WT | B |
| | HCV A156S | C |
| | HCV D168A | D |
| | HCV R155K | D |
| | Replicon | D [3] |
| | Replicon | D [4] |
| (I-51) | WT | A |
| | HCV A156S | A |
| | HCV D168A | B |
| | HCV R155K | B |
| | Replicon | C [3] |
| | Replicon | D [4] |
| (I-52) | WT | B |
| | HCV D168A | D |
| | Replicon | D [3] |
| | Replicon | D [4] |
| (I-53) | WT | A |
| | HCV A156S | A |
| | HCV D168A | A |
| | HCV R155K | A |
| | Replicon | B [3] |
| | Replicon | C [4] |
| (I-54) | WT | A |
| | HCV A156S | A |
| | HCV D168A | B |
| | HCV R155K | B |
| | Replicon | C [3] |
| | Replicon | E [4] |
| (I-55) | WT | A |
| | HCV A156S | A |
| | HCV D168A | B |
| | HCV R155K | B |

[1] Designates $IC_{90}$ value (nM).
[2] Data collected from assay described in Example 14.
[3] Designates $EC_{50}$ value (nM). Data collected from assay described in Example 26.
[4] Designates $EC_{90}$ value (nM). Data collected from assay described in Example 26.

Example 17

Mass spectrometric analysis of HCV wild type or HCV variant C159S in the presence of test compound is performed. 100 pmols of HCV wild type (Bioenza CA) is incubated with test compound for 1 hr and 3 hrs at 10-fold access of test compound to protein. 1 ul aliquots of the samples (total volume of 4.24 ul) are diluted with 10 ul of 0.1% TFA prior to micro C4 ZipTipping directly onto the MALDI target using Sinapinic acid as the desorption matrix (10 mg/mL in 0.1% TFA:Acetonitrile 50:50). Analyses are performed on a Shimadzu Biotech Axima TOF$^2$ (Shimadzu Instruments) matrix-assisted-laser desorption/ionization Time-of-Flight (MALDI-TOF) mass spectrometer. The same procedure is carried out on 100 pmols of HCV C159S mutant of HCV protease for 3 hrs at 10-fold excess of test compound to protein.

Example 18

Modification of Cys159 of Wild-Type HCV Protease Using a Tryptic Digest Strategy HCV is incubated with test compound for 3 hrs prior to tryptic digestion. Iodoacetamide is used as the alkylating agent after compound incubation. For tryptic digests a 2 ul aliquot (0.06 ug/ul) is diluted with 10 ul of 0.1% TFA prior to micro C18 Zip Tipping directly onto the MALDI target using alpha cyano-4-hydroxy cinnamic acid as the matrix (5 mg/mL in 0.1% TFA:Acetonitrile 50:50).

For tryptic digests the instrument is set in Reflectron mode with a pulsed extraction setting of 1800. Calibration is done using the Laser Biolabs Pep Mix standard (1046.54, 1296.69, 1672.92, 2093.09, 2465.20). For CID/PSD analysis the peptide is selected using cursors to set ion gate timing and fragmentation occurred at a laser power about 20% higher and He is used as the collision gas for CID. Calibration for fragments is done using the P14R fragmentation calibration for the Curved field Reflectron.

Example 19

Figure 2:
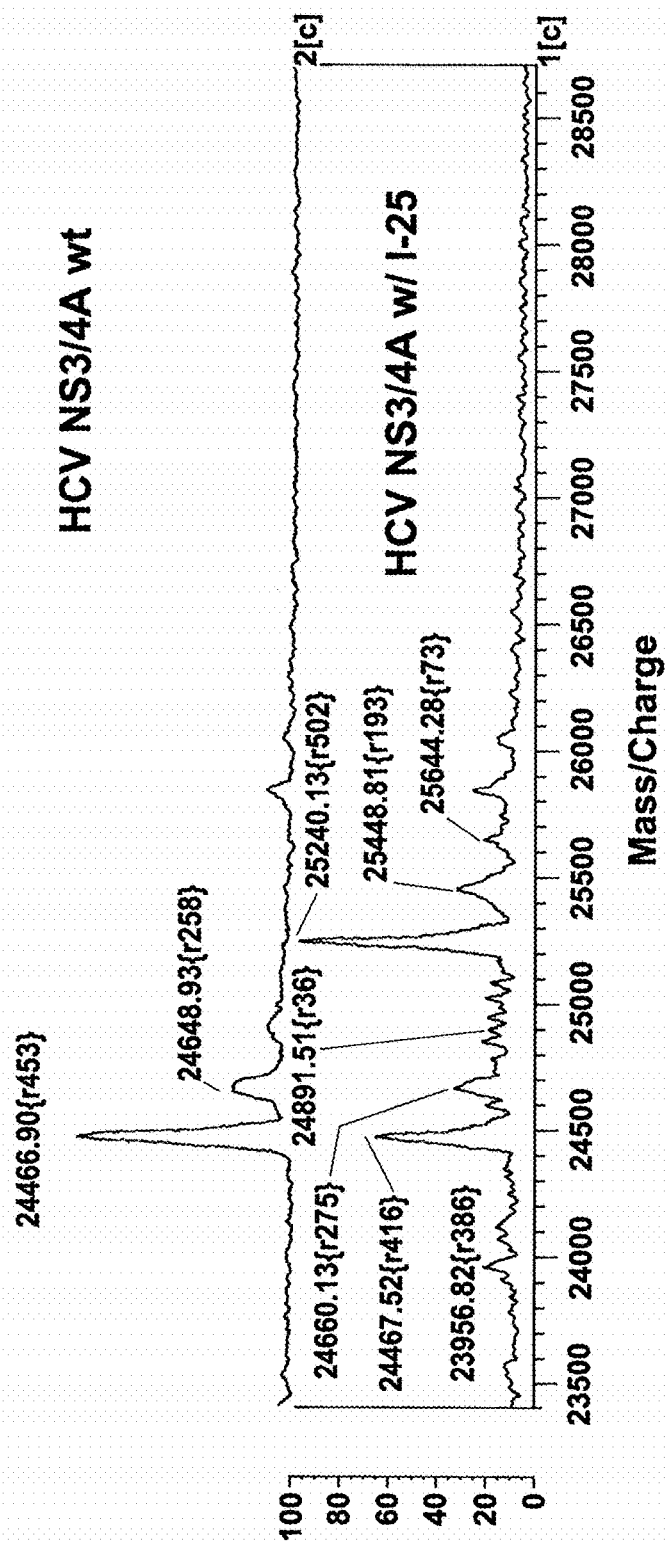
FIG. 2 depicts a mass spectroscopic analysis of HCV NS3/4A wild-type protease in the presence of test compound I-25.
Figure 3:
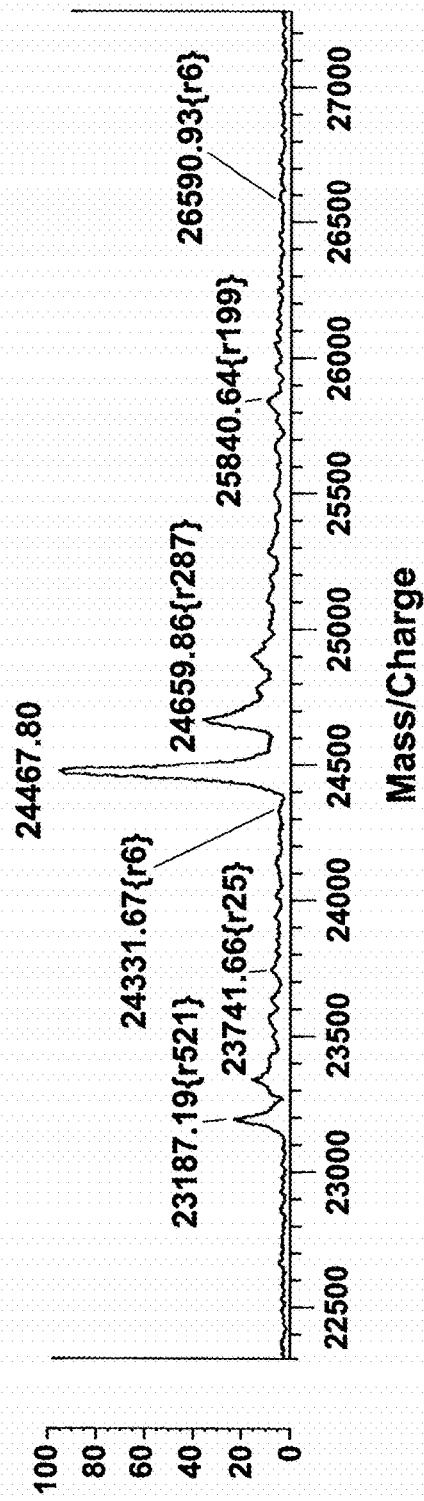
FIG. 3 depicts a mass spectroscopic analysis of HCV NS3/4A protease.

As depicted in FIGS. 1 and 2, mass spectrometric analysis of HCV wild type in the presence of test compounds I-1 and I-25 was performed using the following protocol: HCV NS3/4A wild type (wt) was incubated for 1 hr at a 10× fold access of test compound to protein. 2 ul aliquots of the samples were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). For intact protein mass measurement the instrument was set in linear mode using a pulsed extraction setting of 24,500 and apomyoglobin as the standard to calibrate the instrument.

As depicted in FIG. 1, compared to the protein with no compound, the protein incubated with compound I-1 has reacted significantly to produce a new species at MW 25,218 Da, which is approximately 751 Da heavier and consistent with the mass of compound I-1 at 747 Da.

As depicted in FIG. 2, after 1 hour reaction time there was conversion to a new peak at MH+ of 25,240 Da which is 773 Da heavier and consistent with the mass of compound I-25.

Compounds I-2, I-5, I-6, I-8, I-9, I-10, I-13, I-19, I-20, I-22, I-23, I-24, I-26, and I-27 were tested in a similar fashion, using the methods described in Example 17, and measurable covalent modification of HCV NS3/4A wild type was observed.

Example 20

As depicted in FIGS. 4, 5, 6, and 7, mass spectrometric analysis of HCV mutants in the presence of compound I-11 was performed. HCV Mutants (A156S), (R155K), (D168A), (A156T), and (D168V) were incubated for 3 hrs at a 10× fold access of test compound to protein. 2 ul aliquots of the samples were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). For intact protein mass measurement the instrument was set in linear mode using a pulsed extraction setting of 24,500 and apomyoglobin as the standard to calibrate the instrument.

Figure 4:
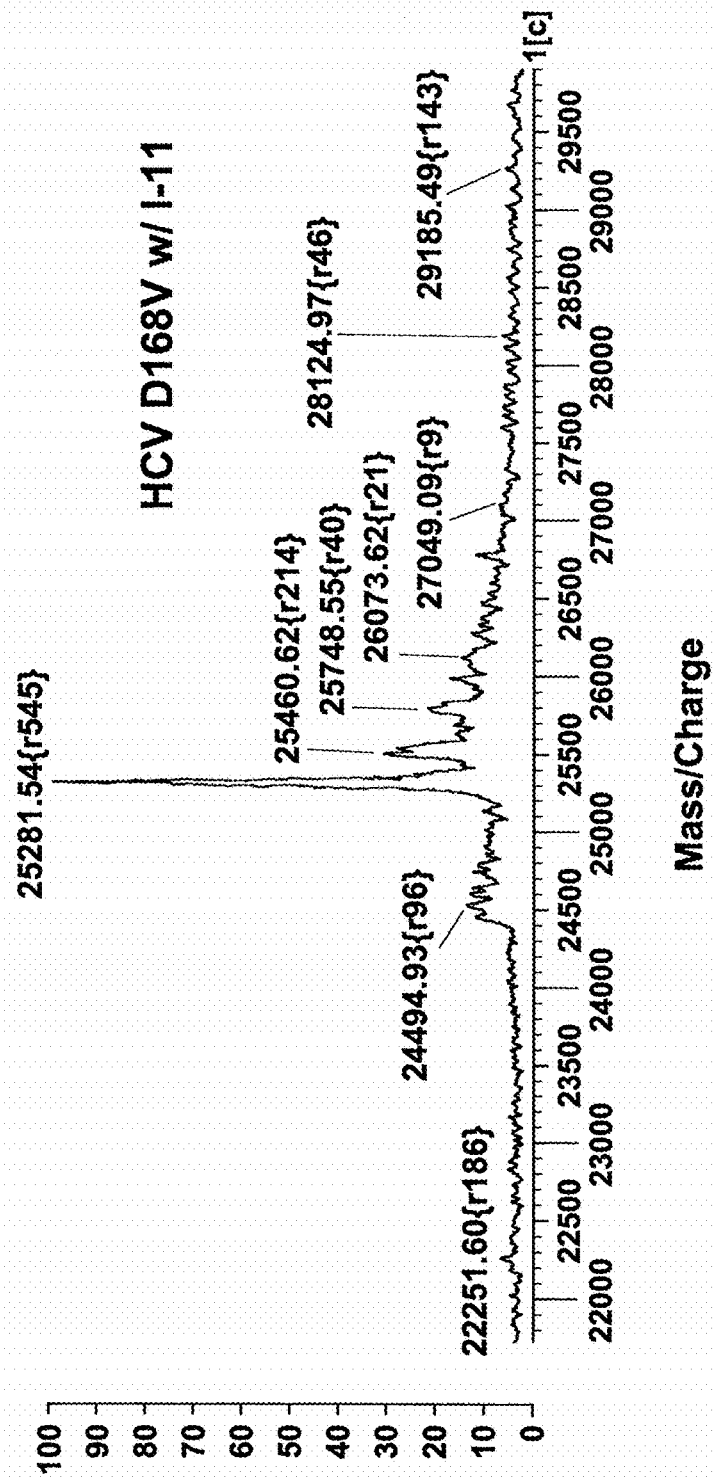
FIG. 4 depicts a mass spectroscopic analysis of HCV NS3/4A mutant D168V protease in the presence of test compound I-11.

As depicted in FIG. 4, for the HCV (D168V) mutant there is complete conversion after 3 hours reaction time. The mass difference between the new species and the unreacted mutant is consistent with the mass of compound I-11.

Figure 5:
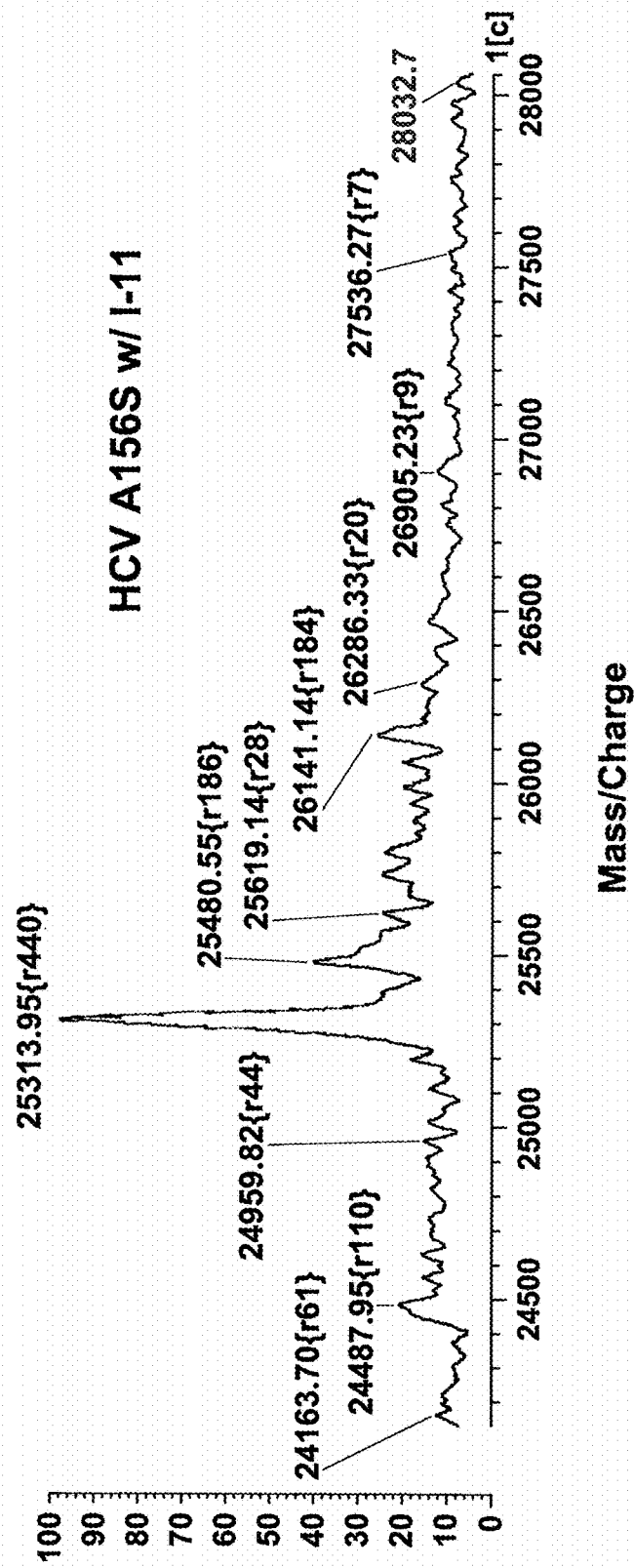
FIG. 5 depicts a mass spectroscopic analysis of HCV NS3/4A mutant A156S protease in the presence of test compound I-11.

As depicted in FIG. 5, for the HCV (A156S) mutant there is complete conversion after 3 hours reaction time. The mass difference between the new species and the unreacted mutant is consistent with the mass of compound I-11.

Figure 6:
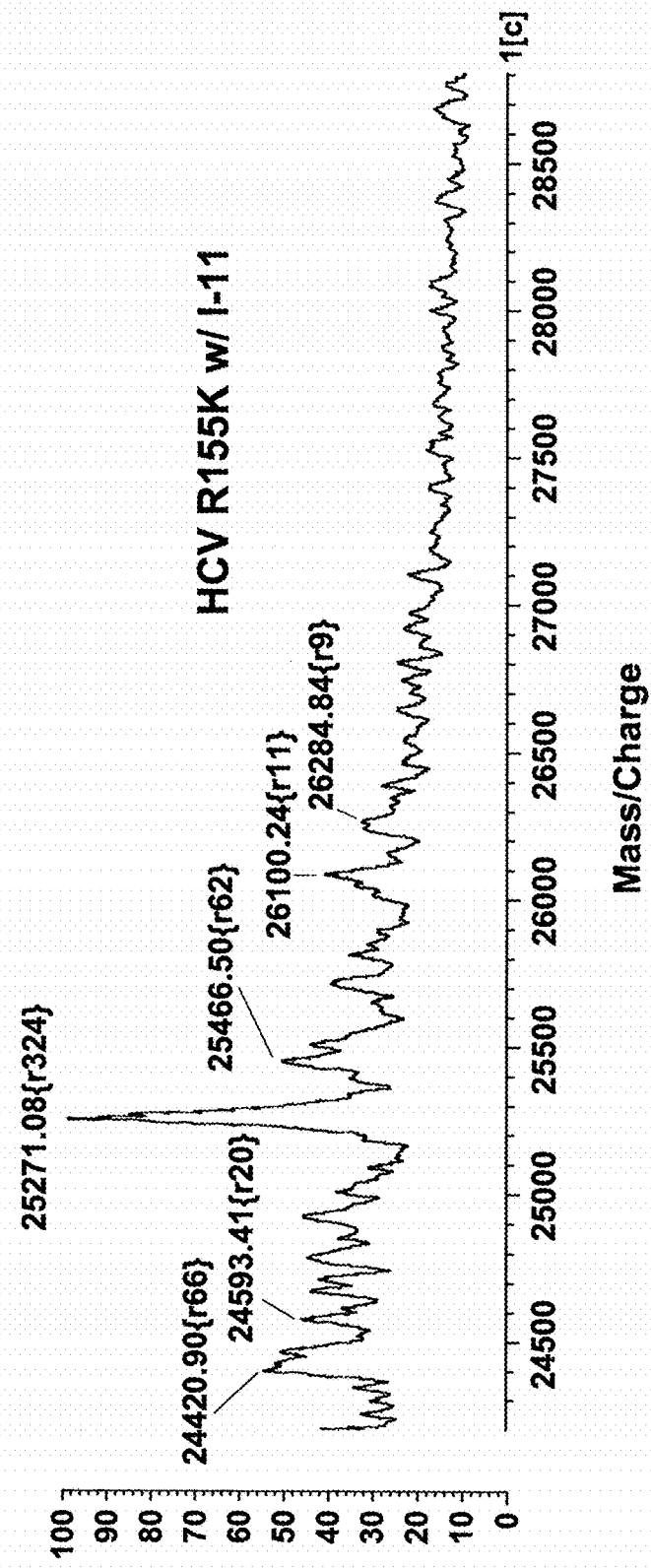
FIG. 6 depicts a mass spectroscopic analysis of HCV NS3/4A mutant R155K protease in the presence of test compound I-11.

As depicted in FIG. 6, for the HCV (R155K) mutant there is good conversion after 3 hours reaction time. The mass difference between the new species and the unreacted mutant is consistent with the mass of compound I-11.

As depicted in FIG. 7, for the HCV (A156T) mutant there is complete conversion after 3 hours reaction time. The mass difference between the new species and the unreacted mutant is consistent with the mass of compound I-11.

Compounds I-19 and I-24 were tested in a similar fashion using the methods described in Example 18, and measurable covalent modification of HCV NS3/4A D168A was observed.

Example 21

Cell Culture

Huh-luc/neo-ET, Huh7-Lunet were obtained from ReBLikon Gmbh (Heidelberg, Germany). Cells were grown in Dulbecco modified Eagle medium (DMEM; Invitrogen) supplemented with 2 mM L-glutamine, nonessential amino acids, 100 U of penicillin/ml, 100 μg of streptomycin/mL, and 10% fetal bovine serum. G418 (Geneticin; Invitrogen) was added at a final concentration of 400 ug/mL. Huh7-Lunet were grown in the absence of G418.

Example 22

Mutant Constructs

Constructs containing clinically relevant mutations were generated by performing site-directed mutagenesis on the pFK-I389-luc-ubi-neo-NS3-3'ET plasmid (ReBLikon Gmbh (Heidelberg, Germany)). using the QuickChange II Site-Directed Mutagenesis Kit (Stratagene, La Jolla, Calif.) according to manufacturer's directions and with the primers described in Table 7, below.

TABLE 7

Primer sequence used to establish Mutant Replicon cell lines.

| | | |
|---|---|---|
| NS3-A156S-F | GCTGTGGGCATCTTTCGGTCTGC CGTGTGCACCCGAGGG | SEQ ID NO: 66 |
| NS3-A156S-R | CCCTCGGGTGCACACGGCAGACC GAAAGATGCCCACAGC | SEQ ID NO: 67 |
| NS3-A156T-F | GCTGTGGGCATCTTTCGGACTGC CGTGTGCACCCGAGGG | SEQ ID NO: 68 |
| NS3-A156T-R | CCCTCGGGTGCACACGGCAGTCC GAAAGATGCCCACAGC | SEQ ID NO: 69 |
| NS3-D168A-F | GGGGTTGCGAAGGCGGTGGCCTT TGTACCCGTCGAGTCT | SEQ ID NO: 70 |
| NS3-D168A-R | AGACTCGACGGGTACAAAGGCCA CCGCCTTCGCAACCCC | SEQ ID NO: 71 |
| NS3-D168V-F | GGGGTTGCGAAGGCGGTGGTCTT TGTACCCGTCGAGTCT | SEQ ID NO: 72 |
| NS3-D168V-R | AGACTCGACGGGTACAAAGACCA CCGCCTTCGCAACCCC | SEQ ID NO: 73 |
| NS3-C159S-F | ATCTTTCGGGCTGCCGTGAGCAC CCGAGGGGTTGCGAAG | SEQ ID NO: 74 |
| NS3-C159S-R | CTTCGCAACCCCTCGGGTGCTCA CGGCAGCCCGAAAGAT | SEQ ID NO: 75 |
| NS3-R155K-F | CACGCTGTGGGCATCTTTAAGGC TGCCGTGTGCACCCGA | SEQ ID NO: 76 |
| NS3-R155K-R | TCGGGTGCACACGGCAGCCTTAA AGATGCCCACAGCGTG | SEQ ID NO: 77 |

Example 23

In Vitro Transcription

In vitro transcripts of HCV positive strands were generated by using the protocol described by Lohmann V et al., J. Virol., 77:3007-3019, 2003. For transcription of positive-strand HCV RNAs, plasmid DNA (pFK 1341 PI-Luc/NS3-3'/ET, obtained from ReBLikon Gmbh (Heidelberg, Germany)), was digested with AseI followed by ScaI. After restriction digest, DNA was extracted with phenol and chloroform, precipitated with ethanol, and dissolved in RNase-free water. In vitro transcription reactions contained 80 mM HEPES (pH 7.5), 12 mM $MgCl_2$, 2 mM spermidine, 40 mM dithiothreitol, a 3.125 mM concentration of each nucleoside triphosphate, 1 U of RNasin. 5 ug of restricted plasmid DNA and 80 U of T7 RNA polymerase (Promega) was used. After 2 h at 37° C., an additional 40 U of T7 polymerase was added, and the reaction was incubated for another 2 h. Transcription was terminated by the addition of 1 U of RNase-free DNase (Promega) per ug of plasmid DNA, followed by incubation for 30 min at 37° C. After extraction with acidic phenol and chloroform, RNA was precipitated with isopropanol and dissolved in RNase-free water. The concentration was determined by measurement of the optical density at 260 nm (OD260), and RNA integrity was checked by denaturing agarose gel electrophoresis.

Example 24

Transfection of HCV Full Length Genome and Selection of Stable Cell Lines $7 \times 10^4$ Huh7-Lunet cells were seeded over night in a 12 well plate, the next day 1 ug of RNA/well was transfected using Mirus Tx (Madison, Wis.) kit. Transfection was performed according to manufacturer's instructions, and 24 hours after transfection cells were either subjected to Luciferase assay or subjected to G418 (400 ug/ml) selection in order to establish stable cell lines.

Example 25

Inhibition of Protease Self Cleavage

Huh-7-Luc-Neo-ET cells were plated in Replicon Assay Medium (RPMI supplemented with 5% FBS, 1× non-essential amino acids and pen/strep) at a density of $1 \times 10^5$ cells/well in 12 well plates. Eight hours later the media was removed and replaced with 1 ml media containing test compound (5 wells per compound) and 0.02% DMSO and the cells were returned to the incubator overnight. Sixteen hours later 1 well from each compound and 1 untreated well were washed with PBS, then lysed and scraped into 30 ul of Cell Extraction Buffer (Biosource, Camarillo, Calif.) plus Complete Protease Inhibitor (Roche, Indianapolis, Ind.). The remaining wells were rinsed 2× with PBS then fed with Replicon Media and returned to the incubator. Cells were washed once every hour by removing the old media and replacing it with fresh media and were lysed and collected at 4, 12, 24, and 48 hours following the first collection.

Cell lysates were separated by SDS-Page (4-20%) and transferred to Immobilon-P PVDF membrane (Millipore Corporation, MA) and blotted with polyclonal anti NS3 antibody (Bioenza, CA). Blots were scanned on an Odyssey infrared scanner from Licor and the FL band and cleavage products were quantified separately using the Licor software provided with the scanner. The cleavage product was calculated as a percentage of the total NS3 in each sample and then normalized to the DMSO control so that the DMSO control reflects 100% activity.

Results and Discussion

When protease activity is inhibited, self-cleavage is abolished and the only protein species detectable is the holoenzyme. After 16 hours of continuous exposure of the replicon cells to NS3 inhibitor compound, the self-cleavage products were undetectable in the treated samples, but readily detectable in the not treated control replicon cells. Prolonged duration of action was demonstrated by exposing the replicon cells to a protease inhibitor for 16 hours, at which time the compound was removed, and the replicon cells were repeatedly washed for several more hours. Covalent irreversible NS3 inhibitors demonstrated sustained inhibition of NS3 internal self-cleavage activity for up to 48 hours, whereas the protease self-cleavage activity rapidly returned when using reversible compounds (FIG. 8).

Figure 8:
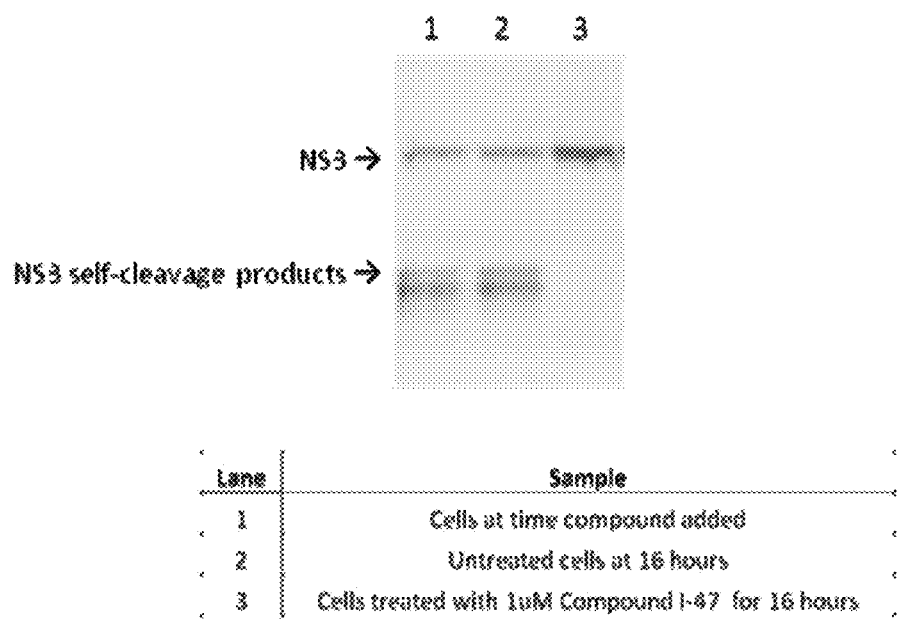
FIG. 8 depicts that the NS3 internal self-cleavage products are inhibited by treatment of replicon cells with Compound I-47 for 16 hours.

FIG. 8 depicts that the NS3 internal self-cleavage products are inhibited by treatment of replicon cells with Compound I-47 for 16 hours.

Figure 9:
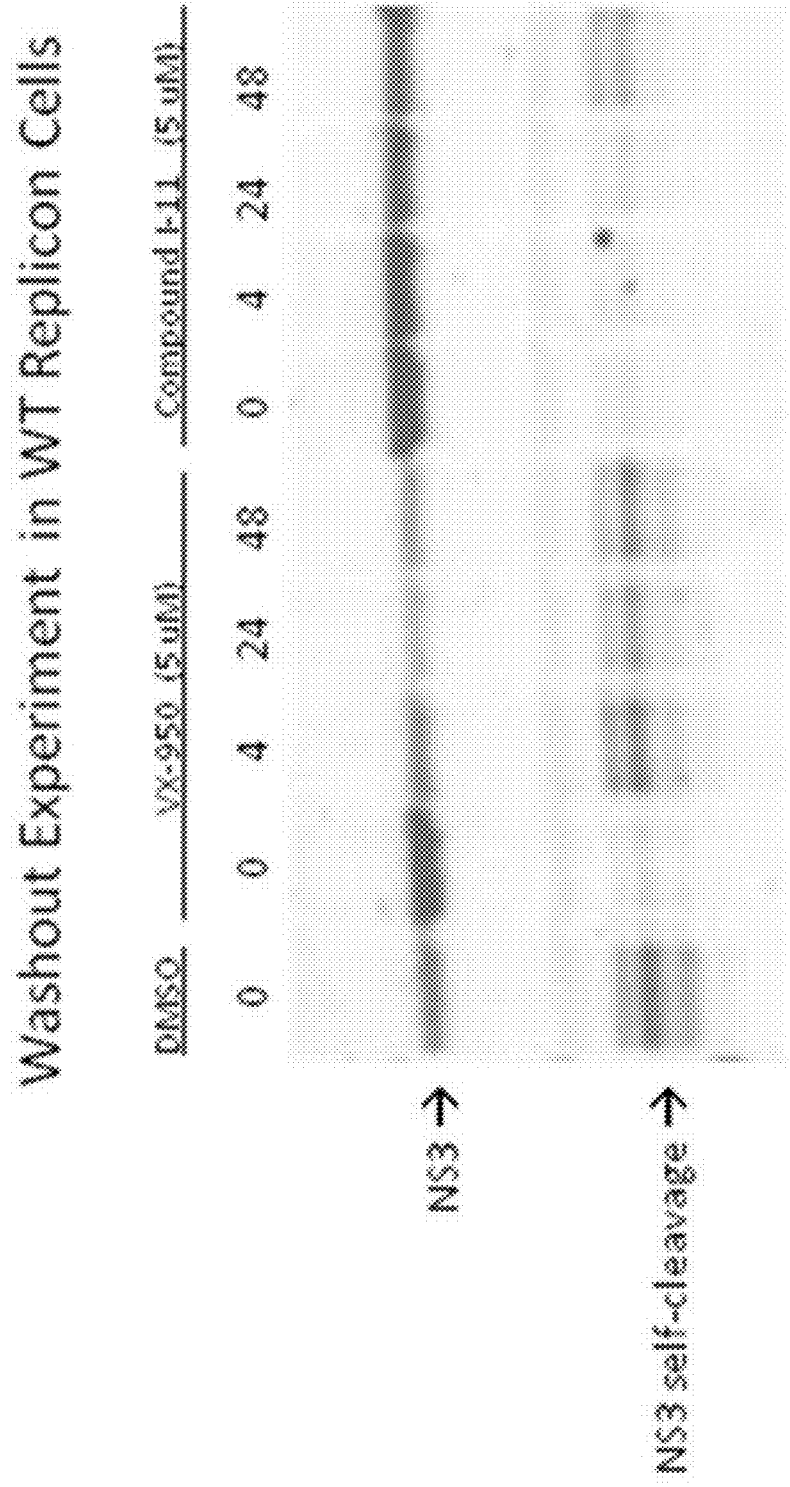

FIG. 9 depicts an irreversible covalent inhibitor (compound I-11) of NS3 protease demonstrate prolonged inhibition of NS3 protease activity in the wild-type replicon cells, as measured by self-cleavage, after the compounds are removed. The compound was incubated with replicon cells for 16 hours and then removed (time 0). Even up to 48 hours after removal of a covalent irreversible NS3 inhibitor, NS3 self-cleaving activity is inhibited by at least 50%, whereas a reversible drug, VX-950, shows virtually complete return of activity in as little as 4 hours after drug removal.

Figure 10:
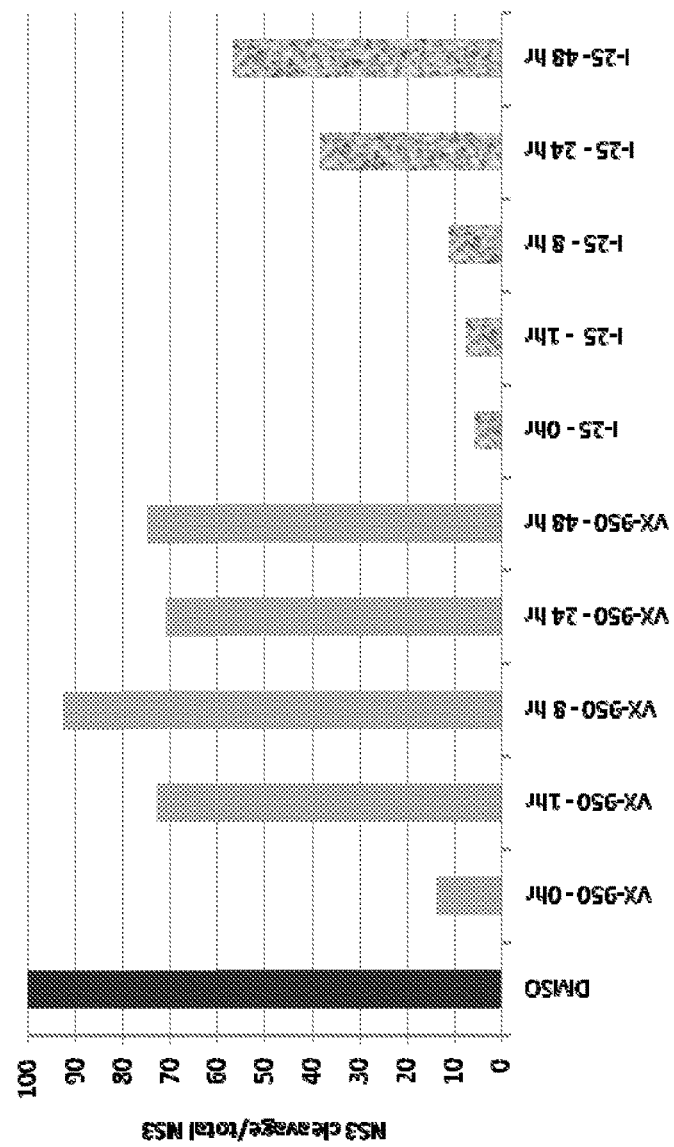
FIG. 10 depicts that an irreversible covalent inhibitor (compound I-25) of NS3 protease demonstrates prolonged inhibition of NS3 protease activity in the wild-type replicon cells, as measured by self-cleavage, after the compounds are removed.

FIG. 10 depicts an irreversible covalent inhibitor (compound I-25) of NS3 protease demonstrate prolonged inhibition of NS3 protease activity in the wild-type replicon cells, as measured by self-cleavage, after the compounds are removed. The compound was incubated with replicon cells for 16 hours and then removed (time 0). Even up to 48 hours after removal of a covalent irreversible NS3 inhibitor, NS3 self-cleaving activity is inhibited by at least 40%, whereas a reversible drug, VX-950, shows virtually complete return of activity in as little as 8 hours after drug removal.

Example 26

Luciferase Assay

The compounds were assayed to evaluate the antiviral activity and cytotoxicity of compounds using replicon-derived luciferase activity. This assay used the cell line ET (luc-ubi-neo/ET), which is a human Huh7 hepatoma cell line that contains an HCV RNA replicon with a stable luciferase (Luc) reporter and cell culture-adaptive mutations. The ET cell line was grown in a 5% $CO_2$ incubator at 37° C. in Dulbecco's modified essential media (DMEM) supplemented with 2 mM L-glutamine, nonessential amino acids, 100 U of penicillin/ml, 100 µg of streptomycin/mL, and 10% fetal bovine serum. G418 (Geneticin; Invitrogen) was added at a final concentration of 400 ug/mL.

All cell culture reagents were obtained from Invitrogen (Carlsbad). Cells were trypsinized (1% trypsin:EDTA) and plated out at $5 \times 10^3$ cells/well in white 96-well assay plates (Costar) dedicated to cell number (cytotoxicity) or antiviral activity assessments. Test compounds were added at six 3-fold concentrations each and the assay was run in DMEM, 5% FBS, 1% pen-strep, 1% glutamine, 1% non essential amino acid. Human interferon alpha-2b (PBL Biolabs, New Brunswick, N.J.) was included in each run as a positive control compound. Cells were processed 72 hr post test compound addition when the cells were still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by Cell Titer Blue Assay (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating hepatitis C viral infection in a patient, comprising the step of administering to a patient in need thereof a compound of formula I:

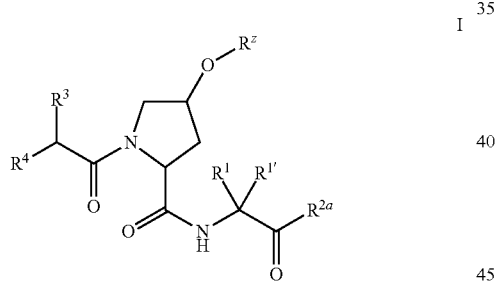

or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{2a}$ is —OH or —NHSO$_2$R$^2$;

$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:

two R on the same nitrogen atom are taken together with the nitrogen to form a 4-7 membered heterocyclic ring having 1-2 heteroatoms independently selected from nitrogen, oxygen, or sulfur;

$R^3$ is -L-Y, wherein -L-Y is selected from the following:

(a) L is a bivalent $C_{2-8}$ straight or branched, hydrocarbon chain wherein L has at least one double bond and one or two methylene units of L are independently replaced by —NRC(O)—, —C(O)NR—, —N(R)SO$_2$—, —SO$_2$N(R)—, —S(O)—, —SO$_2$—, —OC(O)—, —C(O)O, or —C(O)—; and Y is hydrogen or $C_{1-6}$ aliphatic optionally substituted with oxo, halogen, NO$_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN; or (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN;

or $R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or $R^3$ and a ring formed by $R^1$ and $R^1$, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;

$R^4$ is H, —NHC(O)$R^5$, —NHC(O)O$R^6$,

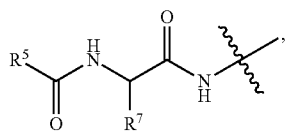

or a natural or unnatural amino acid side-chain group;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

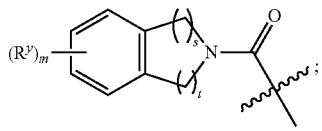

or $R^4$ and $R^z$ are taken together with their intervening atoms to form an optionally substituted, saturated or unsaturated 16-22 membered ring having 2-6 heteroatoms independently selected from nitrogen, oxygen, or sulfur;

wherein the 16-22 membered ring is optionally substituted with $(R^m)_p$, wherein:
p is an integer from 1 to 6, inclusive;
each occurrence of $R^m$ is independently halogen, —OR°, —CN, —N(R°)$_2$, or an optionally substituted group selected from $C_{1-6}$ aliphatic or $C_{3-7}$ cycloalkyl; and each occurrence of $R^y$ is independently selected from halogen, —OR°, —CN, —NO$_2$, —N(R°)$_2$, or optionally substituted $C_{1-4}$ aliphatic;

each R° of $R^m$ and $R^y$ is independently optionally substituted $C_{1-6}$ aliphatic; and m is an integer from 0 to 4, inclusive;
s is an integer from 0 to 4, inclusive;
t is an integer from 0 to 4, inclusive;
wherein the sum of s and t is non-zero.

2. The method according to claim 1, wherein:
L is a bivalent $C_{2-8}$ straight or branched, hydrocarbon chain wherein L has at least one double bond and one or two methylene units of L are independently replaced by —NRC(O)—, —C(O)NR—, —N(R)SO$_2$—, —SO$_2$N(R)—, —S(O)—, —SO$_2$—, —OC(O)—, —C(O)O, or —C(O)—; and Y is hydrogen or $C_{1-6}$ aliphatic optionally substituted with oxo, halogen, NO$_2$, or CN.

3. The method according to claim 1, wherein:
L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one additional methylene unit of L is optionally replaced by cyclopropylene, —O—, —N(R)—, or —C(O)—; and Y is hydrogen or $C_{1-6}$ aliphatic optionally substituted with oxo, halogen, NO$_2$, or CN.

4. The method according to claim 3, wherein L is a bivalent $C_{2-8}$ straight or branched, hydrocarbon chain wherein L has at least one double bond and at least one methylene unit of L is replaced by —C(O)—, and one additional methylene unit of L is optionally replaced by cyclopropylene, —O—, —N(R)—, or —C(O)—.

5. The method according to claim 3, wherein L is a bivalent $C_{2-8}$ straight or branched, hydrocarbon chain wherein L has at least one double bond and at least one methylene unit of L is replaced by —OC(O)—.

6. The method according to claim 1, wherein L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$1—, or —NRC(O)C(=CH$_2$)CH$_2$—; wherein the R group of L is H or optionally substituted $C_{1-6}$ aliphatic; and Y is hydrogen or $C_{1-6}$ aliphatic optionally substituted with oxo, halogen, NO$_2$, or CN.

7. The method according to claim 6, wherein L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, or —NHC(O)C(=CH$_2$)CH$_2$—.

8. The method according to claim 1, wherein L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one additional methylene unit of L is optionally replaced by cyclopropylene, —O—, —N(R)—, or —C(O)—.

9. A method for treating hepatitis C infection in a patient, comprising the step of administering to a patient in need thereof a compound of formula I:

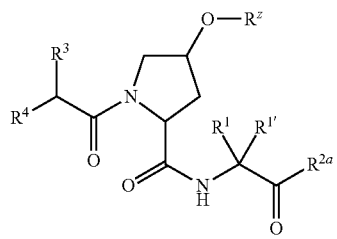

I or a pharmaceutically acceptable salt thereof, wherein:
- $R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
- $R^{2a}$ is —OH or —NHSO$_2$R$^2$;
- $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
- each R is independently hydrogen, optionally substituted $C_{1-6}$ aliphatic, or:
  - two R on the same nitrogen atom are taken together with the nitrogen to form a 4-7 membered heterocyclic ring having 1-2 heteroatoms independently selected from nitrogen, oxygen, or sulfur;
- $R^3$ is -L-Y, wherein:
  - L is a covalent bond, —C(O)—, —N(R)C(O)—, a bivalent $C_{1-8}$ saturated or unsaturated, straight or branched, hydrocarbon chain, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—; and
  - Y is selected from:

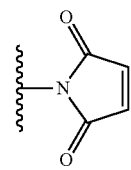 a

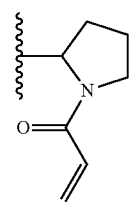 b

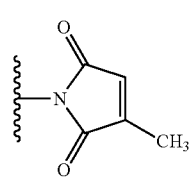 c

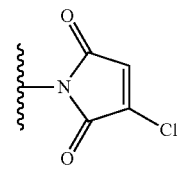 d

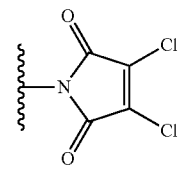 e

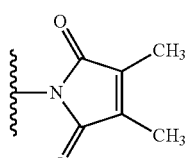 f

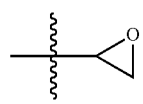 g

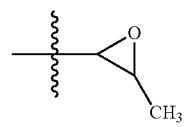 h

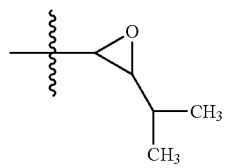 i

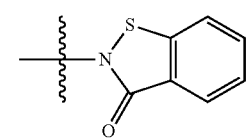 j

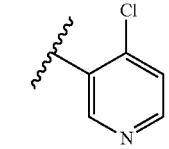 k

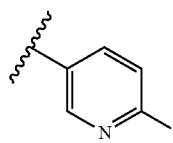 l

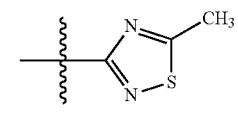 m

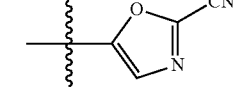 n

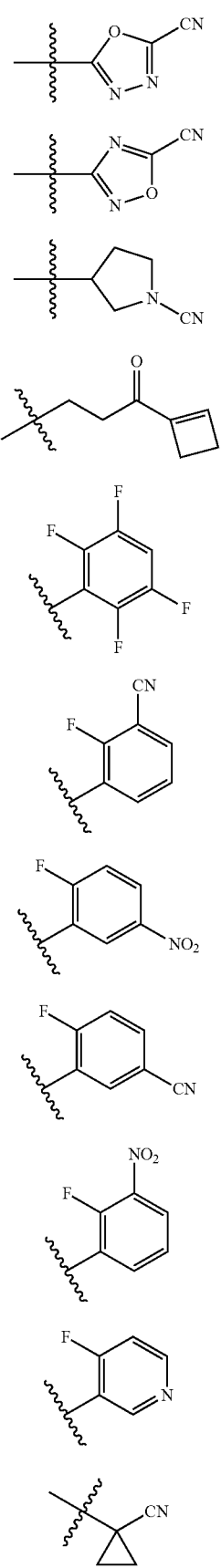
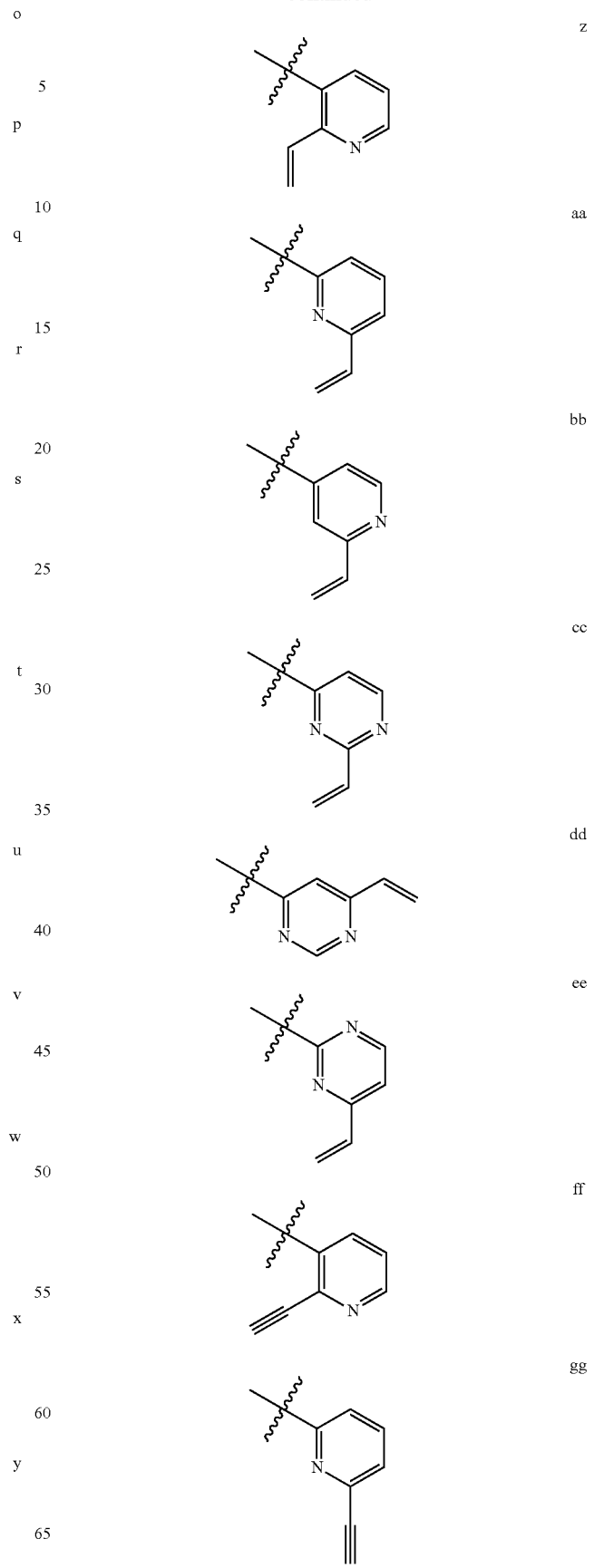

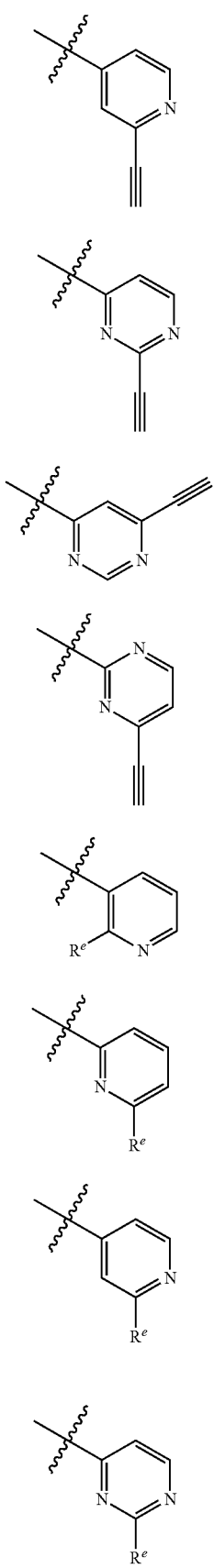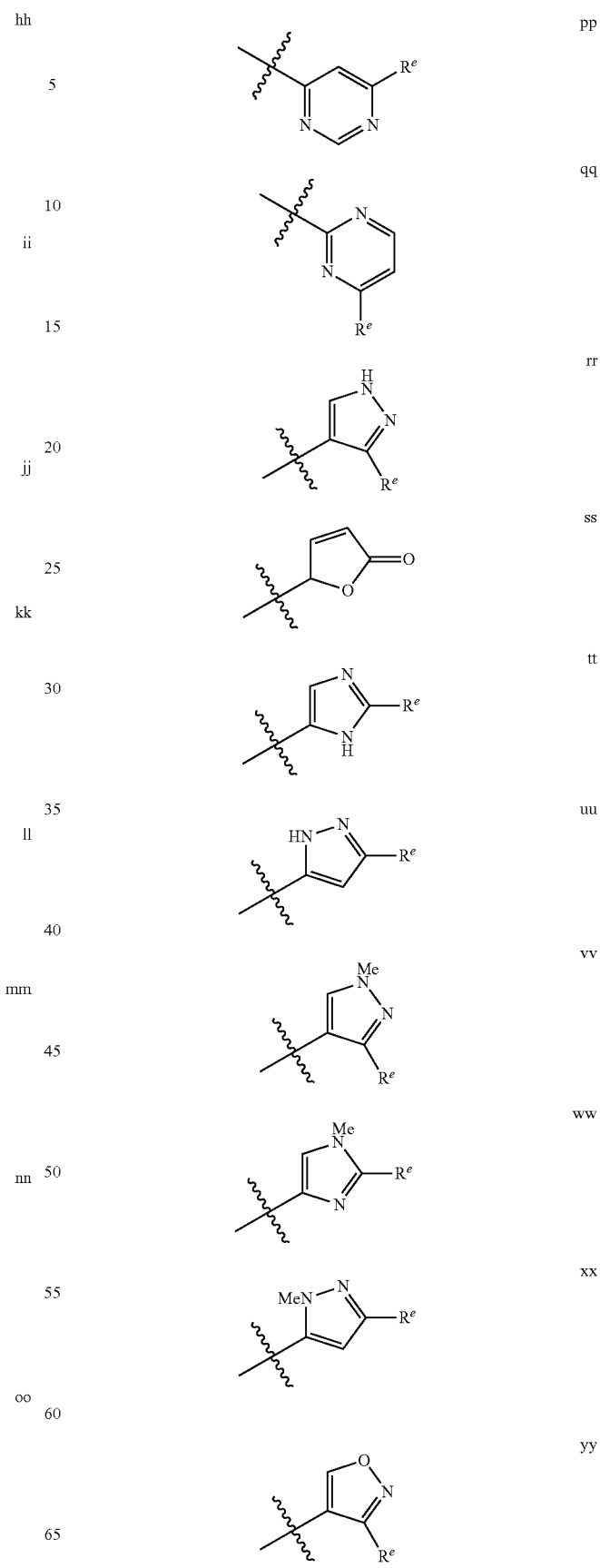

| | | | |
|---|---|---|---|
| zz | 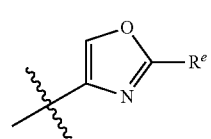 | kkk | 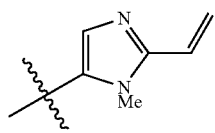 |
| aaa | 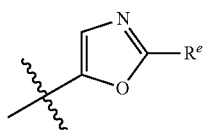 | lll | 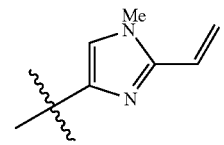 |
| bbb | 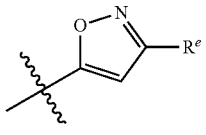 | mmm | 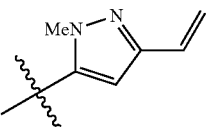 |
| ccc | 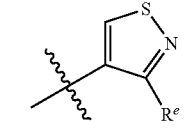 | nnn | 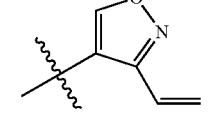 |
| ddd | 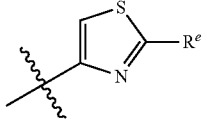 | ooo | 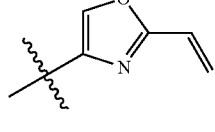 |
| eee | 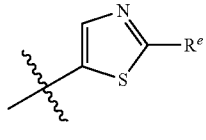 | ppp | 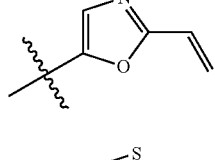 |
| fff | 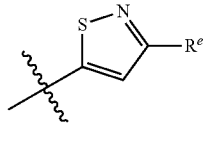 | qqq | 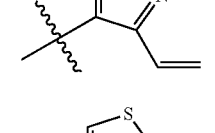 |
| ggg | 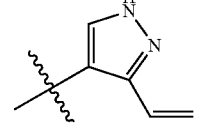 | rrr | 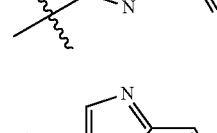 |
| hhh | 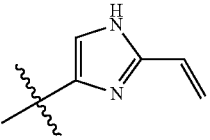 | sss | 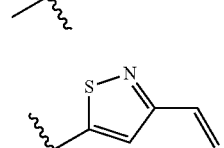 |
| iii | 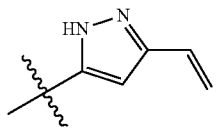 | ttt | 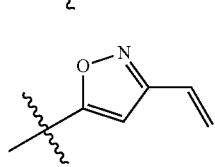 |
| jjj | 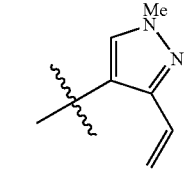 | uuu | |

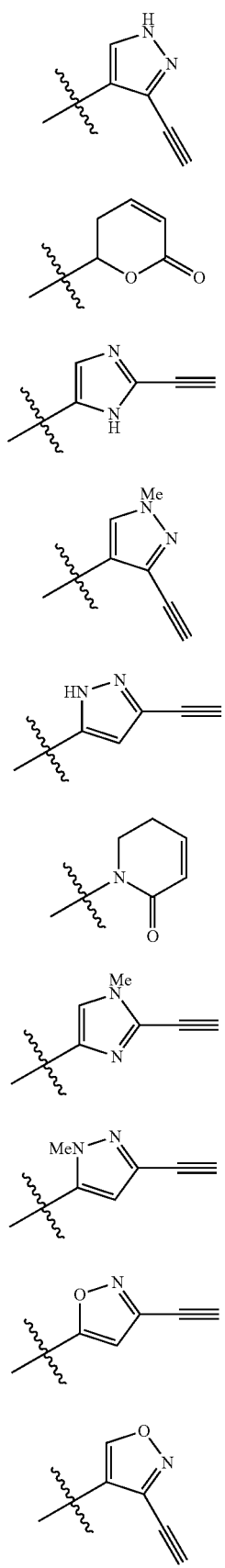
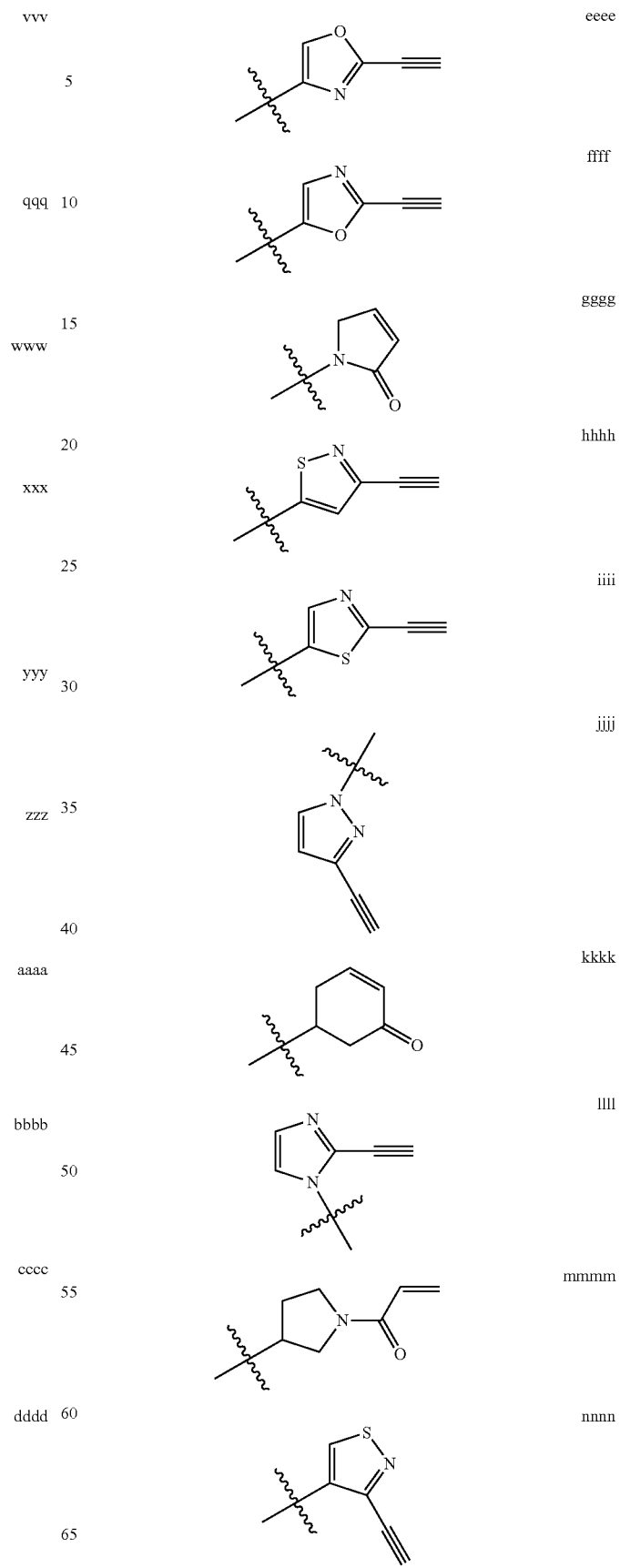

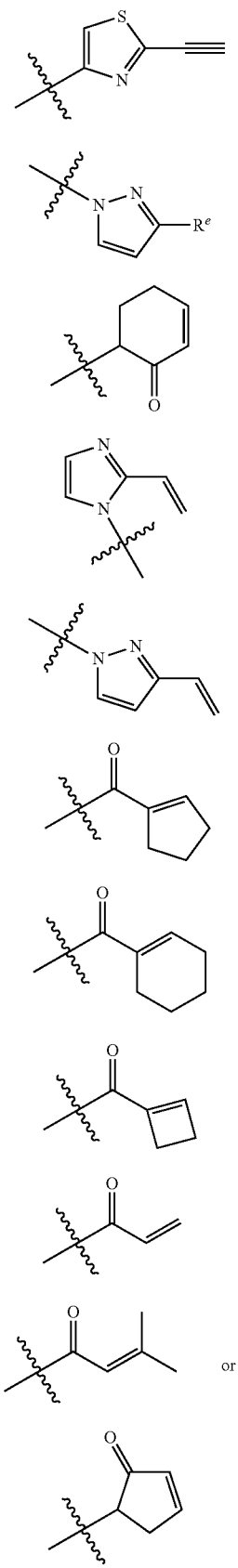

wherein each $R^e$ is independently selected from halogen;
or $R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or $R^3$ and a ring formed by $R^1$ and $R^1$, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;

$R^4$ is H, —NHC(O)$R^5$, —NHC(O)O$R^6$,

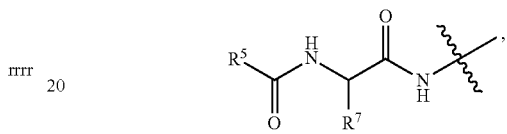

or a natural or unnatural amino acid side-chain group;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

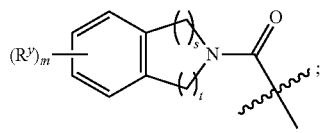

or $R^4$ and $R^z$ are taken together with their intervening atoms to form an optionally substituted, saturated or unsaturated 16-22 membered ring having 2-6 heteroatoms independently selected from nitrogen, oxygen, or sulfur;

wherein the 16-22 membered ring is optionally substituted with $(R^m)_p$, wherein:
p is an integer from 1 to 6, inclusive;
each occurrence of $R^m$ is independently halogen, —OR○, —CN, —N(R○)$_2$, or an optionally substituted group selected from $C_{1-6}$ aliphatic or $C_{3-7}$ cycloalkyl; and each occurrence of $R^y$ is independently selected from halogen, —$OR_\circ$, —CN, —$NO_2$, —$N(R_\circ)_2$, or optionally substituted $C_{1-4}$ aliphatic;

each $R_\circ$ of $R^m$ and $R^y$ is independently optionally substituted $C_{1-6}$ aliphatic; and m is an integer from 0 to 4, inclusive;

s is an integer from 0 to 4, inclusive;

t is an integer from 0 to 4, inclusive;

wherein the sum of s and t is non-zero.

10. The method according to claim 1, wherein said compound is of formula II-a or II-b:

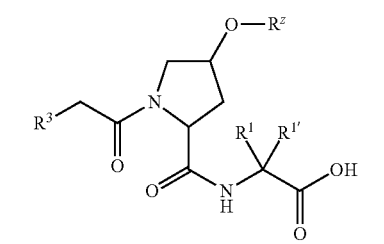

II-a

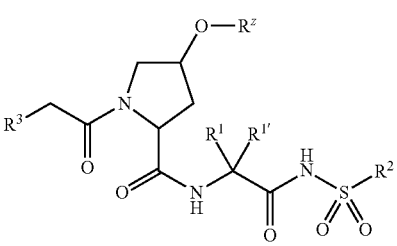

II-b or a pharmaceutically acceptable salt thereof.

11. A method for treating an HCV protease-mediated disorder in a patient, comprising the step of administering to a patient in need thereof a compound selected from the group consisting of:

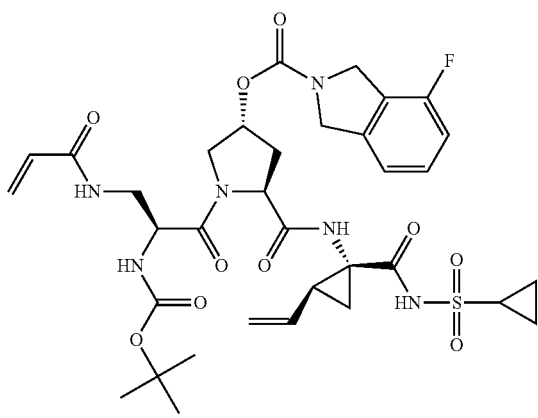

I-1

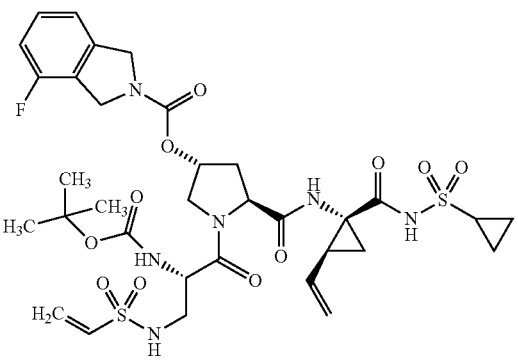

I-2

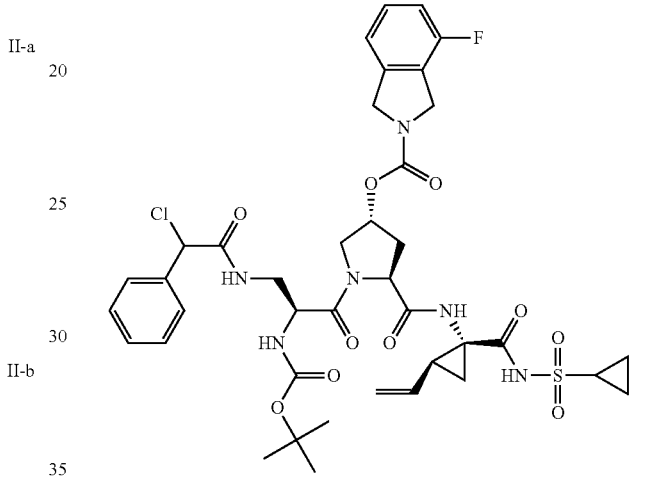

I-3

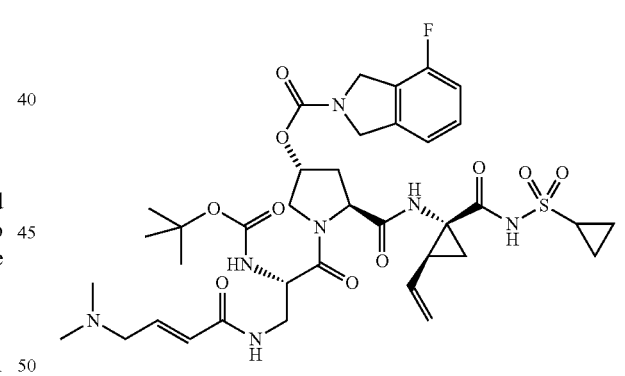

I-4

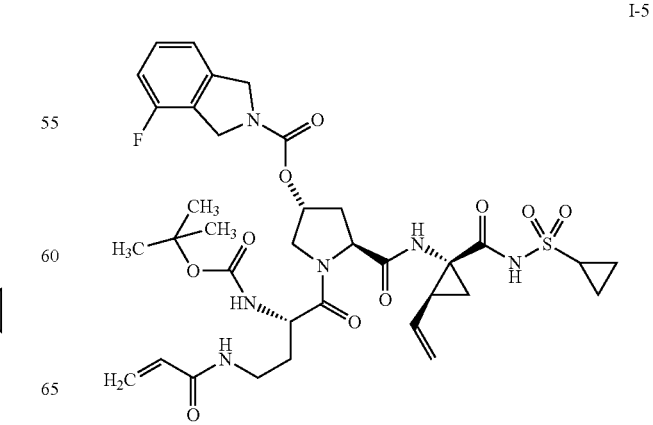

I-5

I-6
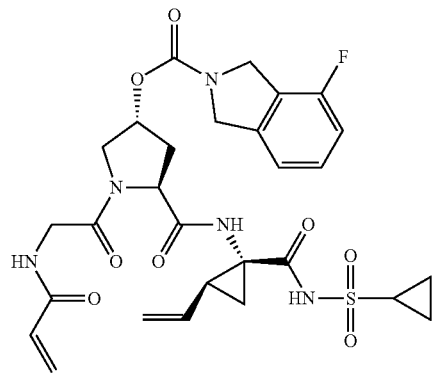
I-9
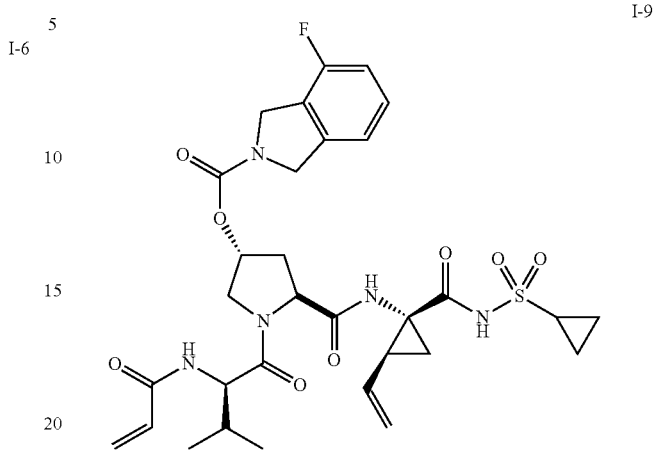
I-7
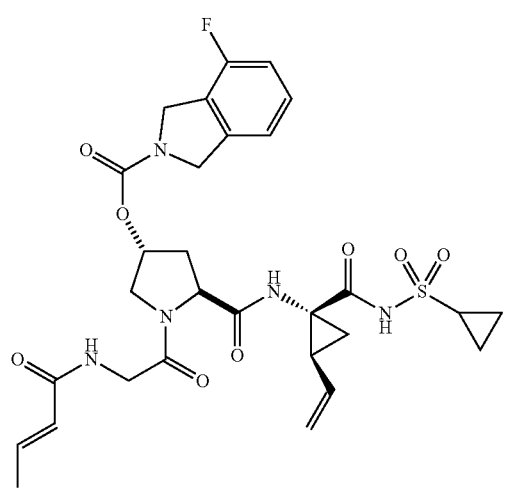
I-10
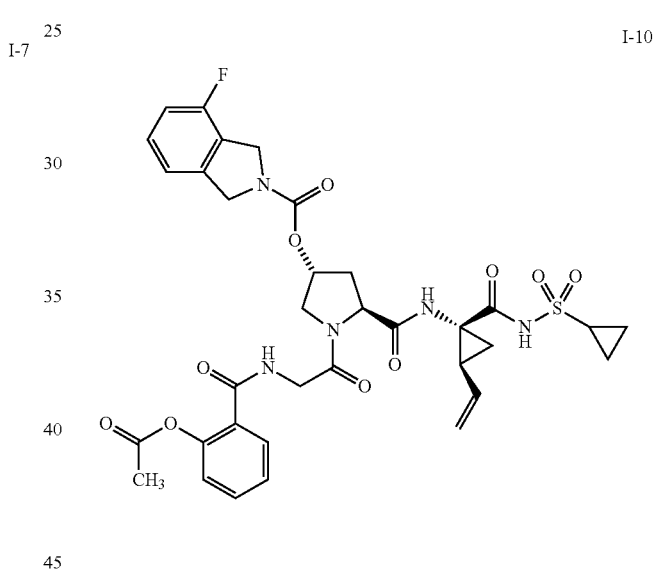
I-8
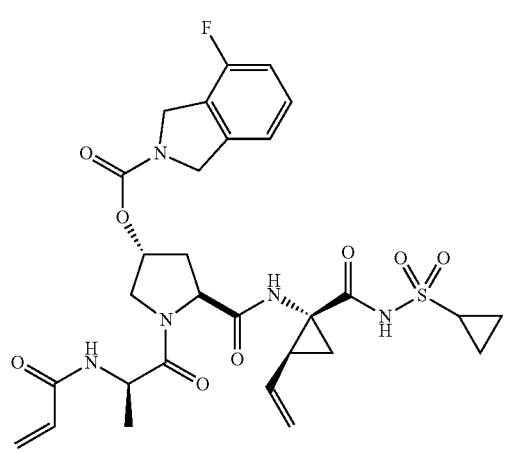
I-11
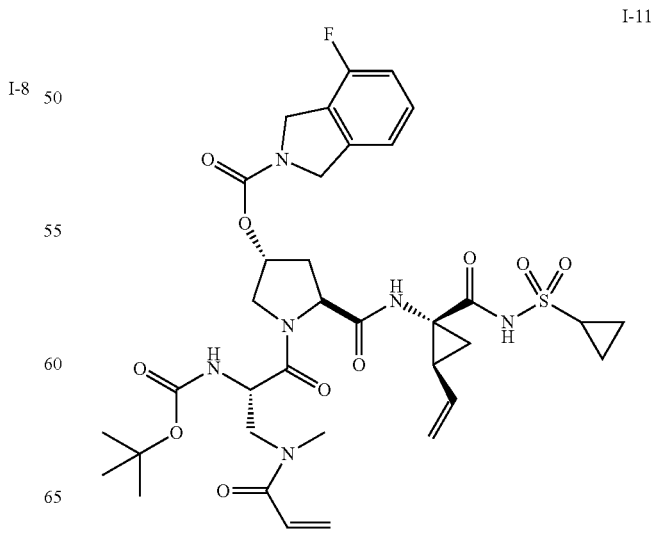

I-12
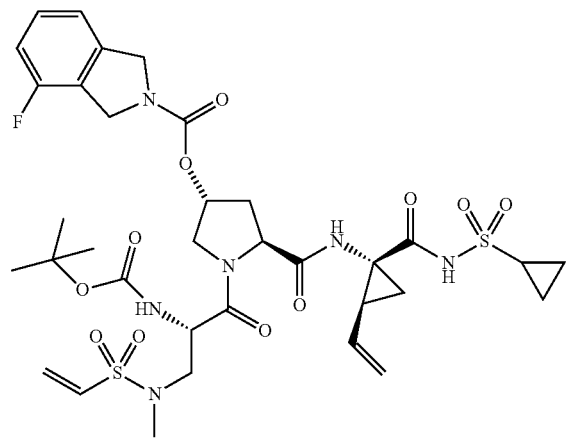
I-15
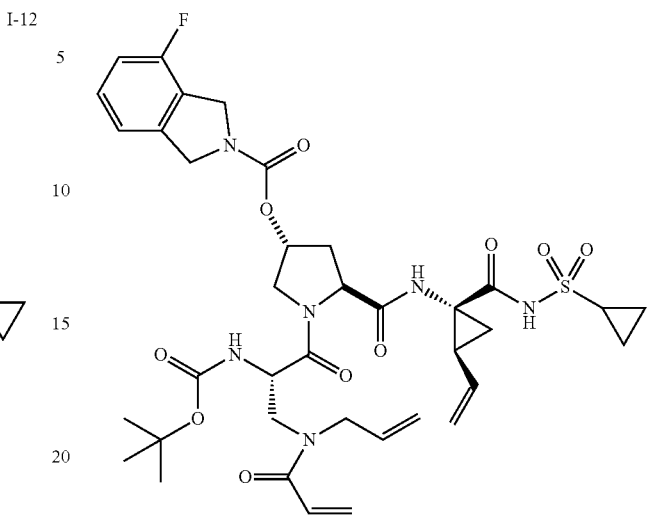
I-13
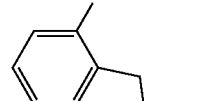
I-16
I-14
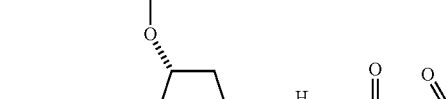
I-17
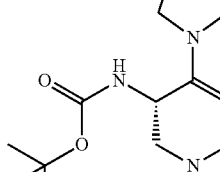

I-18
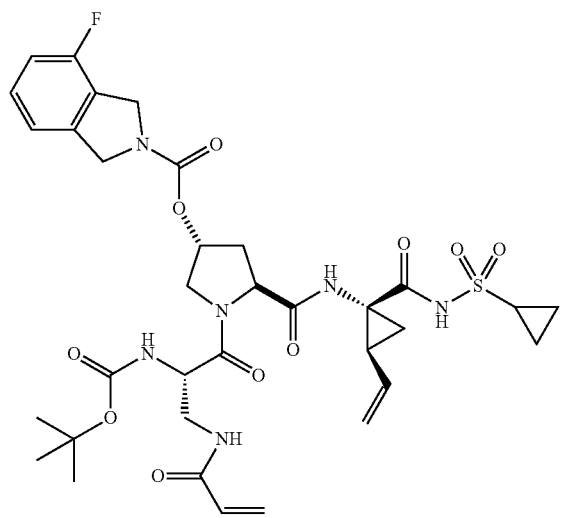
I-21
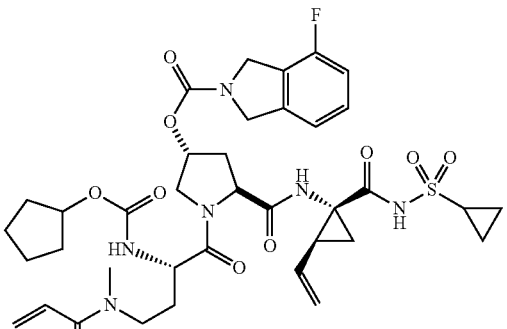
I-19
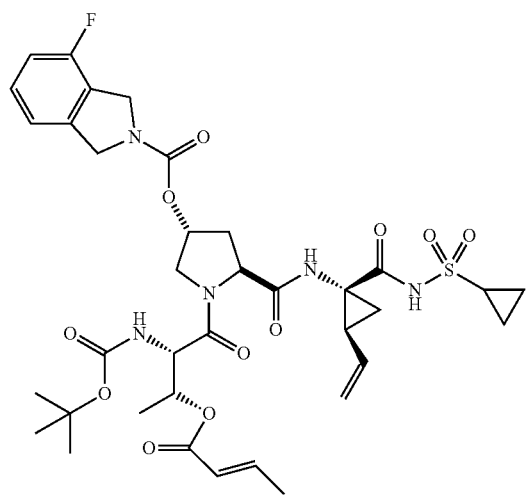
I-22
I-20
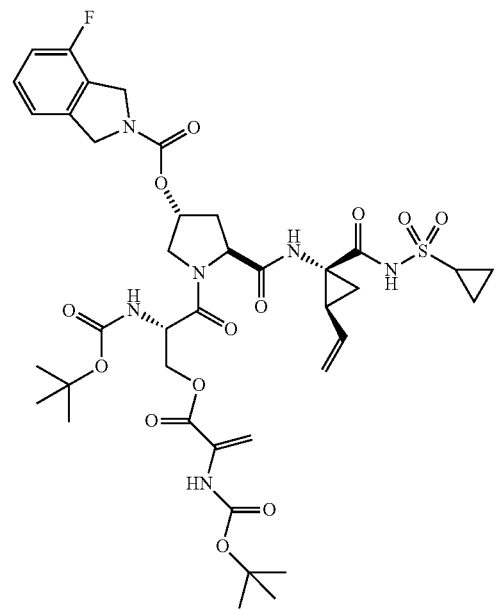
I-23

I-24
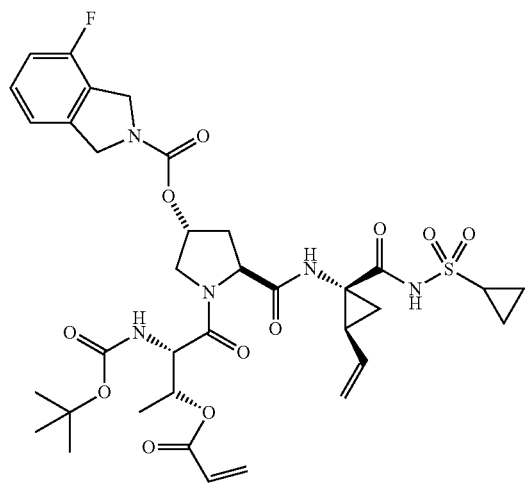
I-25
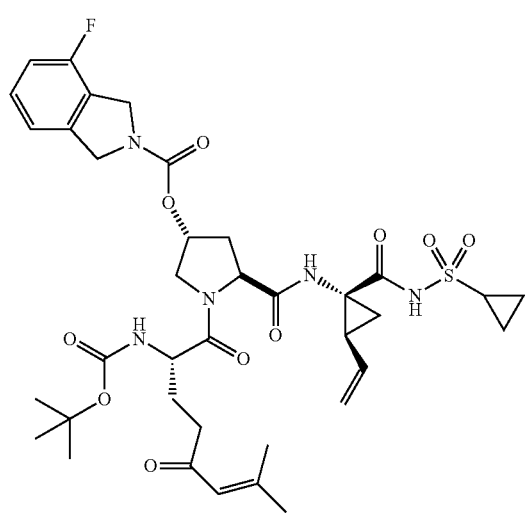
I-26
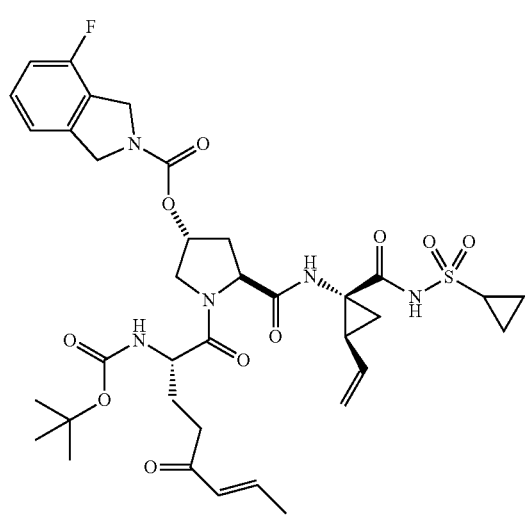
I-27
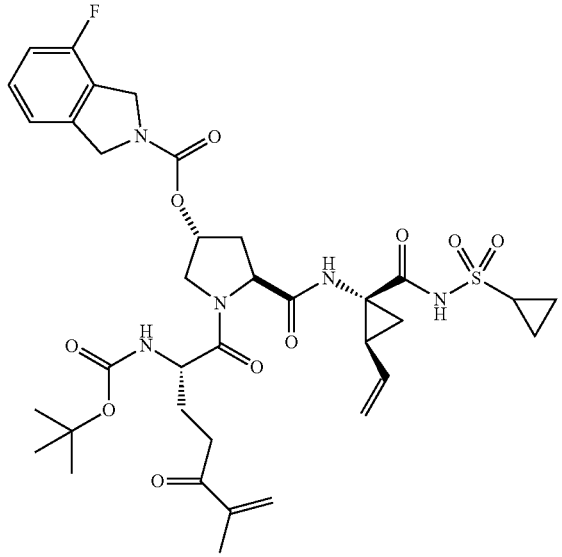
I-28
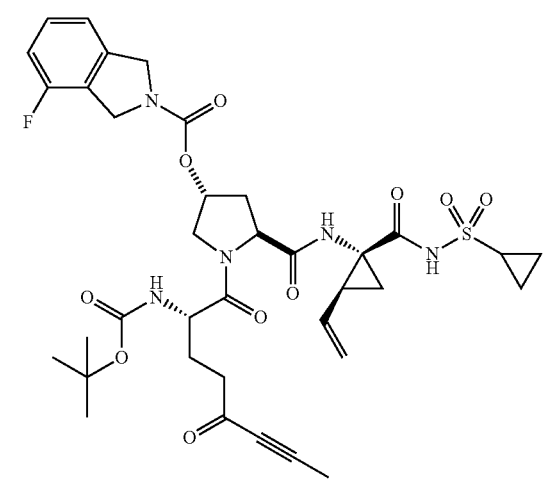
I-29
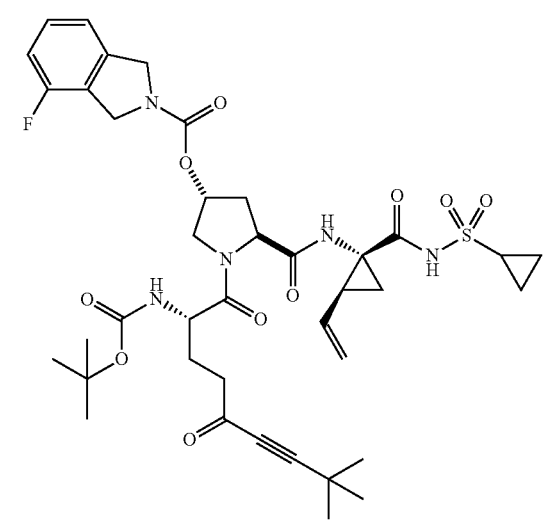

I-30
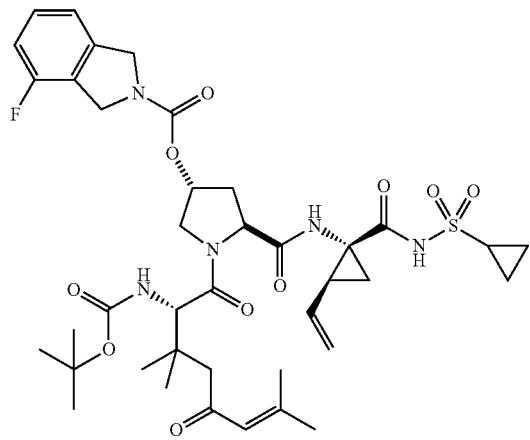
I-33
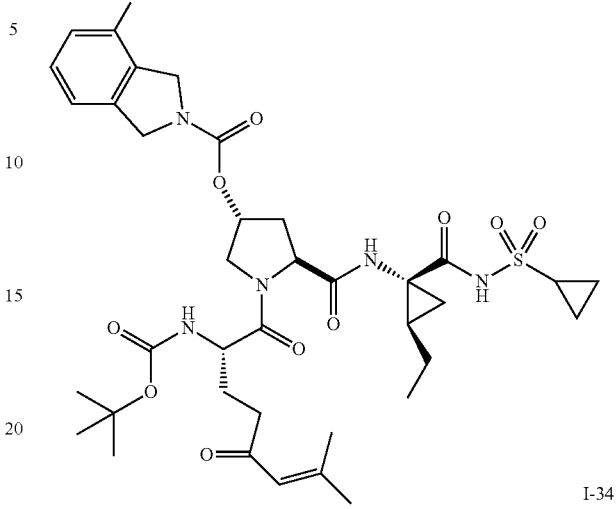
I-31
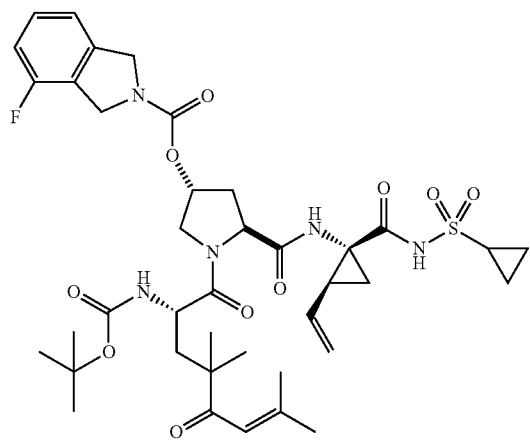
I-34
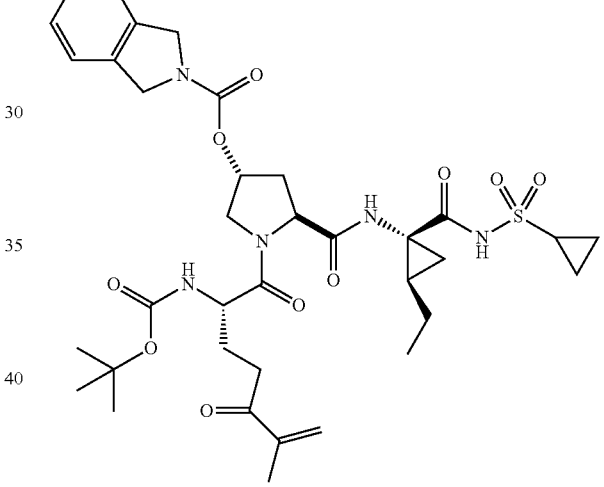
I-32
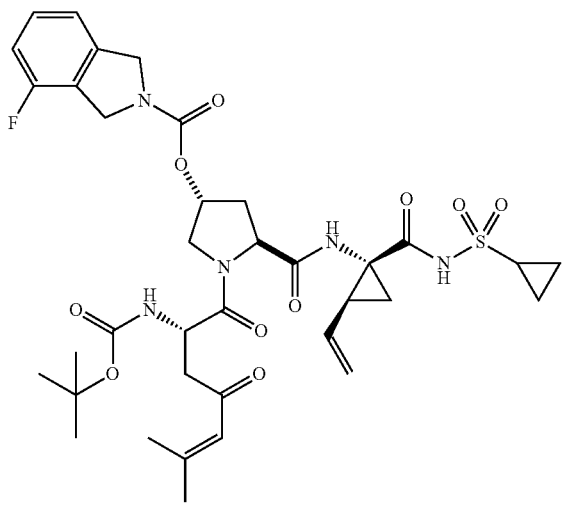
I-35
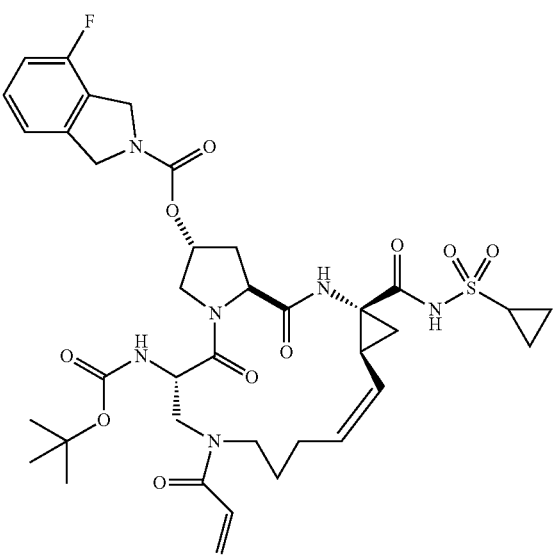

I-36
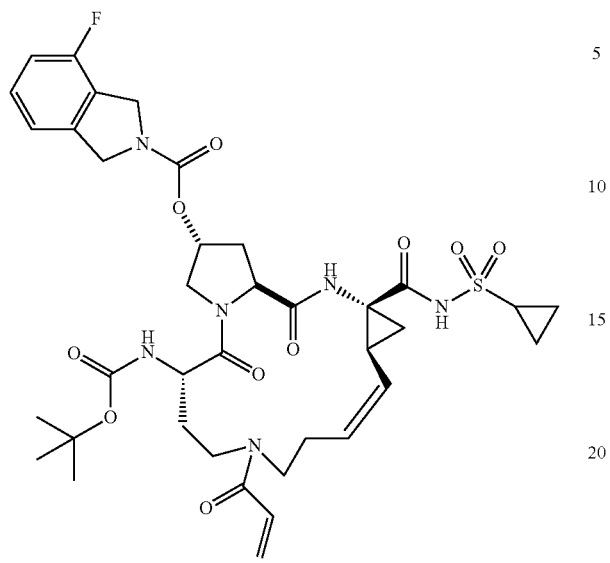
I-39
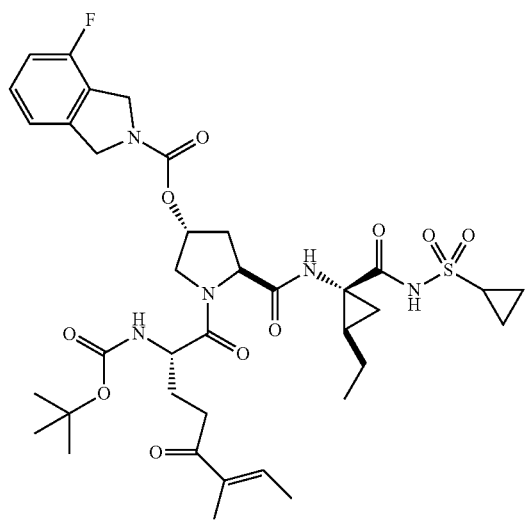
I-37
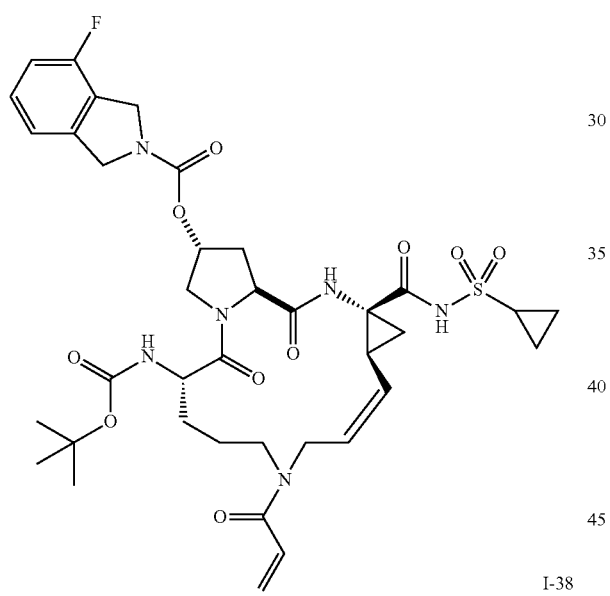
I-40
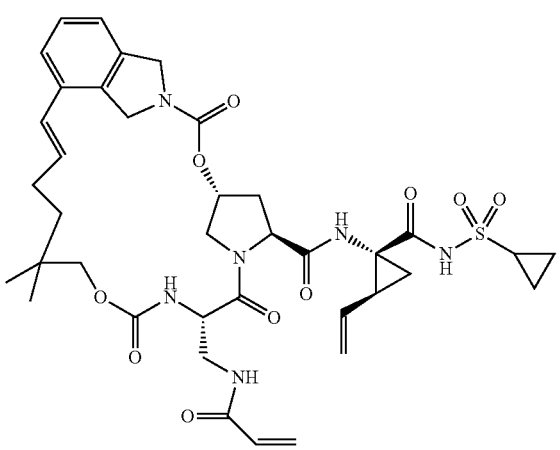
I-38
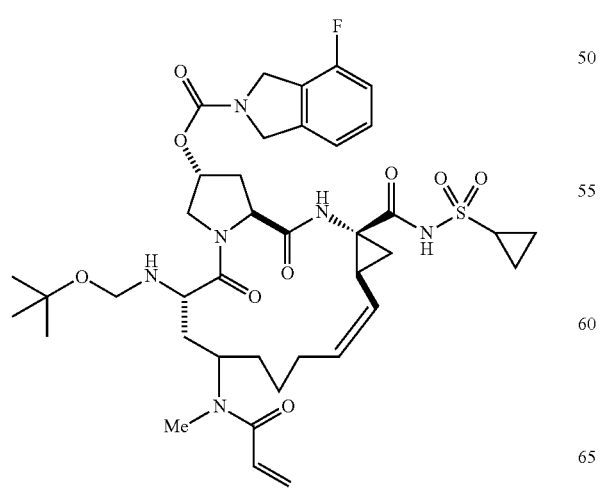
I-41
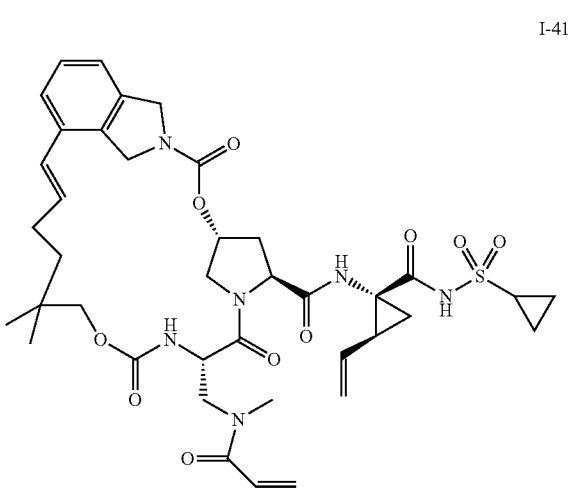

I-42
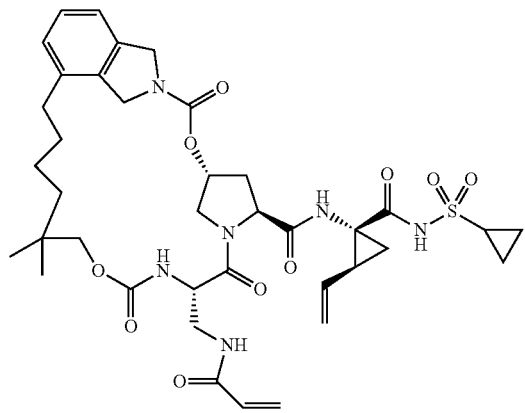
I-45
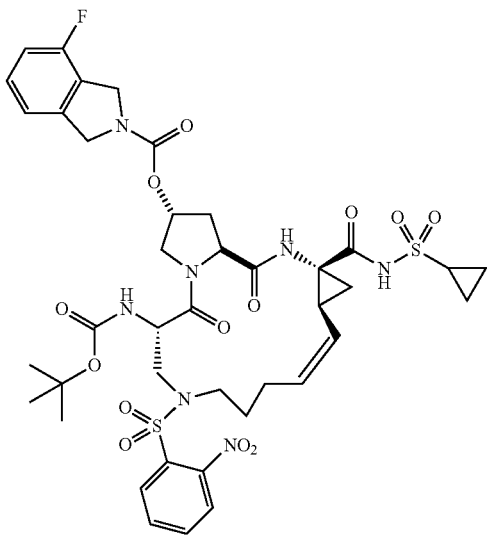
I-43
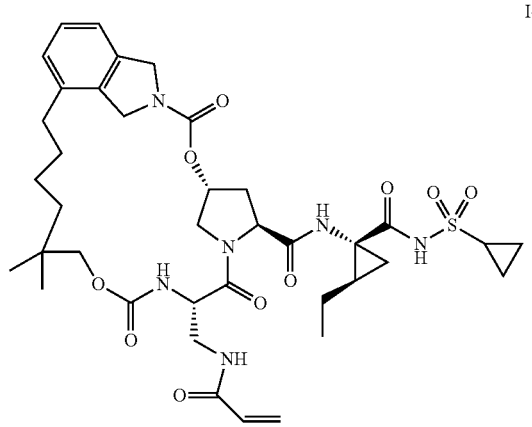
I-46
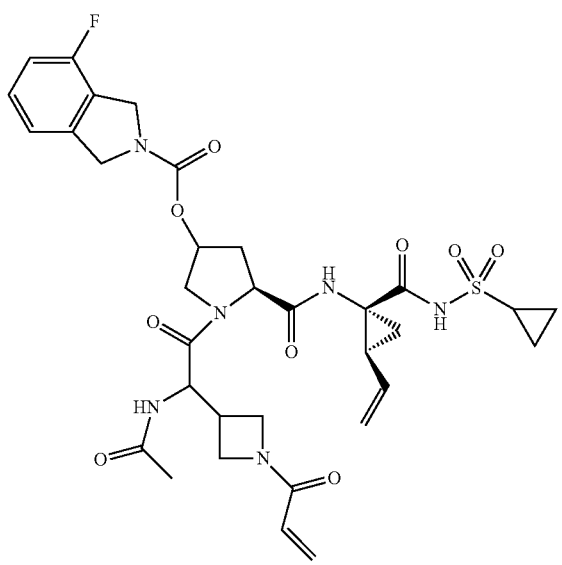
I-44
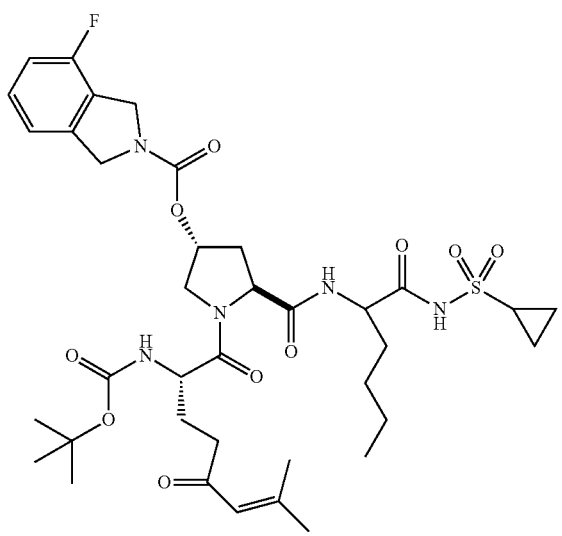
I-47
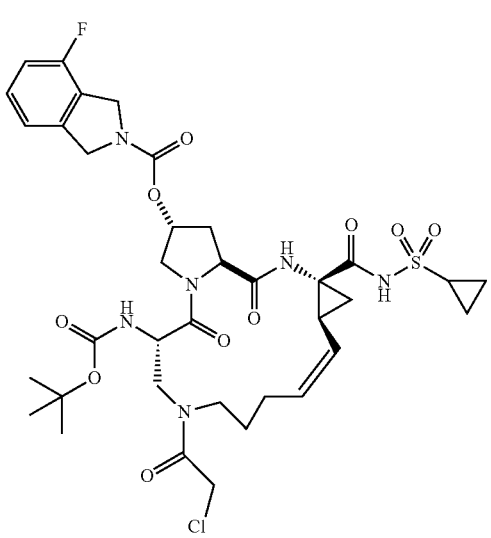

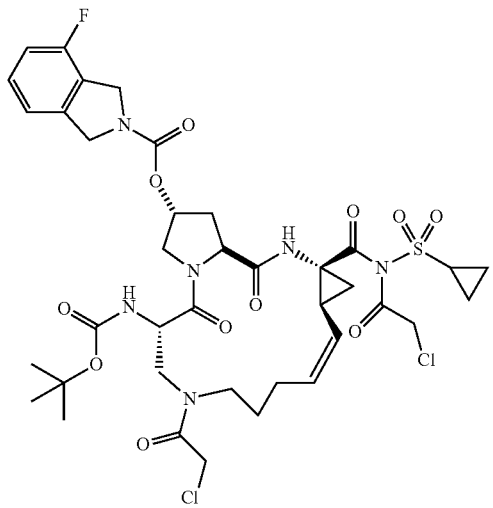
I-48
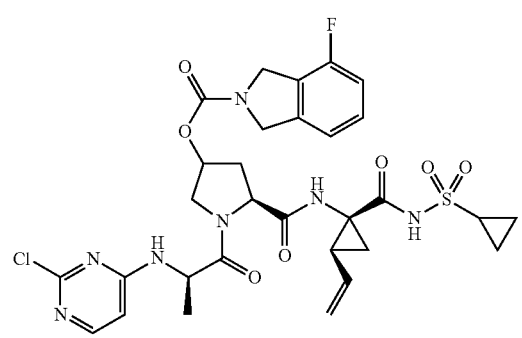
I-49
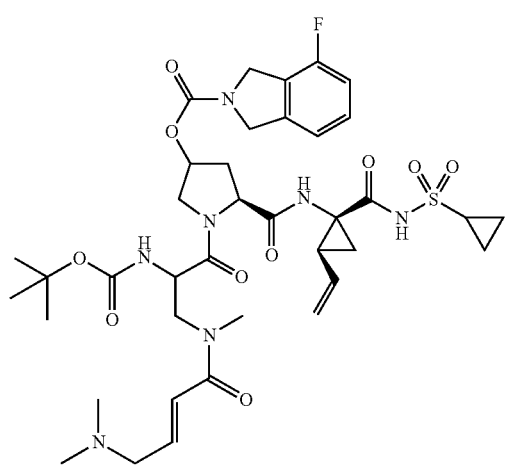
I-50
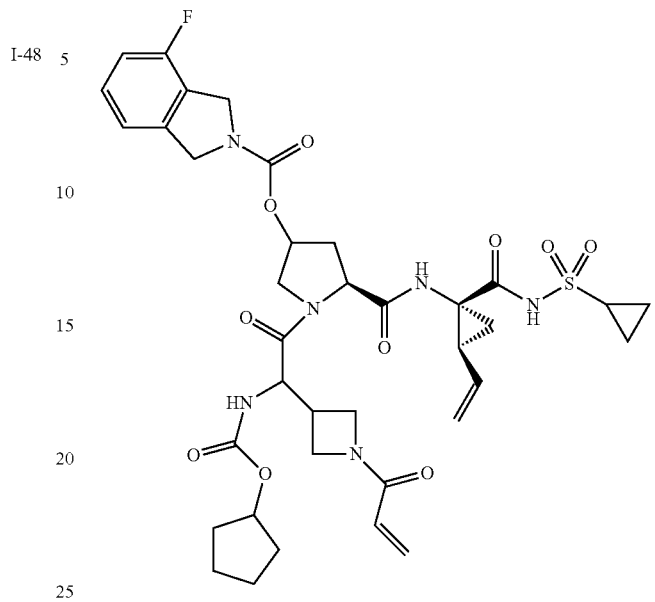
I-51
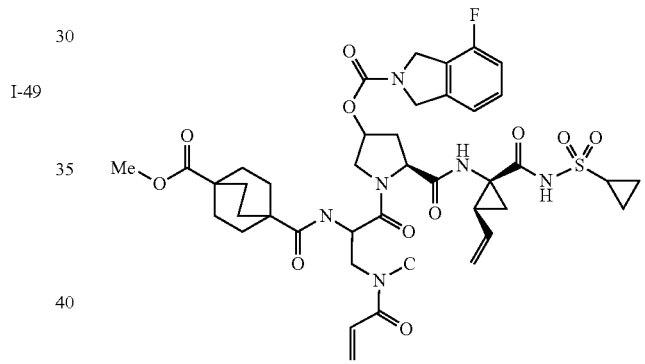
I-52
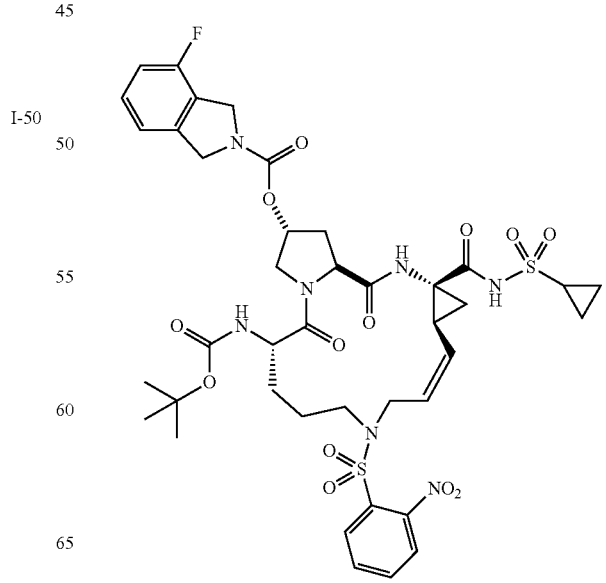
I-54

-continued
I-55
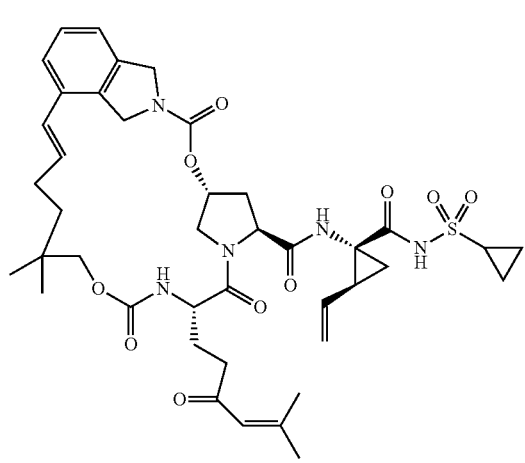
I-56
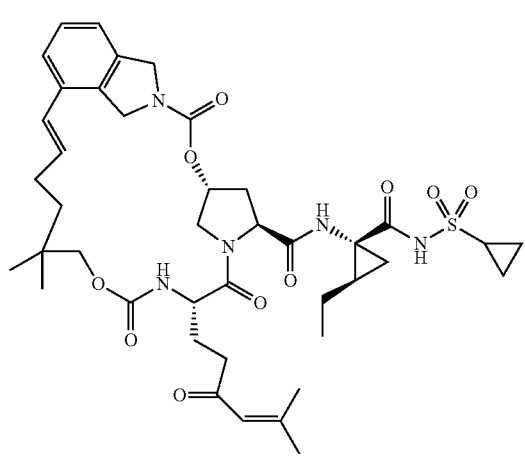
I-57
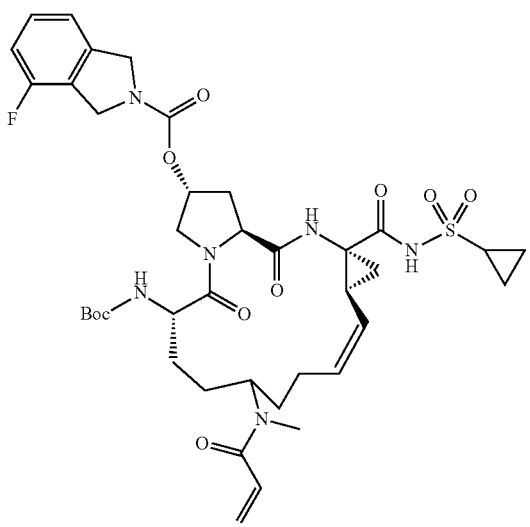
-continued
I-58
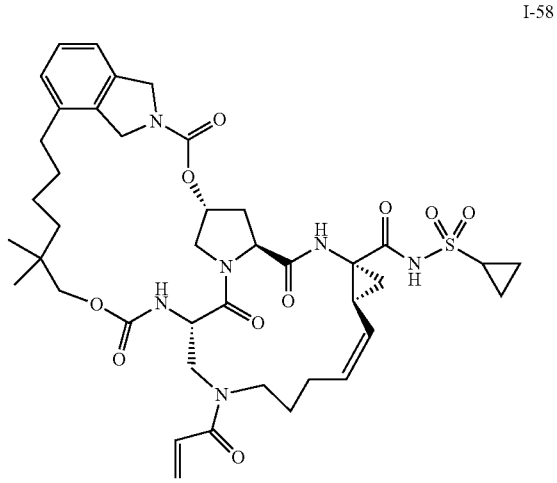
I-59
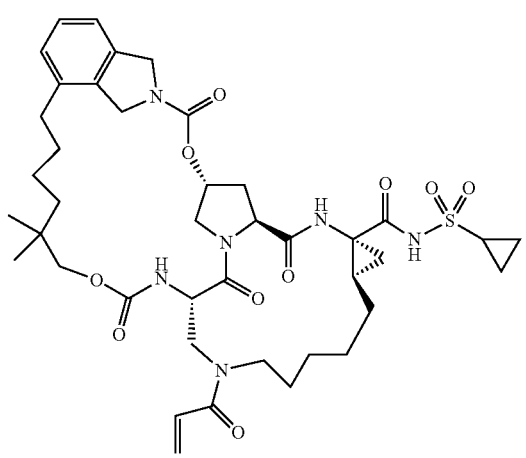
I-60
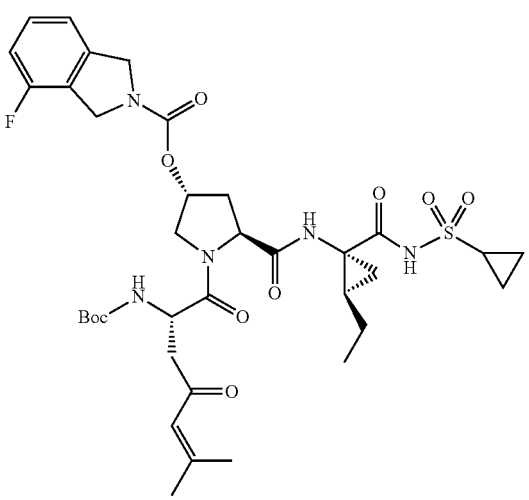

I-61
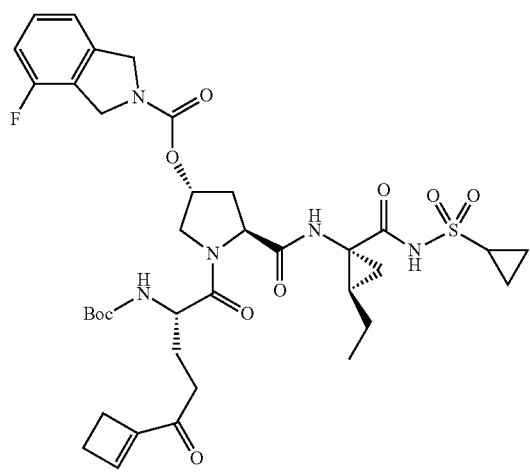
I-62
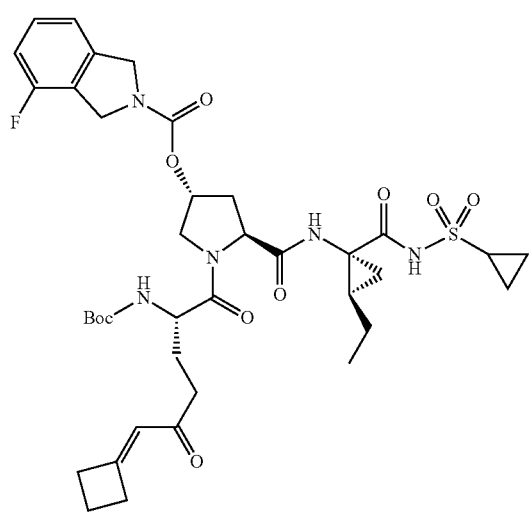
I-63
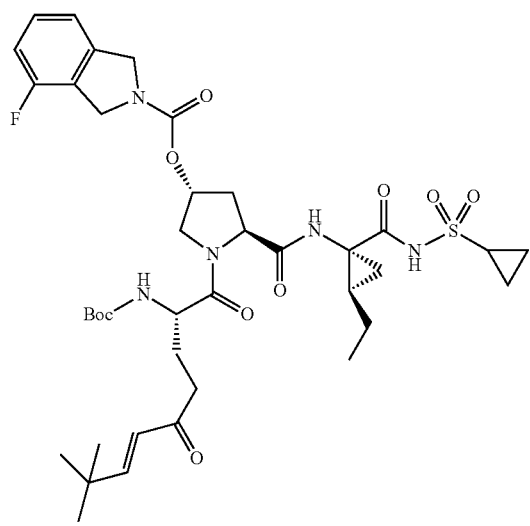
I-64
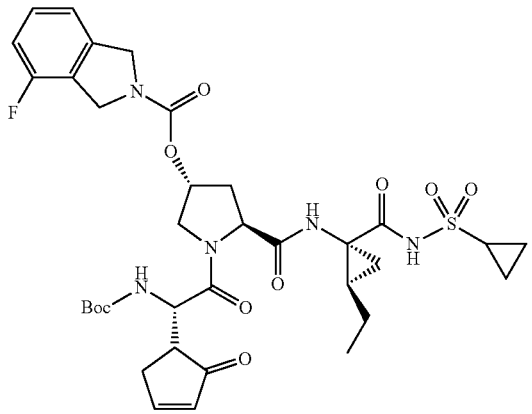
I-65
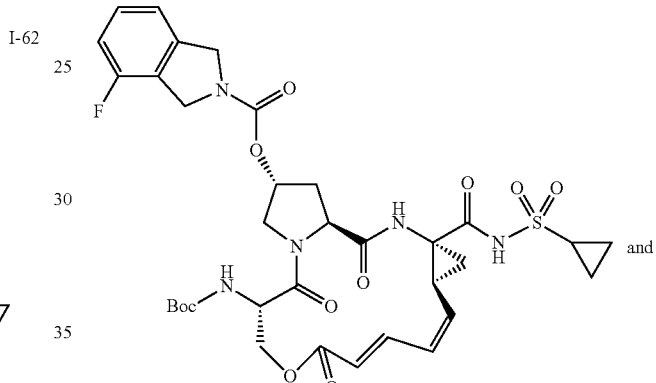
I-66
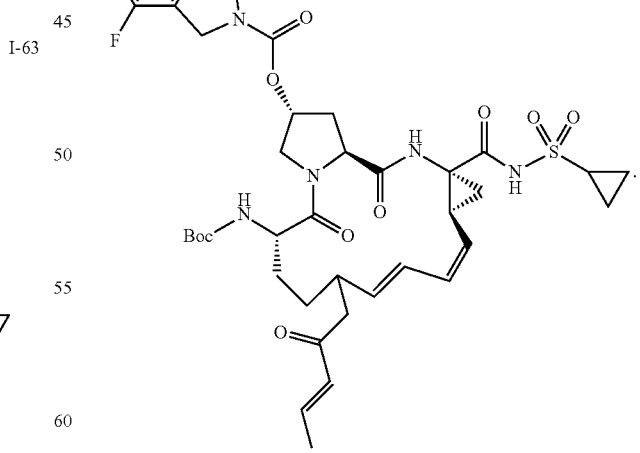
or a pharmaceutically acceptable salt thereof.
12. A method for inhibiting HCV protease, or a mutant thereof, activity comprising the step of administering to a patient in need thereof a compound of formula I:

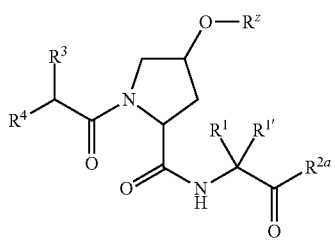

or a pharmaceutically acceptable salt thereof, wherein:
- $R^1$ and $R^{1'}$ are independently hydrogen or optionally substituted $C_{1-6}$ aliphatic, or $R^{1'}$ and $R^1$, are taken together to form an optionally substituted 3-7 membered carbocyclic ring;
- $R^{2a}$ is —OH or —NHSO$_2$R$^2$;
- $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
- each R is independently hydrogen, optionally substituted $C_{1-6}$ aliphatic, or:
  - two R on the same nitrogen atom are taken together with the nitrogen to form a 4-7 membered heterocyclic ring having 1-2 heteroatoms independently selected from nitrogen, oxygen, or sulfur;
- $R^3$ is -L-Y, wherein -L-Y is selected from the following:
  - (a) L is a bivalent $C_{2-8}$ straight or branched, hydrocarbon chain wherein L has at least one double bond and one or two methylene units of L are independently replaced by —NRC(O)—, —C(O)NR—, —N(R)SO$_2$—, —SO$_2$N(R)—, —S(O)—, —SO$_2$—, —OC(O)—, —C(O)O, or —C(O)—; and Y is hydrogen or $C_{1-6}$ aliphatic optionally substituted with oxo, halogen, NO$_2$, or CN; or
  - (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN; or
  - (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN; or
  - (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, NO$_2$, or CN;
- or $R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or
- $R^3$ and a ring formed by $R^{1'}$ and $R^1$, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;
- $R^4$ is H, —NHC(O)R$^5$, —NHC(O)OR$^6$,

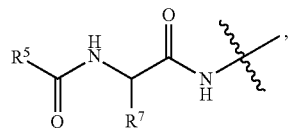

or a natural or unnatural amino acid side-chain group;
- each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
- $R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
- $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
- $R^z$ is

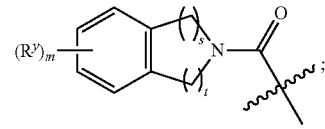

or $R^4$ and $R^z$ are taken together with their intervening atoms to form an optionally substituted, saturated or unsaturated 16-22 membered ring having 2-6 heteroatoms independently selected from nitrogen, oxygen, or sulfur;
- wherein the 16-22 membered ring is optionally substituted with $(R^m)_p$, wherein:
  - p is an integer from 1 to 6, inclusive;
  - each occurrence of $R^m$ is independently halogen, —OR$_\circ$, —CN, —N(R$_\circ$)$_2$, or an optionally substituted group selected from $C_{1-6}$ aliphatic or $C_{3-7}$ cycloalkyl;

each occurrence of $R^m$ is independently selected from halogen, —OR○, —CN, —NO$_2$, —N(R○)$_2$, or optionally substituted $C_{1-4}$ aliphatic;

each R○ of $R^m$ or $R^y$ is independently optionally substituted $C_{1-6}$ aliphatic; and m is an integer from 0 to 4, inclusive;

s is an integer from 0 to 4, inclusive;

t is an integer from 0 to 4, inclusive;

wherein the sum of s and t is non-zero.

13. The method according to claim 12, wherein the HCV protease, or a mutant thereof, activity is inhibited irreversibly by covalently modifying a cysteine residue of HCV protease, wherein the cysteine is Cys159 or at an equivalent position to Cys159 of HCV protease subtype 1b.

14. The method according to claim 12, wherein the HCV protease, or a mutant thereof, activity is inhibited irreversibly by covalently modifying Cys159 of HCV protease.

15. The method according to claim 12, wherein the HCV protease, or a mutant thereof, activity is inhibited irreversibly by covalently modifying Cys16 of HCV protease.

16. The method of claim 1, wherein the step of administering occurs once daily.

17. The method according to claim 1, wherein the disorder is hepatitis C.

18. The method of claim 1 comprising the step of irreversibly inhibiting HCV protease by covalently modifying a cysteine residue of HCV protease, wherein the cysteine is Cys159 or at an equivalent position to Cys159 of HCV protease subtype 1b.

19. The method of claim 18, wherein the HCV protease genotype or subtype is selected from the group consisting of 1a, 1b, 1c, 2a, 2b, 2c, 2i, 2k, 3a, 3b, 3k, 4a, 4d, 4f, 5a, 6a, 6b, 6c, 6d, 6e, 6f, 6g, 6h, 6i, 6j, 6k, 6l, 6m, 6n, 6o, 6p, 6q, 6t, and 7a.

20. The method of claim 19, wherein the HCV protease genotype or subtype is 1a, 1b, 2a, or 3a.

21. The method according to claim 1, comprising the step of irreversibly inhibiting HCV protease by covalently modifying Cys159 of HCV protease.

22. The method according to claim 1, comprising the step of irreversibly inhibiting HCV protease by covalently modifying Cys16 of HCV protease.

23. The method according to claim 1, wherein $R^z$ is

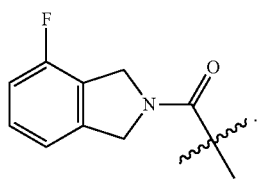 [SMILES: *C(=O)N1Cc2cccc(F)c2C1]

24. The method according to claim 1, wherein $R^4$ and $R^z$ are taken together with their intervening atoms to form an optionally substituted, saturated or unsaturated 16-22 membered ring having 2-6 heteroatoms independently selected from nitrogen, oxygen, or sulfur.

25. The method according to claim 24, wherein the compound is of formula I-e or I-f:

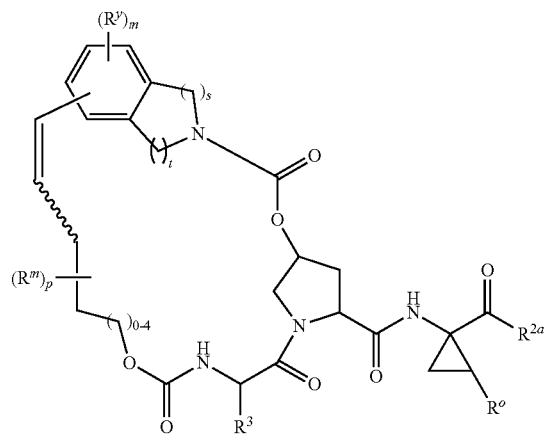

I-e

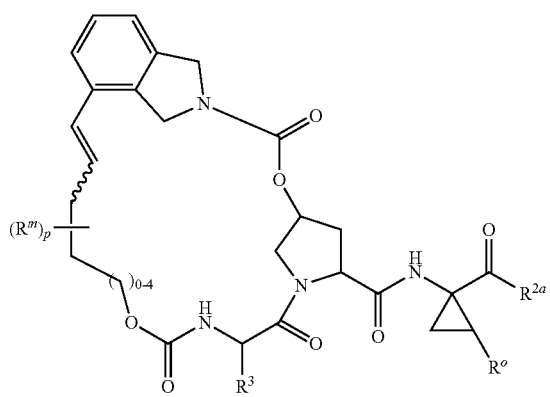

I-f or a pharmaceutically acceptable salt thereof;
wherein:
p is an integer from 1 to 6, inclusive; and
each occurrence of $R^m$ is independently halogen, —OR○, —CN, —N(R○)$_2$, or an optionally substituted group selected from the group consisting of $C_{1-6}$ aliphatic and $C_{3-7}$ cycloalkyl; and
R○ is an optionally substituted group selected from $C_{1-6}$ aliphatic.

26. The method according to claim 1, wherein $R^1$ and $R^1$, are taken together to form an optionally substituted 3-7 membered carbocyclic ring.

27. The method according to claim 26, wherein $R^1$ and $R^1$, are taken together to form:

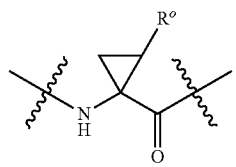

wherein R○ is an optionally substituted group selected from $C_{1-6}$ aliphatic.

28. The method according to claim 27, wherein R○ is vinyl.

29. The method according to claim 27, wherein R○ is ethyl.

30. A method for inhibiting HCV protease, or a mutant thereof, activity comprising the step of administering to a patient in need thereof a compound of formula I:

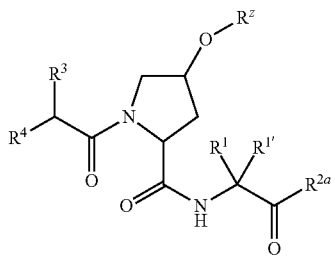

I or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{2a}$ is —OH or —NHSO$_2$R$^2$;

$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:

two R on the same nitrogen atom are taken together with the nitrogen to form a 4-7 membered heterocyclic ring having 1-2 heteroatoms independently selected from nitrogen, oxygen, or sulfur;

$R^3$ is -L-Y, wherein:

L is a covalent bond, —C(O)—, —N(R)C(O)—, a bivalent $C_{1-8}$ saturated or unsaturated, straight or branched, hydrocarbon chain, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—; and Y is selected from:

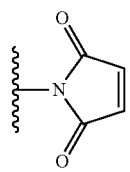
a

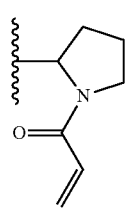
b

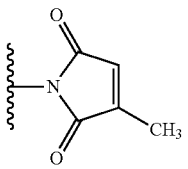
c

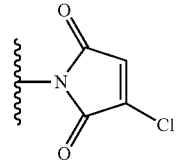
d

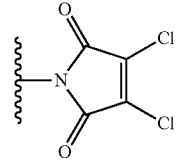
e

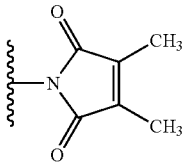
f

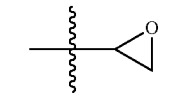
g

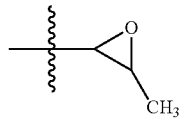
h

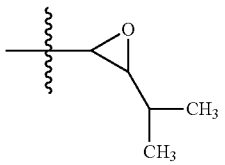
i

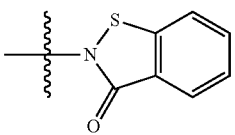
j

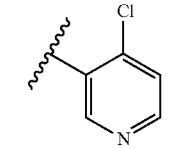
k

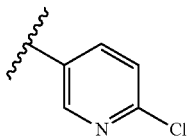
l

| | | | |
|---|---|---|---|
| 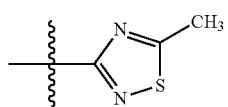 | m | 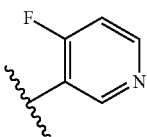 | x |
| 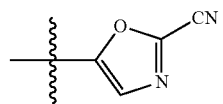 | n | 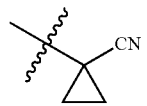 | y |
| 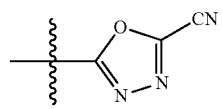 | o | 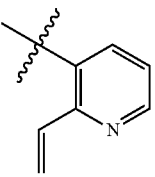 | z |
| 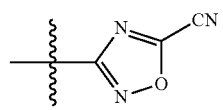 | p | 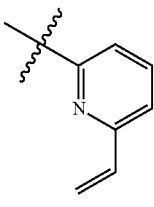 | aa |
| 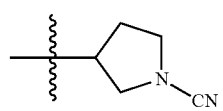 | q | 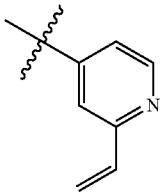 | bb |
| 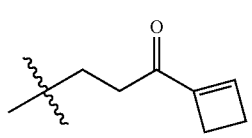 | r | 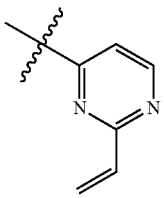 | cc |
| 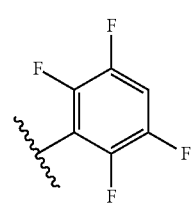 | s | 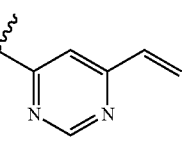 | dd |
| 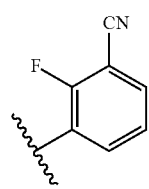 | t | 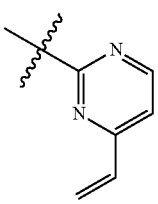 | ee |
| 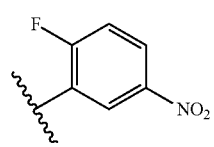 | u | 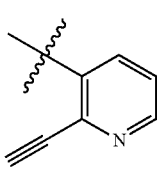 | ff |
| 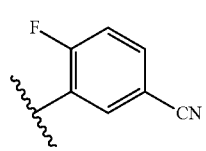 | v | | |
| 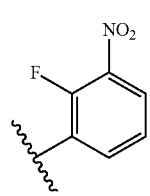 | w | | |

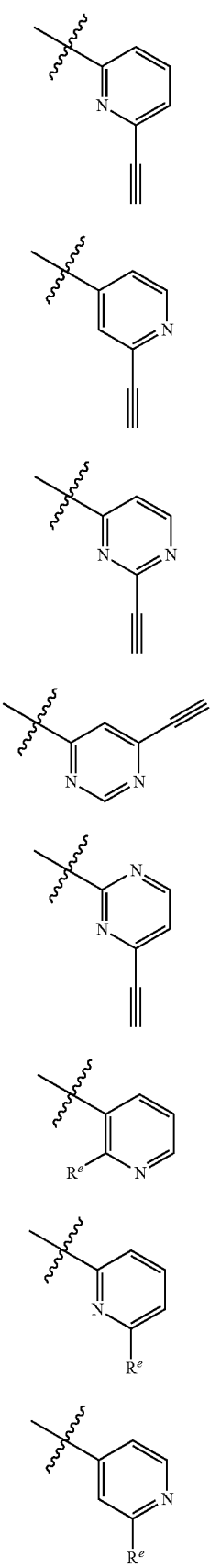
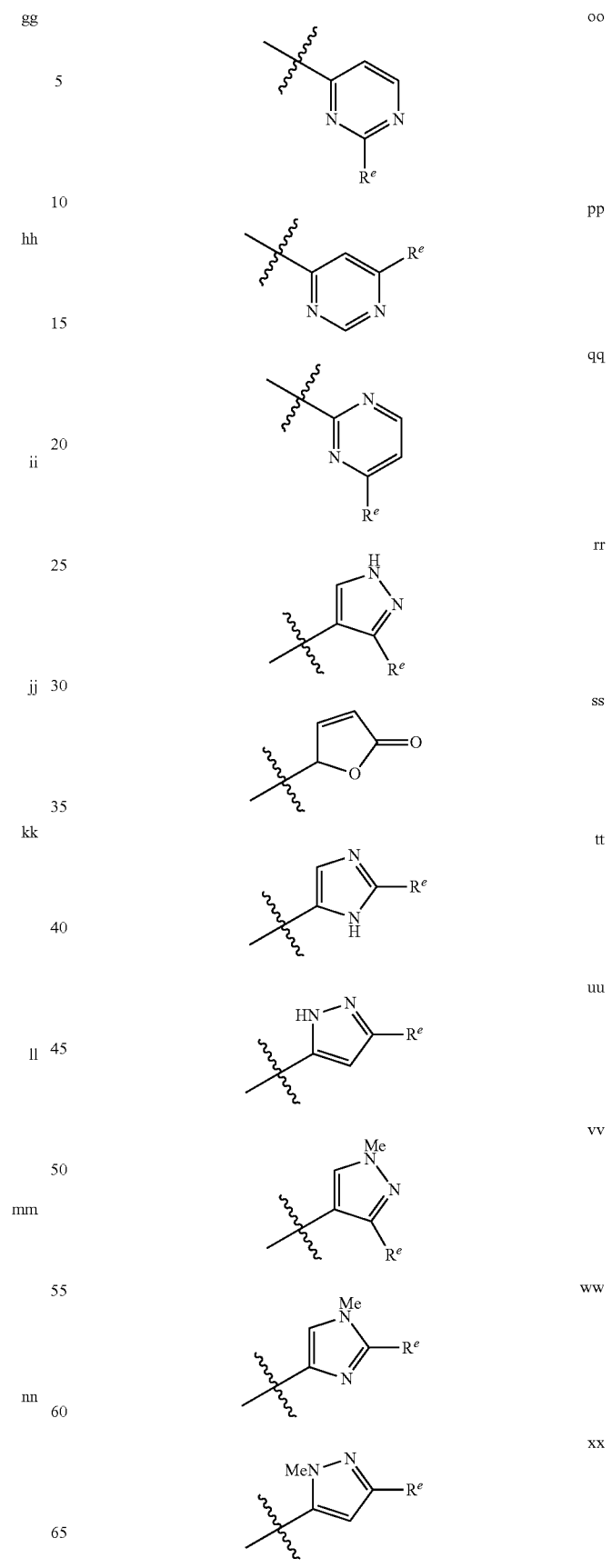

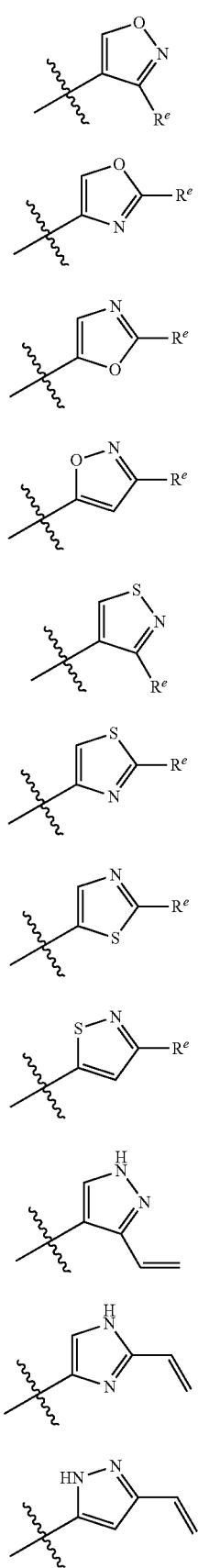
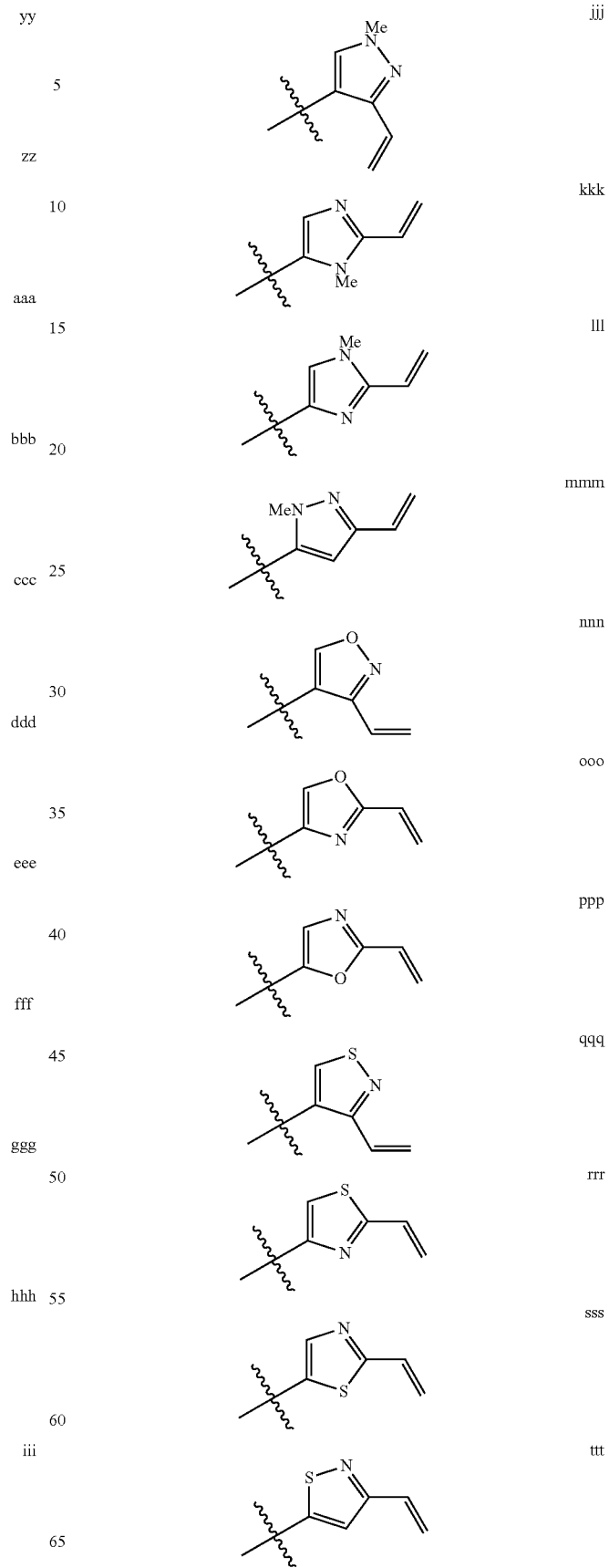

| | | | |
|---|---|---|---|
| uuu | 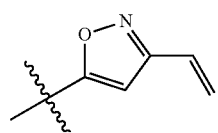 | dddd | 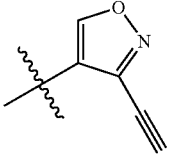 |
| vvv | 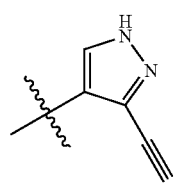 | eeee | 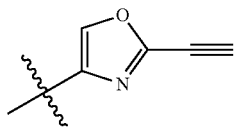 |
| qqq | 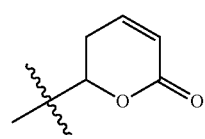 | ffff | 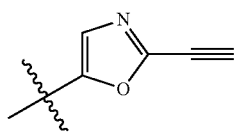 |
| www | 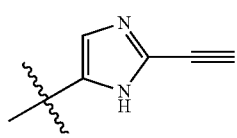 | gggg | 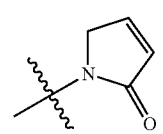 |
| xxx | 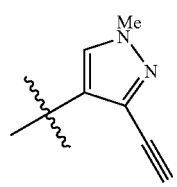 | hhhh | 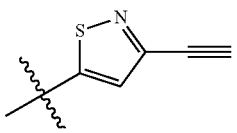 |
| yyy | 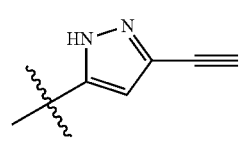 | iiii | 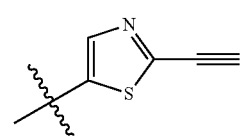 |
| zzz | 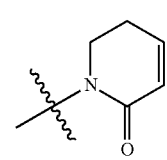 | jjjj | 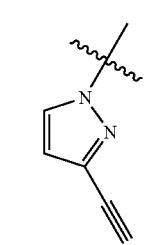 |
| aaaa | 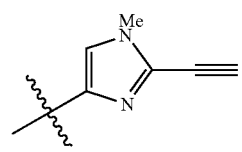 | kkkk | 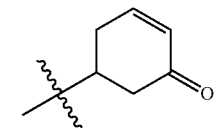 |
| bbbb | 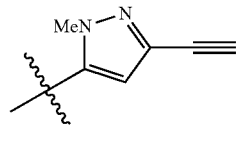 | llll | 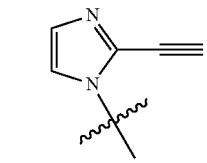 |
| cccc | 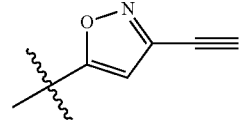 | mmmm | 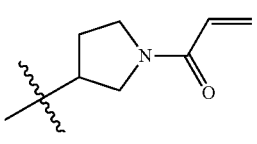 |

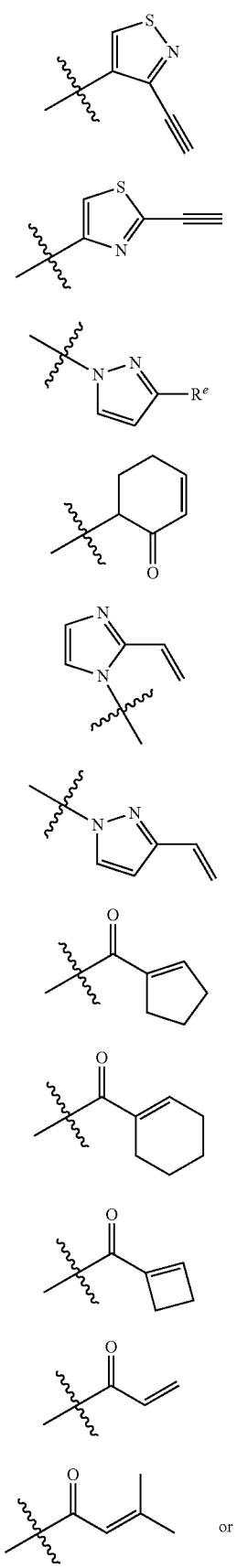

nnnn oooo pppp qqqq rrrr ssss tttt uuuu vvvv wwww xxxx or ddddd

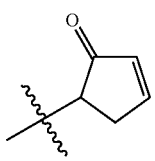

wherein each $R^e$ is independently selected from halogen; or $R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or $R^3$ and a ring formed by $R^1$ and $R^1$, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;

$R^4$ is H, —NHC(O)$R^5$, —NHC(O)O$R^6$,

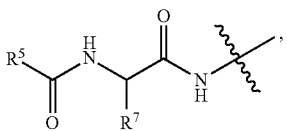

or a natural or unnatural amino acid side-chain group;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

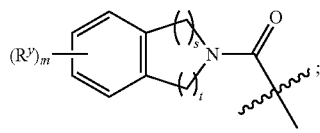

or $R^4$ and $R^z$ are taken together with their intervening atoms to form an optionally substituted, saturated or unsaturated 16-22 membered ring having 2-6 heteroatoms independently selected from nitrogen, oxygen, or sulfur;
  wherein the 16-22 membered ring is optionally substituted with $(R^m)_p$, wherein:
    p is an integer from 1 to 6, inclusive;
    each occurrence of $R^m$ is independently halogen, —OR○, —CN, —N(R○)$_2$, or an optionally substituted group selected from $C_{1-6}$ aliphatic or $C_{3-7}$ cycloalkyl; and
  each occurrence of $R^y$ is independently selected from halogen, —OR○, —CN, —NO$_2$, —N(R○)$_2$, or optionally substituted $C_{1-4}$ aliphatic;
  each R○ of $R^m$ or $R^y$ is independently optionally substituted $C_{1-6}$ aliphatic; and
  m is an integer from 0 to 4, inclusive;
  s is an integer from 0 to 4, inclusive;
  t is an integer from 0 to 4, inclusive;
  wherein the sum of s and t is non-zero.

31. A method for treating hepatitis C infection in a patient, comprising the step of administering to a patient in need thereof a compound of formula I:

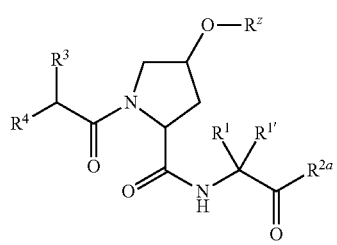

I or a pharmaceutically acceptable salt thereof, wherein:
  $R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
  $R^{2a}$ is —OH or —NHSO$_2$R$^2$;
  $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
  each R is independently hydrogen, optionally substituted $C_{1-6}$ aliphatic, or:
    two R on the same nitrogen atom are taken together with the nitrogen to form a 4-7membered heterocyclic ring having 1-2 heteroatoms independently selected from nitrogen, oxygen, or sulfur;
  $R^3$ is -L-Y, wherein -L-Y is selected from:

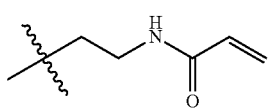

b

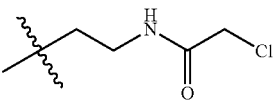

c

-continued

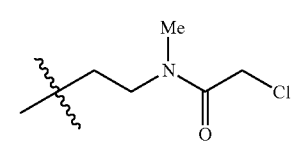

d

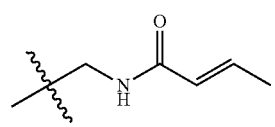

g

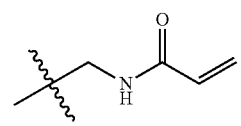

h

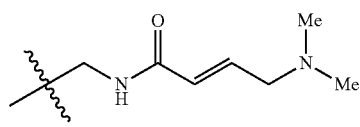

i

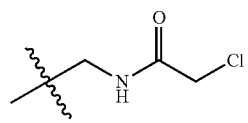

j

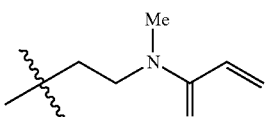

l

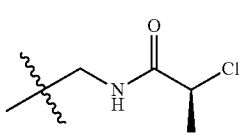

m

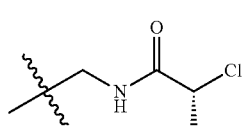

n

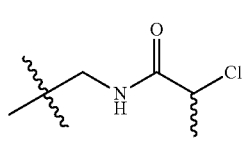

o

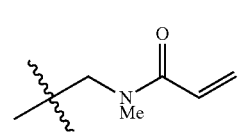

p

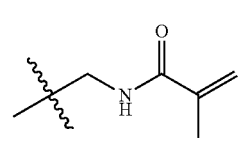

q

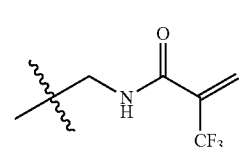

r

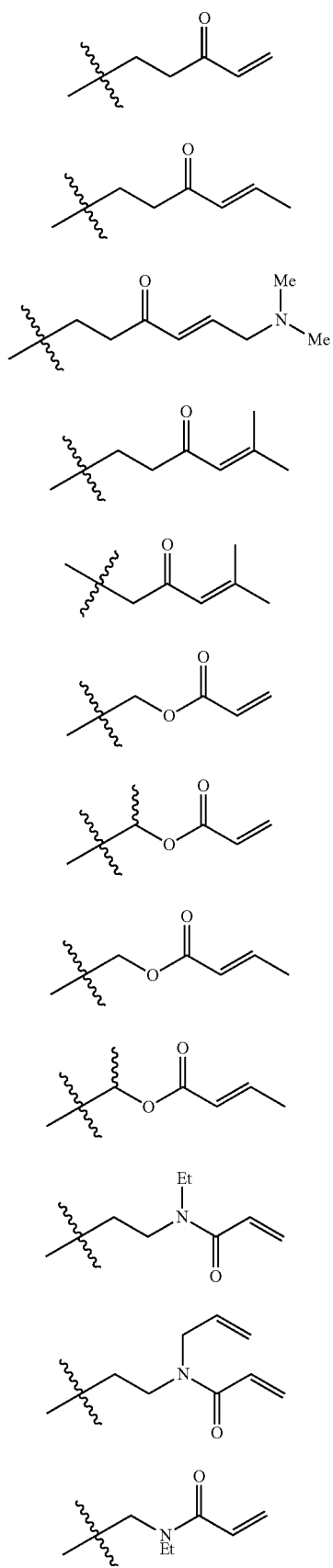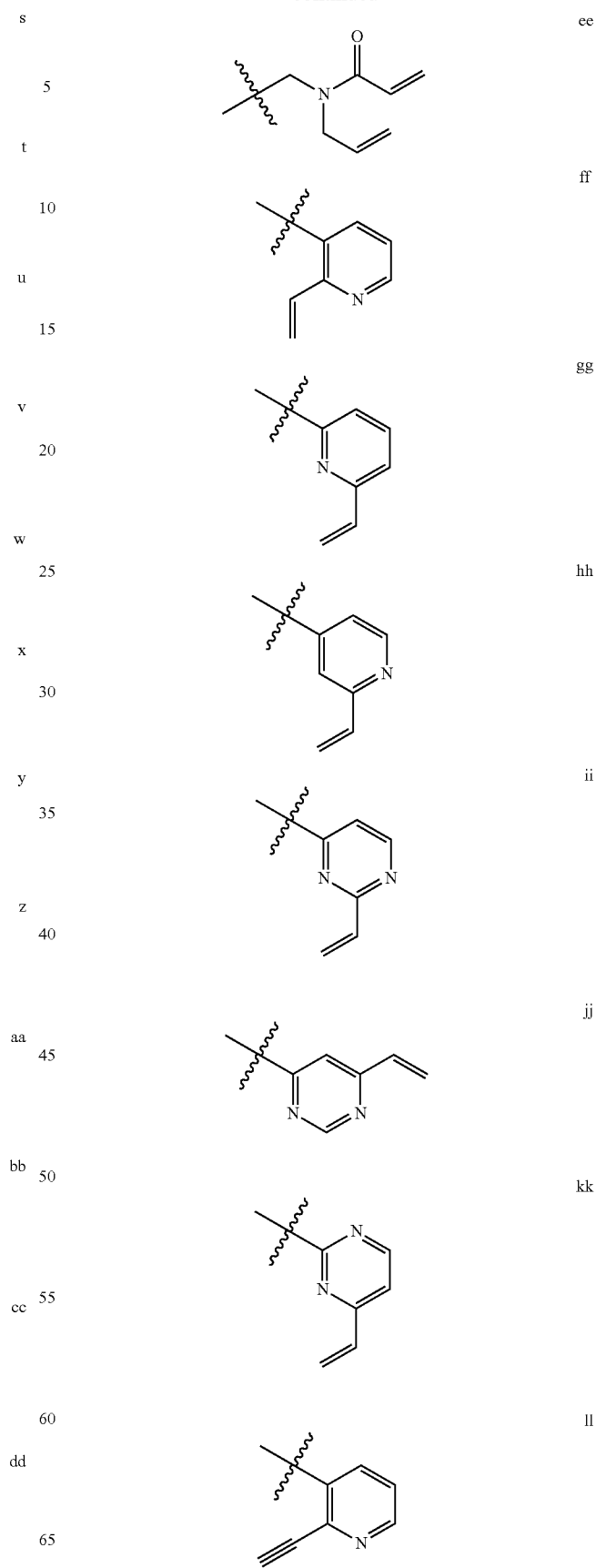

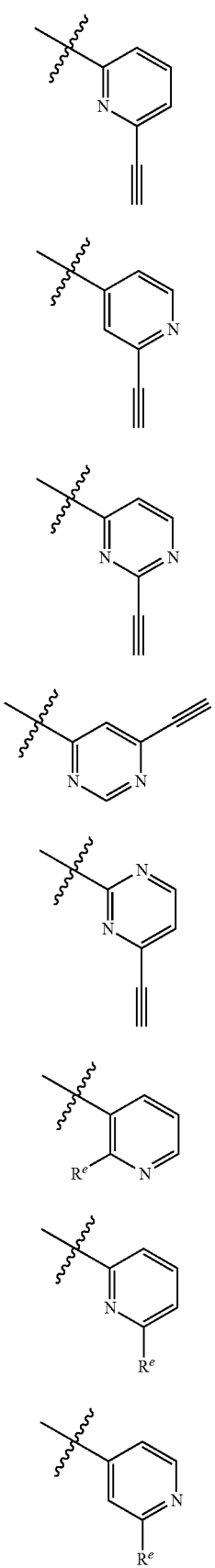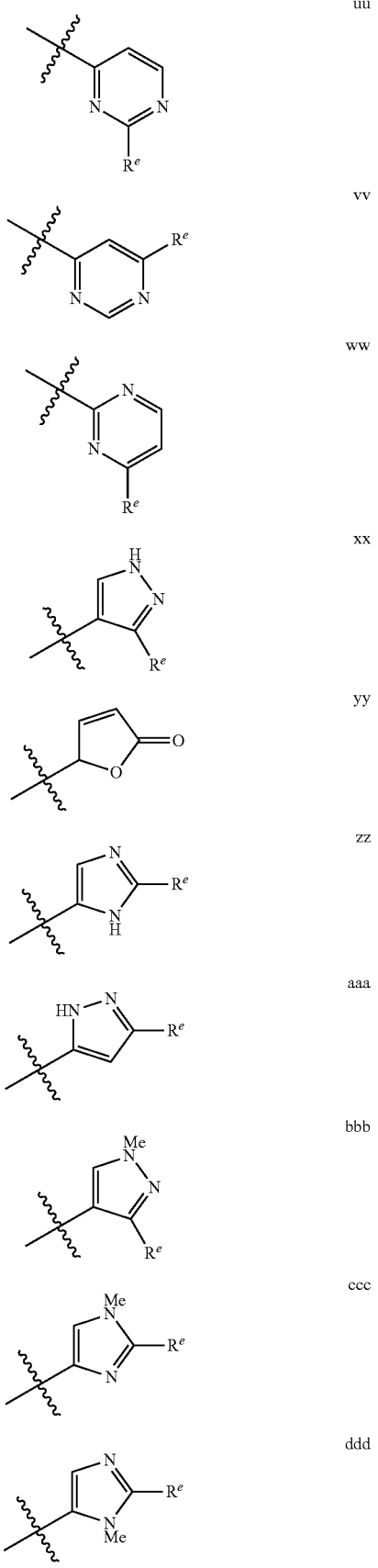

| | | | | |
|---|---|---|---|---|
| eee | 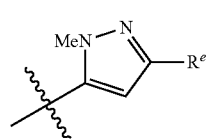 | | ppp | 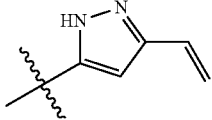 |
| fff | 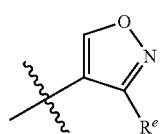 | | | 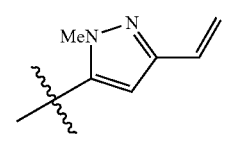 |
| ggg | 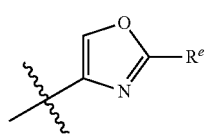 | | qqq | 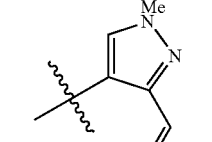 |
| hhh | 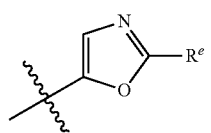 | | rrr | 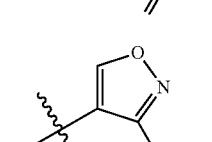 |
| iii | 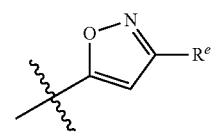 | | sss | 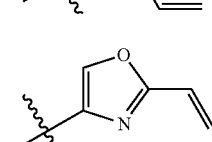 |
| jjj | 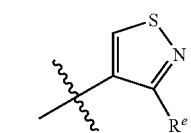 | | ttt | 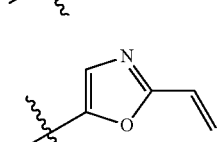 |
| kkk | 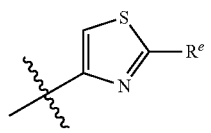 | | uuu | 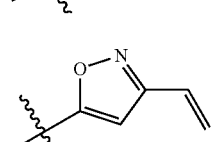 |
| lll | 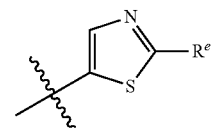 | | vvv | 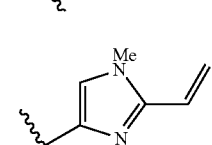 |
| mmm | 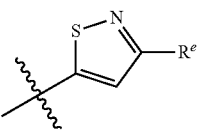 | | www | 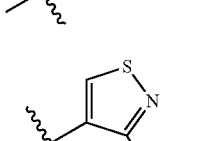 |
| nnn | 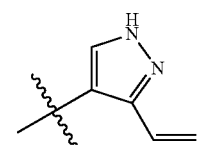 | | xxx | 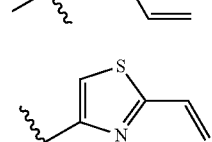 |
| ooo | 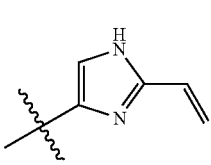 | | yyy | 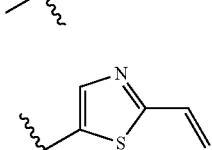 |

289
-continued
| | | |
|---|---|---|
| 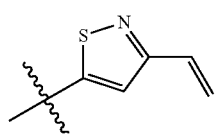 | zzz | |
| 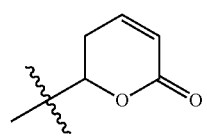 | aaaa | |
| 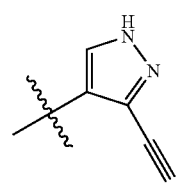 | bbbb | |
| 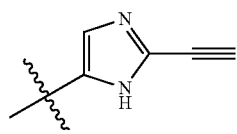 | cccc | |
| 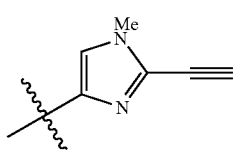 | dddd | |
| 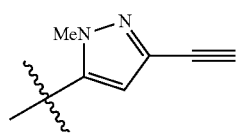 | eeee | |
| 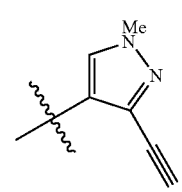 | ffff | |
| 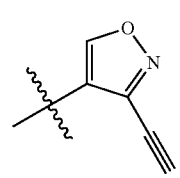 | gggg | |
| 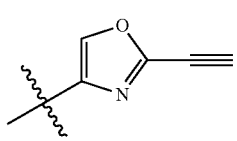 | hhhh | |
| 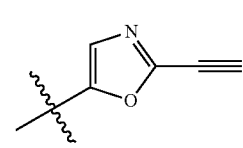 | iiii | |
290
-continued
| | | |
|---|---|---|
| 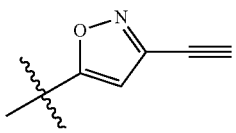 | jjjj | |
| 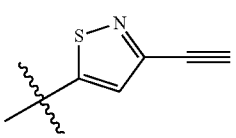 | kkkk | |
| 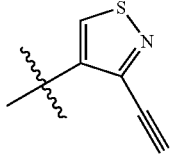 | llll | |
| 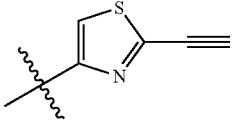 | mmmm | |
| 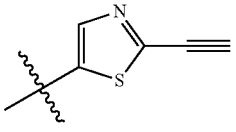 | nnnn | |
| 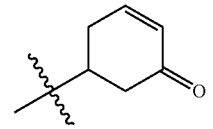 | oooo | |
| 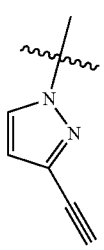 | pppp | |
| 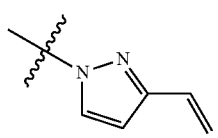 | qqqq | |
| 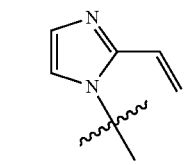 | rrrr | |
| 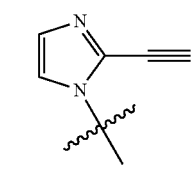 | ssss | |

| | | | |
|---|---|---|---|
| 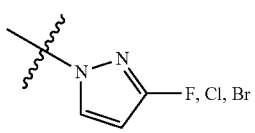 | tttt | 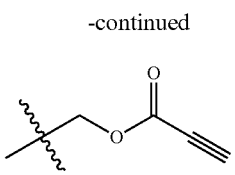 | fffff |
| 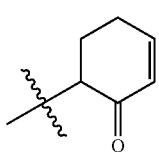 | uuuu | 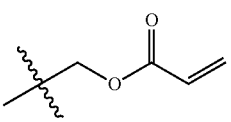 | hhhhh |
| 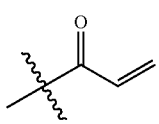 | vvvv | 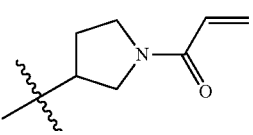 | iiiii |
| 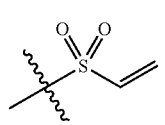 | wwww | 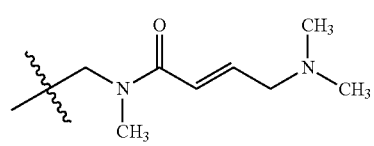 | jjjjj |
| 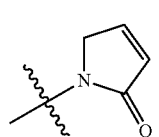 | xxxx | 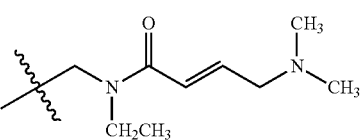 | kkkkk |
| 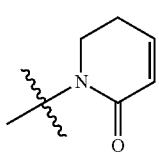 | yyyy | 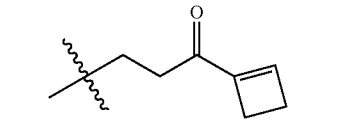 | lllll |
| 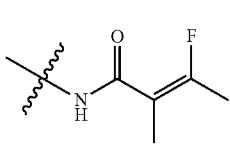 | zzzz | 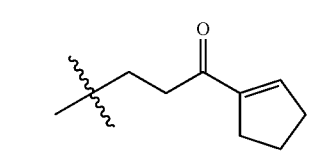 | mmmmm |
| 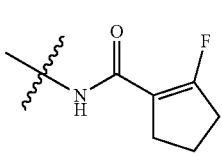 | aaaaa | 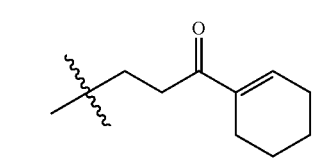 | nnnnn |
| 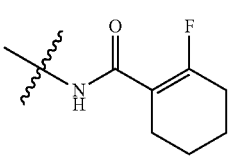 | bbbbb | 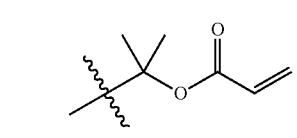 | ooooo |
| 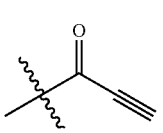 | ddddd | 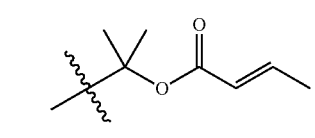 | ppppp |
| 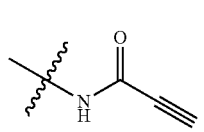 | eeeee | | qqqqq |

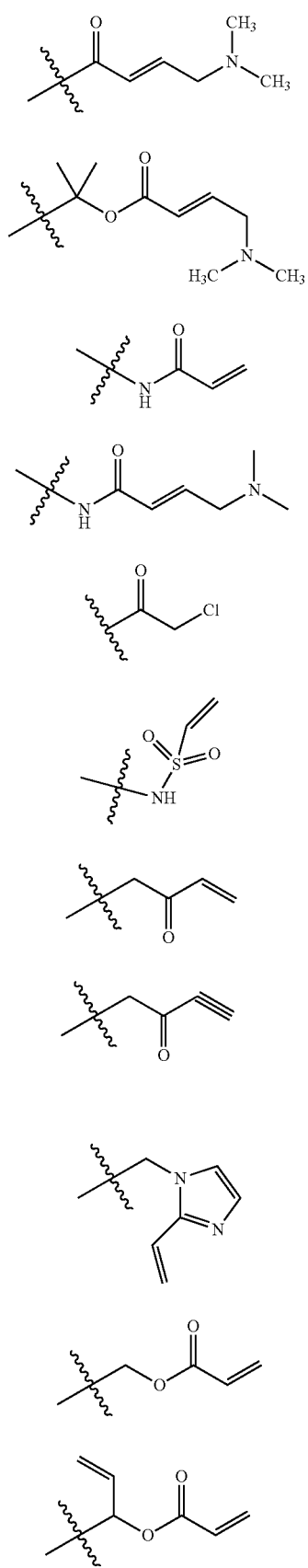
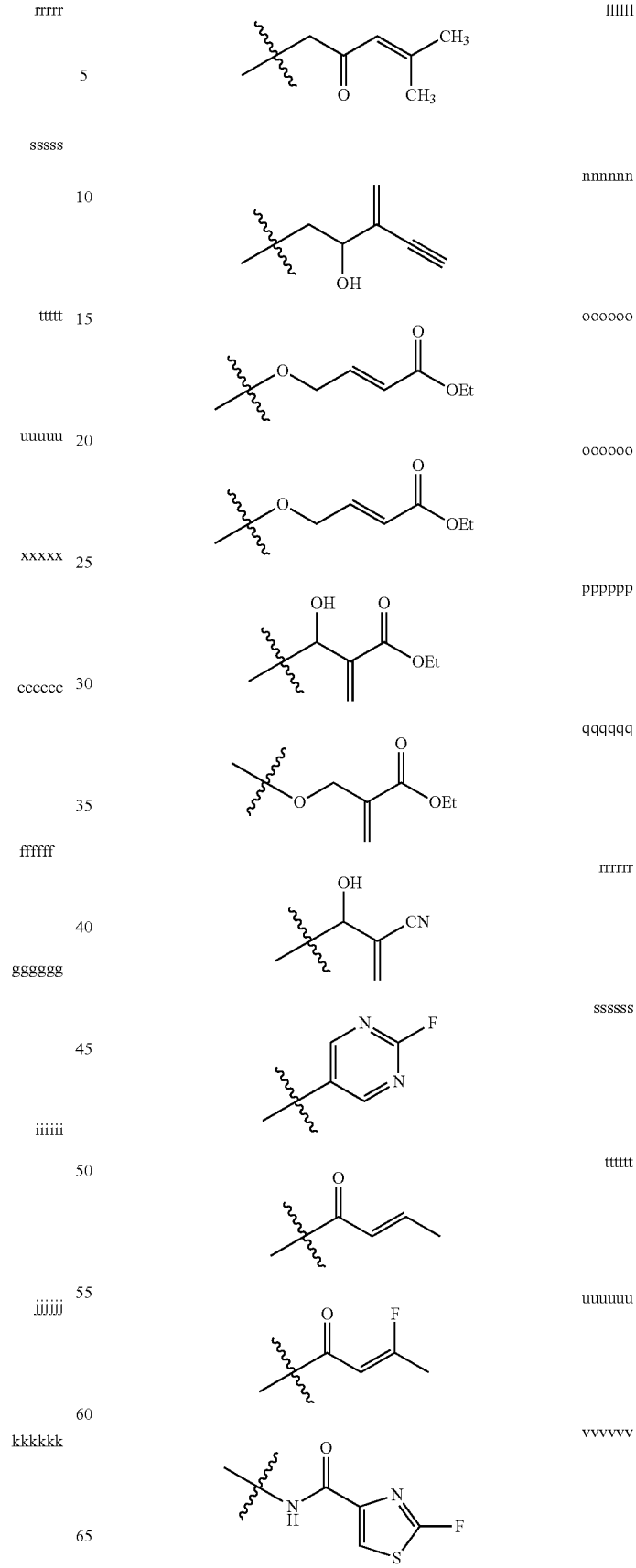

-continued wwwwww

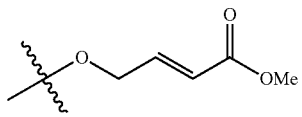

xxxxxx

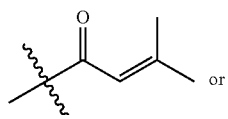 or yyyyyy

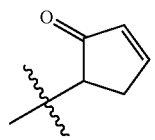

or

R³ and R¹ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or R³ and a ring formed by R¹ and R¹, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;

R⁴ is H, —NHC(O)R⁵, —NHC(O)OR⁶,

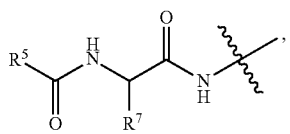

or a natural or unnatural amino acid side-chain group;

each R⁵ is independently —N(R)₂ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

R⁶ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and R⁷ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

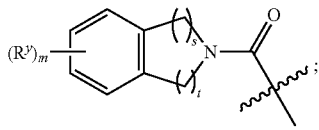

or R⁴ and $R^z$ are taken together with their intervening atoms to form an optionally substituted, saturated or unsaturated 16-22 membered ring having 2-6 heteroatoms independently selected from nitrogen, oxygen, or sulfur;
wherein the 16-22 membered ring is optionally substituted with $(R^m)_p$, wherein:
p is an integer from 1 to 6, inclusive;
each occurrence of $R^m$ is independently halogen, —OR∘, —CN, —N(R∘)₂, or an optionally substituted group selected from $C_{1-6}$ aliphatic or $C_{3-7}$ cycloalkyl; and each occurrence of $R^y$ is independently selected from halogen, —OR∘, —CN, —NO₂, —N(R∘)₂, or optionally substituted $C_{1-4}$ aliphatic;

each R∘ of $R^m$ or $R^m$ is independently optionally substituted $C_{1-6}$ aliphatic; and m is an integer from 0 to 4, inclusive;
s is an integer from 0 to 4, inclusive;
t is an integer from 0 to 4, inclusive;
wherein the sum of s and t is non-zero.

32. A method for inhibiting HCV protease, or a mutant thereof, activity comprising the step of administering to a patient in need thereof a compound of formula I:

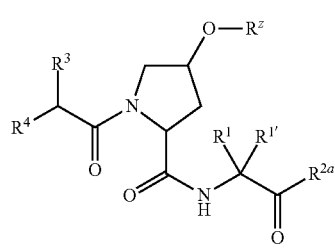

I or a pharmaceutically acceptable salt thereof, wherein:
R¹ and R¹, are independently hydrogen or optionally substituted $C_{1-6}$ aliphatic, or R¹ and R¹, are taken together to form an optionally substituted 3-7 membered carbocyclic ring;
$R^{2a}$ is —OH or —NHSO₂R²;
R² is —N(R)₂ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or:
two R on the same nitrogen atom are taken together with the nitrogen to form a 4-7membered heterocyclic ring having 1-2 heteroatoms independently selected from nitrogen, oxygen, or sulfur;

297
R³ is -L-Y, wherein -L-Y is selected from:
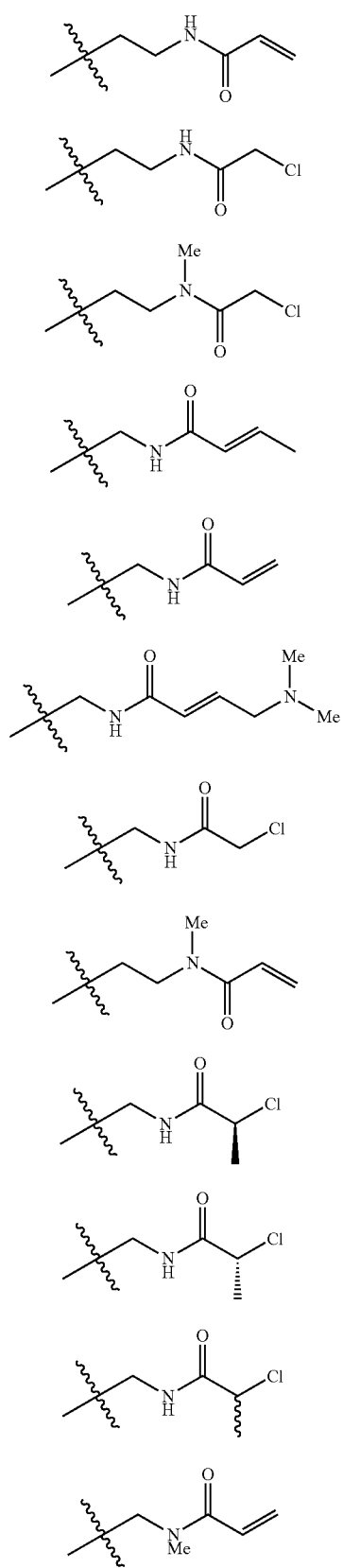
298
-continued
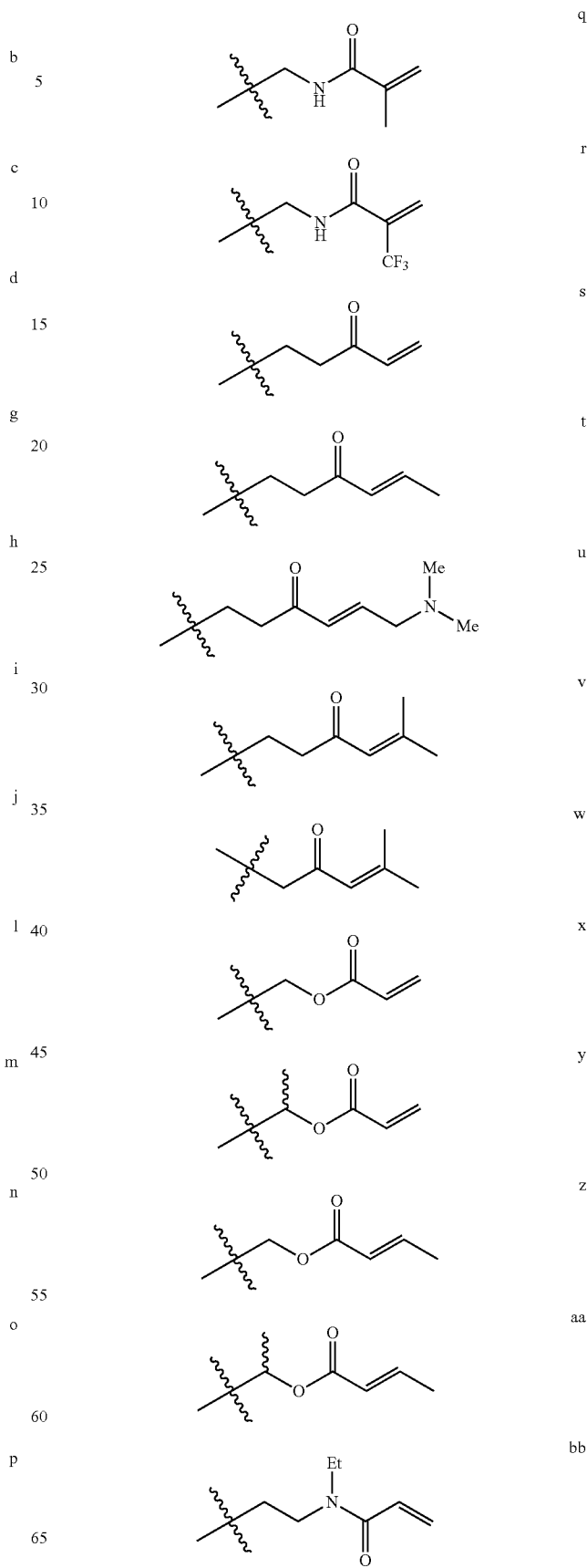

| 299 -continued | | 300 -continued | |
|---|---|---|---|
| 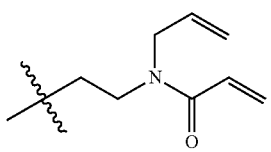 | cc | 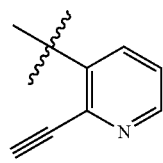 | ll |
| 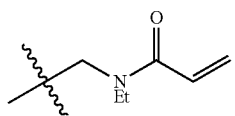 | dd | 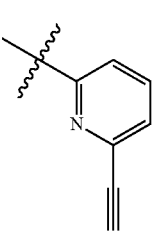 | mm |
| 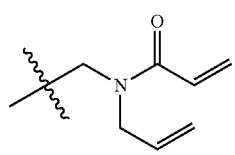 | ee | 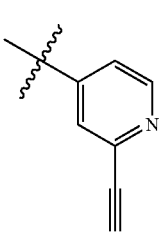 | nn |
| 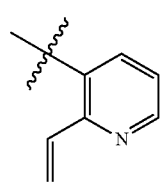 | ff | 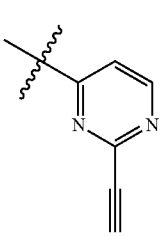 | oo |
| 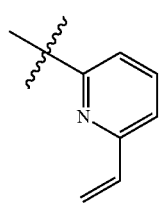 | gg | 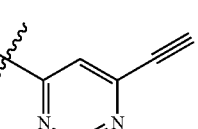 | pp |
| 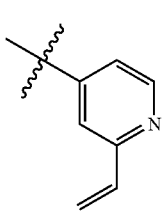 | hh | 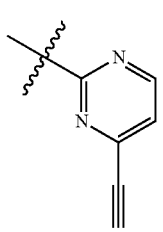 | qq |
| 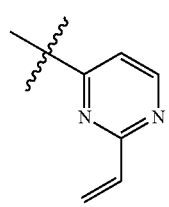 | ii | 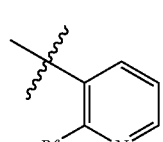 | rr |
| 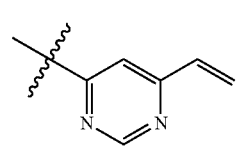 | jj | 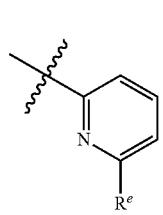 | ss |
| 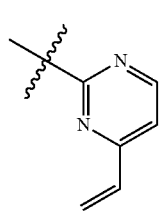 | kk | | |

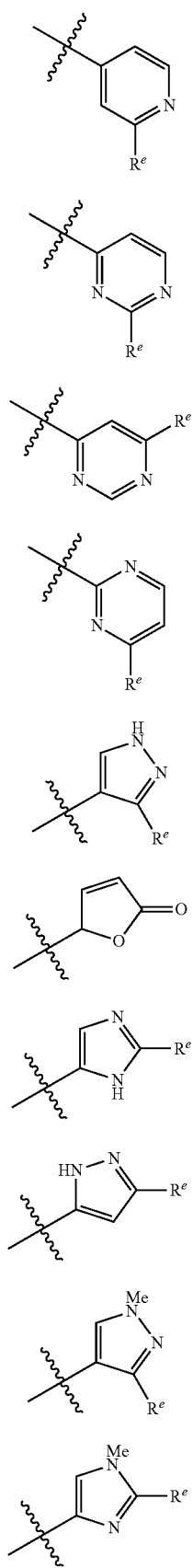
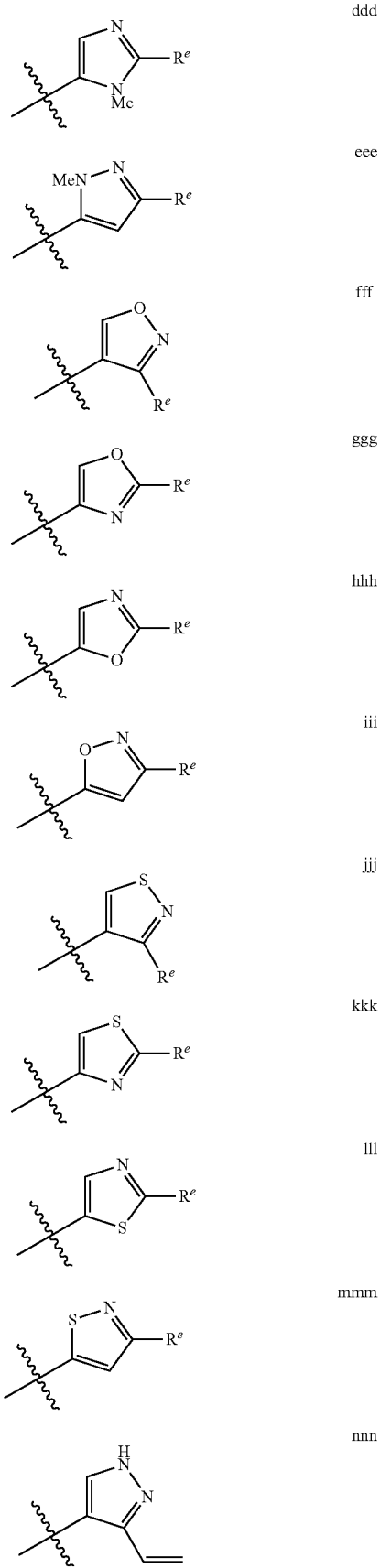

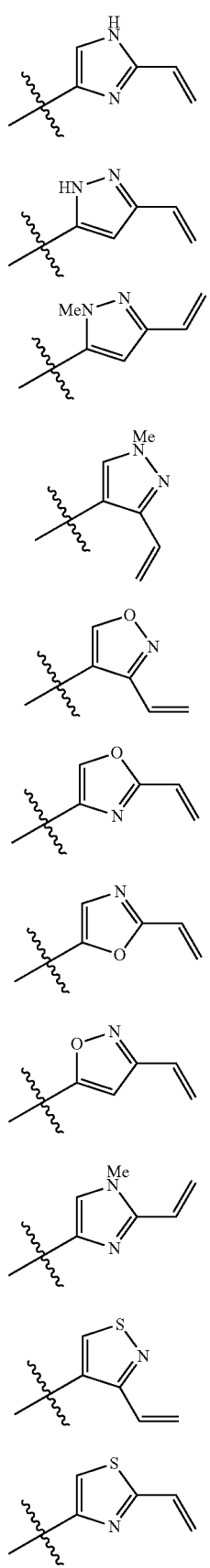
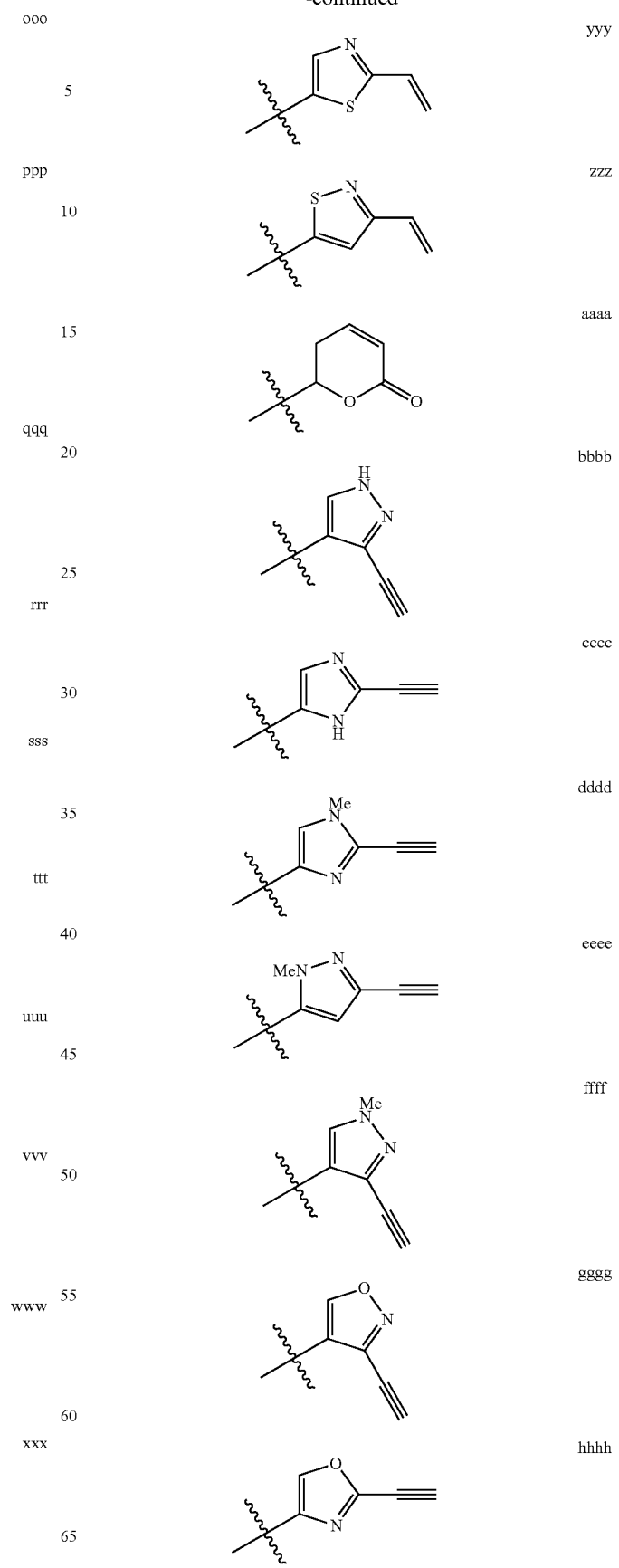

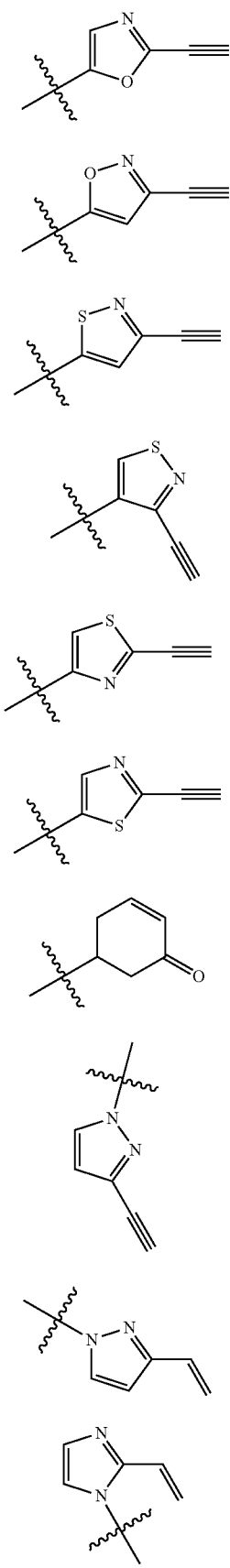
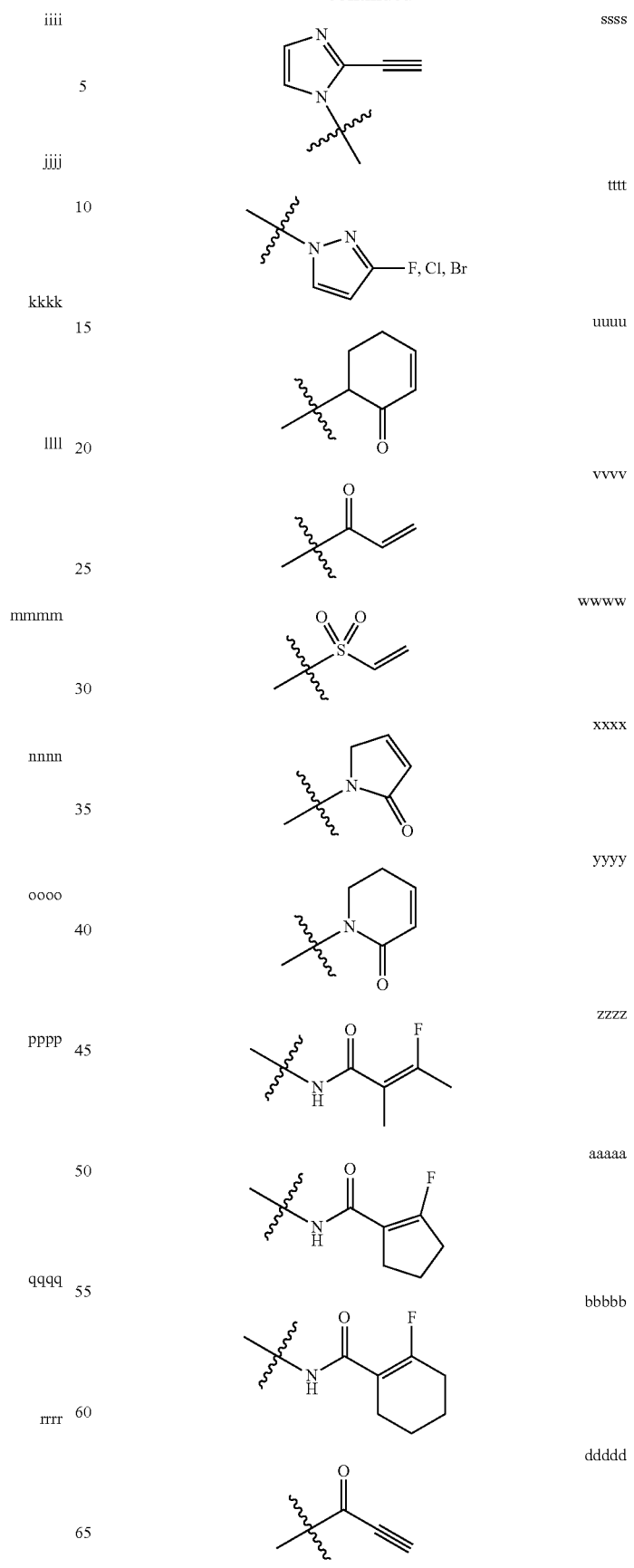

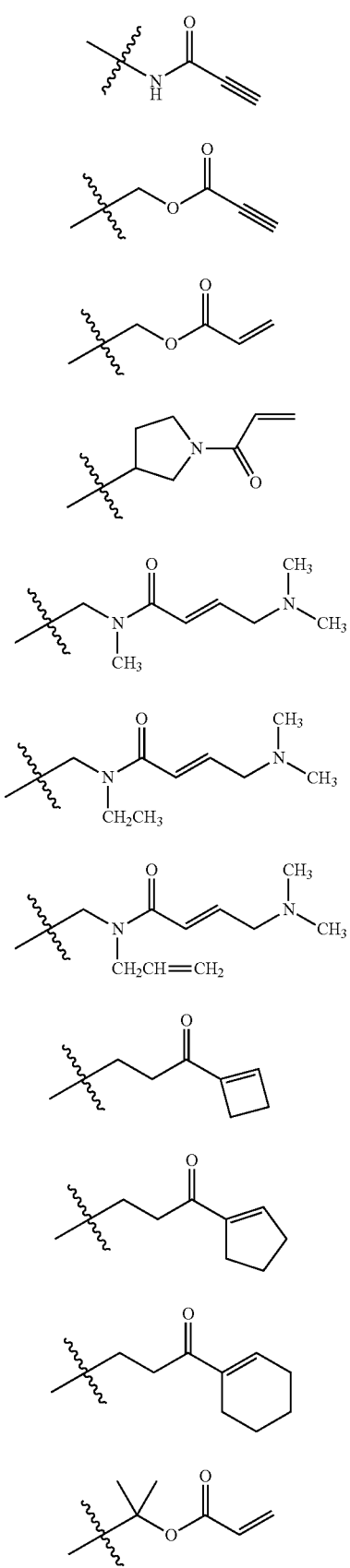
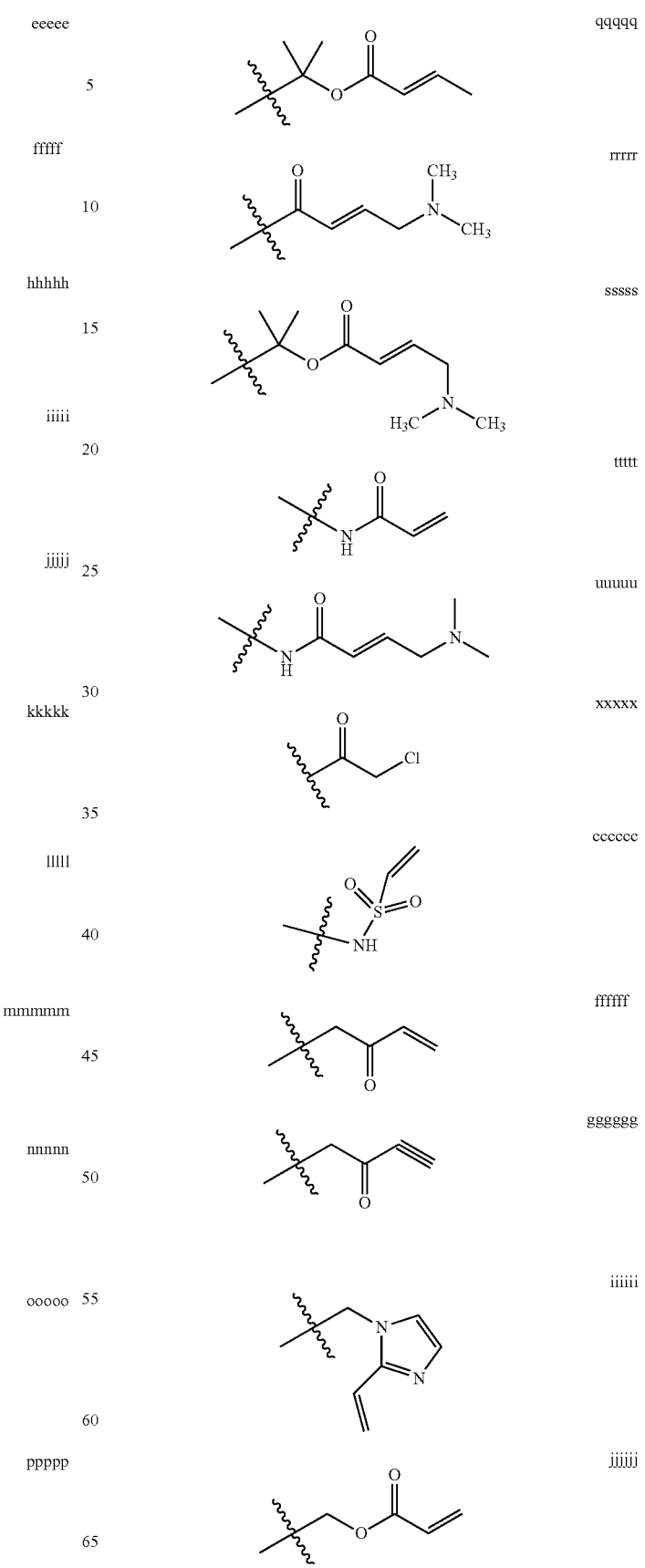

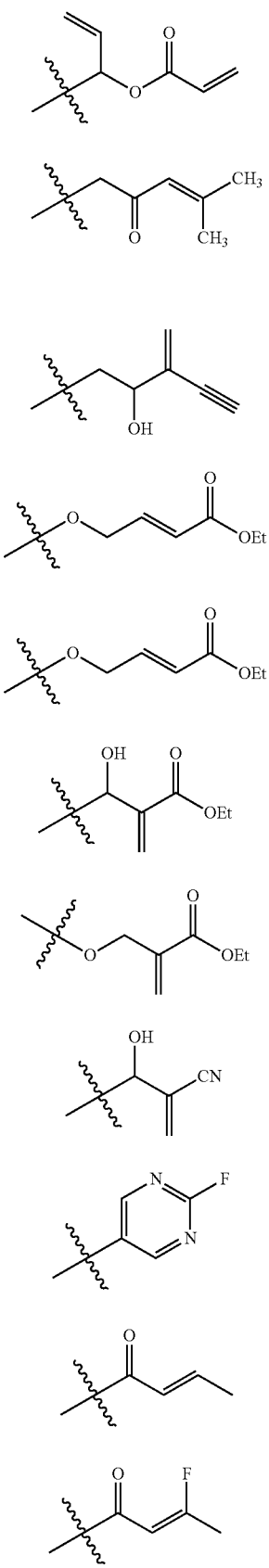
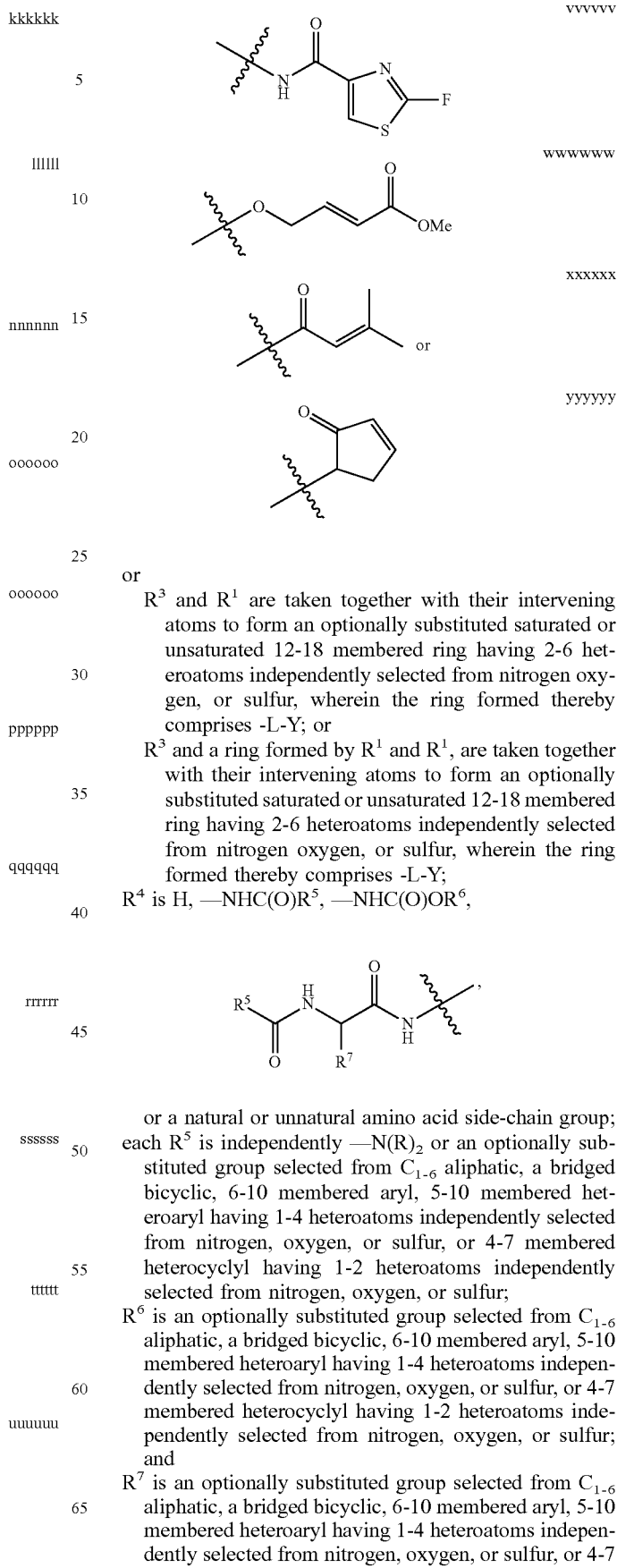

or

R³ and R¹ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or R³ and a ring formed by R¹ and R¹, are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y;

$R^4$ is H, —NHC(O)$R^5$, —NHC(O)O$R^6$, or a natural or unnatural amino acid side-chain group;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^z$ is

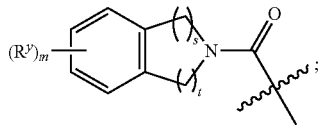

or $R^4$ and $R^z$ are taken together with their intervening atoms to form an optionally substituted, saturated or unsaturated 16-22 membered ring having 2-6 heteroatoms independently selected from nitrogen, oxygen, or sulfur;

wherein the 16-22 membered ring is optionally substituted with $(R^m)_p$, wherein:
p is an integer from 1 to 6, inclusive;
each occurrence of $R^m$ is independently halogen, —OR○, —CN, —N(R○)$_2$, or an optionally substituted group selected from $C_{1-6}$ aliphatic or $C_{3-7}$ cycloalkyl; and each occurrence of $R^y$ is independently selected from halogen, —OR○, —CN, —NO$_2$, —N(R○)$_2$, or optionally substituted $C_{1-4}$ aliphatic;

each R○ of $R^m$ or $R^y$ is independently optionally substituted $C_{1-6}$ aliphatic; and m is an integer from 0 to 4, inclusive;
s is an integer from 0 to 4, inclusive;
t is an integer from 0 to 4, inclusive;
wherein the sum of s and t is non-zero.

* * * * *